(12) United States Patent
Ambarkhane et al.

(10) Patent No.: US 8,546,416 B2
(45) Date of Patent: Oct. 1, 2013

(54) 3-SPIROCYCLIC PIPERIDINE DERIVATIVES AS GHRELIN RECEPTOR AGONISTS

(75) Inventors: Ameet Vijay Ambarkhane, Horsham (GB); Gurdip Bhalay, Horsham (GB); Martin Beckett, Redhill (GB); James Dale, Horsham (GB); Ahmed Hamadi, Horsham (GB); Alessandro Mazzacani, Brighton (GB); Jeffrey McKenna, Horsham (GB); Christopher Thomson, Billingshurst (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/479,596

(22) Filed: May 24, 2012

(65) Prior Publication Data

US 2012/0302540 A1    Nov. 29, 2012

Related U.S. Application Data

(60) Provisional application No. 61/490,848, filed on May 27, 2011, provisional application No. 61/560,960, filed on Nov. 17, 2011, provisional application No. 61/642,116, filed on May 3, 2012.

(51) Int. Cl.
| | |
|---|---|
| *C07D 211/00* | (2006.01) |
| *C07D 213/00* | (2006.01) |
| *C07D 215/00* | (2006.01) |
| *C07D 219/00* | (2006.01) |
| *C07D 221/00* | (2006.01) |
| *C07D 217/00* | (2006.01) |

(52) U.S. Cl.
USPC .......................................... 514/278; 546/15

(58) Field of Classification Search
CPC .. C07D 211/00; C07D 213/00; C07D 215/00; C07D 219/00; C07D 221/00; C07D 217/00
See application file for complete search history.

(56) References Cited

U.S. PATENT DOCUMENTS 5,536,716 A    7/1996    Chen et al.

FOREIGN PATENT DOCUMENTS

| EP | 1159964 | 12/2001 |
| WO | WO 97/11697 | * 4/1997 |
| WO | WO 2004/104001 | 12/2004 |
| WO | WO 2007/092681 | 8/2007 |
| WO | WO 2011/041369 | 4/2011 |

OTHER PUBLICATIONS

Carey, FA. Organic Chemistry 6th Ed. McGraw Hill. 2006, chapter 1, p. 9.*
Nakamura, I. et al. Transition-Metal-Catalyzed Reactions in Heterocyclic Synthesis. Chem. Rev. 2004, vol. 104, p. 2127.*
Kotha, S. et al. Synthesis of spiro-cyclics via ring-closing metathesis. Arkivoc. 2003, vol. iii, p. 67.*
Dorwold, FZ. Side Reactions in Organic Synthesis. Wiley. 2005, preface.*
Maison W et al., "Multicomponent Synthesis of Tripeptides Containing Pipecolic Acid Derivatives: Selective Induction of *cis*- and *trans*-imide Bonds into Peptide Backbones" *J. Chem. Soc Perkin Trans 1*:1867-1871, 2000.
Yang L et al., "Potent 3-Spiropiperidine Growth Hormone Secretagogues" *Bioorganic Medicinal Chemistry Letters* 8(1):107-112, 1998.
Asakawa et al., "Ghrelin is an Appetite-Stimulatory Signal From Stomach with Structural Resemblance to Motilin" *Gastroenterology* 120(2):337-345, 2001.
Trudel et al., "Ghrelin/Motilin-Related Peptide is a Potent Prokinetic to Reverse Gastric Postoperative Ileus in Rat" *Am J. Physiol Gastrointest Liver Physiol* 282(6):G948-G952, 2002.

* cited by examiner

*Primary Examiner* — Rita Desai
*Assistant Examiner* — Ben S Michelson
(74) *Attorney, Agent, or Firm* — Michael G. Smith

(57) ABSTRACT

The invention relates to derivatives of formula (I),

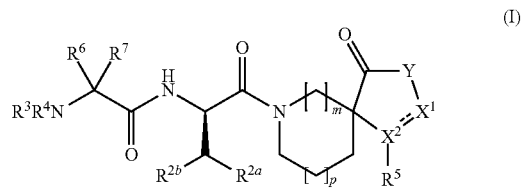

wherein the substituents are as defined in the specification; to processes for the preparation of such derivatives; pharmaceutical compositions comprising such derivatives; such derivatives as a medicament; such derivatives for the treatment of a disorder or a disease mediated by the ghrelin receptor.

11 Claims, 14 Drawing Sheets

3-SPIROCYCLIC PIPERIDINE DERIVATIVES AS GHRELIN RECEPTOR AGONISTS

CROSS-REFERENCE TO RELATED APPLICATIONS

This application claims benefit of priority to U.S. Provisional Applications Ser. No. 61/490,848 filed May 27, 2011, and Ser. No. 61/560,960 filed Nov. 17, 2011, and Ser. No. 61/642,116 filed May 3, 2012; the contents of each of these applications is incorporated herein by reference.

FIELD OF THE INVENTION

The present invention relates to 3-spirocyclic piperidine derivatives; processes for the preparation of such 3-spirocyclic piperidine derivatives; pharmaceutical compositions comprising such 3-spirocyclic piperidine derivatives optionally in combination with one or more other pharmaceutically active compounds; such 3-spirocyclic piperidine derivatives optionally in combination with one or more other pharmaceutically active compounds as a medicament; such 3-spirocyclic piperidine derivatives optionally in combination with one or more other pharmaceutically active compounds for the treatment of disorders/diseases characterized by gastrointestinal (GI) dysmotility; and the use of such 3-spirocyclic piperidine derivatives for the preparation of a pharmaceutical composition (medicament) for the treatment of disorders/diseases characterized by gastrointestinal (GI) dysmotility.

BACKGROUND OF THE INVENTION

Ghrelin is a hormone which has been shown to be the endogenous ligand for a G protein-coupled receptor (GPCR), type 1 growth hormone secretagogue receptor (hGHS-R1a) (Howard et al., Science, 1996, 273, 974-977).

Ghrelin is primarily synthesized in the stomach (Kojima et al., Horm. Res., 2001, 56 (Suppl. 1), 93-97. It has been found that levels of ghrelin are elevated in response to fasting or extended food restriction (Nakazato et al., Nature, 2001, 409, 194-198). A large number of effects of ghrelin in humans have been reported (see for example US patent application US2008/0194672, background section).

Ghrelin has been shown to improve gastrointestinal (GI) motility (Murray et al., Gastroenterology, 2003, 125, 1492-1502) and symptoms associated with conditions of altered GI transit like gastroparesis (e.g. Tack et al., Aliment Pharmacol Ther, 2005, 22: 847-853) and functional dyspepsia (e.g. Akamizu et al., Eur J. Endocrinol. 2008, 158, 491-498). Thus, ghrelin agonists may be useful in treating conditions associated with reduced or restricted GI motility.

Ghrelin has been observed to have additional endocrine effects including modulation of growth hormone (GH) levels (Howard et al., Science, 1996, 273, 974-977; Kojima et al., Nature 1999, 402, 656-660) as well as control of appetite, satiety and energy homeostasis (Cummings, Physiol Behav, 2006, 89, 71-84). Ghrelin receptor agonists may therefore be useful as therapeutics for conditions where modulation of GH release and/or food intake could be beneficial, for example for conditions such as growth retardation, muscle wasting disorders (e.g. sarcopenia or cachexia associated with, for example, cancer, chronic obstructive pulmonary disease (COPD), congestive heart failure (CHF), renal failure or Parkinson's Disease), anorexia and recovery from acute trauma (e.g. burns, spinal cord injury, hip fracture, head trauma and major surgery) or critical illness (DeBoer, 2011, Mol Cell Endocrinol).

Hence, it is the object of this invention to provide novel ghrelin receptor agonists.

WO 97/11697 (Merck) describes 3-spirolactam, 3-spiroamino, 3-spirolactone and 3-spirobenzopyran piperidines and pyrrolidines for the release of growth hormone.

SUMMARY OF THE INVENTION

In a first aspect, there is provided a compound of formula (I),

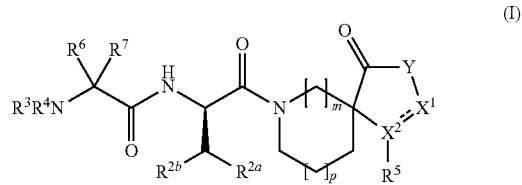

wherein

---- is a single bond or a double bond;

$X^1$ is $(CR^{x1}H)_n$ and $X^2$ is (CH); or $X^1$ is $(CR^{x1}H)_n$ and $X^2$ is N; or $X^1$ is $NR^{x1}$ and $X^2$ is (CH); or $X^1$ is $NR^{x1}$ and $X^2$ is N; or $X^1$ is N and $X^2$ is C; wherein the bond between $X^1$ and $X^2$ is a double bond if $X^1$ is N and $X^2$ is C;

n is 0 or 1;

$R^{x1}$ is selected from hydrogen and $C_{1-6}$alkyl;

m is 1 and p is 0; or m is 1 and p is 1; or m is 2 and p is 1;

Y is $NR^1$ or 0;

$R^1$ is selected from hydrogen, $C_{1-6}$ alkyl, —$C_{1-4}$alkylC(O)$NR^{1a}R^{1b}$, —$C_{1-4}$alkylC(O)O$C_{1-4}$alkyl, —$C_{1-4}$alkylC(O)O$C_{1-4}$haloalkyl, $C_{1-6}$haloalkyl, $C_{3-6}$cycloalkyl, —$C_{1-4}$alkyl-5-6 membered heteroaryl, hydroxy$C_{1-6}$ alkyl, $C_{1-6}$ alkoxy and $C_{1-4}$ alkoxy$C_{1-4}$ alkyl;

wherein the 5-6 membered heteroaryl is unsubstituted or substituted with 1 to 3 substituents independently selected from halogen and $C_{1-6}$alkyl;

$R^{1a}$ and $R^{1b}$ are independently selected from hydrogen, $C_{1-6}$ alkyl and $C_{1-6}$ haloalkyl; or $R^{1a}$ and $R^{1b}$ together with the nitrogen to which they are attached form a 4-6 membered heterocyclic ring containing 0, 1 or 2 additional heteroatoms selected from oxygen, nitrogen and sulphur;

$R^{2a}$ is selected from (i) -A-phenyl;

(ii) -A-5-6 membered heteroaryl;

(iii) -A-4-6 membered heterocyclyl;

(iv) -A-$C_{5-6}$cycloalkyl;

(v) -D-8-10 membered fused bicyclic ring system;

wherein the phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from halogen, hydroxy, $C_{1-6}$alkyl, $C_{1-6}$alkoxy and $C_{1-6}$haloalkyl;

A is selected from a bond, —$(CR^{A1}R^{A2})$—, —$(CR^{A1}R^{A2})$$(CR^{A1}R^{A2})$—, —$(CR^{A1}R^{A2})$—O—, —O—$(CR^{A1}R^{A2})$—$(CR^{A1}R^{A2})$—S—, —$(CR^{A1}R^{A2})$—S(O)—, —$(CR^{A1}R^{A2})$—S(O)$_2$—, —S—$(CR^{A1}R^{A2})$—, —S(O)—$(CR^{A1}R^{A2})$—, —S(O)$_2$—$(CR^{A1}R^{A2})$—, —$NR^{A3}$—$(CR^{A1}R^{A2})$—, —$(CR^{A1}R^{A2})$—$NR^{A3}$— and —$(CR^{A1})$=$(CR^{A1})$—;

D is a bond, —O— or —$(CR^{D1}R^{D2})$—;

$R^{A1}$, $R^{A2}$ and $R^{A3}$ are independently selected from hydrogen, $C_{1-6}$alkyl and halogen;

$R^{D1}$ and $R^{D2}$ are independently selected from hydrogen, $C_{1-6}$alkyl and halogen;

$R^{2b}$ is hydrogen or $C_{1-4}$alkyl;

$R^3$ and $R^4$ are independently selected from hydrogen, $C_{1-6}$alkyl and $C_{3-6}$cycloalkyl; or $R^3$ and $R^4$ together with the nitrogen to which they are attached from a 4-6 membered heterocyclic ring containing 0, 1 or 2 additional heteroatoms selected from oxygen, nitrogen and sulphur; which 4-6 membered heterocyclic ring is unsubstituted or substituted with 1 or 2 halogen substituents;

$R^6$ and $R^7$ are independently selected from hydrogen, $C_{1-6}$alkyl, $C_{1-6}$hydroxyalkyl and $C_{1-6}$haloalkyl;

$R^5$ is selected from phenyl, a 5-6 membered heteroaryl, $C_{3-6}$cycloalkyl and 4-6 membered heterocyclyl; which phenyl, 5-6 membered heteroaryl, $C_{3-6}$cycloalkyl and 4-6 membered heterocyclyl is unsubstituted or substituted with 1 to 3 substituents independently selected from halogen, $C_{1-6}$alkyl, $C_{1-6}$alkoxy and $C_{1-6}$haloalkyl;

or a pharmaceutically acceptable salt thereof.

In a second aspect, there is provided a compound of formula (I),

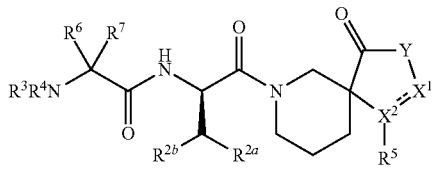

wherein

---- is a single bond or a double bond;

$X^1$ is $(CR^{x1}H)_n$ and $X^2$ is (CH); or $X^1$ is $(CR^{x1}H)_n$ and $X^2$ is N; or $X^1$ is $NR^{x1}$ and $X^2$ is (CH); or $X^1$ is $NR^{x1}$ and $X^2$ is N; or $X^1$ is N and $X^2$ is C; wherein the bond between $X^1$ and $X^2$ is a double bond if $X^1$ is N and $X^2$ is C;

n is 0 or 1;

$R^{x1}$ is selected from hydrogen and $C_{1-6}$alkyl;

Y is $NR^1$ or O;

$R^1$ is selected from hydrogen, $C_{1-6}$ alkyl, —$C_{1-4}$alkylC(O)NR$^{1a}$R$^{1b}$, —$C_{1-4}$alkylC(O)OC$_{1-4}$alkyl, —$C_{1-4}$ alkylC(O)OC$_{1-4}$ haloalkyl, $C_{1-6}$ haloalkyl, $C_{3-6}$ cycloalkyl, hydroxyC$_{1-6}$ alkyl, $C_{1-6}$ alkoxy and $C_{1-4}$ alkoxyC$_{1-4}$ alkyl;

$R^{1a}$ and $R^{1b}$ are independently selected from hydrogen, $C_{1-6}$ alkyl and $C_{1-6}$ haloalkyl; or $R^{1a}$ and $R^{1b}$ together with the nitrogen to which they are attached form a 4-6 membered heterocyclic ring;

$R^{2a}$ is selected from (i) -A-phenyl;

(ii) -A-5-6 membered heteroaryl;

(iii) -A-4-6 membered heterocyclyl;

(iv) -A-$C_{5-6}$cycloalkyl;

(v) -D-8-10 membered fused bicyclic ring system;

wherein the phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from halogen, $C_{1-6}$alkyl, $C_{1-6}$alkoxy and $C_{1-6}$haloalkyl;

A is selected from a bond, —$(CR^{A1}R^{A2})$—, —$(CR^{A1}R^{A2})(CR^{A1}R^{A2})$—, —$(CR^{A1}R^{A2})$—O—, —O—$(CR^{A1}R^{A2})$—, $(CR^{A1}R^{A2})$—S—; —S—$(CR^{A1}R^{A2})$—, —$NR^{A3}$—$(CR^{A1}R^{A2})$—, —$(CR^{A1}R^{A2})$—$NR^{A3}$— and —$(CR^{A1})$═$(CR^{A1})$—;

D is a bond, —O— or —$(CR^{D1}R^{D2})$—;

$R^{A1}$, $R^{A2}$ and $R^{A3}$ are independently selected from hydrogen, $C_{1-6}$alkyl and halogen;

$R^{D1}$ and $R^{D2}$ are independently selected from hydrogen, $C_{1-6}$alkyl and halogen;

$R^{2b}$ is hydrogen or $C_{1-4}$alkyl;

$R^3$ and $R^4$ are independently selected from hydrogen, $C_{1-6}$alkyl and $C_{3-6}$cycloalkyl; or $R^3$ and $R^4$ together with the nitrogen to which they are attached from a 4-6 membered heterocyclic ring; which 4-6 membered heterocyclic ring is unsubstituted or substituted with 1 or 2 halogen substituents;

$R^6$ and $R^7$ are independently selected from hydrogen, $C_{1-6}$alkyl, $C_{1-6}$hydroxyalkyl and $C_{1-6}$haloalkyl; or $R^6$ and $R^7$ together with the carbon atom to which they are attached form a $C_{3-6}$cycloalkyl, which $C_{3-6}$cycloalkyl is unsubstituted or substituted with 1 or 2 halogen substituents; or $R^6$ together with the carbon atom to which it is attached, $R^3$ and the nitrogen to which $R^3$ is attached form a 4-6 membered heterocyclic ring; which 4-6 membered heterocyclic ring is unsubstituted or substituted with 1 or 2 halogen substituents;

$R^5$ is selected from phenyl, a 5-6 membered heteroaryl, $C_{3-6}$cycloalkyl and 4-6 membered heterocyclyl; which phenyl, 5-6 membered heteroaryl, $C_{3-6}$cycloalkyl and 4-6 membered heterocyclyl is unsubstituted or substituted with 1 to 3 substituents independently selected from halogen, $C_{1-6}$alkyl, $C_{1-6}$alkoxy and $C_{1-6}$haloalkyl;

or a pharmaceutically acceptable salt thereof.

In a third aspect, there is provided a compound of formula (I),

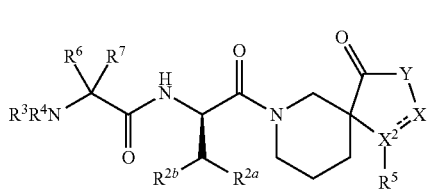

wherein

---- is a single bond or a double bond;

$X^1$ is $(CR^{x1}H)_n$ and $X^2$ is (CH); or $X^1$ is $(CR^{x1}H)_n$ and $X^2$ is N; or $X^1$ is $NR^{x1}$ and $X^2$ is (CH); or $X^1$ is $NR^{x1}$ and $X^2$ is N; or $X^1$ is N and $X^2$ is C; wherein the bond between $X^1$ and $X^2$ is a double bond if $X^1$ is N and $X^2$ is C;

n is 0 or 1;

$R^{x1}$ is selected from hydrogen and $C_{1-6}$alkyl;

Y is $NR^1$ or O;

$R^1$ is selected from hydrogen, $C_{1-6}$ alkyl, —$C_{1-4}$alkylC(O)NR$^{1a}$R$^{1b}$, —$C_{1-4}$alkylC(O)OC$_{1-4}$alkyl, —$C_{1-4}$ alkylC(O)OC$_{1-4}$ haloalkyl, $C_{1-6}$ haloalkyl, $C_{3-6}$ cycloalkyl, hydroxyC$_{1-6}$ alkyl, $C_{1-6}$ alkoxy and $C_{1-4}$ alkoxyC$_{1-4}$ alkyl;

$R^{1a}$ and $R^{1b}$ are independently selected from hydrogen, $C_{1-6}$ alkyl and $C_{1-6}$ haloalkyl; or $R^{1a}$ and $R^{1b}$ together with the nitrogen to which they are attached form a 4-6 membered heterocyclic ring;

$R^{2a}$ is selected from (i) -A-phenyl;

(ii) -A-5-6 membered heteroaryl;

(iii) -A-5-6 membered heterocyclyl;
(iv) -A-$C_{5-6}$cycloalkyl;
(v) -D-8-10 membered fused bicyclic ring system;
wherein the phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from halogen, $C_{1-6}$alkyl, $C_{1-6}$alkoxy and $C_{1-6}$haloalkyl;
A is selected from a bond, —($CR^{A1}R^{A2}$)—, —($CR^{A1}R^{A2}$)($CR^{A1}R^{A2}$)—, —($CR^{A1}R^{A2}$)—O—, —O—($CR^{A1}R^{A2}$)—($CR^{A1}R^{A2}$)—S—; —S—($CR^{A1}R^{A2}$)—, —$NR^{A3}$—($CR^{A1}R^{A2}$)—, —($CR^{A1}R^{A2}$)—$NR^{A3}$— and —($CR^{A1}$)=($CR^{A1}$)—;
D is a bond, —O— or —($CR^{D1}R^{D2}$)—;
$R^{A1}$, $R^{A2}$ and $R^{A3}$ are independently selected from hydrogen, $C_{1-6}$alkyl and halogen;
$R^{D1}$ and $R^{D2}$ are independently selected from hydrogen, $C_{1-6}$alkyl and halogen;
$R^{2b}$ is hydrogen or $C_{1-4}$alkyl;
$R^3$ and $R^4$ are independently selected from hydrogen, $C_{1-6}$alkyl and $C_{3-6}$cycloalkyl; or $R^3$ and $R^4$ together with the nitrogen to which they are attached from a 4-6 membered heterocyclic ring; which 4-6 membered heterocyclic ring is unsubstituted or substituted with 1 or 2 halogen substituents;
$R^6$ and $R^7$ are independently selected from hydrogen, $C_{1-6}$alkyl, $C_{1-6}$hydroxyalkyl and $C_{1-6}$haloalkyl; or $R^6$ and $R^7$ together with the carbon atom to which they are attached form a $C_{3-6}$cycloalkyl, which $C_{3-6}$cycloalkyl is unsubstituted or substituted with 1 or 2 halogen substituents; or $R^6$ together with the carbon atom to which it is attached, $R^3$ and the nitrogen to which $R^3$ is attached form a 4-6 membered heterocyclic ring; which 4-6 membered heterocyclic ring is unsubstituted or substituted with 1 or 2 halogen substituents;
$R^5$ is selected from phenyl, a 5-6 membered heteroaryl, $C_{3-6}$cycloalkyl and 4-6 membered heterocyclyl; which phenyl, 5-6 membered heteroaryl, $C_{3-6}$cycloalkyl and 4-6 membered heterocyclyl is unsubstituted or substituted with 1 to 3 substituents independently selected from halogen, $C_{1-6}$alkyl, $C_{1-6}$alkoxy and $C_{1-6}$haloalkyl;
or a pharmaceutically acceptable salt thereof.

In another aspect, there is provided a compound as defined in the first, second or third aspect for use as a medicine, in particular for the treatment of a disorder or a disease mediated by the ghrelin receptor.

In a further aspect, there is provided a method of treating a disorder or a disease mediated by the ghrelin receptor, comprising administering to the subject in need thereof a therapeutically effective amount of a compound as defined in the first, second or third aspect.

DETAILED DESCRIPTION OF THE INVENTION

Figure 1:
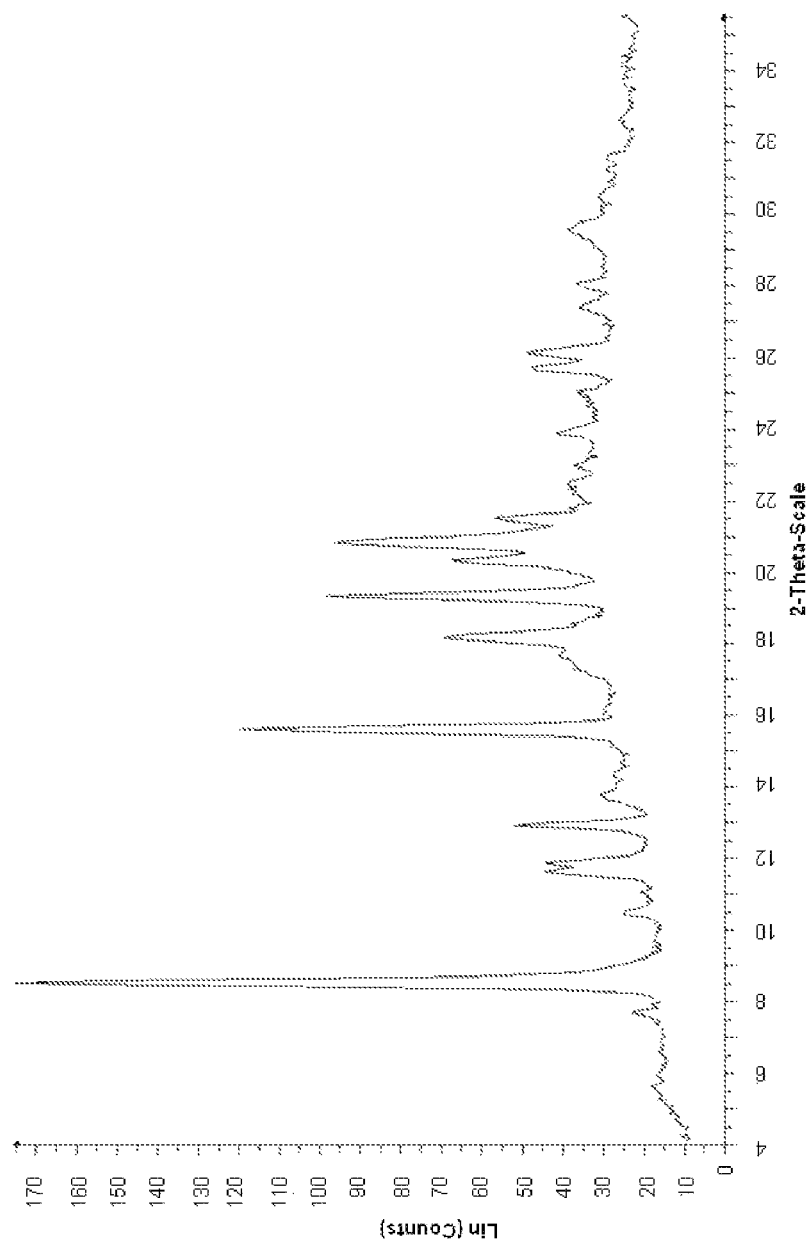
FIG. 1 illustrates the X-ray powder diffraction pattern of the crystalline form I of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

In a first aspect, there is provided a compound of formula (I),

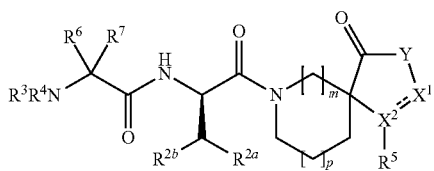

(I)

wherein

---- is a single bond or a double bond;

$X^1$ is $(CR^{x1}H)_n$ and $X^2$ is (CH); or $X^1$ is $(CR^{x1}H)_n$ and $X^2$ is N; or $X^1$ is $NR^{x1}$ and $X^2$ is (CH); or $X^1$ is $NR^{x1}$ and $X^2$ is N; or $X^1$ is N and $X^2$ is C; wherein the bond between $X^1$ and $X^2$ is a double bond if $X^1$ is N and $X^2$ is C;

n is 0 or 1;

$R^{x1}$ is selected from hydrogen and $C_{1-6}$alkyl;

m is 1 and p is 0; or m is 1 and p is 1; or m is 2 and p is 1;

Y is $NR^1$ or O;

$R^1$ is selected from hydrogen, $C_{1-6}$alkyl, —$C_{1-4}$alkylC(O)$NR^{1a}R^{1b}$, —$C_{1-4}$alkylC(O)O$C_{1-4}$alkyl, —$C_{1-4}$alkylC(O)O$C_{1-4}$ haloalkyl, $C_{1-6}$haloalkyl, $C_{3-6}$cycloalkyl, —$C_{1-4}$alkyl-5-6 membered heteroaryl, hydroxy$C_{1-6}$alkyl, $C_{1-6}$alkoxy and $C_{1-4}$alkoxy$C_{1-4}$alkyl;

wherein the 5-6 membered heteroaryl is unsubstituted or substituted with 1 to 3 substituents independently selected from halogen and $C_{1-6}$alkyl; $R^{1a}$ and $R^{1b}$ are independently selected from hydrogen, $C_{1-6}$alkyl and $C_{1-6}$haloalkyl; or $R^{1a}$ and $R^{1b}$ together with the nitrogen to which they are attached form a 4-6 membered heterocyclic ring containing 0, 1 or 2 additional heteroatoms selected from oxygen, nitrogen and sulphur;

$R^{2a}$ is selected from (i) -A-phenyl;

(ii) -A-5-6 membered heteroaryl;

(iii) -A-4-6 membered heterocyclyl;

(iv) -A-$C_{5-6}$cycloalkyl;

(v) -D-8-10 membered fused bicyclic ring system;

wherein the phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from halogen, hydroxy, $C_{1-6}$alkyl, $C_{1-6}$alkoxy and $C_{1-6}$haloalkyl;

A is selected from a bond, —$(CR^{A1}R^{A2})$—, —$(CR^{A1}R^{A2})$—$(CR^{A1}R^{A2})$—, —$(CR^{A1}R^{A2})$—O—, —O—$(CR^{A1}R^{A2})$—$(CR^{A1}R^{A2})$—S—, —$(CR^{A1}R^{A2})$—S(O)—, —$(CR^{A1}R^{A2})$—S(O)$_2$—, —S—$(CR^{A1}R^{A2})$—, —S(O)—$(CR^{A1}R^{A2})$—, —S(O)$_2$—$(CR^{A1}R^{A2})$—, —$NR^{A3}$—$(CR^{A1}R^{A2})$—, —$(CR^{A1}R^{A2})$—$NR^{A3}$— and —$(CR^{A1})$=$(CR^{A1})$—;

D is a bond, —O— or —$(CR^{D1}R^{D2})$—;

$R^{A1}$, $R^{A2}$ and $R^{A3}$ are independently selected from hydrogen, $C_{1-6}$ alkyl and halogen;

$R^{D1}$ and $R^{D2}$ are independently selected from hydrogen, $C_{1-6}$ alkyl and halogen;

$R^{2b}$ is hydrogen or $C_{1-4}$ alkyl;

$R^3$ and $R^4$ are independently selected from hydrogen, $C_{1-6}$alkyl and $C_{3-6}$cycloalkyl; or $R^3$ and $R^4$ together with the nitrogen to which they are attached form a 4-6 membered heterocyclic ring containing 0, 1 or 2 additional heteroatoms selected from oxygen, nitrogen and sulphur; which 4-6 membered heterocyclic ring is unsubstituted or substituted with 1 or 2 halogen substituents;

$R^6$ and $R^7$ are independently selected from hydrogen, $C_{1-6}$ alkyl, $C_{1-6}$ hydroxyalkyl and $C_{1-6}$ haloalkyl;

$R^5$ is selected from phenyl, a 5-6 membered heteroaryl, $C_{3-6}$cycloalkyl and 4-6 membered heterocyclyl; which phenyl, 5-6 membered heteroaryl, $C_{3-6}$cycloalkyl and 4-6 membered heterocyclyl is unsubstituted or substituted with 1 to 3 substituents independently selected from halogen, $C_{1-6}$alkyl, $C_{1-6}$alkoxy and $C_{1-6}$haloalkyl;

or a pharmaceutically acceptable salt thereof.

The term 'halogen' is used herein to describe, unless otherwise stated, a group selected from fluoro, chloro, bromo or iodo.

The term '$C_{1-6}$alkyl' or '$C_{1-4}$alkyl' as used herein as a group or a part of the group refers to a linear or branched saturated hydrocarbon group containing from 1 to 6 or 1 to 4 carbon atoms. Examples of such groups include methyl, ethyl, n-propyl, isopropyl, n-butyl, isobutyl, sec-butyl, tert-butyl, pentyl, hexyl, and the like. Unless a particular structure is specified, the terms propyl, butyl etc. include all straight and branched chain forms having the appropriate number of carbon atoms e.g. propyl includes n-propyl and isopropyl.

The term '$C_{1-6}$alkoxy' as used herein refers to an —O—$C_{1-6}$ alkyl group wherein $C_{1-6}$alkyl is as defined herein. Examples of such groups include methoxy, ethoxy, propoxy, butoxy, and the like. As for alkyl unless a particular structure is specified the terms propoxy, butoxy etc. include all straight and branched chain forms having the appropriate number of carbon atoms e.g. propoxy includes n-propoxy and isopropoxy.

The term '$C_{1-6}$haloalkyl' or '$C_{1-4}$haloalkyl' as used herein refers to a $C_{1-6}$alkyl or $C_{1-4}$alkyl group as defined herein substituted with one or more halogen groups which halogen groups may be the same or different, e.g. —$CF_3$, —$CF_2H$ or —$CH_2CF_3$.

The term '$C_{3-6}$cycloalkyl' or '$C_{5-6}$cycloalkyl' as used herein refers to a saturated monocyclic hydrocarbon ring of 3 to 6 carbon atoms or 5-6 carbon atoms, respectively. Examples of such groups include cyclopropyl, cyclobutyl, cyclopentyl and cyclohexyl.

When m is 1 and p is 0, the compound of formula (I) is

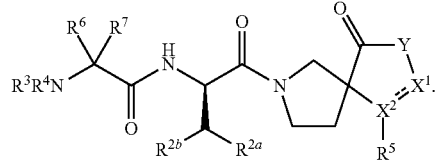

When m is 1 and p is 1, the compound of formula (I) is

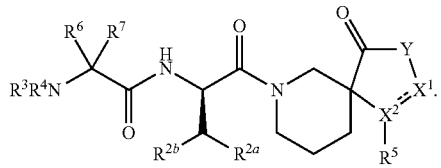

When m is 2 and p is 1, the compound of formula (I) is

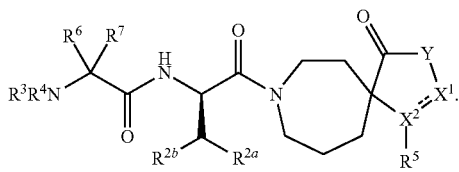

The term hydroxyC$_{1-6}$alkyl as used herein refers to a C$_{1-6}$alkyl group as defined herein substituted with one hydroxy group, e.g. —CH$_2$CH$_2$OH.

The term '5-6 membered heteroaryl' refers to a 5 or 6 membered aromatic ring system which contains 1 to 3 heteroatoms selected from oxygen, nitrogen and sulphur. Examples of 5-membered heteroaryl rings in this instance include furanyl, pyrrolyl, oxazolyl, thiazolyl, imidazolyl, oxadiazolyl, thiadiazolyl, triazolyl, isothiazolyl, isoxazolyl, thienyl, pyrazolyl and tetrazolyl. Examples of 6-membered heteroaryl rings include pyridyl, pyridazinyl, pyrimidinyl, pyrazinyl and triazinyl.

The term '4-6 membered heterocyclic ring' or '4-6 membered heterocyclyl' refers to a 4, 5 or 6 membered saturated or partially unsaturated aliphatic monocyclic ring which contains 1 to 3 heteroatoms selected from oxygen, nitrogen and sulphur. Suitable examples of such groups include azetidinyl, pyrrolidinyl, piperidinyl, piperazinyl, morpholinyl, tetrahydropyranyl and thiomorpholinyl.

The term '8 to 10 membered fused bicyclic ring system' includes but is not limited to the following ring systems indolinyl, indolyl, isoindolinyl, isoindolyl, indenyl, benzofuranyl, benzothiophenyl, indazolyl, benzimidazolyl, benzothiazolyl, benzoxazolyl, benzoxazinyl, benzopyranyl, benzothiopyranyl, quinolinyl, isoquinolinyl, chromenyl, cinnolinyl, phthalazinyl, quinazolinyl, quinoxalinyl, naphthyridinyl, furopyridinyl, naphthyl, dihydrobenzoxazinyl, dihydrochromenyl, dihydrobenzodioxinyl, tetrahydroquinolinyl, tetrahydroquinoxalinyl, tetrahydronaphthalenyl dihydrobenzofuranyl, dihydrobenzopyranyl, dihydrobenzothiopyranyl, dihydrobenzothiophenyl, dihydrodioxinopyridinyl, dihydroindenyl, dihydropyrrolopyridinyl, dihydropyrrolopyrimidinyl, dihydropyrrolopyrazinyl, dihydropyrrolopyridazinyl, pyrrolopyridinyl, pyrrolopyrazinyl, pyrrolopyridazinyl, pyrrolopyrimidinyl, furopyrimidinyl, furopyrazinyl, furopyridazinyl, thienopyridinyl, thienopyrazinyl, thienopyridazinyl, thienopyrimidinyl, pyrazolopyridinyl, pyrazolopyrazinyl, pyrazolopyridazinyl, pyrazolopyrimidinyl, imidazopyridinyl, imidazopyrazinyl, imidazopyridazinyl, imidazopyrimidinyl, thiazolopyridinyl, thiazolopyrazinyl, thiazolopyridazinyl, thiazolopyrimidinyl, oxazolopyridinyl, oxazolopyrazinyl, oxazolopyridazinyl, oxazolopyrimidinyl, pyridopyrazinyl, pyridopyridazinyl, pyridopyrimidinyl, pyridooxazinyl, pyrazinooxazinyl, pyridazinooxazinyl, pyrimidooxazinyl, dihydropyridooxazinyl, dihydropyrazinooxazinyl, dihydropyridazinooxazinyl, dihydropyrimidooxazinyl, dihydropyranopyridinyl, dihydropyranopyrazinyl, dihydropyranopyridazinyl, dihydropyrimidinyl, pyranopyridinyl, pyranopyrimidinyl, pyranopyrazinyl, pyranopyridazinyl, dihydrodioxinopyridinyl, dihydrodioxinopyrazinyl, dihydrodioxinopyridazinyl, dihydrodioxinopyrimidinyl, tetrahydronaphthyridinyl, tetrahydropyridopyridazinyl, tetrahydropyridopyrazinyl, tetrahydropyridopyrimidinyl, tetrahydropyrazinopyridazinyl, tetrahydropteridinyl, tetrahydropyrazinopyrimidinyl, tetrahydroquinolinyl, tetrahydrocinnolinyl, tetrahydroquinazolinyl, tetrahydroquinoxalinyl, thiinopyridinyl, thiinopyrazinyl, thiinopyridazinyl, thiinopyrimidinyl, dihydrothiinopyridinyl, dihydrothiinopyrazinyl, dihydrothiinopyridazinyl, dihydrothiinopyrimidinyl, dihydrofuropyridinyl, dihydrofuropyrazinyl, dihydrofuropyridazinyl, dihydrofuropyrimidinyl, dihydrothienopyridinyl, dihydrothienopyrazinyl, dihydrothienopyridazinyl, dihydrothienopyrimidinyl, dihydrocyclopentapyridinyl, dihydrocyclopentapyrazinyl, dihydrocyclopentapyridazinyl, dihydrocyclopentapyrimidinyl, quinolinonyl, naphtyridinonyl, pyridopyrazinonyl, pyridopyridazinonyl and pyridopyrimidinonyl.

The term "substituted with 1 to 3 substituents", as used herein, means substituted with 1, 2 or 3 substituents.

The term "which contains 1 to 3 heteroatoms", as used herein, means containing 1, 2 or 3 heteroatoms.

The term "polymorph", as used herein, refers to crystalline forms having the same chemical composition but different spatial arrangements of the molecules, atoms, and/or ions forming the crystal.

The term "solvate", as used herein, refers to a crystalline form of a compound of the present invention (including pharmaceutically acceptable salts thereof) with one or more solvent molecules incorporated into the crystalline lattice structure. Such solvent molecules are those commonly used in the pharmaceutical art, which are known to be innocuous to the recipient, e.g., water, ethanol, and the like. The solvent molecules in the solvate may be present in a regular arrangement and/or a non-ordered arrangement. The solvate may comprise either a stoichiometric or non-stoichiometric amount of the solvent molecules. For example, a solvate with a non-stoichiometric amount of solvent molecules may result from partial loss of solvent from the solvate. Solvates may occur as dimers or oligomers comprising more than one molecule of a compound within the crystalline lattice structure.

The term "hydrate", as used herein, refers to a solvate as defined herein wherein the solvent is water.

The term "amorphous", as used herein, refers to a solid form of a molecule, atoms and/or ions that is not crystalline. An amorphous solid does not display a definitive X-ray diffraction pattern.

In one embodiment (i) of the first aspect, the compound is of formula (Ia)

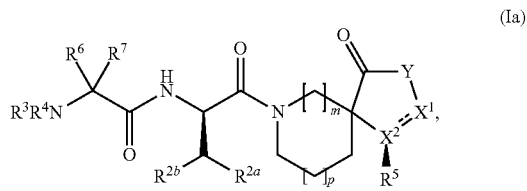

wherein X$^1$ is (CR$^{x1}$H)$_n$ and X$^2$ is (CH) or X$^1$ is NR$^{x1}$ and X$^2$ is (CH).

In one embodiment (ii) of the first aspect, the compound is of formula (Ib)

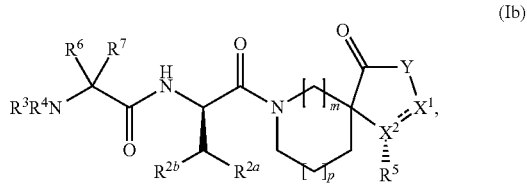

wherein $X^1$ is $(CR^{x1}H)_n$ and $X^2$ is (CH) or $X^1$ is $NR^{x1}$ and $X^2$ is (CH).

In one embodiment (iii) of the first aspect, the compound is of formula (Ic)

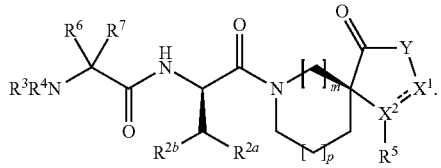

(Ic)

In one embodiment (iv) of the first aspect, the compound is of formula (Id)

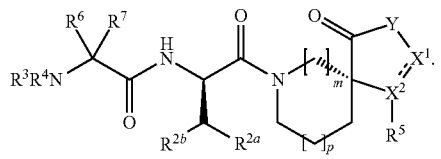

(Id)

In one embodiment (v) of the first aspect, the compound is of formula (Ie)

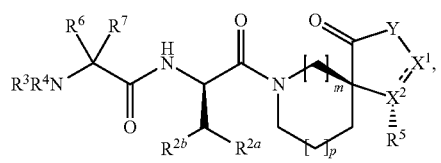

(Ie)

wherein $X^1$ is $(CR^{x1}H)_n$ and $X^2$ is (CH) or $X^1$ is $NR^{x1}$ and $X^2$ is (CH).

In one embodiment (vi) of the first aspect, the compound is of formula (If)

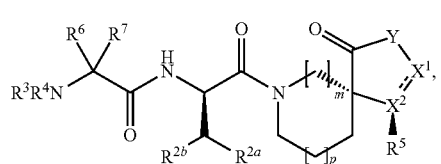

(If)

wherein $X^1$ is $(CR^{x1}H)_n$ and $X^2$ is (CH) or $X^1$ is $NR^{x1}$ and $X^2$ is (CH). The compound of formula (I) is particularly a compound of formula (If).

In one embodiment (vii) of the first aspect, the compound is of formula (Ig)

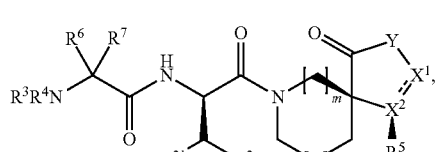

(Ig)

wherein $X^1$ is $(CR^{x1}H)_n$ and $X^2$ is (CH) or $X^1$ is $NR^{x1}$ and $X^2$ is (CH).

In one embodiment (viii) of the first aspect, the compound is of formula (Ih)

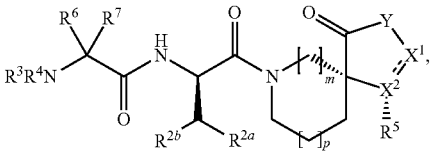

(Ih)

wherein $X^1$ is $(CR^{x1}H)_n$ and $X^2$ is (CH) or $X^1$ is $NR^{x1}$ and $X^2$ is (CH).

In one embodiment (ix) of the first, second or third aspect or of embodiments (i) or (viii) of the first aspect, Y is $NR^1$.

In one embodiment (x) of the first aspect or of embodiments (i) to (ix) of the first aspect, Y is $NR^1$ and $R^1$ is selected from hydrogen, $C_{1-6}$alkyl, $C_{1-6}$haloalkyl, —$C_{1-4}$alkylC(O)$NR^{1a}R^{1b}$, —$C_{1-4}$ alkylC(O)O$C_{1-4}$alkyl, and —$C_{1-4}$alkyl-5-6 membered heteroaryl, wherein the 5-6 membered heteroaryl is unsubstituted or substituted with 1 to 3 substituents independently selected from halogen and $C_{1-6}$alkyl.

In one embodiment (xi) of the second or third aspect or of embodiment (ix) of the second or third aspect, Y is $NR^1$ and $R^1$ is selected from hydrogen, $C_{1-6}$alkyl, —$C_{1-4}$alkylC(O)$NR^{1a}R^{1b}$ and —$C_{1-4}$ alkylC(O)O$C_{1-4}$alkyl.

In one embodiment (xii) of the first aspect or of embodiments (i) to (x) of the first aspect, Y is $NR^1$ and $R^1$ is selected from hydrogen, methyl, isopropyl, ethyl, 2,2-dimethyl-propyl, isobutyl, 2,2,2-trifluoroethyl, methylisoxazolylmethyl, oxazolylmethyl and —$(CH_2)C(O)N(CH_3)_2$.

In one embodiment (xiii) of the second or third aspect or of embodiments (ix) or (xi) of the second or third aspect, Y is $NR^1$ and $R^1$ is selected from hydrogen, methyl, isopropyl, ethyl, —$(CH_2)C(O)N(CH_3)_2$ and —$(CH_2)C(O)O(CH_2)$ $(CH_3)$.

In one embodiment (xiv) of the first, second or third aspect or of embodiments (i) to (xiii) of the first, second or third aspect as applicable, $X^1$ is $(CR^{x1}H)_n$ and n is 1.

In one embodiment (xv) of the first, second or third aspect or of embodiments (i) to (xiv) of the first, second or third aspect as applicable, $R^{x1}$ is selected from hydrogen and $C_{1-6}$ alkyl.

In one embodiment (xvi) of the first, second or third aspect or of embodiments (i) to (xv) of the first, second or third aspect as applicable, $R^5$ is selected from phenyl and pyridinyl, which phenyl or pyridinyl is unsubstituted or substituted with 1 to 3 substituents independently selected from halogen and $C_{1-6}$alkyl.

In one embodiment (xvii) of the first or second aspect or of embodiments (i) to (xvi) of the first or second aspect as applicable, $R^{2a}$ is selected from -A-phenyl, -A-5-6 membered heteroaryl, -A-4-6 membered heterocyclyl, -A-$C_{5-6}$cycloalkyl and a -D-8-10 membered fused bicyclic ring system, which phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from $C_{1-6}$ alkyl, $C_{1-6}$ alkoxy and halogen.

In one embodiment (xviii) of the third aspect or of embodiments (ix) to (xvi) of the third aspect as applicable, $R^{2a}$ is selected from -A-phenyl, -A-5-6 membered heteroaryl, -A-5-6 membered heterocyclyl, -A-$C_{5-6}$cycloalkyl and a -D-8-10 membered fused bicyclic ring system, which phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from $C_{1-6}$ alkyl, $C_{1-6}$ alkoxy and halogen.

In one embodiment (xix) of the third aspect or of embodiments (ix) to (xvi) of the third aspect as applicable, $R^{2a}$ is selected from -A-phenyl and a -D-8-10 membered fused bicyclic ring system, which phenyl and 8-10 membered fused bicyclic ring system are unsubstituted or substituted with 1 to 3 substituents independently selected from $C_{1-6}$ alkyl, $C_{1-6}$ alkoxy and halogen.

In one embodiment (xx) of the first aspect or of embodiments (i) to (xvii) of the first aspect as applicable, $R^{2a}$ is selected from -A-phenyl, -A-pyridyl, -A-tetrahydropyranyl, -A-cyclohexyl, -D-indolyl and -D-dihydroindenyl, which phenyl, pyridyl, tetrahydropyranyl, cyclohexyl, dihydroindenyl and indolyl groups are unsubstituted or substituted with 1 to 3 substituents independently selected from $C_{1-6}$ alkyl, $C_{1-6}$ alkoxy and halogen.

In one embodiment (xxi) of the second or third aspect or of embodiments (ix) to (xix) of the second or third aspect as applicable, $R^{2a}$ is selected from -A-phenyl and -D-indolyl, which phenyl and indolyl groups are unsubstituted or substituted with 1 to 3 substituents independently selected from $C_{1-6}$ alkyl, $C_{1-6}$ alkoxy and halogen.

In one embodiment (xxii) of the first aspect or of embodiments (i) to (xx) of the first aspect as applicable, $R^{2a}$ is -A-phenyl, -A-para-methylphenyl, -A-ortho-methylphenyl, -A-meta-methylphenyl, -A-meta-methoxyphenyl, -A-para-methoxyphenyl, -A-para-chlorophenyl, -A-para-fluorophenyl, -A-ortho,para-difluorophenyl, -A-meta,para-difluorophenyl, -A-cyclohexyl, -A-tetrahydro-2H-pyran-4-yl, -A-pyridin-2-yl, -A-pyridin-3-yl, -D-dihydroindenyl, -D-1H-indol-3-yl or -D-1-methyl-1H-indol-3-yl, preferably -A-phenyl.

In one embodiment (xxiii) of the second or third aspect or of embodiments (ix) to (xxi) of the second or third aspect as applicable,
$R^{2a}$ is

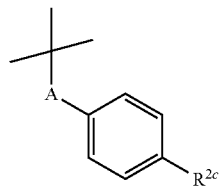

and $R^{2c}$ is selected from hydrogen, $C_{1-6}$ alkyl, $C_{1-6}$ alkoxy and halogen.

In one embodiment (xxiv) of the second or third aspect or of embodiments (ix) to (xxi) of the second or third aspect as applicable,
$R^{2a}$ is

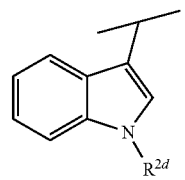

and $R^{2d}$ is selected from hydrogen, $C_{1-4}$ alkyl and halogen.

In one embodiment (xxv) of the first aspect or of embodiments (i) to (xxii) of the first aspect as applicable, -A- is —$(CR^{A1}R^{A2})$—, —$(CR^{A1}R^{A2})(CR^{A1}R^{A2})$—, —O—$(CR^{A1}R^{A2})$—, —$(CR^{A1}R^{A2})$—O—, —S—$(CR^{A1}R^{A2})$—, and —$(CR^{A1})$=$(CR^{A1})$—; D is a bond; and $R^{A1}$, $R^{A2}$ are both hydrogen.

In one embodiment (xxvi) of the first, second or third aspect or of embodiments (i) to (xxv) of the first, second or third aspect as applicable, $R^{2b}$ is hydrogen or methyl, particularly hydrogen.

In one embodiment (xxvii) of the first, second or third aspect or of embodiments (i) to (xxvi) of the first, second or third aspect as applicable, $R^3$ and $R^4$ are both hydrogen.

In one embodiment (xxviii) of the first aspect or of embodiments (i) to (xxvii) of the first aspect as applicable, $R^6$ and $R^7$ are independently selected from hydrogen, $C_{1-6}$alkyl and $C_{1-6}$hydroxyalkyl.

In one embodiment (xxix) of the second or third aspect or of embodiments (ix) to (xxvii) of the second or third aspect as applicable, $R^6$ and $R^7$ are independently selected from hydrogen, $C_{1-6}$alkyl and $C_{1-6}$haloalkyl.

In one embodiment (xxx) of the first, second or third aspect or of embodiments (i) to (xxix) of the first, second or third aspect as applicable, $R^6$ and $R^7$ are both methyl.

In one embodiment of the invention, the compound is selected from

2-Amino-N-[(R)-1-benzyloxymethyl-2-(2-methyl-1-oxo-4-phenyl-2,7-diaza-spiro[4.5]dec-7-yl)-2-oxo-ethyl]-2-methyl-propionamide;

2-Amino-N-((2R)-3-(benzyloxy)-1-(4-(4-fluorophenyl)-2-methyl-1-oxo-2,7-diazaspiro[4.5]decan-7-yl)-1-oxopropan-2-yl)-2-methylpropanamide;

2-Amino-N-((2R)-3-(benzyloxy)-1-oxo-1-(1-oxo-4-phenyl-2,7-diazaspiro[4.5]decan-7-yl)propan-2-yl)-2-methylpropanamide;

2-Amino-N-((2R)-3-(benzyloxy)-1-(2-isopropyl-1-oxo-4-phenyl-2,7-diaza spiro[4.5]decan-7-yl)-1-oxopropan-2-yl)-2-methylpropanamide;

2-Amino-N-((2R)-3-(benzyloxy)-1-(4-(4-chlorophenyl)-2-methyl-1-oxo-2,7-diaza spiro[4.5]decan-7-yl)-1-oxopropan-2-yl)-2-methylpropanamide;

2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide;

2-Amino-2-methyl-N-((2R)-1-(2-methyl-1-oxo-4-phenyl-2,7-diazaspiro[4.5]decan-7-yl)-3-(1-methyl-1H-indol-3-yl)-1-oxopropan-2-yl)propanamide;

2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide;

2-Amino-N-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-yl)-2-methylpropanamide;

2-amino-N-((2R)-3-(benzyloxy)-1-(2-(2-(dimethylamino)-2-oxoethyl)-1-oxo-4-phenyl-2,7-diaza spiro[4.5]decan-7-yl)-1-oxopropan-2-yl)-2-methylpropanamide;

N-((2R)-3-(Benzyloxy)-1-(2-methyl-1-oxo-4-phenyl-2,7-diazaspiro[4.5]decan-7-yl)-1-oxopropan-2-yl)-2-methyl-2-(methylamino) propanamide;

2-Amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide;

2-Amino-N-((2R)-3-(benzyloxy)-1-(2-methyl-1-oxo-4-phenyl-2,7-diazaspiro[4.5]decan-7-yl)-1-oxopropan-2-yl)-2-methylpropanamide;

N-((2R)-3-(1H-indol-3-yl)-1-(2-methyl-1-oxo-4-phenyl-2,7-diazaspiro[4.5]decan-7-yl)-1-oxopropan-2-yl)-2-amino-2-methylpropanamide;

2-amino-2-methyl-N-((2R)-1-(2-methyl-1-oxo-4-phenyl-2, 7-diazaspiro[4.5]decan-7-yl)-1-oxo-5-phenylpentan-2-yl) propanamide;

2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide;

2-amino-2-methyl-N-((2R)-1-(2-methyl-1-oxo-4-phenyl-2, 7-diazaspiro[4.5]decan-7-yl)-1-oxo-4-phenylbutan-2-yl) propanamide;

2-amino-N-((2R)-1-(4-(4-fluorophenyl)-2-methyl-1-oxo-2, 7-diazaspiro[4.5]decan-7-yl)-3-(4-methylbenzyloxy)-1-oxopropan-2-yl)-2-methylpropanamide;

2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2, 7-diazaspiro[4.5]decan-7-yl)-1-oxo-5-phenylpentan-2-yl)-2-methylpropanamide;

2-amino-2-methyl-N-((2R)-1-(2-methyl-1-oxo-4-phenyl-2, 7-diazaspiro[4.5]decan-7-yl)-1-oxo-5-phenylpentan-2-yl) propanamide;

2-amino-N-((2R)-1-(4-(4-fluorophenyl)-2-isopropyl-1-oxo-2,7-diazaspiro[4.5]decan-7-yl)-3-(1H-indol-3-yl)-1-oxopropan-2-yl)-2-methylpropanamide;

2-amino-2-methyl-N-((2R)-1-(2-methyl-1-oxo-3-phenyl-2, 6-diazaspiro[3.5]nonan-6-yl)-3-(1-methyl-1H-indol-3-yl)-1-oxopropan-2-yl)propanamide;

2-Amino-N-{(R)-1-benzyloxymethyl-2-[2-(2,2-dimethlypropyl)-1-oxo-4-phenyl-2,7-diaza-spiro[4.5]dec-7-yl]-2-oxo-ethyl}-2-methyl-propionamide;

2-amino-N-((2R)-3-(benzyloxy)-1-(2-methyl-1-oxo-4-phenyl-2,7-diazaspiro[4.5]decan-7-yl)-1-oxobutan-2-yl)-2-methylpropanamide;

2-amino-N-((2R)-3-(benzyloxy)-1-(1-(4-fluorophenyl)-2-methyl-3-oxo-2,6-diazaspiro[3.5]nonan-6-yl)-1-oxopropan-2-yl)-2-methylpropanamide;

2-Amino-N-{(R)-1-benzyloxymethyl-2-(2-isobutyl-1-oxo-4-phenyl-2,7-diaza-spiro[4.5]dec-7-yl)-2-oxo-ethyl}-2-methyl-propionamide;

2-Amino-N-{(R)-1-benzyloxymethyl-2-[4-(4-chloro-phenyl)-2-methyl-1-oxo-2,7-diaza-spiro[4.5]dec-7-yl]-2-oxo-ethyl}-2-methyl-propionamide;

2-Amino-N-[(R)-1-benzyloxymethyl-2-(2-isopropyl-1-oxo-4-phenyl-2,7-diaza-spiro[4.5]dec-7-yl)-2-oxo-ethyl]-2-methyl-propionamide;

2-Amino-N-[(R)-1-benzyloxymethyl-2-(3-methyl-4-oxo-1-phenyl-2,3,7-triaza-spiro[4.5]dec-1-en-7-yl)-2-oxo-ethyl]-2-methyl-propionamide;

2-Amino-N-[(R)-1-benzyloxymethyl-2-(3-methyl-4-oxo-1-phenyl-1,3,7-triaza-spiro[4.5]dec-7-yl)-2-oxo-ethyl]-2-methyl-propionamide;

2-Amino-N-[(R)-1-benzyloxymethyl-2-oxo-2-(1-oxo-4-phenyl-2,7-diaza-spiro[4.5]dec-7-yl)ethyl]-2-methylpropionamide;

2-amino-N-((2R)-3-(benzyloxy)-1-(2-methyl-1-oxo-4-o-tolyl-2,7-diazaspiro[4.5]decan-7-yl)-1-oxopropan-2-yl)-2-methylpropanamide;

2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide;

2-amino-2-methyl-N-((2R)-1-(2-methyl-1-oxo-4-phenyl-2, 7-diazaspiro[4.5]decan-7-yl)-3-(4-methylbenzyloxy)-1-oxopropan-2-yl)propanamide;

2-amino-N-((2R)-3-(4-chlorobenzyloxy)-1-(4-(4-fluorophenyl)-2-methyl-1-oxo-2,7-diazaspiro[4.5]decan-7-yl)-1-oxopropan-2-yl)-2-methylpropanamide;

2-amino-N-((2R)-3-(benzyloxy)-1-(2-methyl-1-oxo-4-(pyridin-3-yl)-2,7-diazaspiro[4.5]decan-7-yl)-1-oxopropan-2-yl)-2-methylpropanamide;

2-amino-N-((2R)-3-(cyclohexylmethoxy)-1-(2-methyl-1-oxo-4-phenyl-2,7-diazaspiro[4.5]decan-7-yl)-1-oxopropan-2-yl)-2-methylpropanamide;

2-amino-N-((2R)-3-(benzyloxy)-1-(3-methyl-4-oxo-1-phenyl-1,3,7-triazaspiro[4.5]decan-7-yl)-1-oxopropan-2-yl)-2-methylpropanamide;

2-amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide;

2-amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide;

N-((2R)-3-(1H-Indol-3-yl)-1-(2-isopropyl-1-oxo-4-phenyl-2,7-diazaspiro[4.5]decan-7-yl)-1-oxopropan-2-yl)-2-amino-2-methylpropanamide;

2-Amino-N-[(R)-1-benzyloxymethyl-2-(2-methyl-1-oxo-4-phenyl-2,7-diaza-spiro[4.5]dec-7-yl)-2-oxo-ethyl]-3-hydroxy-2-methyl-propionamide;

2-Amino-N-[(R)-1-(4-methoxy-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-2-[4-(4-fluoro-phenyl)-2-methyl-1-oxo-2,7-diaza-spiro[4.5]dec-7-yl]-1-(4-ethoxy-benzyloxymethyl)-2-oxo-ethyl]-2-methyl-propionamide;

2-Amino-N-[(R)-1-(4-fluoro-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-1-(3,4-difluoro-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-1-(2,4-difluoro-benzyloxymethyl)-2-(2-methyl-1-oxo-4-phenyl-2,7-diaza-spiro[4.5]dec-7-yl)-2-oxo-ethyl]-2-methyl-propionamide;

2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide;

2-amino-N-((2R)-3-(2,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-3-(4-fluorobenzyloxy)-1-(2-methyl-1-oxo-4-p-tolyl-2,7-diazaspiro[4.5]decan-7-yl)-1-oxopropan-2-yl)-2-methylpropanamide;

2-amino-N-((2R)-3-(benzyloxy)-1-(4-(3,5-difluorophenyl)-2-methyl-1-oxo-2,7-diazaspiro[4.5]decan-7-yl)-1-oxopropan-2-yl)-2-methylpropanamide;

2-amino-N-((2R)-3-(3,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-3-(benzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-1-(4-(3,4-difluorophenyl)-2-methyl-1-oxo-2,7-diazaspiro[4.5]decan-7-yl)-3-(4-fluorobenzyloxy)-1-oxopropan-2-yl)-2-methylpropanamide;

2-amino-N-(1-(4-(4-fluorophenyl)-2-methyl-1-oxo-2,7-diazaspiro[4.5]decan-7-yl)-1-oxo-4-(tetrahydro-2H-pyran-4-yl)butan-2-yl)-2-methylpropanamide;

2-amino-N-((2R)-3-(benzyloxy)-1-(4-(4-fluorophenyl)-2-((5-methylisoxazol-3-yl)methyl)-1-oxo-2,7-diazaspiro[4.5]decan-7-yl)-1-oxopropan-2-yl)-2-methylpropanamide;

2-amino-N-((2R)-3-(benzyloxy)-1-(4-(4-fluorophenyl)-2-(oxazol-2-ylmethyl)-1-oxo-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-3-(2-methylbenzyloxy)-1-oxopropan-2-yl)-2-methylpropanamide;

2-amino-N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methylpropanamide;

N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methyl-2-(methylamino)propanamide;

N-((2R)-3-(benzyloxy)-1-(4-(4-fluorophenyl)-2-methyl-1-oxo-2,7-diazaspiro[4.5]decan-7-yl)-1-oxopropan-2-yl)-2-methyl-2-(methylamino)propanamide;

2-amino-N-((2R)-3-(benzyloxy)-1-(4-(4-fluorophenyl)-1-oxo-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-3-(3-methylbenzyloxy)-1-oxopropan-2-yl)-2-methylpropanamide;

2-Amino-N-((R)-3-(2,3-dihydro-1H-inden-2-yl)-1-(2-methyl-1-oxo-4-phenyl-2,7-diazaspiro[4.5]decan-7-yl)-1-oxopropan-2-yl)-2-methylpropanamide;

2-amino-N-((2R)-1-(4-(4-fluorophenyl)-1-oxo-2,7-diazaspiro[4.5]decan-7-yl)-1-oxo-5-phenylpentan-2-yl)-2-methylpropanamide;

2-amino-N-((2R)-4-cyclohexyl-1-(4-(4-fluorophenyl)-2-methyl-1-oxo-2,7-diazaspiro[4.5]decan-7-yl)-1-oxobutan-2-yl)-2-methylpropanamide;

2-amino-2-methyl-N-((2R)-1-(2-methyl-1-oxo-4-p-tolyl-2,7-diazaspiro[4.5]decan-7-yl)-3-(2-methylbenzyloxy)-1-oxopropan-2-yl)propanamide;

2-amino-2-methyl-N-((2R)-1-(2-methyl-1-oxo-4-phenyl-2,7-diazaspiro[4.5]decan-7-yl)-1-oxo-5-phenylpent-4-en-2-yl)propanamide;

2-Amino-N-((S)-3-(benzylthio)-1-(2-methyl-1-oxo-4-phenyl-2,7-diazaspiro[4.5]decan-7-yl)-1-oxopropan-2-yl)-2-methylpropanamide;

N-((2R)-3-(4-fluorobenzyloxy)-1-(2-methyl-1-oxo-4-phenyl-2,7-diazaspiro[4.5]decan-7-yl)-1-oxopropan-2-yl)-2-methyl-2-(methylamino)propanamide;

2-amino-N-((2R)-3-(benzyloxy)-1-(2-methyl-1-oxo-4-p-tolyl-2,7-diazaspiro[4.5]decan-7-yl)-1-oxobutan-2-yl)-2-methylpropanamide;

2-amino-2-methyl-N-((R)-1-(2-methyl-1-oxo-4-phenyl-2,7-diazaspiro[4.5]decan-7-yl)-1-oxo-3-(pyridin-2-ylmethoxy)propan-2-yl)propanamide;

2-Amino-N-((R)-3-(benzyloxy)-1-oxo-1-(1-oxo-4-phenyl-2-(2,2,2-trifluoroethyl)-2,7-diazaspiro[4.5]decan-7-yl)propan-2-yl)-2-methylpropanamide;

2-Amino-N-((R)-3-(benzyloxy)-1-(2-methyl-1-oxo-4-phenyl-2,7-diazaspiro[4.5]decan-7-yl)-1-oxopropan-2-yl)-2-methylbutanamide;

N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methyl-2-(methylamino)propanamide;

2-Amino-2-methyl-N-((R)-1-(2-methyl-1-oxo-4-phenyl-2,7-diazaspiro[4.5]decan-7-yl)-1-oxo-4-phenoxybutan-2-yl)propanamide;

or a pharmaceutically acceptable salt thereof.

In one embodiment of the invention, the compound is one of the Examples wherein each chiral centre, if present, is in (R) or (S) form.

In one embodiment of the invention, the compound is selected from

2-Amino-N-[(R)-1-benzyloxymethyl-2-((4R,5S)-2-methyl-1-oxo-4-phenyl-2,7-diaza-spiro[4.5]dec-7-yl)-2-oxoethyl]-2-methyl-propionamide;

2-Amino-N-[(R)-1-benzyloxymethyl-2-((4S,5R)-2-methyl-1-oxo-4-phenyl-2,7-diaza-spiro[4.5]dec-7-yl)-2-oxoethyl]-2-methyl-propionamide;

2-Amino-N-((2R)-3-(benzyloxy)-1-((4S,5R)-4-(4-fluorophenyl)-2-methyl-1-oxo-2,7-diazaspiro[4.5]decan-7-yl)-1-oxopropan-2-yl)-2-methylpropanamide;

2-amino-N-((2R,3S)-3-(benzyloxy)-1-(2-methyl-1-oxo-4-phenyl-2,7-diazaspiro[4.5]decan-7-yl)-1-oxobutan-2-yl)-2-methylpropanamide;

(R)-2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-3-hydroxy-2-methyl-propionamide;

(R)-2-Amino-N-[(R)-1-benzyloxymethyl-2-((4R,5S)-2-methyl-1-oxo-4-phenyl-2,7-diaza-spiro[4.5]dec-7-yl)-2-oxo-ethyl]-3-hydroxy-2-methyl-propionamide;

(S)-2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-3-hydroxy-2-methyl-propionamide;

(S)-2-Amino-N-[(R)-1-benzyloxymethyl-2-((4R,5S)-2-methyl-1-oxo-4-phenyl-2,7-diaza-spiro[4.5]dec-7-yl)-2-oxo-ethyl]-3-hydroxy-2-methyl-propionamide;

2-Amino-N-[(R)-1-(4-methoxy-benzyloxymethyl)-2-((4S,5R)-2-methyl-1-oxo-4-phenyl-2,7-diaza-spiro[4.5]dec-7-yl)-2-oxo-ethyl]-2-methyl-propionamide;

2-Amino-N-[(R)-1-(4-methoxy-benzyloxymethyl)-2-((4R,5S)-2-methyl-1-oxo-4-phenyl-2,7-diaza-spiro[4.5]dec-7-yl)-2-oxo-ethyl]-2-methyl-propionamide;

2-Amino-N-[(R)-1-(4-fluoro-benzyloxymethyl)-2-((4S,5R)-2-methyl-1-oxo-4-phenyl-2,7-diaza-spiro[4.5]dec-7-yl)-2-oxo-ethyl]-2-methyl-propionamide;

2-Amino-N-[(R)-1-(4-fluoro-benzyloxymethyl)-2-((4R,5S)-2-methyl-1-oxo-4-phenyl-2,7-diaza-spiro[4.5]dec-7-yl)-2-oxo-ethyl]-2-methyl-propionamide;

2-Amino-N-((R)-3-(2,3-dihydro-1H-inden-2-yl)-1-((4S,5R)-2-methyl-1-oxo-4-phenyl-2,7-diazaspiro[4.5]decan-7-yl)-1-oxopropan-2-yl)-2-methylpropanamide;

2-amino-2-methyl-N-((R,Z)-1-((4S,5R)-2-methyl-1-oxo-4-phenyl-2,7-diazaspiro[4.5]decan-7-yl)-1-oxo-5-phenylpent-4-en-2-yl)propanamide;

2-Amino-N-((S)-3-(benzylthio)-1-((4S,5R)-2-methyl-1-oxo-4-phenyl-2,7-diazaspiro[4.5]decan-7-yl)-1-oxopropan-2-yl)-2-methylpropanamide;

2-amino-N-((2R,3S)-3-(benzyloxy)-1-(2-methyl-1-oxo-4-p-tolyl-2,7-diazaspiro[4.5]decan-7-yl)-1-oxobutan-2-yl)-2-methylpropanamide;

2-amino-2-methyl-N-((R)-1-((4S,5R)-2-methyl-1-oxo-4-phenyl-2,7-diazaspiro[4.5]decan-7-yl)-1-oxo-3-(pyridin-2-ylmethoxy)propan-2-yl)propanamide;

2-amino-2-methyl-N-((R)-1-((4S,5R)-2-methyl-1-oxo-4-phenyl-2,7-diazaspiro[4.5]decan-7-yl)-1-oxo-3-(pyridin-3-ylmethoxy)propan-2-yl)propanamide;

2-Amino-N-((R)-3-(benzyloxy)-1-oxo-1-((4S,5R)-1-oxo-4-phenyl-2-(2,2,2-trifluoroethyl)-2,7-diazaspiro[4.5]decan-7-yl)propan-2-yl)-2-methylpropanamide;

(R)-2-Amino-N-((R)-3-(benzyloxy)-1-((4S,5R)-2-methyl-1-oxo-4-phenyl-2,7-diazaspiro[4.5]decan-7-yl)-1-oxopropan-2-yl)-2-methylbutanamide;

2-Amino-2-methyl-N-((R)-1-((4S,5R)-2-methyl-1-oxo-4-phenyl-2,7-diazaspiro[4.5]decan-7-yl)-1-oxo-4-phenoxybutan-2-yl)propanamide;

or a pharmaceutically acceptable salt thereof.

In another aspect, there is provided a process for preparing a compound as defined in the first, second or third aspect.

Compounds of formula (I) wherein $R^3$ and $R^4$ are hydrogen may be prepared according to the following Scheme 1.

Scheme 1

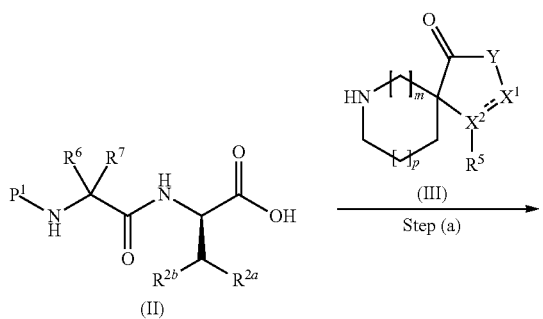

wherein $R^{2a}$, $R^{2b}$, $R^5$, $R^6$, $R^7$, $X^1$, $X^2$, m, p and Y are defined as in the first aspect or wherein m and p are both 1 and $R^{2a}$, $R^{2b}$, $R^5$, $R^6$, $R^7$, $X^1$, $X^2$ and Y are defined as in the second or third aspect, and $P^1$ represents a suitable protection group, for example a BOC (tert-butoxy carbonyl) group.

Step (a) involves reacting a compound of formula (II) in a suitable solvent such as DMF in the presence of a suitable amide coupling reagent, for example ®T3P, and a suitable base such as DIPEA with a compound of formula (III) at a suitable temperature such as room temperature.

Step (b) involves the removal of a suitable protection group $P^1$ which is well known in the art. For example, when $P^1$ is BOC, a compound of formula (IV) is treated in a suitable solvent, for example DCM, under acidic conditions, for example by the addition of TFA, at a suitable temperature such as room temperature.

Compounds of formula (III) wherein $X^1$ is $(CR^{x1}H)_n$, n is 1, $X^2$ is CH and Y is $NR^1$ may be prepared according to the following Scheme 2.

Scheme 2

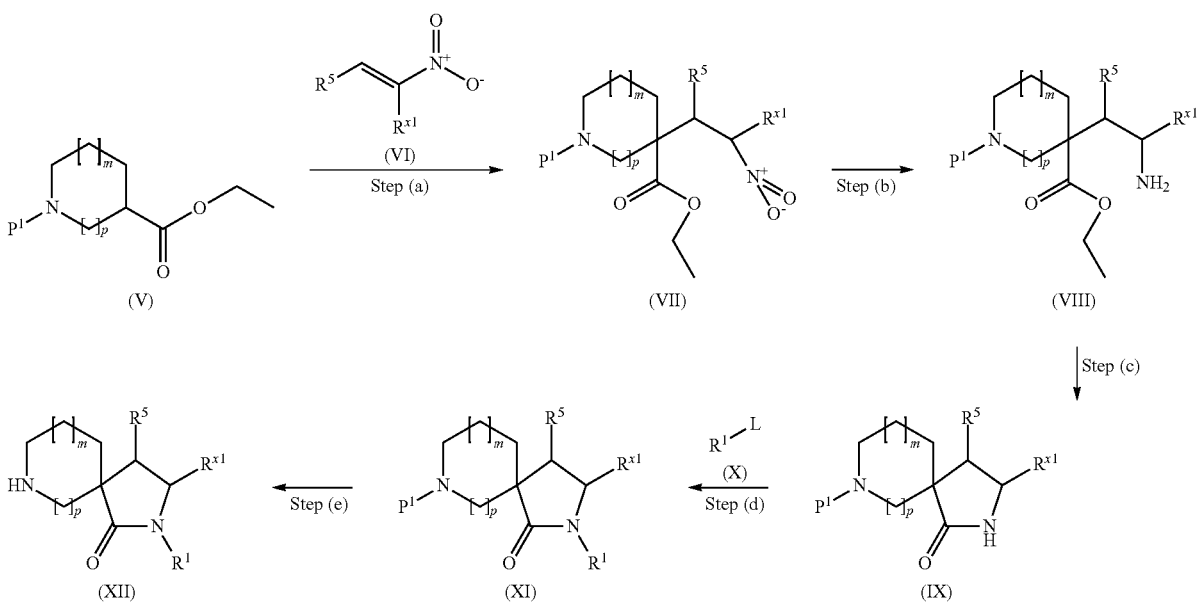

wherein $R^1$, $R^5$, m, p and $R^{x1}$ are defined as in the first aspect or wherein m and p are both 1 and $R^1$, $R^5$, and $R^{x1}$ are defined as in the second or third aspect, $P^1$ represents a suitable protection group, for example a BOC group, and L represents a suitable leaving group, for example a halogen group such as chloro.

Step (a) involves deprotonation of a compound of formula (V) with a suitable base such as lithium bis(trimethylsilyl) amide in a suitable solvent such as THF, at appropriate low temperature, followed by quenching of the formed anion with a compound of formula (VI).

Step (b) involves reduction of a compound of formula (VII) in a suitable solvent such as MeOH, with a suitable reducing agent such as nickel boride at a suitable temperature such as 0° C.

Step (c) involves cyclisation of a compound of formula (VIII) by heating at reflux in a suitable solvent such as toluene.

Step (d) involves deprotonation of a compound of formula (IX) with a suitable base such as sodium hydride in a suitable solvent such as THF, at a suitable temperature, such as room temperature, followed by quenching of the formed anion with a compound of formula (X).

-continued

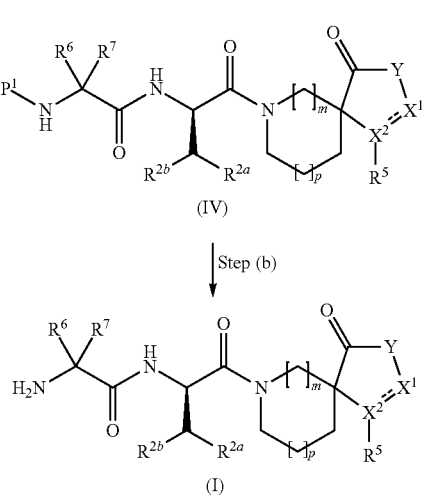

Step (e) involves the removal of a suitable protection group $P^1$ which is well known in the art. For example, when $P^1$ is BOC, a compound of formula (XI) is treated in a suitable solvent, for example DCM, under acidic conditions, for example by the addition of TFA, at a suitable temperature such as room temperature.

Compounds of formula (III) wherein $X^1$ is $(CR^{x1}H)_n$, n is 0, $X^2$ is CH and Y is $NR^1$ may be prepared according to the following Scheme 3.

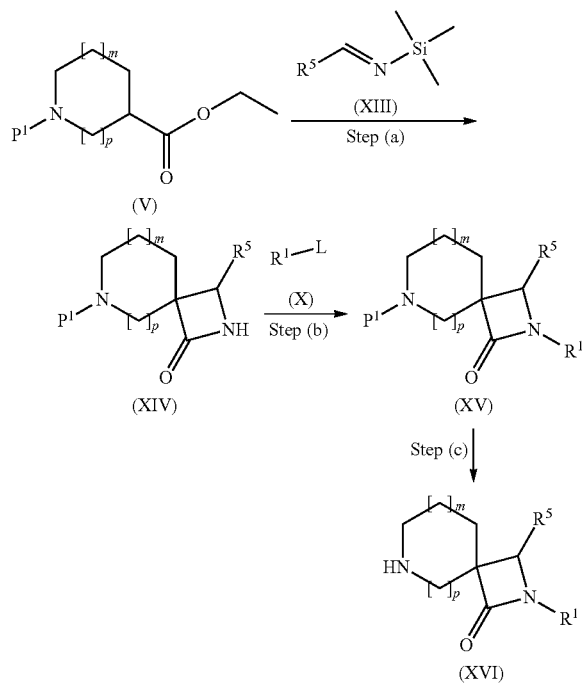

Scheme 3 wherein $R^1$, $R^5$ and m and p are defined as in the first aspect or wherein m and p are both 1 and $R^1$ and $R^5$ are defined as in the second or third aspect, $P^1$ represents a suitable protection group, for example a BOC group, and L represents a suitable leaving group, for example a halogen group such as chloro.

Step (a) involves deprotonation of a compound of formula (V) with a suitable base such as lithium bis(trimethylsilyl) amide in a suitable solvent such as THF, at a suitable temperature, such as −78° C., followed by quenching of the formed anion with a compound of formula XIII.

Step (b) involves deprotonation of a compound of formula (XIV) with a suitable base such as sodium hydride in a suitable solvent such as THF, at a suitable temperature, such as room temperature, followed by quenching of the formed anion with a compound of formula (X).

Step (c) involves the removal of a suitable protection group $P^1$ which is well known in the art. For example, when $P^1$ is BOC, a compound of formula (XV) is treated in a suitable solvent, for example DCM, under acidic conditions, for example by the addition of TFA, at a suitable temperature such as room temperature.

Compounds of formula (II) may be prepared according to known procedures. For example, where $R^{2a}$ is benzyloxy or indolyl, procedures as described in WO1998/58949 (Pfizer) may be used.

Compounds of formula (V), (VI) and (XIII) are commercially available or may be prepared according to procedures known to a person skilled in the art.

Compounds as defined in the first, second or third aspect may exist as stereoisomers. As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be arranged in an E or Z configuration. If the compound contains a disubstituted cycloalkyl, the cycloalkyl substituent may have a cis- or trans-configuration. All tautomeric forms are also intended to be included.

As used herein, the terms "salt" or "salts" refer to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, L-malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of compounds as defined in the first, second or third aspect can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds as defined in the first, second or third aspect that contain groups capable of acting as donors and/or acceptors for hydrogen bonds may be capable of forming co-crystals with suitable co-crystal formers. These co-crystals may be prepared from compounds as defined in the first, second or third aspect by known co-crystal forming procedures. Such procedures include grinding, heating, co-subliming, co-melting, or contacting in solution compounds as defined in the first, second or third aspect with the co-crystal former under crystallization conditions and isolating co-crystals thereby formed. Suitable co-crystal formers include those described in WO 2004/078163. Hence the invention further provides co-crystals comprising a compound as defined in the first, second or third aspect.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound as defined in the first, second or third aspect refers to an amount of the compound as defined in the first, second or third aspect that will elicit the biological or medical response of a subject, for example, increase of an enzyme or a protein activity, or ameliorate symptoms, alleviate conditions, slow or delay disease progression, or prevent a disease, etc. In an non-limiting embodiment, the term "a therapeutically effective amount" refers to the amount of the compound of the present invention that, when administered to a cell, or a tissue, or a non-cellular biological material, or a medium, is effective to at least partially increase the activity of the ghrelin receptor; or at least partially increase the expression of ghrelin.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds as defined in the first, second or third aspect, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The compounds of the present invention, including salts, hydrates and solvates thereof, may inherently or by design form polymorphs.

The compounds as defined in the first, second or third aspect are ghrelin receptor agonists. Hence, the compounds as defined in the first, second or third aspect may be useful in the treatment of disorders/diseases where ghrelin or ghrelin receptor agonists have a beneficial effect.

Thus, the compounds as defined in the first, second or third aspect may be useful in the treatment of disorders/diseases characterized by gastrointestinal (GI) dysmotility (Sanger, Drug Discov Today, 2008, 13, 234-239; De Smet et al. Pharmacol Ther, 2009, 123, 207-22; Camilleri et al. Nat Rev Gastroenterol Hepatol, 2009, 6, 343-352). In particular, the compounds as defined in the first, second or third aspect may be useful in the treatment of disorders/diseases characterized by gastrointestinal (GI) dysmotility selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers, Crohn's disease, and emesis. It has been reported that ghrelin and ghrelin receptor agonists have favorable therapeutic effects on both dysmotility and the associated symptoms in functional gastrointestinal diseases (Murray et al. Gastroenterology, 2003, 125, 1492-1502; Tack et al. Aliment Pharmacol Ther, 2005, 22: 847-853; Akamizu et al. Eur J Endocrinol. 2008, 158, 491-498; Ejskaer et al. 2009 29, 1179-1187; Popescu et al. 2010, 53, 126-134; Ejskjaer et al. Neurogastroenterol Motil, 22, 1069-e281).

The compounds as defined in the first, second or third aspect may also be useful in the treatment of muscle wasting disorders like cachexia resulting from, for example, cancer, congestive heart failure, AIDS, chronic liver failure, renal failure, Parkinson's Disease or chronic obstructive pulmonary disease (COPD) and age-related frailty (i.e. sarcopenia) (DeBoer, 2011 Mol Cell Endocrinol); reducing cachexia and protein loss due to acute or chronic illness (U.S. Pat. No. 6,194,578); treating or preventing frailty associated with aging or obesity (U.S. Pat. No. 6,194,578); to improve muscle strength and mobility (U.S. Pat. No. 6,194,578); for the treatment of endocrine disorders associated with GH deficiency, e.g. fibromyalgia (Cuatrecasas, Pediatr Endocrinol Rev. 2009, 4, 529-533), Alzheimer's Disease (Sevigny et al. 2008 71, 1702-1708) and short stature/dwarfism (Pihoker et al. 1997, J Endocrinol, 155, 79-86); and the treatment of 'eating disorders' including anorexia nervosa (Hotta et al. 2009, 56, 1119-1128).

The compounds as defined in the first, second or third aspect may also have cardioprotective effects providing therapeutic benefit for the treatment of cardiovascular diseases (e.g. for the prevention of congestive heart failure (U.S. Pat. No. 6,329,342; U.S. Pat. No. 6,194,578)) and atherogenesis (Garcia and Korbonits, Curr Opin Pharmacol 2006, 6, 142-147; Cao et al. Trends Endocrinol Metab, 2006, 17, 13-15; Isgaard and Granata, Mol Cell Endocrinol 2011). Furthermore, ghrelin has been shown to have protective effects by inhibiting cardiomyocyte and endothelial cell apoptosis (Baldanzi et al. J Cell Biol, 2002, 159, 1029-1037), and to improve left ventricular (LV) function during ischemia-reperfusion (I/R) injury (Frascarelli et al. Basic Res Cardiol, 2003, 98, 401-405). In rats with heart failure (HF), ghrelin has been shown to improve LV dysfunction and attenuates the development of cardiac cachexia (Nagaya et al. Circulation, 2001, 104, 1430-1435). Similarly, in short term studies, ghrelin has been shown to improve cardiac function and to decrease systemic vascular resistance in patients with chronic HF (Nagaya et al. Endocrinol Metab, 2001, 86, 5854-5859). In the vasculature, ghrelin has been shown to exert vasodilatory effects (Nagaya et al. Am J Physiol Regul integr Comp Physiol, 2001, 280, R1483-R1487) and possible anti-inflammatory effects that may be of potential importance for the development of atherosclerosis (Dixit et al. J Clin Invest, 2004, 114, 57-66).

The compounds as defined in the first, second or third aspect may also have therapeutic potential for the protection from sepsis (Chorny et al. 2008, J Immunol, 180, 8369-8377) and associated injuries such as to the lung (Wu et al., 2007, 176, 805-813); gastroprotection from mucosal damage and acceleration of healing, for example acid-induced ulceration (Ceranowicz et al. J Physiol Pharmacol, 60, 87-98); for the stimulation of hair growth (EP1818061 A1); for the inhibition of tumor cell growth (Ghe et al. J Endocrinol, 2000, 165, 139-146; Cassoni et al. J Clin Endocrinol, 2002, 143, 484-491); for the acceleration of recovery of patients following major surgery (U.S. Pat. No. 6,194,578); accelerating the recovery of burn patients (U.S. Pat. No. 6,194,578); attenuating protein catabolic responses after major surgery (U.S. Pat. No. 6,194,578); treating central nervous system disorders of patients undergoing a medical procedure in combination with antidepressants (US 2002/0002137 A1); acceleration of bone fracture repair and cartilage growth (U.S. Pat. No. 6,194,578); treatment or prevention of osteoporosis; stimulation of the immune system; accelerating wound healing (U.S. Pat. No. 6,194,578); treatment of intrauterine growth retardation; treatment of growth retardation associated with the Prader-Willi syndrome, Turner's syndrome and Noonan's syndrome; treatment of schizophrenia, depressions and Alzheimer's disease; treatment of pulmonary dysfunction and ventilation dependency; treatment of hyperinsulinemia including nesidioblastosis; adjuvant treatment for ovulation induction; prevention of the age-related decline of thymic function; maintenance of skin thickness (U.S. Pat. No. 6,194,578); improvement of sleep quality (U.S. Pat. No. 6,071,926); metabolic homeostasis or renal homeostasis (e.g. in the frail elderly, U.S. Pat. No. 6,194,578); improving glycemic control (U.S. Pat. No. 6,251,902); treatment of lupus erythematosus and inflammatory bowel disease (US 2002/0013320); as well as stimulation of osteoblasts.

Hence, the invention relates in a second aspect to compounds as defined in the first, second or third aspect for use in medicine. Particularly, the compounds of the first, second or third aspect have valuable pharmacological properties, as described hereinbefore and hereinafter. The invention thus provides:

a compound of the first, second or third aspect as defined herein, as a pharmaceutical/for use in medicine;

a compound of the first, second or third aspect as defined herein, as a medicament/for use as a medicament;

a compound of the first, second or third aspect as defined herein, for the treatment of/for use in the treatment of disorders/diseases where ghrelin or ghrelin receptor agonists have a beneficial effect;

a compound of the first, second or third aspect as defined herein, for the treatment of/for use in the treatment of disorders/diseases characterized by gastrointestinal (GI) dysmotility;

a compound of the first, second or third aspect as defined herein, for the treatment of/for use in the treatment of a disorder or disease selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis;

a compound of the first, second or third aspect as defined herein, for the treatment of/for use in the treatment of gastroparesis;

the use of a compound of the first, second or third aspect as defined herein, for the manufacture of a medicament in the treatment of disorders/diseases where ghrelin or ghrelin receptor agonists have a beneficial effect;

the use of a compound of the first, second or third aspect as defined herein, for the manufacture of a medicament for the treatment of a disorder or disease selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis;

the use of a compound of the first, second or third aspect as defined herein, for the manufacture of a medicament for the treatment of a disorder or disease selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis;

the use of a compound of the first, second or third aspect as defined herein, for the treatment of one or more disorders/diseases where ghrelin or ghrelin receptor agonists have a beneficial effect;

the use of a compound of the first, second or third aspect as defined herein, for the treatment of gastroparesis (e.g. of diabetic, idiopathic or surgical origin), ileus (including postoperative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis;

the use of a compound of the first, second or third aspect as defined herein, for the treatment of a disorder or disease selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis;

a method for the treatment of disorders/diseases where ghrelin or ghrelin receptor agonists have a beneficial effect comprising the step of administering to a subject a therapeutically effective amount of a compound of the first, second or third aspect as defined herein;

a method for the treatment of a disorder or disease selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis comprising the step of administering to a subject a therapeutically effective amount of a compound of the first, second or third aspect as defined herein;

a method of modulating ghrelin receptor activity in a subject, comprising the step of administering to a subject a therapeutically effective amount of a compound of the first, second or third aspect as defined herein;

When used as a medicine, a compound as defined in the first, second or third aspect, or a pharmaceutically acceptable salt thereof, are usually formulated as a pharmaceutical composition. Hence, the invention relates in a third aspect to pharmaceutical compositions comprising a compound as defined in the first, second or third aspect, and one or more pharmaceutically acceptable carrier. The pharmaceutical composition can be formulated for particular routes of administration such as oral administration, parenteral administration, intranasal, sublingual and rectal administration, etc, in particular intranasal and sublingual administration. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound as defined in the first, second or third aspect in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The invention thus provides
a pharmaceutical composition comprising a compound as defined in the first, second or third aspect and one or more carriers/excipients;
a pharmaceutical composition comprising a therapeutically effective amount of a compound as defined in the first, second or third aspect, and one or more pharmaceutically acceptable carriers/excipients.

Treatment as defined herein may be applied as a sole therapy or may involve, in addition to a compound as defined in the first, second or third aspect, administration of other active ingredients. Such therapy may for example include in combination with a compound as defined in the first, second or third aspect, one or more of the following categories of active ingredients:
Dopamine $D_2$ antagonists, eg domperidone, metoclopramide and itopride;
$5HT_4$ receptor agonists, eg cisapride, cinitapride, mosapride, renzapride, prucalopride, tegaserod, and compounds described in WO 2005068461, US 2005228014 and WO 2005080389, US 2006100426, US 2006100236, US 2006135764, US 2005277671, WO 2005092882, WO 2005073222, JP 2005104896, JP 2005082508, WO 2005021539, JP 2004277319, JP 2004277318, WO 2004026869, EP 1362857;
$5HT_3$ agonists eg pumosetrag;
$CCK_4$ receptor antagonists, eg loxiglumide and dexloxiglumide;
Motilin receptor agonists, eg motilin, atilmotilin, erythromycin, alemcinal, mitemcinal, KOS-2187 and compounds described in WO 2005060693;
μ-opioid antagonists eg alvimopan and methylnaltrexone
Opioid agonists, eg asimadoline, loperamide and codeine;
CRF-1 receptor antagonists, eg GSK876008 and compounds described in WO 2004069257, WO 9940089, U.S. Pat. No. 6,844,351, WO 2005013997, WO 2005014557, WO 2005023806, WO 2005026126, WO 2005028480, WO 2005044793, WO 2005051954, WO 2005051954, WO 2005115399, WO 2005028480, WO 2005023806, WO 2006044958, WO 2010015655 and WO 2010015628;
Glutamate receptor antagonists, eg AZD9272 and compounds described in WO 9902497, WO 2000020001, WO 200304758 and WO 2005030723;
Neurokinin receptor antagonists, eg casopitant, nepadutrent saredutant, DNK-333, SLV-317, SLV321, SLV317 and compounds described in EP 96-810237;
$5HT_3$ receptor antagonists eg alosetron, cilansetron, ramosetron, azasetron, ondansetron, granisetron tropisetron and DDP225;
Histamine $H_2$ antagonists, eg famotidine, cimetidine, ranitidine and nizatidine
Histamine $H_4$ antagonists. eg JNJ7777120, JNJ10191584 and compounds described in US 2006111416, WO 2006050965, WO 2005092066, WO 2005054239 US 2005070550, US 2005070527, EP 1505064;
Proton pump inhibitors, eg omeprazole, lansoprazole, rabeprazole, tentoprazole, pantoprazole, esomeprazole, revaprazan soraprazan and AGN201904;
Chloride channel activators, eg lubiprostone;
Guanylate cyclase activators, eg linaclotide;
Muscarinic antagonists, eg darifenacin, solifenacin, atropine, dicycloverine, hycosine butyl bromide, propantheline, oxybutinin, cimetropium bromide, pinaverium bromide and otilonium bromide;
Antispasmodics, eg mebeverine, tiropramide, alverine and peppermint oil;
Stimulant laxatives, eg bisacodyl;
Osmotic laxatives, eg activated charcoal with sorbitol, lactulose, magnesium hydroxide and phosphate buffered saline;
Faecal softeners, eg senna concentrate, liquid paraffin and arachis oil;
Absorbents and fibre supplements, eg bulk fibre laxatives such as bran, methylcellulose, ispaghula husk and sterculia;
Antacids, eg aluminium, magnesium and calcium antacids, simeticone and alginate containing preparations;
GI relaxants, eg cholestyramine resin;
Bismuth compounds, eg bismuth subsalicylate;
Vanilloid receptor antagonists, eg compounds described in WO 2002076946, WO 2004033435, WO 2005121116 and WO 2005120510;
Anticonvulsants, eg carbamazepine, oxcarbemazepine, lamotrigine, gabapentin, and pregabalin;
NSAIDS, eg aspirin, acetometaphen, ibuprofen, diclofenac, naproxen, flurbiprofen, indomethacin, piricoxam, ketoprofen, sulindac and diflunisal;
COX-2 inhibitors eg celecoxib, rofecoxib, lumiracoxib, valdecoxib, etoricoxib and compounds described in WO 2004048314;
opiates, eg morphine, buprenorphine, diamorphine, dihydrocodeine, fentanyl and pethidine; $GABA_b$ modulators, eg racemic and (R)-baclofen, AZD3355, XP19986 and compounds described in WO 2006001750 and WO 2004000856;
CB receptor ligands, eg compounds described in WO 2002042248 and WO 2003066603;
Calcium channel blockers, eg ziconotide, AGI0-003, PD-217014 and compounds described in WO 2006038594, WO 2006030211 and WO 2005068448;
Sodium channel blockers, eg lamotrigine and compounds described in WO 2006023757, WO 2005097136, JP 2005206590 and WO 2005047270; tricyclic antidepressants, e.g. clomipramine, amoxapine, nortripyline, amitriptyline, imipramine, desipramine, doxepin, trimipramine and protripyline;

selective serotonin reuptake inhibitors, eg fluoxetine, paroxetine, citaprolam, sertaline, fluvoxamine, duloxetine;

anxiolytic agents, eg milnacipran, tianeptine, MCI-225 and dextofisopam;

CGRP antagonists, eg olcegepant and cizolirtine;

5HT$_{1d}$ antagonists, eg almotriptan, eletriptan, frovatriptan, naratriptan, rizatriptan, sumatriptan and zolmatriptan;

bradykinin receptor antagonists, eg compounds described in WO 2000075107, WO 2002092556 and WO 20050851298.

Compounds of the first, second or third aspect may further be used in combination with other pharmacologically active agents to enhance the absorption or activity of the co-medicant through improvements in gastric emptying, for example to enhance the exposure rate of anti-migraine drugs like triptans (sumatriptan, zolmitriptan, avitriptan, rizatriptan, etc) or anti-diabetes therapies (e.g. insulin secretagogues or sensitizers, etc.

Compounds of the first, second or third aspect may further be used in combination with proton pump inhibitors (PPIs), for example esomeprazole, lansoprazole, omeprazole, pantoprazole and rabeprazole, histamine H2 receptor blockers (such as ranitidine, famotidine and cimetidine) or antacids for the treatment of gastrointestinal diseases like GERD.

A ghrelin receptor agonist as defined in the first, second or third aspect may also be combined with another therapeutic agent that is useful in the treatment of disorders associated with obesity such as hypertension, hyperlipidaemias, dyslipidaemias, diabetes, sleep apnoea, asthma, heart disorders, atherosclerosis, macro and micro vascular diseases, liver steatosis, cancer, joint disorders, and gallbladder disorders. For example, a Ghrelin receptor modulator of formula I may be used in combination with another therapeutic agent that lowers blood pressure or that decreases the ratio of LDL:HDL or an agent that causes a decrease in circulating levels of LDL-cholesterol, such as, inhibitors of HMG-CoA reductase (3-hydroxy-3-methylglutaryl coenzyme A reductase). Suitably the HMG-CoA reductase inhibitor is a statin. In the present application, the term "cholesterol-lowering agent" also includes chemical modifications of the HMG-CoA reductase inhibitors, such as esters, prodrugs and metabolites, whether active or inactive. In patients with diabetes mellitus the compounds of the invention may also be combined with therapeutic agents used to treat complications related to microangiopathies.

A ghrelin receptor agonist as defined in the first, second or third aspect may be used alongside other therapies for the treatment of obesity and its associated complications, the metabolic syndrome and type 2 diabetes. These include, but shall not be limited to, biguanide drugs (for example, metformin), insulin (synthetic insulin analogues) oral antihyperglycemics (these are divided into prandial glucose regulators and α-glucosidase inhibitors) and sulfonylureas, for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide.

A ghrelin receptor agonist as defined in the first, second or third aspect may also be used in combination with an inhibitor of the ileal bile acid transport system (IBAT inhibitor). The present invention also includes a Ghrelin ghrelin receptor agonist as defined in the first, second or third aspect in combination with a bile acid binding resin. The present invention also includes a ghrelin receptor agonist as defined in the first, second or third aspect in combination with a bile acid sequestering agent, for example, colestipol or cholestyramine or cholestagel.

According to an additional further aspect of the present invention there is provided a combination treatment comprising the administration of an effective amount of a compound as defined in the first, second or third aspect, or a pharmaceutically acceptable salt thereof, optionally together with a pharmaceutically acceptable diluent or carrier, with the simultaneous, sequential or separate administration of one or more of the following agents selected from: a CETP (cholesteryl ester transfer protein) inhibitor; a cholesterol absorption antagonist; a MTP (microsomal transfer protein) inhibitor; a nicotinic acid derivative, including slow release and combination products; a phytosterol compound; probucol; an anticoagulant; an omega-3 fatty acid; another anti-obesity compound for example sibutramine, phentermine, orlistat, bupropion, ephedrine, thyroxine; an antihypertensive compound for example an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, an AT-I blocker, a saluretic, a diuretic or a vasodilator; a CBI receptor antagonist/inverse agonist; a melanin concentrating hormone (MCH) modulator; a melanocortin-4 receptor agonist; an NPY receptor modulator; an orexin receptor modulator; a diacylglycerol acyltransferase-1 inhibitor; a diacylglycerol acyltransferase-2 inhibitor; a phosphoinositide-dependent protein kinase (PDK) modulator; or modulators of nuclear receptors for example LXR, FXR, RXR, GR, ERR[alpha], [beta], PP ARa, [beta], [gamma] and RORalpha; a monoamine transmission-modulating agent, for example a selective serotonin reuptake inhibitor (SSRI), a noradrenaline reuptake inhibitor (NARI), a noradrenaline-serotonin reuptake inhibitor (SNRI), a monoamine oxidase inhibitor (MAOI), a tricyclic antidepressive agent (TCA), a noradrenergic and specific serotonergic antidepressant (NaSSA); an antipsychotic agent for example olanzapine and clozapine; a serotonin receptor modulator; a leptin/leptin receptor modulator; a Ghrelin/Ghrelin receptor modulator; a DPP-IV inhibitor for example Saxagliptin, Sitagliptin, Vildagliptin or Alogliptin; an SGLT-2 inhibitor for example Dapagliflozin; a GLK activator; or a pharmaceutically acceptable salt, solvate, solvate of such a salt or a prodrug thereof, optionally together with a pharmaceutically acceptable diluent or carrier to a patient.

The invention hence relates in a fourth aspect to combinations comprising a compound as defined in the first, second or third aspect and one or more additional active ingredients. The invention thus provides a combination in particular a pharmaceutical combination, comprising a therapeutically effective amount of a compound as defined in the first, second or third aspect and one or more therapeutically active agents;

a combined pharmaceutical composition, adapted for simultaneous or sequential administration, comprising a therapeutically effective amount of a compound as defined in the first, second or third aspect as defined herein; therapeutically effective amount(s) of one or more combination partners; one or more pharmaceutically acceptable excipients;

a combined pharmaceutical composition as defined herein (i) as a pharmaceutical, (ii) for use in the treatment of a ghrelin mediated disease, (iii) in a method of treatment of a ghrelin mediated disease.

According to an additional further aspect of the present invention there is provided a combination treatment comprising the administration of a therapeutically effective amount of a ghrelin receptor agonist as defined in the first, second or third aspect, optionally together with a pharmaceutically acceptable diluent or carrier, with the simultaneous, sequential or separate administration of very low calorie diets (VLCD) or low-calorie diets (LCD).

Therefore, the invention also provides a method for the treatment of obesity and its associated complications in a patient which comprises administering an effective amount of a compound as defined in the first, second or third aspect, in simultaneous, sequential or separate administration with an effective amount of a compound from one of the other classes of compounds described in this combination.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound as defined in the first, second or third aspect, can be prepared and administered as described in the art such as in the documents cited above.

In one further embodiment, the additional active ingredient is a hormonal medicine.

The pharmaceutical composition or combination of the present invention are typically in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-3}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

EXPERIMENTAL

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

EXAMPLES

General Conditions:

Mass spectra were run on LCMS systems using electrospray ionization. These were either Agilent 1100 HPLC/Micromass Platform Mass Spectrometer combinations or Waters Acquity HPLC with SQD Mass Spectrometer. $[M+H]^+$ refers to mono-isotopic molecular weights.

NMR spectra were run on open access Bruker AVANCE 400 NMR spectrometers using ICON-NMR. Spectra were measured at 298K and were referenced using the solvent peak.

XRPD measurements were run on a Bruker D8 GADDS Discover with Copper Kα radiations. Wavelength: 1.54056 A (Cu); Generator setting: 40.00 KV, 40.00 mA; Monochromator; Detector: HI-STAR; Frame Size: 1024 pixels, direct beam X: 513.5 pixels, direct beam Y: 515.50 pixels; Sample Detector distance 30.35 cm, two frames merged. An amount of 2-5 mg of the tested compound was placed on an objective slide and centered in the X-ray beam. Experiment method: 2-Theta start: 4.0 degree; 2-Theta end: 35.6 degree; Integration stepsize: 0.05 degree; Step time: 120 seconds; Temperature: Room Temperature One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

TGA measurements were run on a TA Instrument Q5000. The TGA thermogram was recorded as follows: 0.5-2 mg of test substance was weighed into the open sample pan. The sample was loaded into the furnace, the temperature equilibrated to 30° C. and heated to 300° C. at a heating rate of 10° C./min, under a flow of nitrogen at 25 mL/min.

DSC measurements were run on a TA Instrument Q1000. Unless otherwise stated through the document, the DSC thermogram was recorded as follows: 0.5-2 mg of test substance was weighed into the closed sample pan. An empty sample pan was used as reference. The temperature of the apparatus was adjusted to about 40° C. and heated to 300° C. at a heating rate of 10° C./min, under a nitrogen flow of 50 mL/min. The instrument was calibrated for temperature and enthalpy with Indium, at least 99.9999% pure. The heat flow, which was normalized by a sample weight, was plotted versus the measured sample temperature. The data were reported in units of watts/gram ("W/g"). The plot was made with the endothermic peaks pointing down. The endothermic melt peak was evaluated for extrapolated onset temperature, peak temperature, and heat of fusion in this analysis.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations:
AA ammonium acetate
BOC tertiary butyl carboxy
br broad
conc concentrated
d doublet
dd doublet of doublets
DBU 1,8-Diazabicyclo[5.4.0]undec-7-ene
DCM dichloromethane
DEA diethylamine
DIPEA diisopropylethylamine
DMF N,N-dimethylformamide
DMSO dimethylsulfoxide
DSC differential scanning calorimetry
EtOAc ethyl acetate
EtOH ethanol
h hour(s)
HCl hydrogen hydrochloride acid
HPLC high pressure liquid chromatography
Int. intermediate
LCMS liquid chromatography and mass spectrometry
LDA lithium diisopropylamide
LHMDS lithium bis(trimethylsilyl)amide
MeOH methanol
MS mass spectrometry
m multiplet
min minutes
ml milliliter(s)
m/z mass to charge ratio
NBS N-bromosuccinimide
$NH_4Cl$ ammonium chloride
NMR nuclear magnetic resonance
O/N overnight
ppm parts per million
PS polymer supported
PE-AX PE-anion exchange (e.g. Isolute® PE-AX columns from Biotage)
RT room temperature
Rf retention factor
Rt retention time
s singlet
SFC Supercritical Fluid Chromatography
SCX-2 strong cation exchange (e.g. Isolute® SCX-2 columns from Biotage)
t triplet
®T3P propylphosphonic anhydride
TBME tert-butyl methyl ether
TBSCl tert-butyldimethylsilyl chloride
TEA triethylamine
TFA trifluoroacetic acid
TGA thermogravimetric analysis
THF tetrahydrofuran
TLC thin layer chromatography
XRPD X-ray powder diffraction Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

If not indicated otherwise, the analytical HPLC conditions are as follows:

Method LowpH_v002

| | |
|---|---|
| Column | Phenomenex Gemini C18 50 × 4.6 mm, 3.0 μm |
| Column Temperature | 50° C. |
| Eluents | A: $H_2O$, B: methanol, both containing 0.1% TFA |
| Flow Rate | 1.0 ml/min |
| Gradient | 5% to 95% B in 2.0 min, 0.2 min 95% B |

Method 2minLC_v003

| | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 ml/min |
| Gradient | 0.20 min 5% B; 5% to 95% B in 1.30 min, 0.25 min 95% B |

Method LowpH_30_v001

| | |
|---|---|
| Column | Phenomenex Gemini C18 50 × 4.6 mm, 3.0 μm |
| Column Temperature | 40° C. |
| Eluents | A: $H_2O$, B: acetonitrile, both containing 0.1% TFA |
| Flow Rate | 1.2 ml/min |
| Gradient | 30% to 95% B in 2.0 min, 0.2 min 95% B |

Method LowpH_30_v002

| | |
|---|---|
| Column | Phenomenex Gemini C18 50 × 4.6 mm, 3.0 m |
| Column Temperature | 50° C. |
| Eluents | A: $H_2O$, B: methanol, both containing 0.1% TFA |
| Flow Rate | 1.0 mL/min |
| Gradient | 30% to 95% B in 2.0 min, 0.2 min 95% B |

Method IC45MeOH_DEA

| | |
|---|---|
| Column: | Chiralpak IC-H, 250 × 10 mm, 5 μm |
| Mobile Phase: | 45% MeOH + 0.1% DEA/55% $CO_2$ |
| Detection: | UV @ 220 nm |
| Flow rate: | 10 ml/min |

Method LUXC2__45MeOH_AA

| Column: | Phenomenex Lux-C2, 250 × 10 mm, 5 μm |
|---|---|
| Mobile Phase: | 45% MeOH (20 mM ammonium acetate)/55% $CO_2$ |
| Detection: | UV @ 220 nm |
| Flow rate: | 10 ml/min |

Method LUXC2__50MeOH_AA

| Column: | Phenomenex LUX C2 250 × 10 mm, 5 μm |
|---|---|
| Mobile phase: | 50% methanol + 20 mM Ammonium Acetate/50% CO2 |
| Flow: | 10 ml/min |
| Detection: | UV @ 220 nm |

Method IC35MeOH_AA

| Column: | Chiralpak IC, 250 × 10 mm, 5 μm (2 columns coupled together) |
|---|---|
| Mobile phase: | 35% methanol + 20 mM Ammonium Acetate/65% CO2 |
| Flow: | 10 ml/min |
| Detection: | UV @ 220 nm |

Method IC40MeOH_AA

| Column: | Chiralpak IC, 250 × 10 mm, 5 μm (2 columns coupled together) |
|---|---|
| Mobile phase: | 40% methanol + 20 mM Ammonium Acetate/60% CO2 |
| Flow: | 10 ml/min |
| Detection: | UV @ 220 nm |

Method AD25MeOH_DEA

| Column: | Chiralpak AD-H, 250 × 10 mm, 5 μm (2 columns coupled together) |
|---|---|
| Mobile phase: | 25% methanol + 0.1% DEA/75% CO2 |
| Flow: | 10 ml/min |
| Detection: | UV @ 220 nm |

Method IC35IPA_DEA

| Column: | Chiralpak IC 250 × 10 mm, 5 μm (2 Columns in series) |
|---|---|
| Mobile phase: | 35% methanol + 0.1% v/v DEA/65% CO2 |
| Flow: | 10 ml/min |
| Detection: | UV @ 220 nm |

Method AD30IPA_AmmAc

| Column: | Chiralcel AD-H 250 × 10 mm, 5 μm |
|---|---|
| Mobile phase: | 30% isopropanol + 20 mM ammonium acetate/70% CO2 |
| Flow: | 10 ml/min |
| Detection: | UV @ 220 nm |

Method AD40IPA_AmmAc

| Column: | Chiralcel AD-H 250 × 10 mm, 5 μm |
|---|---|
| Mobile phase: | 40% isopropanol + 20 mM ammonium acetate/60% CO2 |
| Flow: | 10 ml/min |
| Detection: | UV @ 220 nm |

Method OD30MeOH_AA

| Column: | Chiralcel OD-H 250 × 10 mm, 5 μm |
|---|---|
| Mobile phase: | 30% Methanol + 20 mM ammonium acetate/70% CO2 |
| Flow: | 10 ml/min |
| Detection: | UV @ 220 nm |

Method OD30MeOH_AA__1

| Column: | OD-H 250 × 20 mm, 5 μm |
|---|---|
| Mobile phase: | 30% Methanol + 20 mM ammonium acetate/70% CO2 |
| Flow: | 70 ml/min |

Method OD40MeOH_AA

| Column: | Chiralcel OD-H 250 × 10 mm, 5 μm |
|---|---|
| Mobile phase: | 40% methanol + 0.1% DEA/60% CO2 |
| Flow: | 10 ml/min |
| Detection: | UV @ 220 nm |

Method OD50MeOH_AA

| Column: | Chiralcel OD-H 250 × 10 mm, 5 μm |
|---|---|
| Mobile phase: | 50% methanol + 20 mM Ammonium Acetate)/50% CO2 |
| Flow: | 10 ml/min |
| Detection: | UV @ 220 nm |

Method AD45IPA_DEA

| Column: | Chiralcel AD-H 250 × 10 mm, 5 μm |
|---|---|
| Mobile phase: | 45% isopropanol + 0.1% v/v DEA/55% CO2 |
| Flow: | 10 ml/min |
| Detection: | UV @ 220 nm |

Method OD40IPA_AA

| Column: | Chiralcel OD-H 250 × 10 mm, 5 μm |
|---|---|
| Mobile phase: | 40% isopropanol + 20 mM Ammonium Acetate/60% CO2 |
| Flow: | 10 ml/min |
| Detection: | UV @ 220 nm |

Method OD30MeOH_DEA

| Column: | Chiralcel OD-H 250 × 10 mm, 5 μm |
|---|---|
| Mobile phase: | 30% Methanol + 0.1% v/v DEA/70% CO2 |
| Flow: | 10 ml/min |
| Detection: | UV @ 220 nm |

Method OD_35_MeOH_DEA

| Column: | Chiralpak AD-3 150 × 2.1 mm, 3 µm |
|---|---|
| Mobile phase: | 5% Methanol + 0.1% v/v DEA/95% CO2 |
| Flow: | 0.4 ml/min |
| Detection: | UV @ 220 nm and 254 nm |

Method OD45MeOH_AA

| Column: | OD-H 4.6 × 100 mm, 5 µm, |
|---|---|
| Mobile Phase: | 45% MeOH (20 mM ammonium acetate)/55% CO2, |
| Flow rate: | 60 ml/min, |

Method OD45MeOH_AA_1

| Column: | OD-H 20 × 250 mm, 5 µm |
|---|---|
| Mobile phase: | 45% MeOH (20 mM ammonium acetate)/55% CO2 |
| Flow: | 60 ml/min |

Method: OJ15MeOH_AA

| Column: | Chiralcel OJ-H 250 × 10 mm, 5 µm |
|---|---|
| Mobile phase: | 15% methanol + 20 mM Ammonium Acetate/85% CO2 |
| Flow: | 10 ml/min |
| Detection: | UV @ 220 nm |

Method AD50IPA_DEA

| Column: | Chiralcel AD-H 250 × 10 mm, 5 µm |
|---|---|
| Mobile phase: | 50% isopropanol + 0.1% v/v DEA/50% CO2 |
| Flow: | 10 ml/min |
| Detection: | UV @ 220 nm |

Method OD35IPA_AA

| Column: | Chiralcel OD-H 250 × 10 mm, 5 µm |
|---|---|
| Mobile phase: | 35% 2-propanol + 20 mM Ammoniumn Acetate/65% CO2 |
| Flow: | 10 ml/min |
| Detection: | UV @ 220 nm |

Method OD40MeOH_DEA

| Column: | Chiralcel OD-H 250 × 10 mm, 5 µm |
|---|---|
| Mobile phase: | 40% methanol + 0.1% DEA/60% CO2 |
| Flow: | 10 ml/min |
| Detection: | UV @ 220 nm |

Method OD25IPA_DEA

| Column: | Chiralcel OD-H 250 × 10 mm, 5 µm |
|---|---|
| Mobile phase: | 25% isopropanol + 0.1% v/v DEA/75% CO2 |
| Flow: | 10 ml/min |
| Detection: | UV @ 220 nm |

Method OD30IPA_DEA

| Column: | Chiralcel OD-H 250 × 10 mm, 5 µm |
|---|---|
| Mobile phase: | 30% isopropanol + 0.1% v/v DEA/70% CO2 |
| Flow: | 10 ml/min |
| Detection: | UV @ 220 nm |

Method OD45IPA_DEA

| Column: | Chiralcel OD-H 250 × 10 mm, 5 µm |
|---|---|
| Mobile phase: | 45% isopropanol + 0.1% v/v DEA/55% CO2 |
| Flow: | 10 ml/min |
| Detection: | UV @ 220 nm |

Preparation of Final Compounds

Example 1.0(i) and 1.0(ii)

Diastereomers 2-Amino-N-[(R)-1-benzyloxymethyl-2-((4R,5S)-2-methyl-1-oxo-4-phenyl-2,7-diaza-spiro[4.5]dec-7-yl)-2-oxo-ethyl]-2-methyl-propionamide and 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide

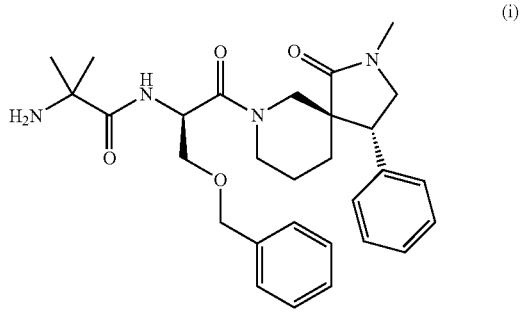

(4R,5S)-stereoisomer

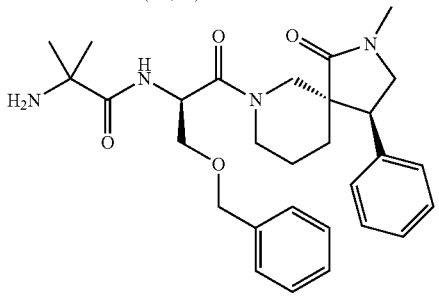

(4S,5R)-stereoisomer

Step 1: tert-Butyl 1-((2R)-3-(benzyloxy)-1-(2-methyl-1-oxo-4-phenyl-2,7-diazaspiro[4.5]decan-7-yl)-1-oxopropan-2-ylamino)-2-methyl-1-oxopropan-2-ylcarbamate A mixture comprising (R)-3-(benzyloxy)-2-(2-(tert-butoxycarbonylamino)-2-methyl propanamido)propanoic acid (Intermediate 3A) (800 mg, 2.103 mmol) and a racemic mixture of (4R,5S)-2-Methyl-4-phenyl-2,7-diazaspiro[4.5]decan-1-one and (4S,5R)-2-Methyl-4-phenyl-2,7-diazaspiro[4.5]decan-1-one (Intermediate 1A) (514 mg, 2.103 mmol) in DMF (10 ml) was treated with DIPEA (1.102 ml, 6.31 mmol) and ®T3P (amide coupling agent 50% in DMF, 2.455 ml, 4.21 mmol) and stirred at RT for 1 hour. The resulting mixture was concentrated in vacuo and the residue was suspended in water (50 ml) and extracted with EtOAc (2×100 ml). The combined organic extracts were dried (MgSO$_4$) and concentrated in vacuo. Purification by chromatography on silica eluting with 0-100% EtOAc in iso-hexane afforded the title compound as a white foam.

LC-MS Rt 2.59 mins; MS m/z 608[M+H]+; Method Low-pH_v002.

Step 2: 2-Amino-N-((2R)-3-(benzyloxy)-1-(2-methyl-1-oxo-4-phenyl-2,7-diazaspiro[4.5]decan-7-yl)-1-oxopropan-2-yl)-2-methylpropanamide tert-Butyl 1-((2R)-3-(benzyloxy)-1-(2-methyl-1-oxo-4-phenyl-2,7-diazaspiro[4.5]decan-7-yl)-1-oxopropan-2-ylamino)-2-methyl-1-oxopropan-2-ylcarbamate (1.18 g, 1.945 mmol) in DCM (15 ml) was treated with TFA (7 ml, 91 mmol) and stirred at RT for 1 hour. The solvent was removed in vacuo and the residue was partitioned between EtOAc (200 ml) and sat. sodium bicarbonate solution (100 ml). The organic portion was dried (MgSO$_4$) and concentrated in vacuo to afford the title compound as a diastereomeric mixture;

LC-MS Rt 2.09 mins; MS m/z 508[M+H]+; Method Low-pH_v002.

Separation of the diastereomers by Supercritical Fluid Chromatography using the following conditions afforded the compounds listed hereinafter:

| | |
|---|---|
| Mobile Phase: | 45% MeOH + 20 mM ammonium acetate/65% CO$_2$ |
| Column: | Chiralcel OD-H, 250 × 10 mm id, 5 μm |
| Detection: | UV @ 220 nm |
| Flow rate: | 10 ml/min |

Example 1.0(i)

First eluted peak Rt=3.31 minutes. Diastereomer 1: 2-Amino-N-[(R)-1-benzyloxymethyl-2-((4R,5S)-2-methyl-1-oxo-4-phenyl-2,7-diaza-spiro[4.5]dec-7-yl)-2-oxo-ethyl]-2-methyl-propionamide LC-MS Rt 2.10 mins; MS m/z 508 [M+H]+; Method Low pH_v002

Example 1.0(ii)

Second eluted peak Rt=7.31 minutes. Diastereomer 2: 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide Rt 2.09 mins; MS m/z 508 [M+H]+; Method Low pH_v002

$^1$H NMR (d6-DMSO, 500 MHz, 398K) δ1.09-1.23 (2H, m), 1.26 (3H, s), 1.27 (3H, m), 1.40-1.51 (1H, m), 1.58-1.69 (1H, m), 2.86 (3H, s), 3.02-3.13 (1H, br m), 3.19 (1H, ddd), 3.25-3.36 (2H, m), 3.60-3.87 (4H, m), 3.90-4.03 (1H, br m), 4.53 (2H, m), 4.97 (1H, dd), 7.10-7.18 (2H, m), 7.19-7.36 (8H, m).

The stereochemistry of Examples 1.0(i) and 1.0(ii) was assigned using X-ray crystal structure analysis.

In another embodiment of the invention there is provided crystalline forms I, II, III and IV of the L-malate salt of the compound of Example 1.0(ii), 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide, and a process to make said crystalline forms. The disclosed crystalline L-malate salt forms provide a significant improvement in processing properties compared to the free base amorphous form, and physicochemical properties (e.g. higher melting point, increased aqueous solubility).

Process to Make Crystalline Forms of the L-Malate Salt of the Compound of Example 1.0(ii)

Method A:

20 mg of 2-Amino-N-[(R)-1-benzyloxymethyl-2-((4S, 5R)-2-methyl-1-oxo-4-phenyl-2,7-diaza-spiro[4.5]dec-7-yl)-2-oxo-ethyl]-2-methyl-propionamide was taken in a vial 5.6 mg of L-Malic acid was added. 500 uL of Ethyl acetate was added and the solids were dissolved by gentle warming. Crystals start appearing on standing at room temperature, the slurry was temperature cycled over 5-50° C. Additional 400 uL of Ethyl acetate was added, liquid was then decanted after centrifugation. Solids were dried under vacuum oven at 40° C. for 30 min. XRPD pattern indicated crystalline solids with a unique pattern (FIG. 1).

Crystalline form I was obtained as a solvate.

Figure 2:
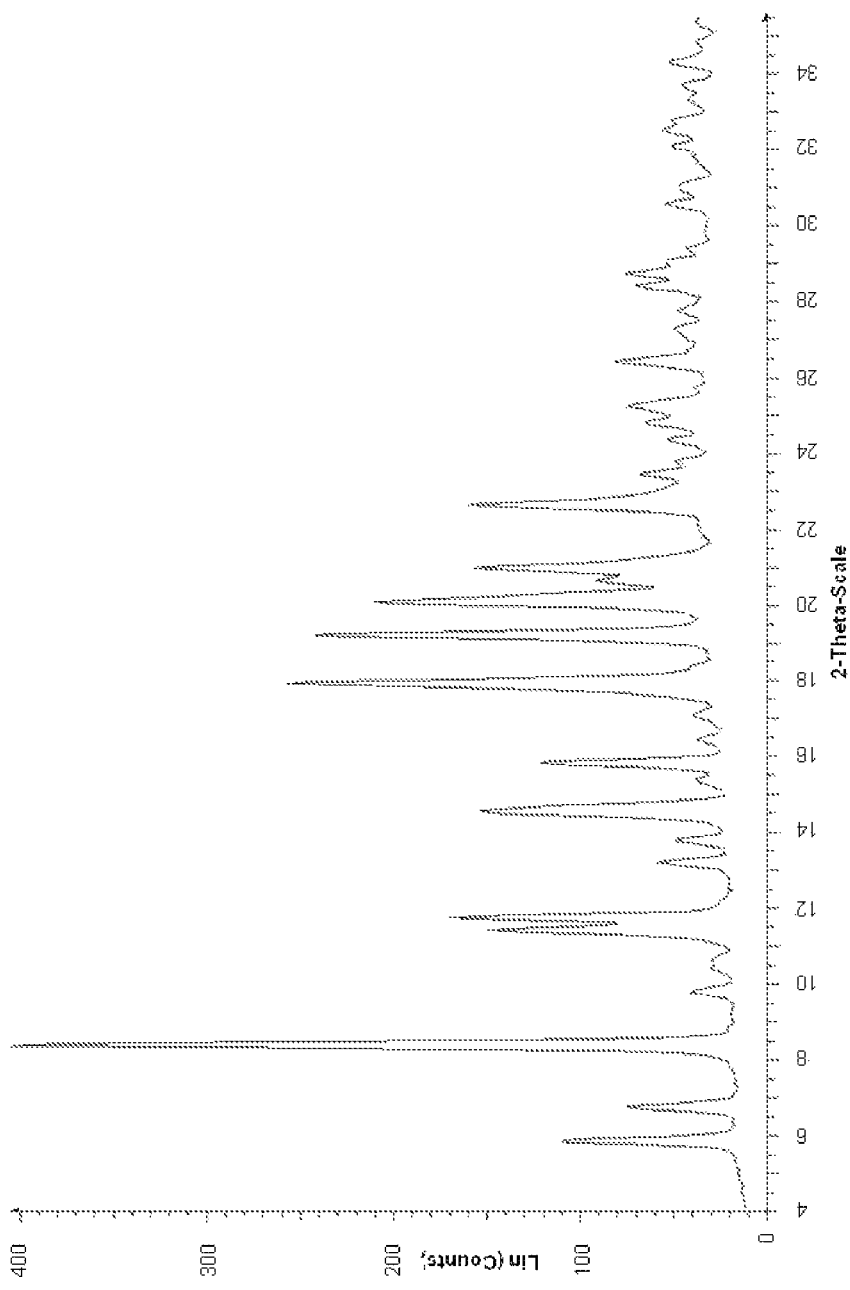
FIG. 2 illustrates the X-ray powder diffraction pattern of the crystalline form II of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Method B:

20 mg of 2-Amino-N-[(R)-1-benzyloxymethyl-2-((4S, 5R)-2-methyl-1-oxo-4-phenyl-2,7-diaza-spiro[4.5]dec-7-yl)-2-oxo-ethyl]-2-methyl-propionamide was taken in a vial 5.6 mg of L-Malic acid was added. 500 uL of Acetone was added and the solids were dissolved by gentle warming. Crystals start appearing on standing at room temperature, the slurry was temperature cycled over 5-50° C. Additional 400 uL of Acetone was added, liquid was then decanted after centrifugation. Solids were dried under vacuum oven at 40° C. for 30 min. XRPD pattern indicated crystalline solids with a unique pattern (FIG. 2). Crystalline form II was obtained.

Figure 3:
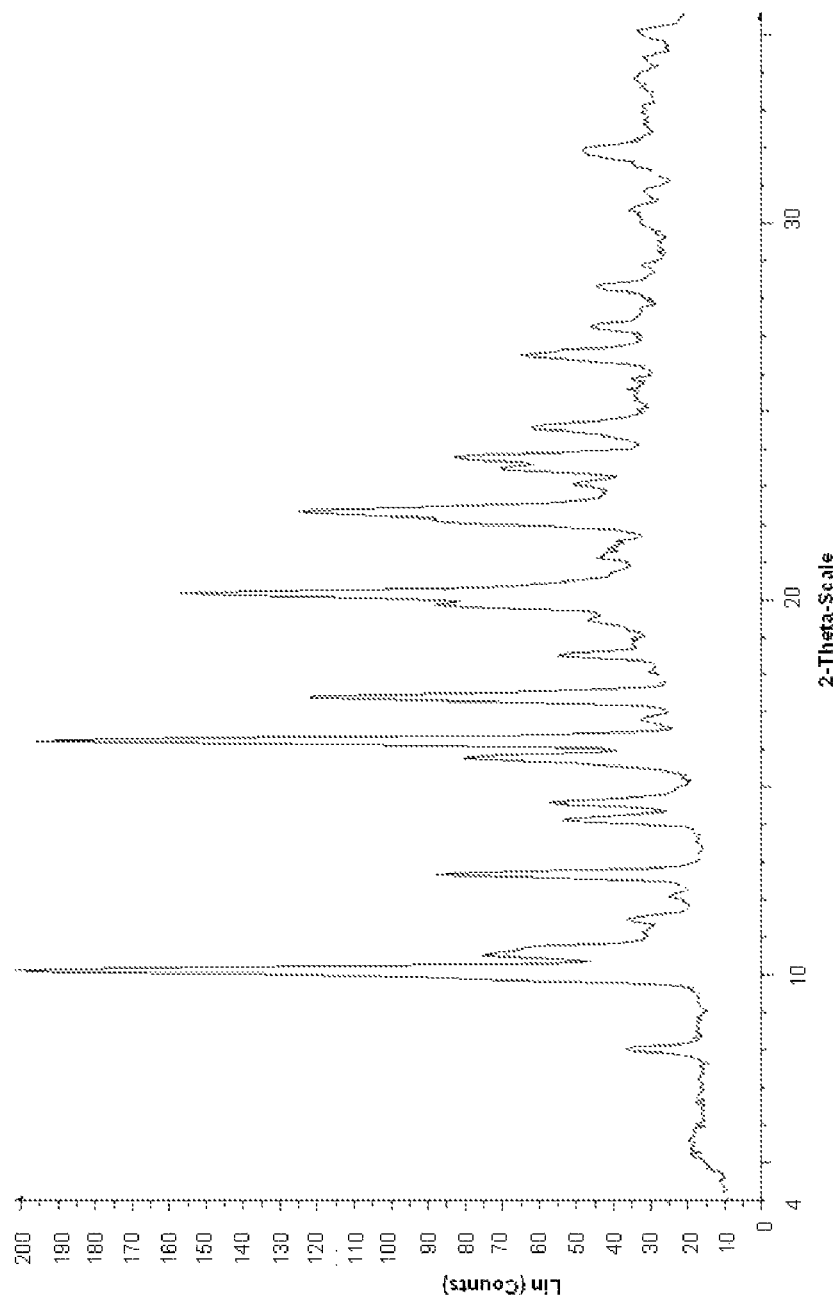
FIG. 3 illustrates the X-ray powder diffraction pattern of the crystalline form III of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Method C:

About 306 mg of salt was formed by addition of equimolar amounts of 2-Amino-N-[(R)-1-benzyloxymethyl-2-((4S, 5R)-2-methyl-1-oxo-4-phenyl-2,7-diaza-spiro[4.5]dec-7-yl)-2-oxo-ethyl]-2-methyl-propionamide and L-Malic acid; it was then dissolved in MeOH/BuOAc. The solids formed were then removed by filtration under vacuum at 100° C. for 2 h to yield white powder 220 mg. Crystalline form III was obtained (FIG. 3).

Figure 4:
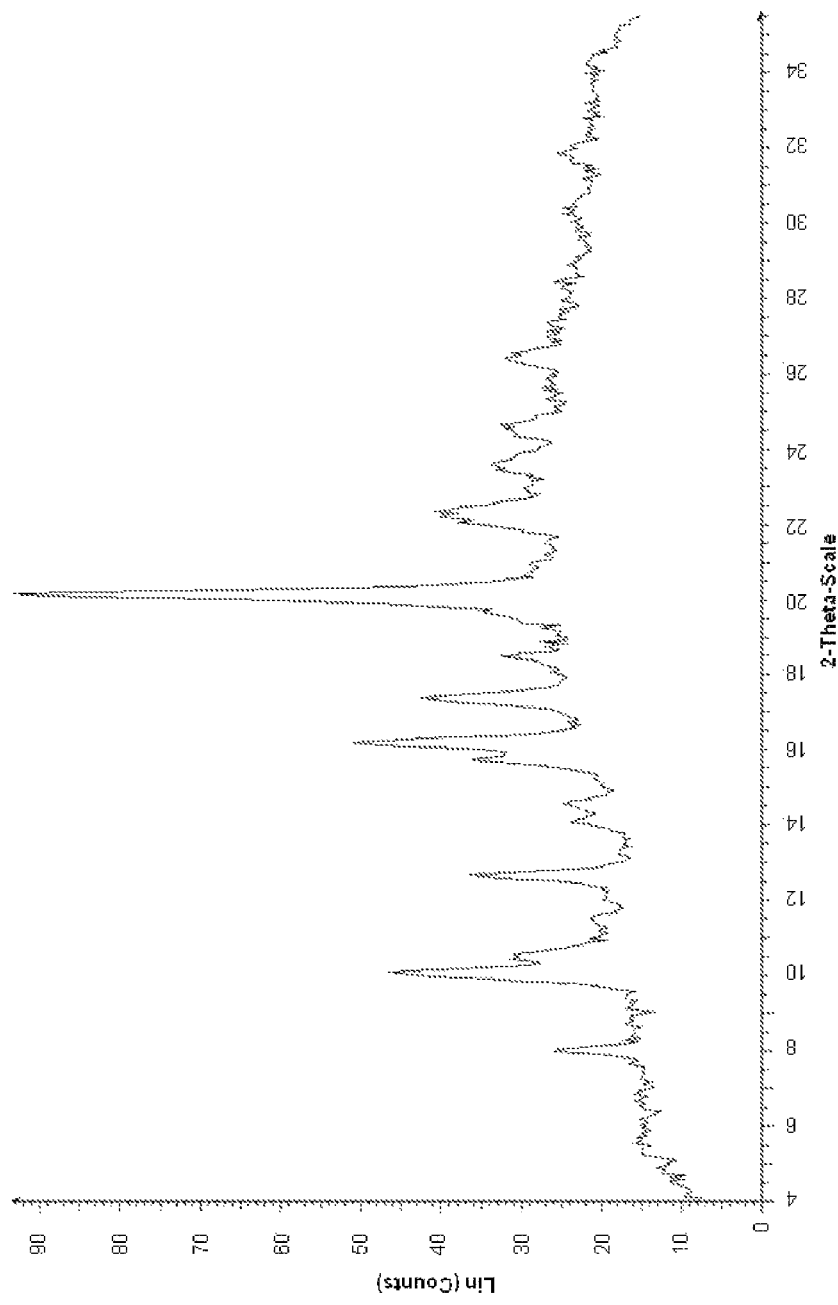
FIG. 4 illustrates the X-ray powder diffraction pattern of the crystalline form IV of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Method D:

100 mg of 2-Amino-N-[(R)-1-benzyloxymethyl-2-((4S, 5R)-2-methyl-1-oxo-4-phenyl-2,7-diaza-spiro[4.5]dec-7-yl)-2-oxo-ethyl]-2-methyl-propionamide was taken in a vial and 27.1 mg of L-Malic acid were added. The components were dissolved by the addition of 2 mL ethyl acetate along with gentle warming. Crystals start appearing rapidly. The slurry was stirred at 45° C. for 10 h. It was then cooled to RT and crystals further 2 mL of ethyl acetate was added. The slurry was then filtered and dried under vacuum. XRPD and TGA results indicated presence of a solvate. The solids were dried further at 100° C. for another 60 min. Crystalline desolvate was isolated with the purity of around 97%. Crystalline form IV was obtained (FIG. 4).

TABLE A

XRPD data of Example 1.0(ii) L-malate salt crystalline form I (Method A)

| Angle 2-Theta ° | d value Angstrom |
|---|---|
| 8.493 | 10.40220 |
| 15.574 | 5.68525 |
| 19.339 | 4.58586 |
| 20.842 | 4.25847 | error +/−0.2°.

TABLE B

XRPD data of Example 1.0(ii) malate
salt crystalline form II (Method B)

| Angle 2-Theta ° | d value Angstrom |
|---|---|
| 8.383 | 10.53930 |
| 11.724 | 7.54226 |
| 17.918 | 4.94627 |
| 19.237 | 4.61015 | error +/−0.2°.

TABLE C

XRPD data of Example 1.0(ii) malate
salt crystalline form III (Method C)

| Angle 2-Theta ° | d value Angstrom |
|---|---|
| 10.084 | 8.76420 |
| 16.209 | 5.46375 |
| 20.166 | 4.39979 |
| 22.325 | 3.97880 | error +/−0.2°.

TABLE D

XRPD data of Example 1.0(ii) malate
salt crystalline form IV (Method D)

| Angle 2-Theta ° | d value Angstrom |
|---|---|
| 10.039 | 8.80389 |
| 16.169 | 5.47723 |
| 17.333 | 5.11200 |
| 20.130 | 4.40759 | error +/−0.2°.

Example 1.2

2-Amino-N-((2R)-3-(benzyloxy)-1-((4S,5R)-4-(4-fluorophenyl)-2-methyl-1-oxo-2,7-diazaspiro[4.5]decan-7-yl)-1-oxopropan-2-yl)-2-methylpropanamide

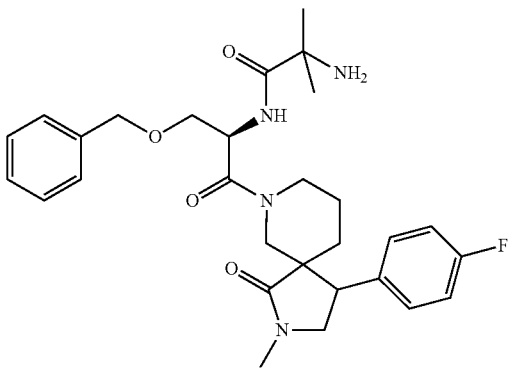 [SMILES: CN1CC(c2ccc(F)cc2)C2(CCCN(C(=O)[C@@H](COCc3ccccc3)NC(=O)C(C)(C)N)C2)C1=O]

Step 1: Tert-butyl 1-((2R)-3-(benzyloxy)-1-(4-(4-fluorophenyl)-2-methyl-1-oxo-2,7-diazaspiro[4.5]decan-7-yl)-1-oxopropan-2-ylamino)-2-methyl-1-oxopropan-2-ylcarbamate To a stirred solution of (R)-3-benzyloxy-2-(2-tert-butoxycarbonylamino-2-methylpropionylamino)-propionic acid (Intermediate 3A) (344 mg, 0.904 mmol) and 4-(4-fluorophenyl)-2-methyl-2,7-diazaspiro[4.5]decan-1-one (270 mg, 0.904 mmol) in MeCN (4 mL) was added dropwise a solution of ®T3P (50% in EtOAc) (1.055 ml, 1.807 mmol) at room temperature. The resulting colourless solution was stirred for 20 hours. The reaction mixture was diluted with saturated aqueous sodium bicarbonate solution (10 mL) and DCM (10 mL). The aqueous phase was separated and extracted using DCM (3×10 mL), the combined organic fractions were washed with 10% citric acid (10 mL), dried (MgSO4) and then concentrated under reduced pressure to afford tert-butyl 1-((2R)-3-(benzyloxy)-1-(4-(4-fluorophenyl)-2-methyl-1-oxo-2,7-diazaspiro[4.5]decan-7-yl)-1-oxopropan-2-ylamino)-2-methyl-1-oxopropan-2-ylcarbamate (546 mg, 97%) as a white amorphous solid.

LCMS Method 2minLC_v003, Rt 1.24 mins; MS m/z 625.8 [M+H]+

Step 2: 2-Amino-N-((2R)-3-(benzyloxy)-1-(4-(4-fluorophenyl)-2-methyl-1-oxo-2,7-diazaspiro[4.5]decan-7-yl)-1-oxopropan-2-yl)-2-methylpropanamide To a stirred solution of tert-butyl 1-((2R)-3-(benzyloxy)-1-(4-(4-fluorophenyl)-2-methyl-1-oxo-2,7-diazaspiro[4.5]decan-7-yl)-1-oxopropan-2-ylamino)-2-methyl-1-oxopropan-2-ylcarbamate (540 mg, 0.864 mmol) in DCM (5 mL) at room temperature was added TFA (0.666 ml, 8.64 mmol) dropwise. The resulting pale-yellow solution was stirred at room temperature for 3 days. The reaction mixture was concentrated in-vacuo, then diluted with saturated aqueous sodium bicarbonate solution (10 mL) and DCM (10 mL). The aqueous phase was separated and extracted using DCM (3×10 mL), the combined organic fractions were dried (MgSO4), then concentrated under reduced pressure to afford 2-amino-N-((2R)-3-(benzyloxy)-1-(4-(4-fluorophenyl)-2-methyl-1-oxo-2,7-diazaspiro[4.5]decan-7-yl)-1-oxopropan-2-yl)-2-methylpropan as a colourless oil.

The title compound was isolated by SFC chromatography.
SFC Rt 5.75 mins; Method AD25MeOH_DEA
LCMS Method 2minLC_v003; Rt 0.97 min; MS m/z 525 [M+H]+;
$^1$H NMR (d6-DMSO, 500 MHz, 398K) δ 1.01-2.52 (2H, br signal), 1.11-1.21 (2H, m), 1.26 (3H, s), 1.27 (3H, s), 1.43-1.52 (1H, m), 1.61-1.70 (1H, m), 2.86 (3H, s), 3.02-3.14 (1H, m), 3.14-3.26 (1H, dt), 3.29-3.37 (2H, m), 3.65 (1H, dd), 3.68-3.84 (3H, m), 3.90-4.08 (1 h, br m), 4.50-4.60 (2H, m), 4.96 (1H, t), 7.05 (2H, dd), 7.19 (2H, dd), 7.23-7.38 (5H, m).

The absolute stereochemistry was determined by X-ray of 4-(4-fluorophenyl)-2-methyl-2,7-diazaspiro[4.5]decan-1-one.

In another embodiment of the invention there is provided a crystalline form I of the L-malate salt of the compound of Example 1.2, 2-Amino-N-((2R)-3-(benzyloxy)-1-((4S,5R)-4-(4-fluorophenyl)-2-methyl-1-oxo-2,7-diazaspiro[4.5]decan-7-yl)-1-oxopropan-2-yl)-2-methylpropanamide, and a process to make said crystalline form. The disclosed crystalline L-malate salt form provides a significant improvement in processing properties compared to the free base amorphous form, and physicochemical properties (e.g. higher melting point, increased aqueous solubility).

Figure 9:
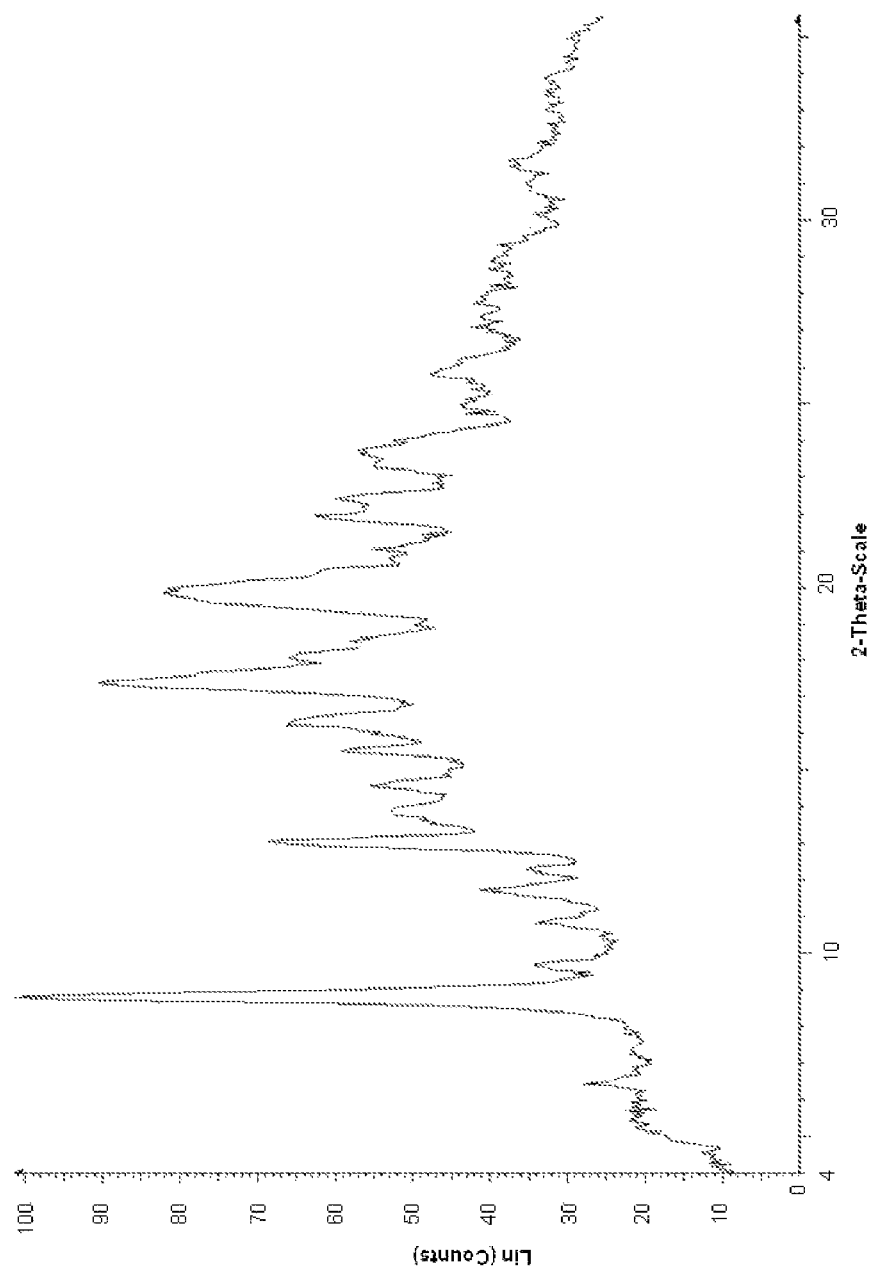
FIG. 9 illustrates the X-ray powder diffraction pattern of the crystalline form I of 2-amino-N-((2R)-3-(benzyloxy)-1-((4S,5R)4-(4-fluorophenyl)-2-methyl-1-oxo-2,7-diazaspiro[4.5]decan-7-yl)-1-oxopropan-2-yl)-2-methylpropanamide L-malate salt.
Figure 10:
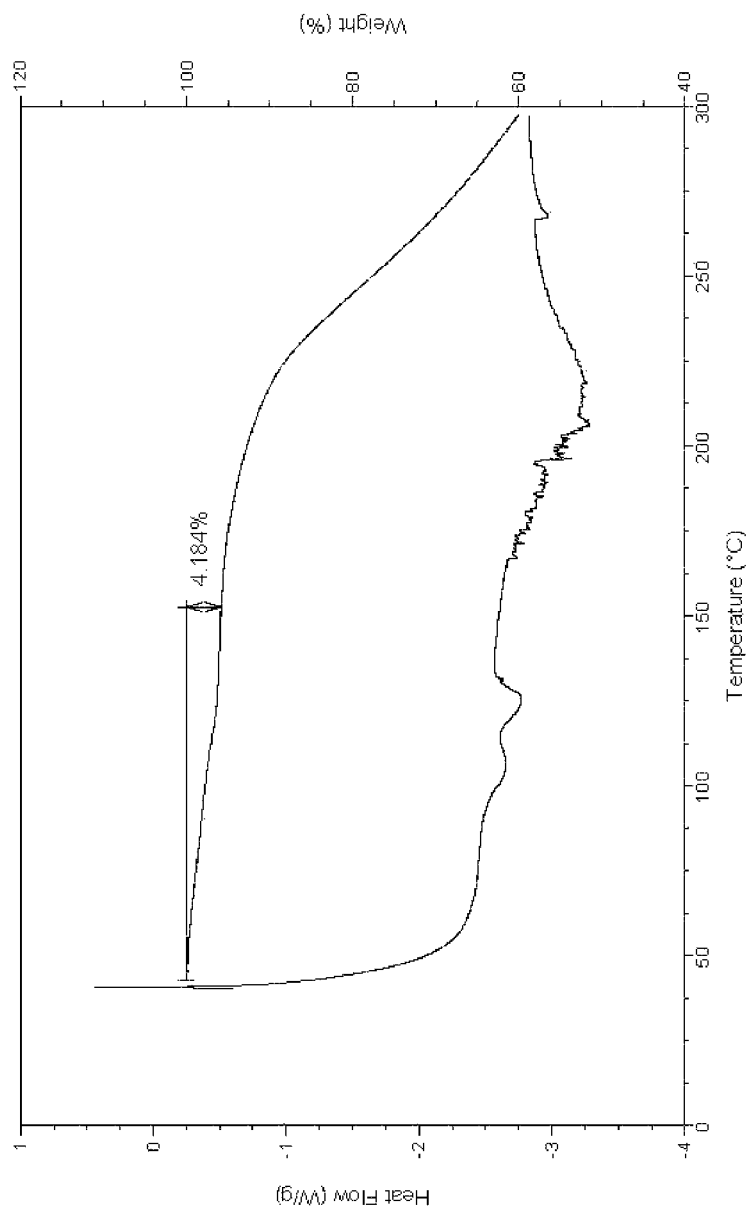
FIG. 10 illustrates the differential scanning calorimetry (DSC) and the thermogravimetric analysis (TGA) of the crystalline form I of 2-amino-N-((2R)-3-(benzyloxy)-1-((4S,5R)-4-(4-fluorophenyl)-2-methyl-1-oxo-2,7-diazaspiro[4.5]decan-7-yl)-1-oxopropan-2-yl)-2-methylpropanamide L-malate salt.

Process to Make Crystalline Forms of the L-Malate Salt of the Compound of Example 1.2:

50 mg of 2-Amino-N-((2R)-3-(benzyloxy)-1-((4S,5R)-4-(4-fluorophenyl)-2-methyl-1-oxo-2,7-diazaspiro[4.5]decan-7-yl)-1-oxopropan-2-yl)-2-methylpropanamide were weighed into a glass vial, 12.8 mg L-Malic acid (counterion) was weighed into each vial. Solids were then dissolved in 0.2 mL of Methanol which was then evaporated under vacuum. 500 uL of acetone was added to each vial. The vials were then temperature cycled over 5-35° C. for 2 days. Solids from vials were isolated by centrifugation and dried under vacuum then characterised (FIG. 9)

TABLE A

XRPD data of Example 1.2 L-malate salt crystalline form I

| Angle 2-Theta ° | d value Angstrom |
|---|---|
| 8.767 | 10.07782 |
| 12.998 | 6.80554 |
| 17.354 | 5.10588 |
| 19.847 | 4.46962 | error +/−0.2°.

The compounds of the following tabulated Examples (Table 1) were prepared by a similar method to that of Example 1.0 from Intermediates 3A, 3B, 3C, 3D, 3E, 3F, 3G, 3H, 3K 4G, 3J and the appropriate spiropiperidine (either commercially available or preparations described hereinafter), or using intermediate 5A as the appropriate commercially available BOC protected amino acid (in a manner obvious to someone skilled in the art).

TABLE 1

| Ex. | Structure | Name | NMR/[M + H]+ LC-MS Method SFC Method |
|---|---|---|---|
| 1.1 | 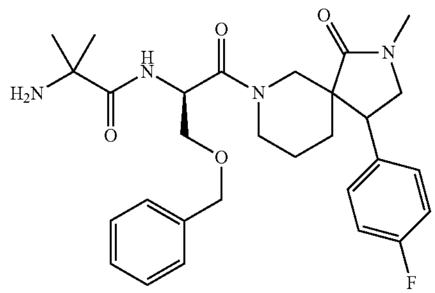 [SMILES: CN1CC(c2ccc(F)cc2)C2(CCCN(C(=O)[C@@H](COCc3ccccc3)NC(=O)C(C)(C)N)C2)C1=O] | Diastereomeric mixture of 2-Amino-N-((2R)-3-(benzyloxy)-1-(4-(4-fluorophenyl)-2-methyl-1-oxo-2,7-diazaspiro[4.5]decan-7-yl)-1-oxopropan-2-yl)-2-methylpropanamide | Method LowpH_30_v002 Rt 1.62 mins; MS m/z 525 [M + H]+; |
| 1.2 | 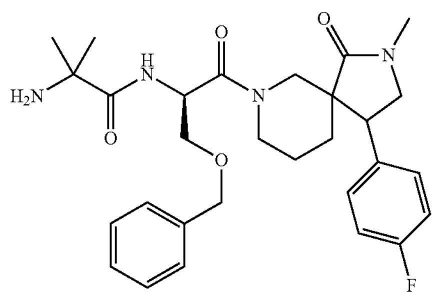 [SMILES: CN1CC(c2ccc(F)cc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(4-(4-fluorophenyl)-2-methyl-1-oxo-2,7-diazaspiro[4.5]decan-7-yl)-1-oxopropan-2-yl)-2-methylpropanamide (Separated by SFC) | MMethod 2minLC_v003RRt 0.97 min; MS m/z 525 [M + H]+; SFC Rt 5.75 mins; Method AD25MEOH_DEA |
| 1.3 | 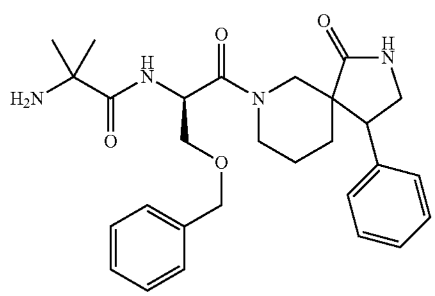 [SMILES: CC(C)(N)C(=O)N[C@H](COCc1ccccc1)C(=O)N1CCCC2(C1)C(=O)NCC2c1ccccc1] | Single diastereomer of 2-Amino-N-((2R)-3-(benzyloxy)-1-oxo-1-(1-oxo-4-phenyl-2,7-diazaspiro[4.5]decan-7-yl)propan-2-yl)-2-methylpropanamide (Separated by SFC) | MMethod 2minLC_v003 RRt 0.93 min; MS m/z 493 [M + H]+; SFC Rt 7.74 mins; Method IC45MeOH_DEA |
| 1.4 | 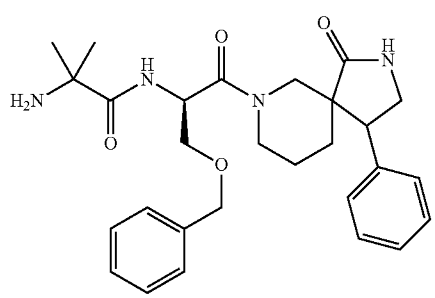 [SMILES: CC(C)(N)C(=O)N[C@H](COCc1ccccc1)C(=O)N1CCCC2(C1)C(=O)NCC2c1ccccc1] | Single diastereomer of 2-Amino-N-((2R)-3-(benzyloxy)-1-oxo-1-(1-oxo-4-phenyl-2,7-diazaspiro[4.5]decan-7-yl)propan-2-yl)-2-methylpropanamide (Separated by SFC) | SFC Rt 9.39 min Method IC45MeOH_DEA |

TABLE 1-continued

| Ex. | Structure | Name | NMR/[M + H]+ LC-MS Method SFC Method |
|---|---|---|---|
| 1.5 | 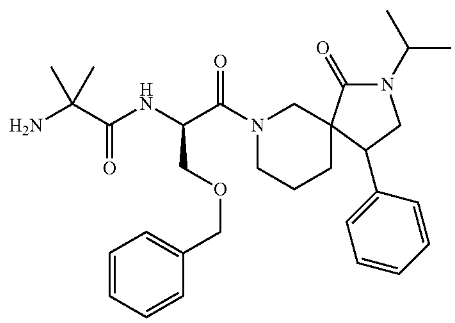 [SMILES: CC(C)N1CC(c2ccccc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(2-isopropyl-1-oxo-4-phenyl-2,7-diaza-spiro[4.5]decan-7-yl)-1-oxopropan-2-yl)-2-methylpropanamide (Separated by SFC) | Method 2minLC__v003 Rt 1.02 min; MS m/z 535 [M + H]+; SFC Rt 5.72 mins; Method IC35IPA__DEA |
| 1.6 | 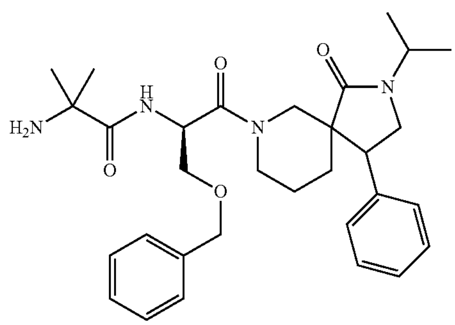 [SMILES: CC(C)N1CC(c2ccccc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(2-isopropyl-1-oxo-4-phenyl-2,7-diaza-spiro[4.5]decan-7-yl)-1-oxopropan-2-yl)-2-methylpropanamide (Separated by SFC) | Method 2minLC__v003 Rt 1.02 min; MS m/z 535 [M + H]+; SFC Rt 7.07 mins; Method IC35IPA__DEA |
| 1.7 | 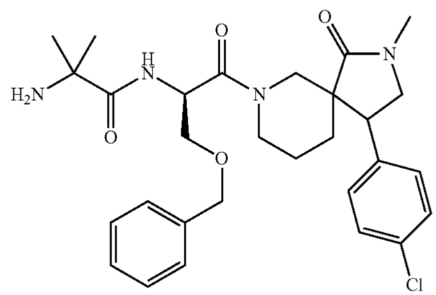 | Single diastereomer of 2-Amino-N-((2R)-3-(benzyloxy)-1-(4-(4-chlorophenyl)-2-methyl-1-oxo-2,7-diaza-spiro[4.5]decan-7-yl)-1-oxopropan-2-yl)-2-methylpropanamide (Separated by SFC) | Method 2minLC__v003 Rt 1.01 mins; MS m/z 541 [M + H]+; SFC Rt 5.43 mins; Method IC45MEOH__DEA |
| 1.8 | 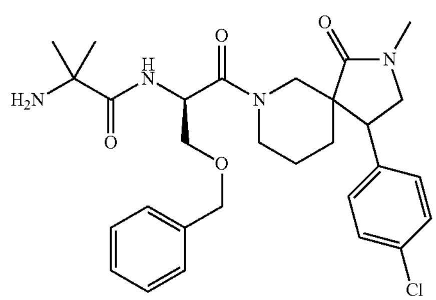 | Single diastereomer of 2-Amino-N-((2R)-3-(benzyloxy)-1-(4-(4-chlorophenyl)-2-methyl-1-oxo-2,7-diaza-spiro[4.5]decan-7-yl)-1-oxopropan-2-yl)-2-methylpropanamide (Separated by SFC) | Method 2minLC__v003 Rt 1.00 min; MS m/z 541 [M + H]+; SFC Rt 7.8 mins; Method IC45MEOH__DEA |

TABLE 1-continued

| Ex. | Structure | Name | NMR/[M + H]+ LC-MS Method SFC Method |
|---|---|---|---|
| 1.9 | 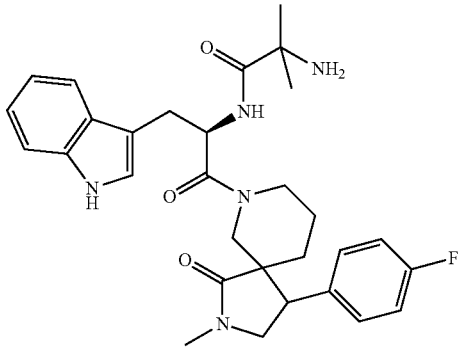 [SMILES: CN1CC(c2ccc(F)cc2)C2(CCCN(C(=O)[C@@H](Cc3c[nH]c4ccccc34)NC(=O)C(C)(C)N)C2)C1=O] | Diastereomeric mixture of 2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide | Method LowpH__v002 Rt 2.1 mins; MS m/z 534 [M + H]+; |
| 1.10 | 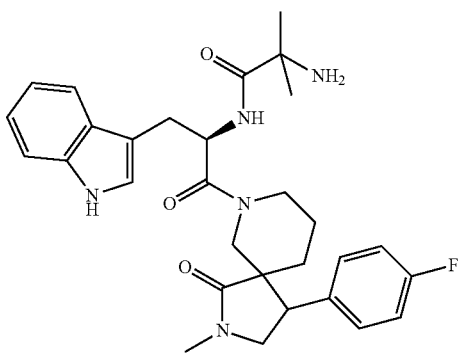 [SMILES: CN1CC(c2ccc(F)cc2)C2(CCCN(C(=O)[C@@H](Cc3c[nH]c4ccccc34)NC(=O)C(C)(C)N)C2)C1=O] | Single diastereomer of 2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide (Separated by SFC) | Method LowpH__v002 Rt 2.09 mins; MS m/z 534 [M + H]+; SFC Rt 7.13 mins; Method AD30IPA__AmmAc |
| 1.11 | 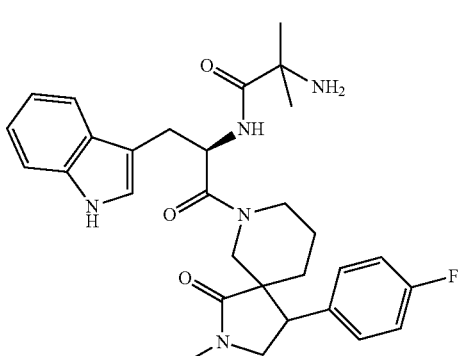 | Single diastereomer of 2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide (Separated by SFC) | Method LowpH__v002 Rt 2.08 mins; MS m/z 534 [M + H]+; SFC Rt 3.6 mins; Method AD30IPA__AmmAc |
| 1.12 | 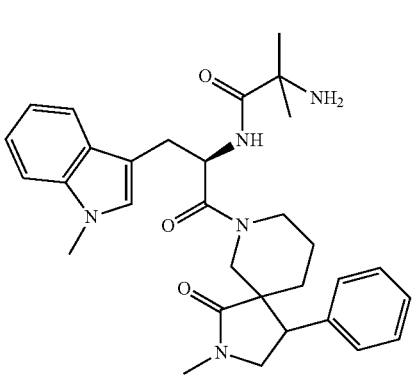 [SMILES: CN1CC(c2ccccc2)C2(CCCN(C(=O)[C@@H](Cc3cn(C)c4ccccc34)NC(=O)C(C)(C)N)C2)C1=O] | Diastereomeric mixture of 2-Amino-2-methyl-N-((2R)-1-(2-methyl-1-oxo-4-phenyl-2,7-diazaspiro[4.5]decan-7-yl)-3-(1-methyl-1H-indol-3-yl)-1-oxopropan-2-yl)propanamide | Method LowpH__v002 Rt 2.15 mins; MS m/z 530 [M + H]+; |

| Ex. | Structure | Name | NMR/[M + H]+ LC-MS Method SFC Method |
|---|---|---|---|
| 1.13 | 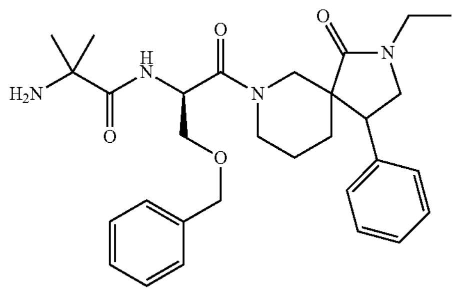 [SMILES: CCN1CC(c2ccccc2)C2(CCCN(C(=O)[C@@H](COCc3ccccc3)NC(=O)C(C)(C)N)C2)C1=O] | Diastereomeric mixture of 2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide | Method 2minLC__v003 Rt 0.98 min; MS m/z 521 [M + H]+; |
| 1.14 | 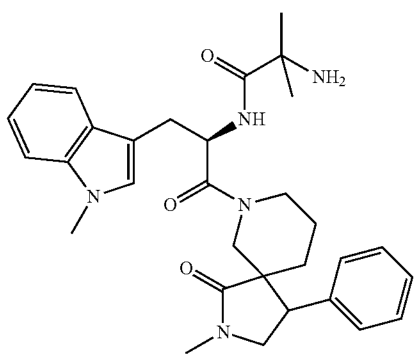 [SMILES: CN1CC(c2ccccc2)C2(CCCN(C(=O)[C@@H](Cc3cn(C)c4ccccc34)NC(=O)C(C)(C)N)C2)C1=O] | Single diastereomer of 2-Amino-2-methyl-N-((2R)-1-(2-methyl-1-oxo-4-phenyl-2,7-diazaspiro[4.5]decan-7-yl)-3-(1-methyl-1H-indol-3-yl)-1-oxopropan-2-yl)propanamide (Separated by SFC) | Method LowpH__v002 Rt 2.13 mins; MS m/z 530 [M + H]+; SFC Rt 4.29 mins; Method AD40IPA__AmmAc |
| 1.15 | 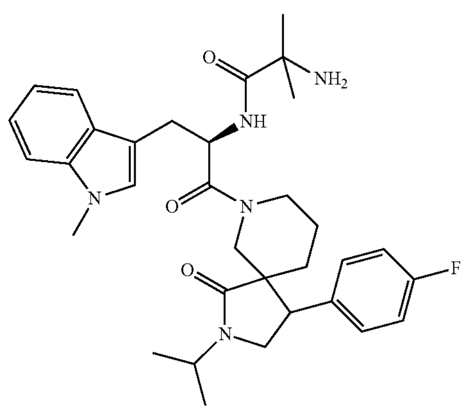 [SMILES: CC(C)N1CC(c2ccc(F)cc2)C2(CCCN(C(=O)[C@@H](Cc3cn(C)c4ccccc34)NC(=O)C(C)(C)N)C2)C1=O] | Single diastereomer of 2-Amino-N-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-yl)-2-methyl propanamide (Separated by SFC) | Method LowpH__v002 Rt 2.27 mins; MS m/z 576 [M + H]+; SFC Rt 3.57 mins; Method OD30MEOH__AA |
| 1.16 | 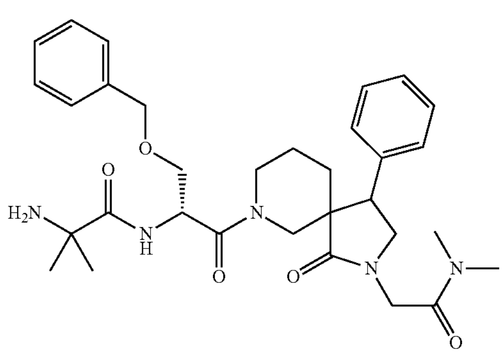 [SMILES: CN(C)C(=O)CN1CC(c2ccccc2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(2-(2-(dimethylamino)-2-oxoethyl)-1-oxo-4-phenyl-2,7-diaza-spiro[4.5]decan-7-yl)-1-oxopropan-2-yl)-2-methylpropanamide (Separated by SFC) | Method LowpH__v002 Rt 2.11 mins; MS m/z 578 [M + H]+; SFC Rt 6.4 mins; Method OD50MeOH__AA |

TABLE 1-continued

| Ex. | Structure | Name | NMR/[M + H]+ LC-MS Method SFC Method |
|---|---|---|---|
| 1.17 | 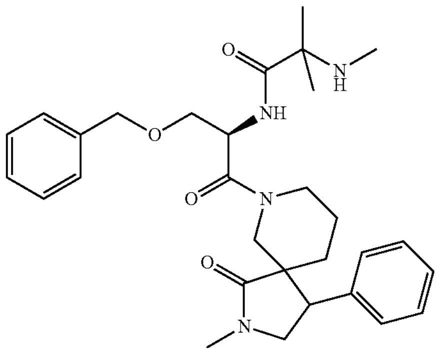 [SMILES: CNC(C)(C)C(=O)N[C@H](COCc1ccccc1)C(=O)N1CCCC2(C1)C(=O)N(C)CC2c1ccccc1] | Single diastereomer of N-((2R)-3-(Benzyloxy)-1-(2-methyl-1-oxo-4-phenyl-2,7-diazaspiro[4.5]decan-7-yl)-1-oxopropan-2-yl)-2-methyl-2-(methylamino)propanamide (Separated by SFC) | Method LowpH_v002 Rt 2.12 mins; MS m/z 521 [M + H]+; SFC Rt 5.13 mins; Method OD30MEOH_AA |
| 1.18 | 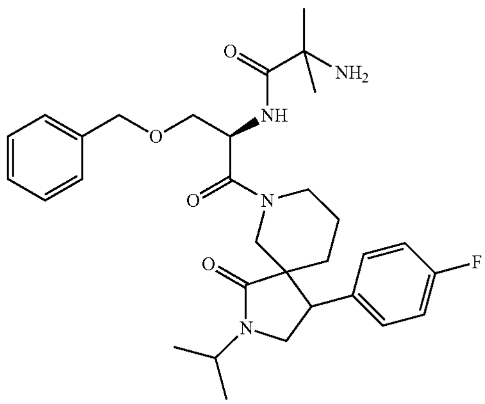 [SMILES: CC(C)N1CC(c2ccc(F)cc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide (Separated by SFC) | Method LowpH_v002 Rt 2.2 mins; MS m/z 553 [M + H]+; SFC Rt 8.91 mins; Method IC40MeOH_AA |
| 1.19 | 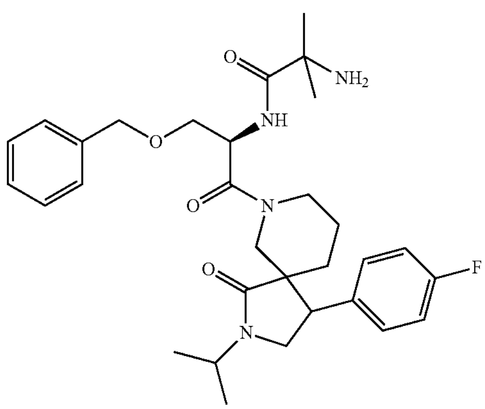 [SMILES: CC(C)N1CC(c2ccc(F)cc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide (Separated by SFC) | Method LowpH_v002 Rt 2.21 mins; MS m/z 553 [M + H]+; SFC Rt 11.54 mins; Method IC40MeOH_AA |
| 1.20 | 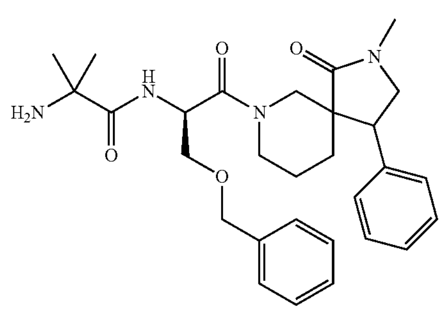 [SMILES: CN1CC(c2ccccc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(2-methyl-1-oxo-4-phenyl-2,7-diazaspiro[4.5]decan-7-yl)-1-oxopropan-2-yl)-2-methylpropanamide (Separated by SFC) | Method LowpH_v002 Rt 2.07 mins, m/z 507.5 [M + H]+ SFC Rt 5.04 min Method LUXC2_45MeOH_AA |

TABLE 1-continued

| Ex. | Structure | Name | NMR/[M + H]+ LC-MS Method SFC Method |
|---|---|---|---|
| 1.21 | 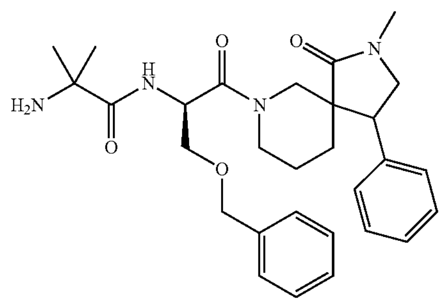 [SMILES: CN1CC(c2ccccc2)C2(CCCN(C(=O)[C@@H](COCc3ccccc3)NC(=O)C(C)(C)N)C2)C1=O] | Single diastereomer of 2-Amino-N-((2R)-3-(benzyloxy)-1-(2-methyl-1-oxo-4-phenyl-2,7-diazaspiro[4.5]decan-7-yl)-1-oxopropan-2-yl)-2-methylpropanamide (Separated by SFC) | Method LowpH_v002 Rt 2.07 mins, m/z 507.5 [M + H]+ SFC Rt 6.47 min Method LUXC2_45MeOH_AA |
| 1.22 | 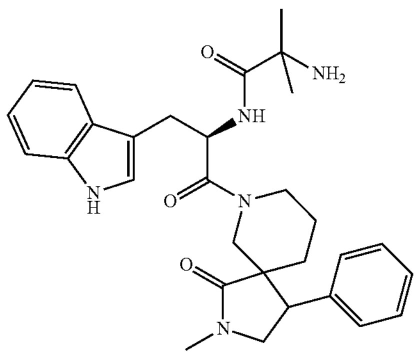 [SMILES: CN1CC(c2ccccc2)C2(CCCN(C(=O)[C@@H](Cc3c[nH]c4ccccc34)NC(=O)C(C)(C)N)C2)C1=O] | Single diastereomer of N-((2R)-3-(1H-indol-3-yl)-1-(2-methyl-1-oxo-4-phenyl-2,7-diazaspiro[4.5]decan-7-yl)-1-oxopropan-2-yl)-2-amino-2-methylpropanamide | Method LowpH_v002 Rt 2.04 mins, m/z 516.5 [M + H]+ SFC Rt 4.55 min Method AD30IPA_AA |
| 1.23 | 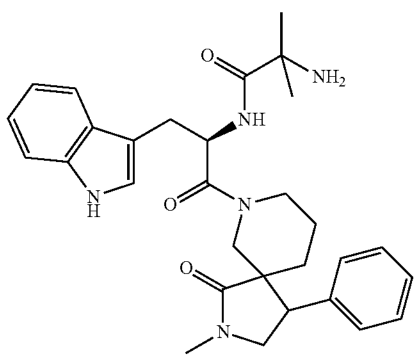 | Single diastereomer of N-((2R)-3-(1H-indol-3-yl)-1-(2-methyl-1-oxo-4-phenyl-2,7-diazaspiro[4.5]decan-7-yl)-1-oxopropan-2-yl)-2-amino-2-methylpropanamide | Method LowpH_v002 Rt 2.06 mins, m/z 516.5 [M + H]+ SFC Rt 7.42 min Method AD30IPA_AA |
| 1.24 | 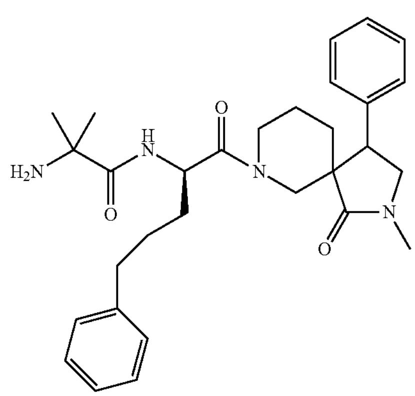 [SMILES: CN1CC(c2ccccc2)C2(CCCN(C(=O)[C@@H](CCCc3ccccc3)NC(=O)C(C)(C)N)C2)C1=O] | Diastereomeric mixture of 2-amino-2-methyl-N-((2R)-1-(2-methyl-1-oxo-4-phenyl-2,7-diazaspiro[4.5]decan-7-yl)-1-oxo-5-phenylpentan-2-yl)propanamide | Method LowpH_v002 Rt 2.15 mins, m/z 505.53 [M + H]+ |

TABLE 1-continued

| Ex. | Structure | Name | NMR/[M + H]+ LC-MS Method SFC Method |
|---|---|---|---|
| 1.25 | 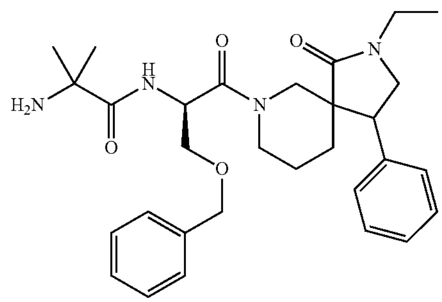 [SMILES: CCN1CC(c2ccccc2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide | Method 2minLC__v003 Rt 0.99 mins, m/z 521.4 [M + H]+ SFC Rt 12.51 min Method IC35MeOH__AA |
| 1.26 | 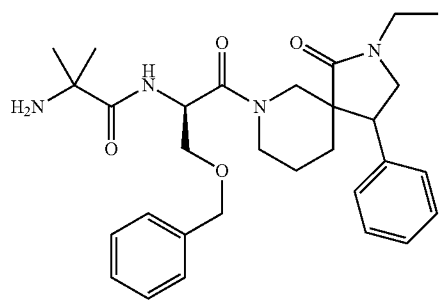 [SMILES: CCN1CC(c2ccccc2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide | Method 2minLC__v003 Rt 0.99 mins, m/z 521.4 [M + H]+ SFC Rt 14.64 min Method IC35MeOH__AA |
| 1.27 | 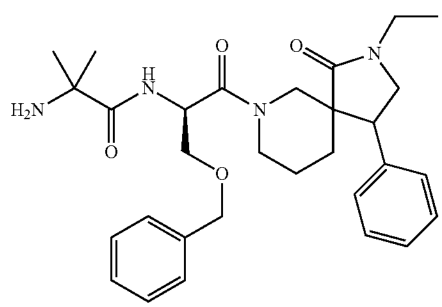 [SMILES: CCN1CC(c2ccccc2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide | Method 2minLC__v003 Rt 0.99 mins, m/z 521.4 [M + H]+ SFC Rt 19.00 min Method IC35MeOH__AA |
| 1.28 | 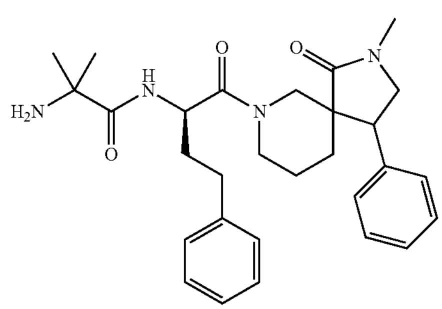 [SMILES: CN1CC(c2ccccc2)C2(CCCN(C(=O)[C@@H](CCc3ccccc3)NC(=O)C(C)(C)N)C2)C1=O] | Single diastereomer of 2-amino-2-methyl-N-((2R)-1-(2-methyl-1-oxo-4-phenyl-2,7-diazaspiro[4.5]decan-7-yl)-1-oxo-4-phenylbutan-2-yl)propanamide | Method 2minLC__v003 Rt 0.96 mins, m/z 491.4 [M + H]+ SFC Rt 5.31 min Method LUXC2__50MeOH__AA |
| 1.29 | 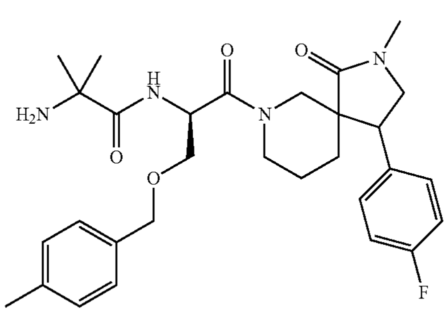 [SMILES: Cc1ccc(COC[C@@H](NC(=O)C(C)(C)N)C(=O)N2CCCC3(C2)C(=O)N(C)CC3c2ccc(F)cc2)cc1] | Single diastereomer of 2-amino-N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methylpropanamide | Method 10minLC__v003 Rt 3.41 min; MS m/z 539.4 [M + H]+; SFC Rt 4.84 min Method OD50MeOH__AA |

TABLE 1-continued

| Ex. | Structure | Name | NMR/[M + H]+ LC-MS Method SFC Method |
|---|---|---|---|
| 1.30 | 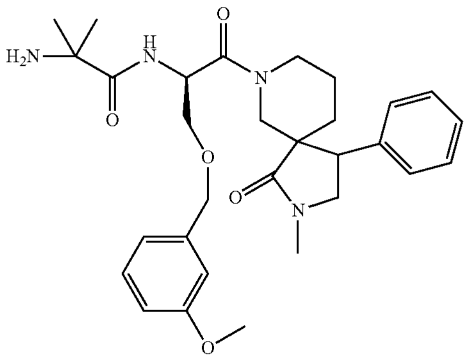 [SMILES: COc1cccc(COC[C@@H](NC(=O)C(C)(C)N)C(=O)N2CCCC3(C2)C(=O)N(C)CC3c2ccccc2)c1] | Diastereomeric mixture of 2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide | Method LowpH_v002 Rt 2.12 mins, m/z 537.52 [M + H]+ |
| 1.31 | 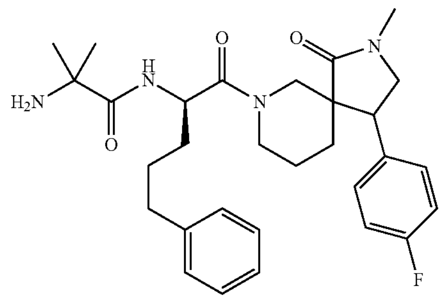 [SMILES: CN1CC(c2ccc(F)cc2)C2(CCCN(C(=O)[C@@H](CCCc3ccccc3)NC(=O)C(C)(C)N)C2)C1=O] | Diastereomeric mixture of 2-amino-N-((2R)-1-(4-(4-fluorophenyl)-2-methyl-1-oxo-2,7-diazaspiro[4.5]decan-7-yl)-1-oxo-5-phenylpentan-2-yl)-2-methylpropanamide | Method 2minLC_v003 Rt 0.98 mins, m/z 523.4 [M + H]+ |
| 1.32 | 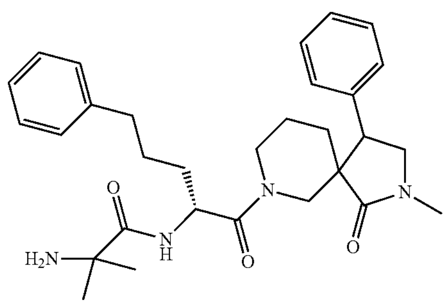 [SMILES: CN1CC(c2ccccc2)C2(CCCN(C(=O)[C@@H](CCCc3ccccc3)NC(=O)C(C)(C)N)C2)C1=O] | Single diastereomer of 2-amino-2-methyl-N-((2R)-1-(2-methyl-1-oxo-4-phenyl-2,7-diazaspiro[4.5]decan-7-yl)-1-oxo-5-phenylpentan-2-yl)propanamide | Method LowpH_v002 Rt 2.22 mins, m/z 505.47 [M + H]+ SFC Rt 5.38 mins Method LUXC2_45MeOH_AA |
| 1.33 | 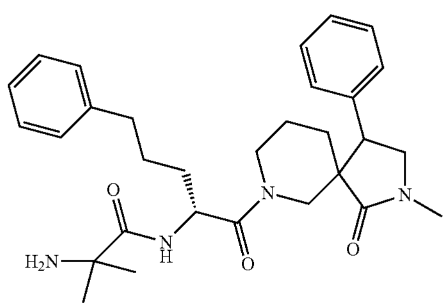 | Single diastereomer of 2-amino-2-methyl-N-((2R)-1-(2-methyl-1-oxo-4-phenyl-2,7-diazaspiro[4.5]decan-7-yl)-1-oxo-5-phenylpentan-2-yl)propanamide | Method LowpH_v002 Rt 2.22 mins, m/z 521.4 [M + H]+ SFC Rt 8.32 mins Method LUXC2_45MeOH_AA |
| 1.34 | 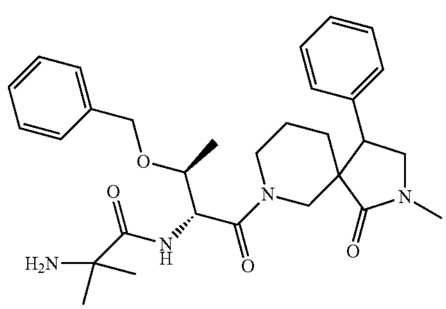 [SMILES: C[C@H](OCc1ccccc1)[C@@H](NC(=O)C(C)(C)N)C(=O)N1CCCC2(C1)C(=O)N(C)CC2c1ccccc1] | Single diastereomer of 2-amino-N-((2R,3S)-3-(benzyloxy)-1-(2-methyl-1-oxo-4-phenyl-2,7-diazaspiro[4.5]decan-7-yl)-1-oxobutan-2-yl)-2-methylpropanamide | Method LowpH 2MinLC_v003 Rt 0.98 mins, m/z 521.4 [M + H]+ SFC Rt 4.15 mins Method AD30IPA_AmmAc |

TABLE 1-continued

| Ex. | Structure | Name | NMR/[M + H]+ LC-MS Method SFC Method |
|---|---|---|---|
| 1.35 | 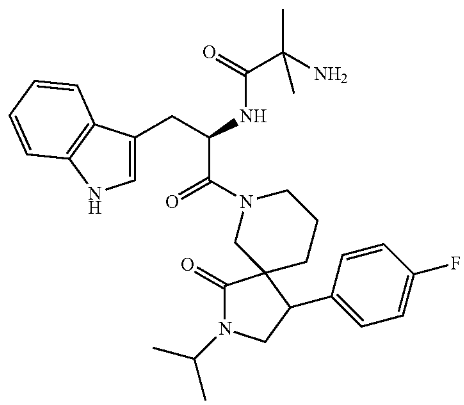 [SMILES: CC(C)N1CC(c2ccc(F)cc2)C2(CCCN(C(=O)[C@@H](Cc3c[nH]c4ccccc34)NC(=O)C(C)(C)N)C2)C1=O] | Single diastereomer of 2-amino-N-((2R)-1-(4-(4-fluorophenyl)-2-isopropyl-1-oxo-2,7-diazaspiro[4.5]decan-7-yl)-3-(1H-indol-3-yl)-1-oxopropan-2-yl)-2-methylpropanamide | Method LowpH_v002 Rt 2.18 mins, m/z 562.5 [M + H]+ SFC Rt 4.66 min Method OD30MEOH_AA |
| 1.36 | 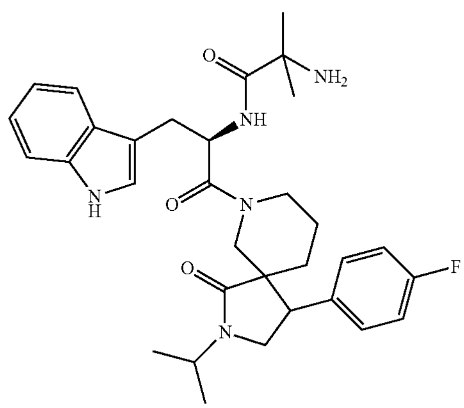 | Single diastereomer of 2-amino-N-((2R)-1-(4-(4-fluorophenyl)-2-isopropyl-1-oxo-2,7-diazaspiro[4.5]decan-7-yl)-3-(1H-indol-3-yl)-1-oxopropan-2-yl)-2-methylpropanamide | Method LowpH_v002 Rt 2.19 mins, m/z 562.5 [M + H]+ SFC Rt 3.27 min Method OD30MEOH_AA |
| 1.37 | 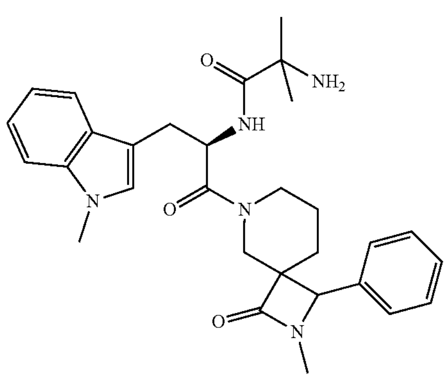 [SMILES: CN1C(=O)C2(CCCN(C(=O)[C@@H](Cc3cn(C)c4ccccc34)NC(=O)C(C)(C)N)C2)C1c1ccccc1] | Single diastereomer of 2-amino-2-methyl-N-((2R)-1-(2-methyl-1-oxo-3-phenyl-2,6-diazaspiro[3.5]nonan-6-yl)-3-(1-methyl-1H-indol-3-yl)-1-oxopropan-2-yl)propanamide | Method LowpH_v002 Rt 2.16 mins, m/z 516.5 [M + H]+ SFC Rt 8.73 min Method LUXC2_50MeOH_AA |
| 1.38 | 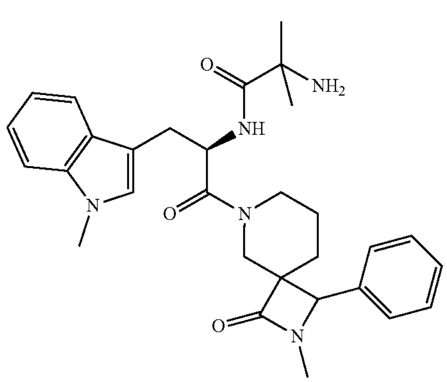 [SMILES: CN1C(=O)C2(CCCN(C(=O)[C@@H](Cc3cn(C)c4ccccc34)NC(=O)C(C)(C)N)C2)C1c1ccccc1] | Single diastereomer of 2-amino-2-methyl-N-((2R)-1-(2-methyl-1-oxo-3-phenyl-2,6-diazaspiro[3.5]nonan-6-yl)-3-(1-methyl-1H-indol-3-yl)-1-oxopropan-2-yl)propanamide | Method LowpH_v002 Rt 2.15 mins, m/z 516.5 [M + H]+ SFC Rt 5.33 min Method LUXC2_50MeOH_AA |

TABLE 1-continued

| Ex. | Structure | Name | NMR/[M + H]+ LC-MS Method SFC Method |
|---|---|---|---|
| 1.39 | 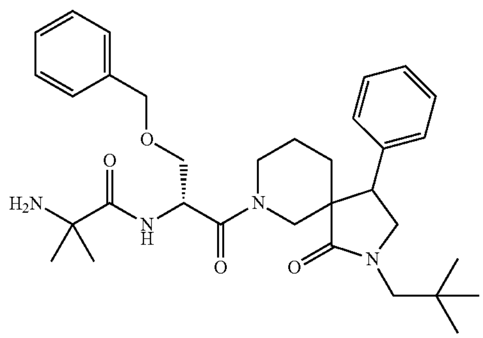 [SMILES: CC(C)(C)CN1CC(c2ccccc2)C2(CCCN(C(=O)[C@@H](COCc3ccccc3)NC(=O)C(C)(C)N)C2)C1=O] | Single diastereomer of 2-Amino-N-{(R)-1-benzyloxymethyl-2-[2-(2,2-dimethly-propyl)-1-oxo-4-phenyl-2,7-diaza-spiro[4.5]dec-7-yl]-2-oxo-ethyl}-2-methyl-propionamide | Method LowpH_v002 Rt 2.34 mins m/z 563.65 [M + H]+ SFC Rt 2.35 mins Method OJ15MEOH_AA |
| 1.40 | 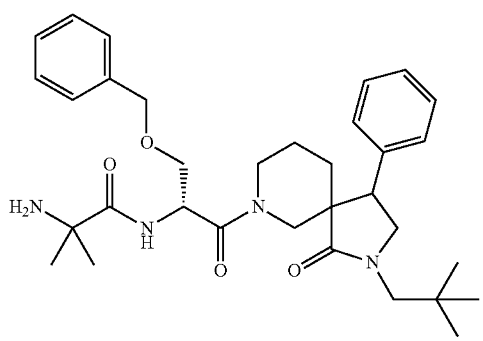 [SMILES: CC(C)(C)CN1CC(c2ccccc2)C2(CCCN(C(=O)[C@@H](COCc3ccccc3)NC(=O)C(C)(C)N)C2)C1=O] | Single diastereomer of 2-Amino-N-{(R)-1-benzyloxymethyl-2-[2-(2,2-dimethly-propyl)-1-oxo-4-phenyl-2,7-diaza-spiro[4.5]dec-7-yl]-2-oxo-ethyl}-2-methyl-propionamide | Method LowpH_v002 Rt 2.34 mins M/z 563.61 [MH+] SFC Rt 4.6 mins Method OJ15MEOH_AA |
| 1.41 | 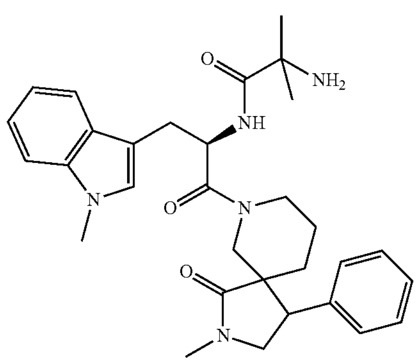 [SMILES: CN1CC(c2ccccc2)C2(CCCN(C(=O)[C@@H](Cc3cn(C)c4ccccc34)NC(=O)C(C)(C)N)C2)C1=O] | Single diastereomer of 2-amino-2-methyl-N-((2R)-1-(2-methyl-1-oxo-4-phenyl-2,7-diazaspiro[4.5]decan-7-yl)-3-(1-methyl-1H-indol-3-yl)-1-oxopropan-2-yl)propanamide | Method LowpH_v002 Rt 2.14 mins, m/z 530.5 [M + H]+ SFC Rt 9.06 min Method AD40IPA_AmmAc |
| 1.42 | 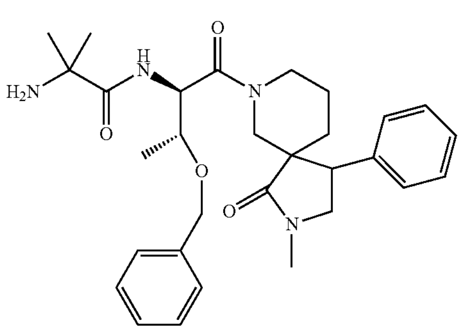 [SMILES: C[C@@H](OCc1ccccc1)[C@@H](NC(=O)C(C)(C)N)C(=O)N1CCCC2(C1)C(=O)N(C)CC2c1ccccc1] | Diastereomeric mixture of 2-amino-N-((2R,3R)-3-(benzyloxy)-1-(2-methyl-1-oxo-4-phenyl-2,7-diazaspiro[4.5]decan-7-yl)-1-oxobutan-2-yl)-2-methylpropanamide | Method LowpH_v002 Rt 2.12 mins, m/z 521.56 [M + H]+ |

TABLE 1-continued

| Ex. | Structure | Name | NMR/[M + H]+ LC-MS Method SFC Method |
|---|---|---|---|
| 1.43 | 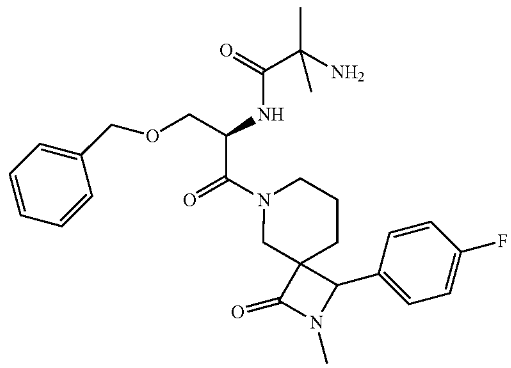 [SMILES: CN1C(=O)C2(CCCN(C(=O)[C@@H](COCc3ccccc3)NC(=O)C(C)(C)N)C2)C1c1ccc(F)cc1] | Diastereomeric mixture of 2-amino-N-((2R)-3-(benzyloxy)-1-(1-(4-fluorophenyl)-2-methyl-3-oxo-2,6-diazaspiro[3.5]nonan-6-yl)-1-oxopropan-2-yl)-2-methylpropanamide | Method LowpH_v002 Rt 2.13 mins, m/z 511.45 [M + H]+ |
| 1.44 | 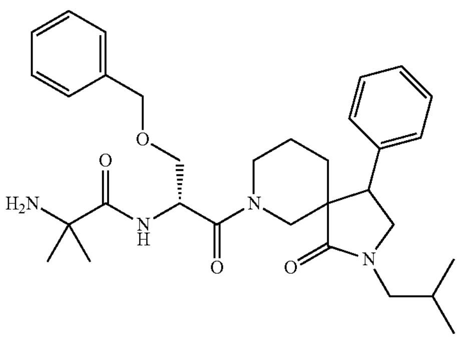 [SMILES: CC(C)CN1CC(c2ccccc2)C2(CCCN(C(=O)[C@@H](COCc3ccccc3)NC(=O)C(C)(C)N)C2)C1=O] | Single diastereomer of 2-Amino-N-{(R)-1-benzyloxymethyl-2-(2-isobutyl-1-oxo-4-phenyl-2,7-diaza-spiro[4.5]dec-7-yl)-2-oxo-ethyl}-2-methyl-propionamide | Method LowpH_v002 Rt 2.28 mins M/z 549.56 [M + H]+ SFC Rt 3.7 mins Method LUXC2_50MEOH_AA |
| 1.45 | 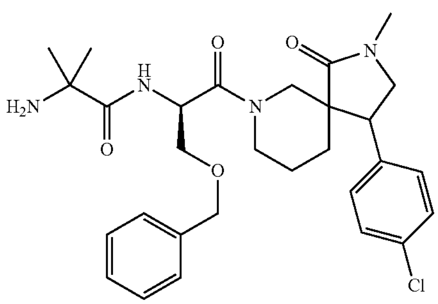 [SMILES: CN1CC(c2ccc(Cl)cc2)C2(CCCN(C(=O)[C@@H](COCc3ccccc3)NC(=O)C(C)(C)N)C2)C1=O] | Diastereomeric mixture of 2-Amino-N-{(R)-1-benzyloxymethyl-2-[4-(4-chloro-phenyl)-2-methyl-1-oxo-2,7-diaza-spiro[4.5]dec-7-yl]-2-oxo-ethyl}-2-methyl-propionamide | Method LowpH_30_v002 Rt 1.67 mins, m/z 541.59 [M + H]+ |
| 1.46 | 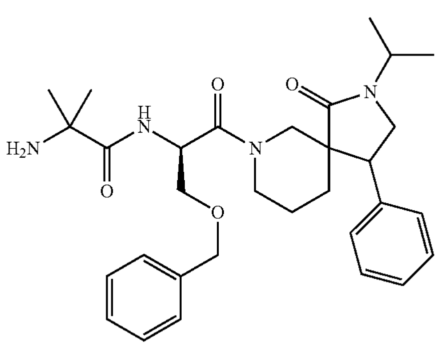 [SMILES: CC(C)N1CC(c2ccccc2)C2(CCCN(C(=O)[C@@H](COCc3ccccc3)NC(=O)C(C)(C)N)C2)C1=O] | Diastereomeric mixture of 2-Amino-N-[(R)-1-benzyloxymethyl-2-(2-isopropyl-1-oxo-4-phenyl-2,7-diaza-spiro[4.5]dec-7-yl)-2-oxo-ethyl]-2-methyl-propionamide | Method LowpH_30_v002, Rt 1.77 mins, m/z 535.62 [M + H]+ |

TABLE 1-continued

| Ex. | Structure | Name | NMR/[M + H]+ LC-MS Method SFC Method |
|---|---|---|---|
| 1.47 | 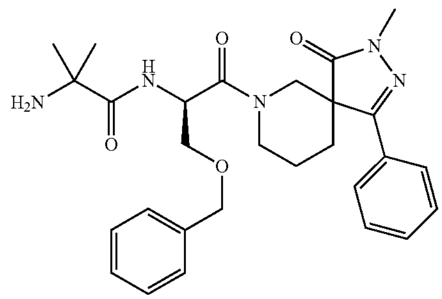 [SMILES: CN1N=C(c2ccccc2)C2(CCCN(C(=O)[C@@H](COCc3ccccc3)NC(=O)C(C)(C)N)C2)C1=O] | Diastereomeric mixture of 2-Amino-N-[(R)-1-benzyloxymethyl-2-(3-methyl-4-oxo-1-phenyl-2,3,7-triaza-spiro[4.5]dec-1-en-7-yl)-2-oxo-ethyl]-2-methyl-propionamide | Method LowpH__v002 Rt 2.10 mins, m/z 506.46 [M + H]+ |
| 1.48 | 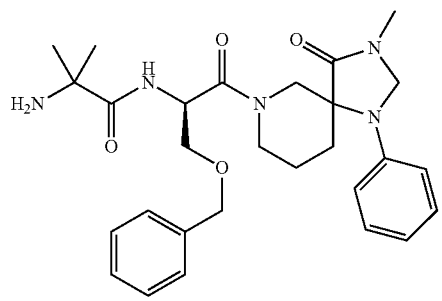 [SMILES: CN1CN(c2ccccc2)C2(CCCN(C(=O)[C@@H](COCc3ccccc3)NC(=O)C(C)(C)N)C2)C1=O] | Diastereomeric mixture of 2-Amino-N-[(R)-1-benzyloxymethyl-2-(3-methyl-4-oxo-1-phenyl-1,3,7-triaza-spiro[4.5]dec-7-yl)-2-oxo-ethyl)-2-methyl-propionamide | Method LowpH__v002 Rt 2.10 mins, m/z 508.48 [M + H]+ |
| 1.49 | 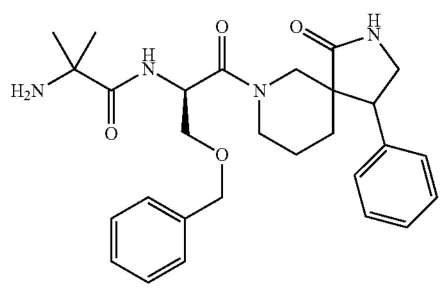 [SMILES: CC(C)(N)C(=O)N[C@H](COCc1ccccc1)C(=O)N1CCCC2(C1)C(=O)NCC2c1ccccc1] | Single diastereomer of 2-Amino-N-[(R)-1-benzyloxymethyl-2-oxo-2-(1-oxo-4-phenyl-2,7-diaza-spiro[4.5]dec-7-yl)-ethyl]-2-methyl-propionamide | SFC Rt 5.61 min Method IC45MeOH__DEA |
| 1.50 | 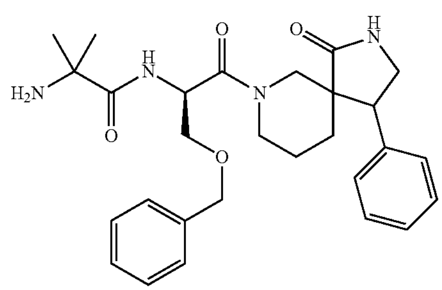 [SMILES: CC(C)(N)C(=O)N[C@H](COCc1ccccc1)C(=O)N1CCCC2(C1)C(=O)NCC2c1ccccc1] | Single diastereomer of 2-Amino-N-[(R)-1-benzyloxymethyl-2-oxo-2-(1-oxo-4-phenyl-2,7-diaza-spiro[4.5]dec-7-yl)-ethyl]-2-methyl-propionamide | SFC Rt 6.14 min Method IC45MeOH__DEA |
| 1.51 | 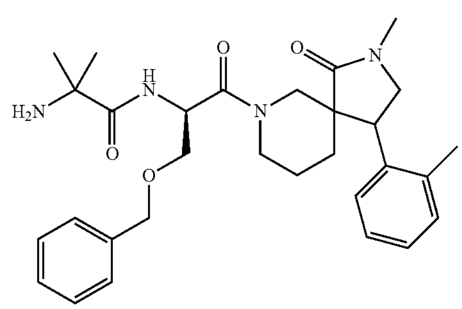 [SMILES: Cc1ccccc1C1CN(C)C(=O)C12CCCN(C(=O)[C@@H](COCc1ccccc1)NC(=O)C(C)(C)N)C2] | Single diastereomer of 2-amino-N-((2R)-3-(benzyloxy)-1-(2-methyl-1-oxo-4-o-tolyl-2,7-diazaspiro[4.5]decan-7-yl)-1-oxopropan-2-yl)-2-methylpropanamide | Method 2minLC__v003 Rt 0.99 min; MS m/z 521.5 [M + H]+; SFC Rt 2.23 min Method AD50IPA__DEA |

TABLE 1-continued

| Ex. | Structure | Name | NMR/[M + H]+ LC-MS Method SFC Method |
|---|---|---|---|
| 1.52 | 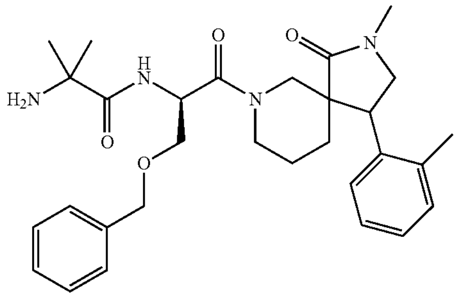 [SMILES: Cc1ccccc1C1CN(C)C(=O)C12CCCN(C(=O)[C@@H](COCc1ccccc1)NC(=O)C(C)(C)N)C2] | Single diastereomer of 2-amino-N-((2R)-3-(benzyloxy)-1-(2-methyl-1-oxo-4-o-tolyl-2,7-diazaspiro[4.5]decan-7-yl)-1-oxopropan-2-yl)-2-methylpropanamide | Method 2minLC_v003 Rt 1.00 min; MS m/z 521.5 [M + H]+; SFC Rt 3.31 min Method AD50IPA_DEA |
| 1.53 | 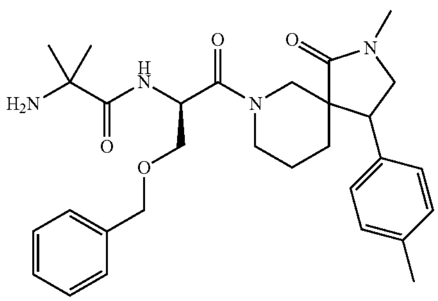 [SMILES: Cc1ccc(C2CN(C)C(=O)C23CCCN(C(=O)[C@@H](COCc2ccccc2)NC(=O)C(C)(C)N)C3)cc1] | Single diastereomer of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide | Method 2minLC_v003 Rt 0.99 min; MS m/z 521.5 [M + H]+; SFC Rt 3.4 min Method OD45MEOH_AA |
| 1.54 | 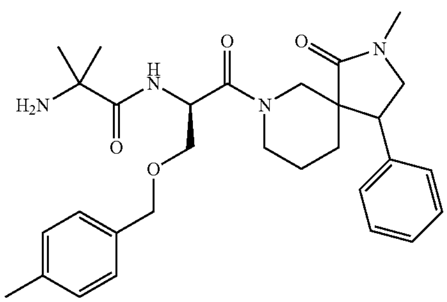 [SMILES: Cc1ccc(COC[C@@H](NC(=O)C(C)(C)N)C(=O)N2CCCC3(C2)C(=O)N(C)CC3c2ccccc2)cc1] | Single diastereomer of 2-amino-2-methyl-N-((2R)-1-(2-methyl-1-oxo-4-phenyl-2,7-diazaspiro[4.5]decan-7-yl)-3-(4-methylbenzyloxy)-1-oxopropan-2-yl)propanamide | Method 2minLC_v003 Rt 1.00 min, MS m/z 521.5 [M + H]+; SFC Rt 2.2 min Method OD45MEOH_AA_1 |
| 1.55 | 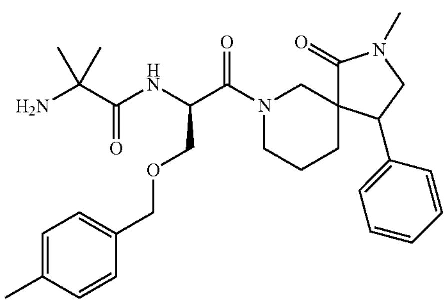 [SMILES: Cc1ccc(COC[C@@H](NC(=O)C(C)(C)N)C(=O)N2CCCC3(C2)C(=O)N(C)CC3c2ccccc2)cc1] | Single diastereomer of 2-amino-2-methyl-N-((2R)-1-(2-methyl-1-oxo-4-phenyl-2,7-diazaspiro[4.5]decan-7-yl)-3-(4-methylbenzyloxy)-1-oxopropan-2-yl)propanamide | Method 2minLC_v003 Rt 0.99 min, MS m/z 521.2 [M + H]+; SFC Rt 4.7 min Method OD45MEOH_AA_1 |
| 1.56 | 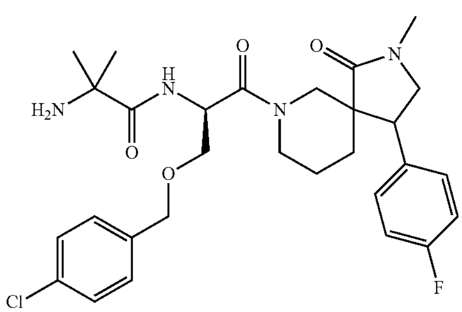 [SMILES: CN1CC(c2ccc(F)cc2)C2(CCCN(C(=O)[C@@H](COCc3ccc(Cl)cc3)NC(=O)C(C)(C)N)C2)C1=O] | Single diastereomer of 2-amino-N-((2R)-3-(4-chlorobenzyloxy)-1-(4-(4-fluorophenyl)-2-methyl-1-oxo-2,7-diazaspiro[4.5]decan-7-yl)-1-oxopropan-2-yl)-2-methylpropanamide | Method 2minLC_v003 Rt 1.05 min; MS m/z 559.3 [M + H]+; SFC Rt 2.3 min Method OD30MEOH_AA_1 |

TABLE 1-continued

| Ex. | Structure | Name | NMR/[M + H]+ LC-MS Method SFC Method |
|---|---|---|---|
| 1.57 | 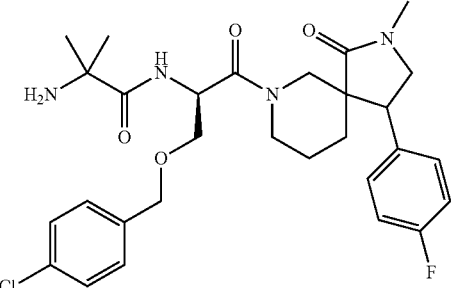 | Single diastereomer of 2-amino-N-((2R)-3-(4-chlorobenzyloxy)-1-(4-(4-fluorophenyl)-2-methyl-1-oxo-2,7-diazaspiro[4.5]decan-7-yl)-1-oxopropan-2-yl)-2-methylpropanamide | Method 2minLC__v003 Rt 1.05 min; MS m/z 559.4 [M + H]+; SFC Rt 3.1 min Method OD30MEOH__AA__1 |
| 1.58 | 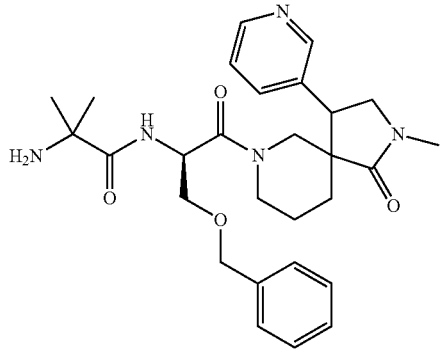 [SMILES: CN1CC(c2cccnc2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(2-methyl-1-oxo-4-(pyridin-3-yl)-2,7-diazaspiro[4.5]decan-7-yl)-1-oxopropan-2-yl)-2-methylpropanamide | Method 2minLC__v003 Rt 0.72 mins, m/z 508.7 [M + H]+ SFC Rt 3.84 min Method OD35MeOH__DEA |
| 1.59 | 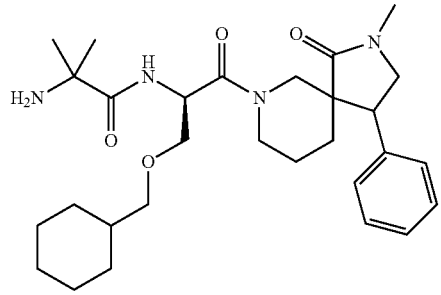 [SMILES: CN1CC(c2ccccc2)C2(CCCN(C(=O)[C@@H](COCC3CCCCC3)NC(=O)C(C)(C)N)C2)C1=O] | Single diastereomer of 2-amino-N-((2R)-3-(cyclohexylmethoxy)-1-(2-methyl-1-oxo-4-phenyl-2,7-diazaspiro[4.5]decan-7-yl)-1-oxopropan-2-yl)-2-methylpropanamide | Method 2minLC__v003 Rt 1.04 mins, m/z 513.6 [M + H]+ SFC Rt 3.24 min Method OD35IPA__AA |
| 1.60 | 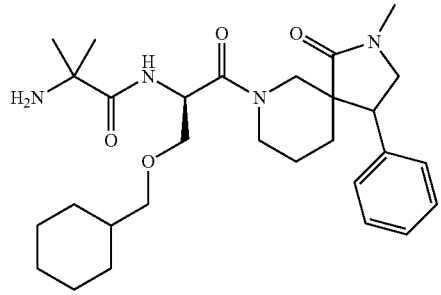 [SMILES: CN1CC(c2ccccc2)C2(CCCN(C(=O)[C@@H](COCC3CCCCC3)NC(=O)C(C)(C)N)C2)C1=O] | Single diastereomer of 2-amino-N-((2R)-3-(cyclohexylmethoxy)-1-(2-methyl-1-oxo-4-phenyl-2,7-diazaspiro[4.5]decan-7-yl)-1-oxopropan-2-yl)-2-methylpropanamide | Method 2minLC__v003 Rt 1.06 mins, m/z 513.6 [M + H]+ SFC Rt 6.31 min Method OD35IPA__AA |
| 1.61 | 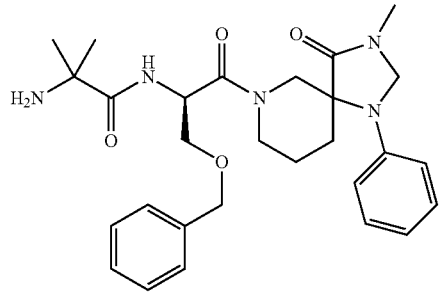 [SMILES: CN1CN(c2ccccc2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(3-methyl-4-oxo-1-phenyl-1,3,7-triazaspiro[4.5]decan-7-yl)-1-oxopropan-2-yl)-2-methylpropanamide | SFC Rt 4.37 min Method AD45IPA__DEA |

TABLE 1-continued

| Ex. | Structure | Name | NMR/[M + H]+ LC-MS Method SFC Method |
|---|---|---|---|
| 1.62 | 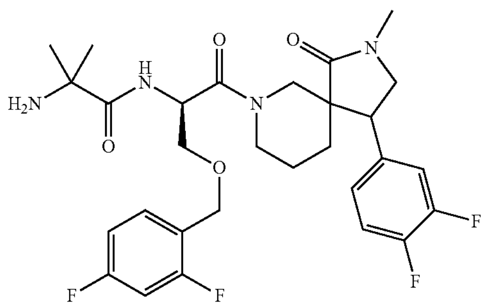 [SMILES: CN1CC(c2ccc(F)c(F)c2)C2(CCCN(C(=O)[C@@H](COCc3ccc(F)cc3F)NC(=O)C(C)(C)N)C2)C1=O] | Diasteromeric mixture of 2-amino-N-((2R)-3-(2,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide | Method 2minLC_v003; Rt 1.00 mins; MS m/z 579.2 [M + H]+ |
| 1.63 | 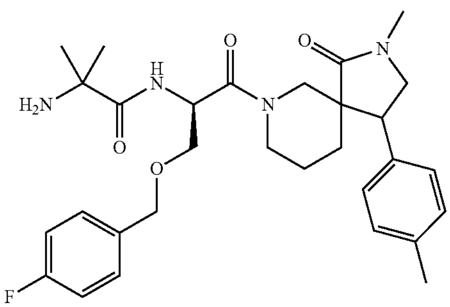 [SMILES: Cc1ccc(C2CN(C)C(=O)C23CCCN(C(=O)[C@@H](COCc2ccc(F)cc2)NC(=O)C(C)(C)N)C3)cc1] | Single diastereomer of 2-amino-N-((2R)-3-(4-fluorobenzyloxy)-1-(2-methyl-1-oxo-4-p-tolyl-2,7-diazaspiro[4.5]decan-7-yl)-1-oxopropan-2-yl)-2-methylpropanamide | Method 2minLowpH; Rt 0.80 min; MS m/z 539.7 [M + H]+; SFC Rt 11.12 min; Method OD25IPA_DEA |
| 1.64 | 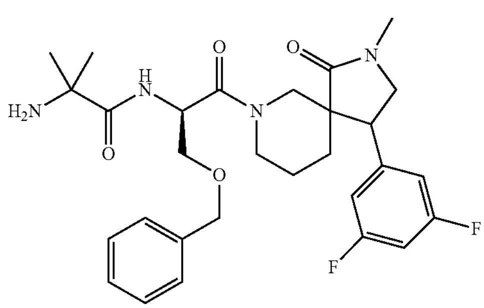 [SMILES: CN1CC(c2cc(F)cc(F)c2)C2(CCCN(C(=O)[C@@H](COCc3ccccc3)NC(=O)C(C)(C)N)C2)C1=O] | Diastereomeric mixture of 2-amino-N-((2R)-3-(benzyloxy)-1-(4-(3,5-difluorophenyl)-2-methyl-1-oxo-2,7-diazaspiro[4.5]decan-7-yl)-1-oxopropan-2-yl)-2-methylpropanamide | Method 2minLC_v003; Rt 0.98 min; MS m/z 543.4 [M + H]+ |
| 1.65 | 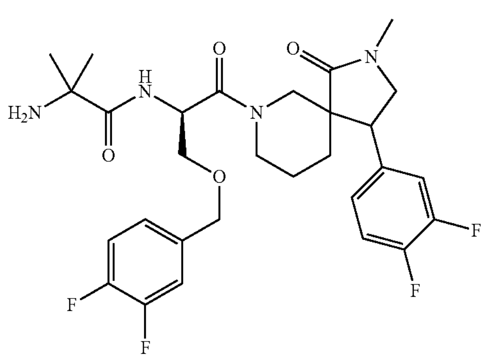 [SMILES: CN1CC(c2ccc(F)c(F)c2)C2(CCCN(C(=O)[C@@H](COCc3ccc(F)c(F)c3)NC(=O)C(C)(C)N)C2)C1=O] | Diastereomeric mixture of 2-amino-N-((2R)-3-(3,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide | Method 2minLC_v003; Rt 1.00 mins; MS m/z 579.4 [M + H]+ |

TABLE 1-continued

| Ex. | Structure | Name | NMR/[M + H]+ LC-MS Method SFC Method |
|---|---|---|---|
| 1.66 | 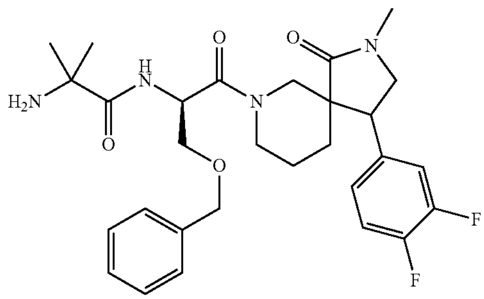 [SMILES: CN1CC(c2ccc(F)c(F)c2)C2(CCCN(C(=O)[C@@H](COCc3ccccc3)NC(=O)C(C)(C)N)C2)C1=O] | Single diastereomer of 2-amino-N-((2R)-3-(benzyloxy)-1-(4-(3,4-difluorophenyl)-2-methyl-1-oxo-2,7-diazaspiro[4.5]decan-7-yl)-1-oxopropan-2-yl)-2-methylpropanamide | Method 2minLC_v003; Rt 0.78 mins; MS m/z 543.1 [M + H]+; SFC Rt 4.94 mins; Method OD45IPA_DEA |
| 1.67 | 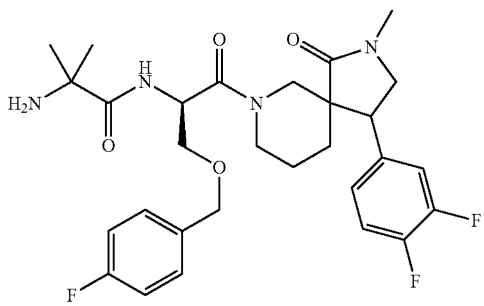 [SMILES: CN1CC(c2ccc(F)c(F)c2)C2(CCCN(C(=O)[C@@H](COCc3ccc(F)cc3)NC(=O)C(C)(C)N)C2)C1=O] | Single diastereomer of 2-amino-N-((2R)-1-(4-(3,4-difluorophenyl)-2-methyl-1-oxo-2,7-diazaspiro[4.5]decan-7-yl)-3-(4-fluorobenzyloxy)-1-oxopropan-2-yl)-2-methylpropanamide | Method 2minLowpH; Rt 0.78 mins; MS m/z 562.3 [M + H]+; SFC Rt 4.95 mins Method OD30IPA_DEA |
| 1.68 | 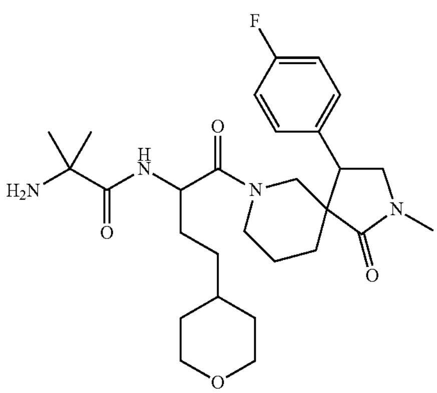 [SMILES: CN1CC(c2ccc(F)cc2)C2(CCCN(C(=O)C(CCC3CCOCC3)NC(=O)C(C)(C)N)C2)C1=O] | Diastereomer mixture of 2-amino-N-(1-(4-(4-fluorophenyl)-2-methyl-1-oxo-2,7-diazaspiro[4.5]decan-7-yl)-1-oxo-4-(tetrahydro-2H-pyran-4-yl)butan-2-yl)-2-methylpropanamide | Method 2minLowpH; Rt 0.70 mins, MS m/z 517.6 [M + 1]+ |
| 1.69 | 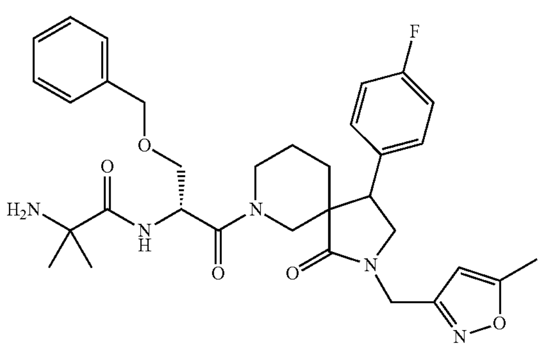 [SMILES: Cc1cc(CN2CC(c3ccc(F)cc3)C3(CCCN(C(=O)[C@@H](COCc4ccccc4)NC(=O)C(C)(C)N)C3)C2=O)no1] | Diastereomer mixture of 2-amino-N-((2R)-3-(benzyloxy)-1-(4-(4-fluorophenyl)-2-((5-methylisoxazol-3-yl)methyl)-1-oxo-2,7-diazaspiro[4.5]decan-7-yl)-1-oxopropan-2-yl)-2-methylpropanamide | Method 2minLowpH; Rt 0.81 mins; MS m/z 606.1 [M + H+] |

TABLE 1-continued

| Ex. | Structure | Name | NMR/[M + H]+ LC-MS Method SFC Method |
|---|---|---|---|
| 1.70 | 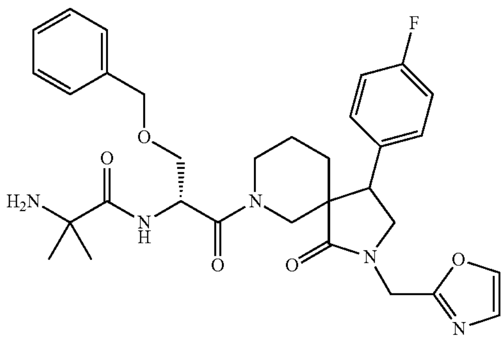 [SMILES: CC(C)(N)C(=O)N[C@H](COCc1ccccc1)C(=O)N1CCCC2(C1)C(=O)N(Cc1ncco1)CC2c1ccc(F)cc1] | Diastereomeric mixture of 2-amino-N-((2R)-3-(benzyloxy)-1-(4-(4-fluorophenyl)-2-(oxazol-2-ylmethyl)-1-oxo-2,7-diazaspiro[4.5]decan-7-yl)-1-oxopropan-2-yl)-2-methylpropanamide | Method 2minLowpH; Rt 0.77 mins; M/z 592.4 [M + H]+ |
| 1.71 | 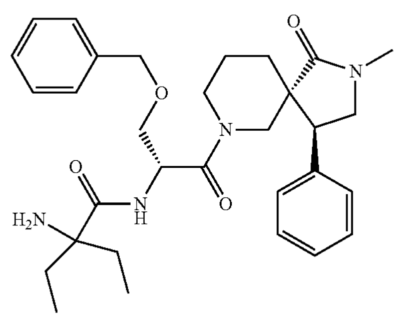 [SMILES: CCC(N)(CC)C(=O)N[C@H](COCc1ccccc1)C(=O)N1CCC[C@@]2(C1)C(=O)N(C)C[C@H]2c1ccccc1] | 2-amino-N-((R)-3-(benzyloxy)-1-((4S,5R)-2-methyl-1-oxo-4-phenyl-2,7-diazaspiro[4.5]decan-7-yl)-1-oxopropan-2-yl)-2-ethylbutanamide | Method 2minLowpH Rt 3.43 mins; M/z 535.4 [M + H]+ |
| 1.72 | 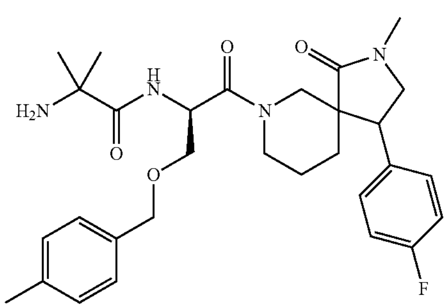 [SMILES: Cc1ccc(COC[C@@H](NC(=O)C(C)(C)N)C(=O)N2CCCC3(C2)C(=O)N(C)CC3c2ccc(F)cc2)cc1] | 2-amino-N-((2R)-1-(4-(4-fluorophenyl)-2-methyl-1-oxo-2,7-diazaspiro[4.5]decan-7-yl)-3-((4-methylbenzyl)oxy)-1-oxopropan-2-yl)-2-methylpropanamide | Method 10minLC_v003 Rt 0.76 mins; M/z 561.3 [M + H]+ |
| 1.73 | 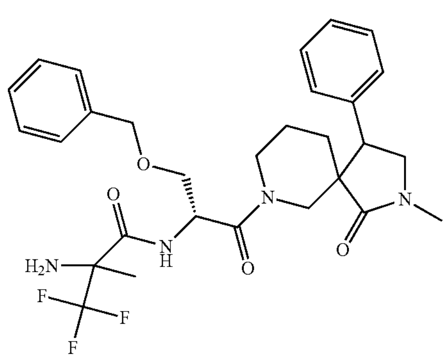 [SMILES: CN1CC(c2ccccc2)C2(CCCN(C(=O)[C@@H](COCc3ccccc3)NC(=O)C(C)(N)C(F)(F)F)C2)C1=O] | 2-amino-N-((2R)-3-(benzyloxy)-1-(2-methyl-1-oxo-4-phenyl-2,7-diazaspiro[4.5]decan-7-yl)-1-oxopropan-2-yl)-3,3,3-trifluoro-2-methylpropanamide | Method 2minLC_v003 Rt 1.05 mins; M/z 561.3 [M + H]+ |

TABLE 1-continued

| Ex. | Structure | Name | NMR/[M + H]+<br>LC-MS Method<br>SFC Method |
|---|---|---|---|
| 1.74 | 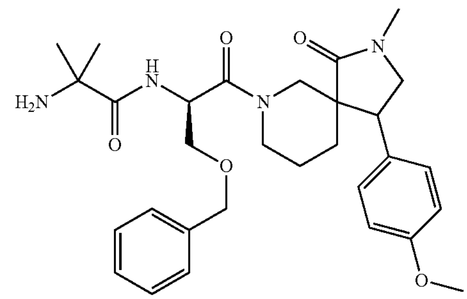 [SMILES: COc1ccc(C2CN(C)C(=O)C23CCCN(C(=O)[C@@H](COCc2ccccc2)NC(=O)C(C)(C)N)C3)cc1] | 2-amino-N-((2R)-3-(benzyloxy)-1-(4-(4-methoxyphenyl)-2-methyl-1-oxo-2,7-diazaspiro[4.5]decan-7-yl)-1-oxopropan-2-yl)-2-methylpropanamide | Method LowpH__v002<br>Rt 2.11 mins; M/z 537.6<br>[M + H]+ |
| 1.75 | 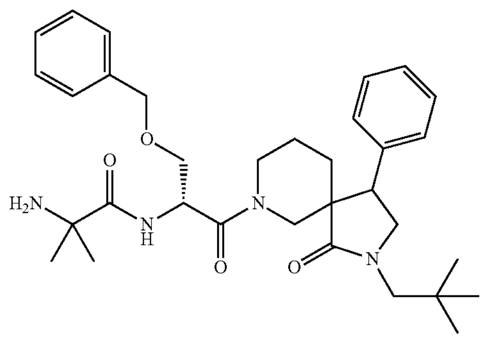 [SMILES: CC(C)(C)CN1CC(c2ccccc2)C2(CCCN(C(=O)[C@@H](COCc3ccccc3)NC(=O)C(C)(C)N)C2)C1=O] | 2-amino-N-((2R)-3-(benzyloxy)-1-(2-neopentyl-1-oxo-4-phenyl-2,7-diazaspiro[4.5]decan-7-yl)-1-oxopropan-2-yl)-2-methylpropanamide | Method LowpH__v002<br>Rt 2.34 mins; M/z 563.6<br>[M + H]+ |

Example 1.9

Diastereomer mixture of 2-Amino-N-[(R)-2-[4-(4-fluoro-phenyl)-2-methyl-1-oxo-2,7-diaza-spiro[4.5]dec-7-yl]-1-(1H-indol-3-ylmethyl)-2-oxo-ethyl]-2-methyl-propionamide

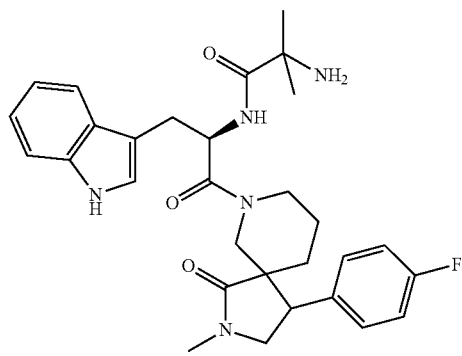 [SMILES: CN1CC(c2ccc(F)cc2)C2(CCCN(C(=O)[C@@H](Cc3c[nH]c4ccccc34)NC(=O)C(C)(C)N)C2)C1=O]

Step 1: Tert-butyl 1-((2R)-1-(4-(4-fluorophenyl)-2-methyl-1-oxo-2,7-diazaspiro[4.5]decan-7-yl)-3-(1H-indol-3-yl)-1-oxopropan-2-ylamino)-2-methyl-1-oxopropan-2-

A mixture comprising 4-(4-fluorophenyl)-2-methyl-2,7-diazaspiro[4.5]decan-1-one (ASW MedChem) (269 mg, 0.899 mmol), (R)-2-(2-(tert-butoxycarbonylamino)-2-methylpropanamido)-3-(1H-indol-3-yl)propanoic acid (Intermediate 3C) (350 mg, 0.899 mmol) and DIPEA (0.628 ml, 3.59 mmol) in DMF (4 ml) was treated with ®T3P (50% in DMF, 0.525 ml, 1.797 mmol) and stirred at RT for 24 hours. The reaction mixture was diluted with water (5 ml) and extracted with EtOAc. The organic portion was dried (MgSO$_4$) and concentrated in vacuo. Purification of the crude product by chromatography on silica eluting with 1% MeOH in DCM afforded the title compound;

LC-MS Rt 2.57 mins; MS m/z 634 [M+H]+; Method LowpH_v002.

Step 2: 2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide A mixture comprising tert-butyl 1-((2R)-1-(4-(4-fluorophenyl)-2-methyl-1-oxo-2,7-diazaspiro[4.5]decan-7-yl)-3-(1H-indol-3-yl)-1-oxopropan-2-ylamino)-2-methyl-1-oxopropan-2-ylcarbamate (312.3 mg, 0.493 mmol) (step 1) and TFA (0.380 ml, 4.93 mmol) in DCM (3 ml) was stirred at room temperature for 17 hours. TFA (1 mL, 13 mmol) was added to the reaction mixture. After 3 h 45 min the solvent was removed in vacuo to afford a colourless oil. The oil was dissolved with methanol (3 ml) and passed through a 10 g SCX-2 cartridge eluting with 2M NH$_3$ in methanol (70 ml). The solvent was removed in vacuo to yield the title compound as diastereomeric mixture.

LC-MS Rt 2.1 mins; MS m/z 534 [M+H]+; Method LowpH_v002.

Examples 1.10 and 1.11

Separation of the diastereomers of Example 1.9 by Supercritical Fluid Chromatography gave examples 1.10 and 1.11.

Example 1.10

Single diastereomer of 2-amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide

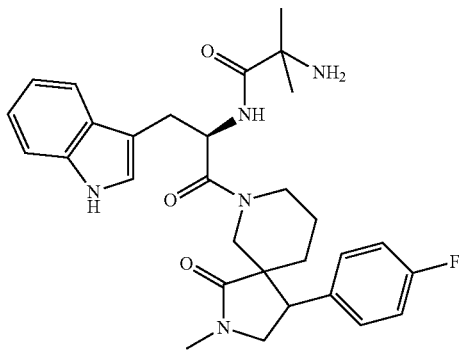 [SMILES: CN1CC(c2ccc(F)cc2)C2(CCCN(C(=O)[C@@H](Cc3c[nH]c4ccccc34)NC(=O)C(C)(C)N)C2)C1=O]

LC-MS Rt 2.09 mins; MS m/z 534[M+H]+; Method Low-pH_v002.

SFC Second eluted peak Rt 7.13 mins; Method AD3OIPA_AmmAc

Example 1.11

Single diastereomer of 2-amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide

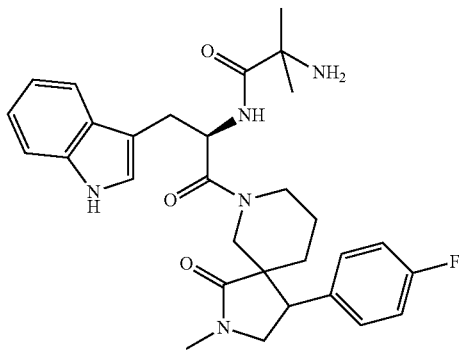 [SMILES: CN1CC(c2ccc(F)cc2)C2(CCCN(C(=O)[C@@H](Cc3c[nH]c4ccccc34)NC(=O)C(C)(C)N)C2)C1=O]

LC-MS Rt 2.08 mins; MS m/z 534[M+H]+; Method Low-pH_v002.

SFC First eluted peak Rt 3.6 mins; Method AD3OIPA_AmmAc $^1$H NMR (d6-DMSO, 500 MHz, 398K) δ 0.98-1.14 (2H, m), 1.21 (3H, s), 1.23 (3H, s), 1.32-1.42 (1H, m), 2.84 (3H, s), 2.88-2.97 (1H, m), 3.05 (1H, dd), 3.16-3.27 (2H, m), 3.55-3.64 (1H, m), 3.65-3.76 (1H, m), 5.02 (1H, t), 6.95-7.10 (6H, m), 7.12 (1H, d), 7.33 (1H, d), 7.58 (1H, d), 10.44 (1H, br s).

Example 1.15

Single diastereomer of 2-Amino-N-[(R)-2-[4-(4-fluoro-phenyl)-2-isopropyl-1-oxo-2,7-diaza-spiro[4.5]dec-7-yl]-1-(1-methyl-1H-indol-3-ylmethyl)-2-oxo-ethyl]-2-methyl-propionamide

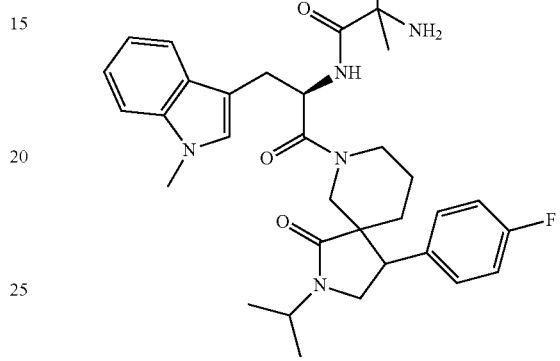

Step 1: Tert-butyl 1-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-ylamino)-2-methyl-1-oxopropan-2-ylcarbamate A mixture comprising 4-(4-fluorophenyl)-2-isopropyl-2,7-diazaspiro[4.5]decan-1-one (ASW MedChem) (243 mg, 0.744 mmol), (R)-2-(2-(tert-butoxycarbonylamino)-2-methylpropanamido)-3-(1-methyl-1H-indol-3-yl)propanoic acid (Intermediate 3D) (300 mg, 0.744 mmol) and DIPEA (0.519 ml, 2.97 mmol) in acetonitrile (3 ml) was treated with ®T3P (50% in DMF, 0.868 ml, 1.487 mmol) and stirred at RT for 19 hours. The reaction mixture was concentrated in vacuo, dissolved in EtOAc and washed with water. The organic portion was dried (MgSO$_4$) and concentrated in vacuo. Purification of the crude product by chromatography on silica eluting with 2% MeOH in DCM afforded the title compound;

LC-MS Rt 2.67 mins; MS m/z 676 [M+H]+; Method Low-pH_v002.

Step 2: 2-Amino-N-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-yl)-2-methylpropanamide A mixture comprising tert-butyl 1-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-ylamino)-2-methyl-1-oxopropan-2-ylcarbamate (378 mg, 0.559 mmol) (step 1) and TFA (0.431 ml, 5.59 mmol) in DCM (3 ml) was stirred at room temperature for 4 hours. The solvent was removed in vacuo to afford a colourless oil. The oil was dissolved with methanol (3 ml) and passed through a 10 g SCX-2 cartridge eluting with 2M NH$_3$ in methanol (70 ml). The solvent was removed in vacuo to yield the title compound as diastereomeric mixture.

Separation of the diastereomers by Supercritical Fluid Chromatography gave a single diastereomer of 2-amino-N-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-yl)-2-methylpropanamide as peak 1.

LC-MS Rt 2.27 mins; MS m/z 576 [M+H]+; Method LowpH_v002.

SFC first eluted peak Rt 3.57 mins; Method OD30MeOH_AA $^1$H NMR (d6-DMSO, 500 MHz, 398K) δ 1.14 (3H, d), 1.23 (3H, d), 1.32 (3H, s), 1.34 (3H, s), 1.49-1.66 (2H, m), 1.73-1.82 (1H, m), 2.04-2.16 (1H, m), 2.52-2.62 (1H, m), 2.85-3.10 (3H, m), 3.21 (1H, dd), 3.30-3.40 (1H, m), 3.44-3.64 (2H, m), 3.71 (3H, s), 4.21 (1H, m), 4.78 (1H, br m), 6.96-7.18 (7H, m), 7.37 (1H, d), 7.57 (1H, d), 7.78 (1H, br signal).

Example 1.16

2-Amino-N-((2R)-3-(benzyloxy)-1-(2-(2-(dimethylamino)-2-oxoethyl)-1-oxo-4-phenyl-2,7-diazaspiro[4.5]decan-7-yl)-1-oxopropan-2-yl)-2-methylpropanamide

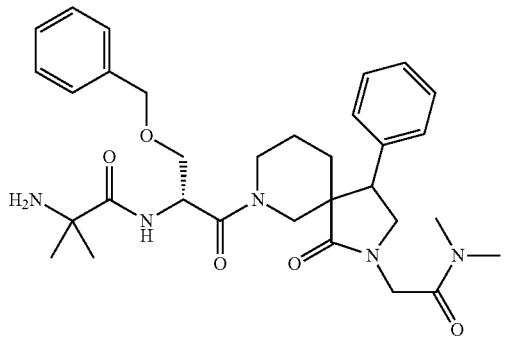

Step 1: Tert-butyl 1-((2R)-3-(benzyloxy)-1-(2-(2-(dimethylamino)-2-oxoethyl)-1-oxo-4-phenyl-2,7-diazaspiro[4.5]decan-7-yl)-1-oxopropan-2-ylamino)-2-methyl-1-oxopropan-2-ylcarbamate A racemic mixture of (4R,5S)—N,N-dimethyl-2-(1-oxo-4-phenyl-2,7-diazaspiro[4.5]decan-2-yl)acetamide and (4S,5R)—N,N-Dimethyl-2-(1-oxo-4-phenyl-2,7-diazaspiro[4.5]decan-2-yl)acetamide (Intermediate 1D) (193 mg; 0.612 mmol) was solubilised in acetonitrile (3 ml). (R)-3-Benzyloxy-2-(2-tert-butoxycarbonylamino-2-methylpropionylamino)-propionic acid (Intermediate 3A) (233 mg; 0.612 mmol) was treated with DIPEA (0.427 ml; 2.448 mmol) and ®T3P (50% in EtOAc), (0.714 ml; 1.224 mmol). The mixture was stirred at RT for 2 hours and concentrated in vacuo. The crude residue was solubilised in ethyl acetate and washed with water (3×50 ml). The organics were washed with brine, dried with magnesium sulfate, filtered and concentrated to yield the title compound.

LC-MS Rt 2.56 mins; MS m/z 678[M+H]+; Method LowpH_v002.olp.

Step 2: 2-Amino-N-((2R)-3-(benzyloxy)-1-(2-(2-(dimethylamino)-2-oxoethyl)-1-oxo-4-phenyl-2,7-diazaspiro[4.5]decan-7-yl)-1-oxopropan-2-yl)-2-methylpropanamide A diasteromeric mixture of tert-butyl 1-((2R)-3-(benzyloxy)-1-(2-(2-(dimethylamino)-2-oxoethyl)-1-oxo-4-phenyl-2,7-diazaspiro[4.5]decan-7-yl)-1-oxopropan-2-ylamino)-2-methyl-1-oxopropan-2-ylcarbamate (386 mg; 0.569 mmol) was solubilised in dichloromethane (3 ml) at room temperature. Trifluoroacetic acid (439 ul; 5.69 mmol) was added and mixture stirred at RT for 72 hours. The solvent was removed in vacuo and the crude product was dissolved in methanol and loaded onto a pre-wetted 10 g SCX-2 cartridge. Methanol (50 ml) was passed through the cartridge and the product was eluted with 2M NH$_3$ in methanol. Concentration of the ammonia fraction afforded the title compound as a diastereomeric mixture. Diastereomers were separated by chiral SFC, collecting the second peak.

SFC Method OD50MeOH_AA, Rt 6.40 mins

LCMS Method LowpH_v002, Rt 2.11 mins; MS m/z 578 [M+H]+

$^1$H NMR (d6-DMSO, 500 MHz, 398K) δ 1.01-2.52 (2H, br signal), 1.12-1.27 (2H, m), 1.29 (3H, s), 1.30 (3H, s), 1.65-1.74 (1H, m), 2.95 (6H, s), 2.99-3.11 (1H, m), 3.14-3.24 (1H, br m), 3.33 (1H, dd), 3.44 (1H, dd), 3.66 (1H, dd), 3.68-3.80 (2H, m), 3.89 (1H, dd), 4.07-4.25 (2H, m), 4.49-4.59 (2H, m), 5.00 (1H, dt), 7.20-7.38 (10H, m).

Examples 1.18 and 1.19

2-Amino-N-{(R)-1-benzyloxymethyl-2-[4-(4-fluorophenyl)-2-isopropyl-1-oxo-2,7-diaza-spiro[4.5]dec-7-yl]-2-oxo-ethyl}-2-methyl-propionamide

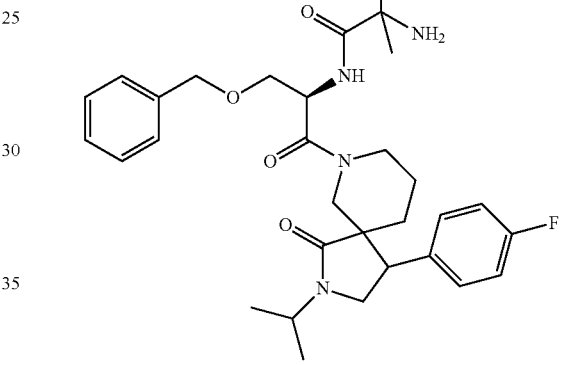

Step 1: Tert-butyl 1-((2R)-3-(benzyloxy)-1-(4-(4-fluorophenyl)-2-isopropyl-1-oxo-2,7-diazaspiro[4.5]decan-7-yl)-1-oxopropan-2-ylamino)-2-methyl-1-oxopropan-2-yl carbamate.

A mixture comprising 4-(4-fluorophenyl)-2-methyl-2,7-diazaspiro[4.5]decan-1-one (ASW MedChem) (258 mg, 0.789 mmol), (R)-3-Benzyloxy-2-(2-tert-butoxycarbonylamino-2-methylpropionylamino)-propionic acid (Intermediate 3A) (300 mg, 0.789 mmol) and DIPEA (0.551 ml, 3.15 mmol) in acetonitrile (3 ml) was treated with ®T3P (50% in DMF, 0.921 ml, 1.577 mmol) and stirred at RT for 19 hours. The reaction mixture was concentrated in vacuo, dissolved with EtOAc and washed with water. The organic portion was dried (MgSO$_4$) and concentrated in vacuo. Purification of the crude product by chromatography on silica eluting with 2% MeOH in DCM afforded the title compound;

LC-MS Rt 2.65 mins; MS m/z 653 [M+H]+; Method LowpH_v002.

Step 2: 2-Amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide A mixture comprising tert-butyl 1-((2R)-3-(benzyloxy)-1-(4-(4-fluorophenyl)-2-isopropyl-1-oxo-2,7-diazaspiro[4.5]decan-7-yl)-1-oxopropan-2-ylamino)-2-methyl-1-oxopropan-2-ylcarbamate (378 mg, 0.579 mmol) (step 1) and TFA (0.892 ml, 11.58 mmol) in DCM (4 ml) was stirred at room temperature for 4 hours. The solvent was removed in vacuo to afford a colourless oil. The oil was dissolved with methanol (3 ml) and passed through a 10 g SCX-2 cartridge eluting with 2M NH₃ in methanol (70 ml). The solvent was removed in vacuo to yield the title compound as diastereomeric mixture.

Separation of the diastereomers by Supercritical Fluid Chromatography gave the following:

Example 1.18

Single diastereomer of 2-amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide

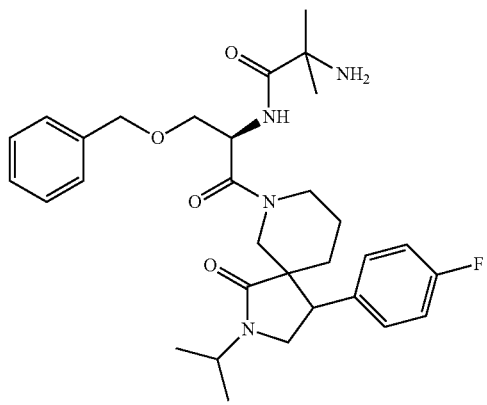 [SMILES: CC(C)N1CC(c2ccc(F)cc2)C2(CCCN(C(=O)[C@@H](COCc3ccccc3)NC(=O)C(C)(C)N)C2)C1=O]

LC-MS Rt 2.2 mins; MS m/z 553[M+H]+; Method LowpH_v002.

SFC First eluted peak Rt 8.91 mins; Method IC40MeOH_AA

Example 1.19

Single diastereomer of 2-amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide

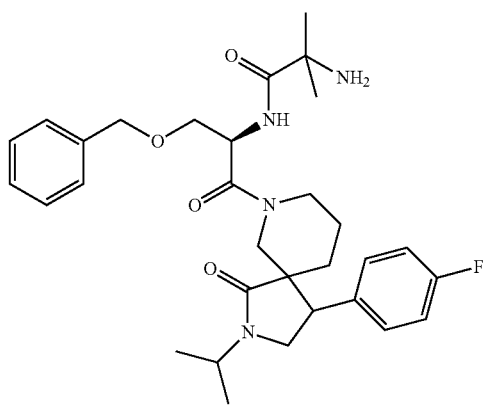 [SMILES: CC(C)N1CC(c2ccc(F)cc2)C2(CCCN(C(=O)[C@@H](COCc3ccccc3)NC(=O)C(C)(C)N)C2)C1=O]

LC-MS Rt 2.2 mins; MS m/z 553[M+H]+; Method LowpH_v002.

SFC Second eluted peak Rt 11.54 mins; Method IC40MeOH_AA

¹H NMR (d6-DMSO, 500 MHz, 398K) δ 1.15 (3H, d), 1.21 (3H, s), 1.22 (3H, d), 1.23 (3H, s), 1.53-1.62 (1H, m), 1.63-1.70 (1H, m), 1.75-1.82 (1H, m), 2.00-2.10 (1H, m), 2.79-2.89 (1H m), 3.00-4.00 (1H, v br signal), 3.15-3.27 (2H, m), 3.42-3.66 (6H, m), 4.22 (1H, m), 4.42-4.52 (2H, m), 4.53-4.71 (1H, m), 7.04 (2H, dd), 7.23 (2H, dd), 7.25-7.36 (5H, m).

Example 1.32

2-Amino-2-methyl-N-((2R)-1-(2-methyl-1-oxo-4-phenyl-2,7-diazaspiro[4.5]decan-7-yl)-1-oxo-5-phenylpentan-2-yl)propanamide

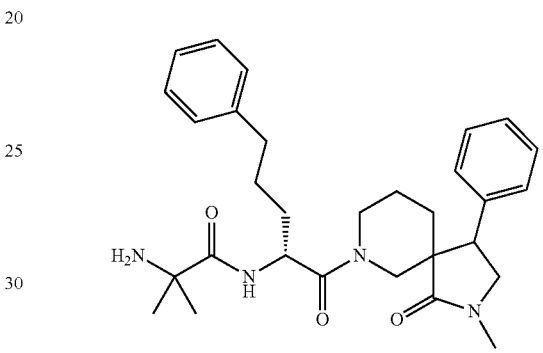

Step 1: Tert-butyl 2-methyl-1-(((2R)-1-(2-methyl-1-oxo-4-phenyl-2,7-diazaspiro[4.5]decan-7-yl)-1-oxo-5-phenylpentan-2-ylamino)-1-oxopropan-2-ylcarbamate The title compound was prepared with (R)-2-(2-(tert-Butoxycarbonylamino)-2-methylpropanamido)-4-phenylpentanoic acid (Intermediate 3F) according to the procedure described in Example 2 Step 1, using ®T3P (50% in EtOAc) and CH₃CN as solvent.

LCMS Rt 2.62 mins; MS m/z [M+H]+ 605.57; Method LowpH_v002

Step 2: Diastereomeric mixture of 2-amino-2-methyl-N-((2R)-1-(2-methyl-1-oxo-4-phenyl-2,7-diazaspiro[4.5]decan-7-yl)-1-oxo-5-phenylpentan-2-yl)propanamide The title compound was prepared according to the procedure described in Example 2 Step 2.

LCMS Rt 2.15 mins; MS m/z [M+H]⁺ 505.53; Method LowpH_v002

Separation of the diastereomers by Supercritical Fluid Chromatography afforded the title compound as the first eluted peak.

SFC Method LUXC2_45MeOH_AA, First eluted peak Rt=5.38 minutes

LCMS Rt 2.22 mins; MS m/z 505.47 [M+H]+; Method 2minLC_v003

¹H NMR (d6-DMSO, 500 MHz, 398K) δ 1.11-1.25 (2H, m), 1.26 (3H, s), 1.28 (3H, s), 1.45-1.54 (1H, m), 1.58-1.73 (4H, m), 1.75-1.84 (1H, m), 2.0-2.73 (2H, v br signal), 2.57-2.70 (2H, m), 2.86 (3H, s), 3.07-3.16 (1H, m), 3.17-3.24 (1H, m), 3.27 (1H, dd), 3.34 (1H, dd), 3.57-3.68 (1H, m), 3.81 (1H, dd), 3.85-3.99 (1H, m), 4.75-4.80 (1H, m), 7.10-7.33 (10H, m), 7.36-8.88 (1H, v br signal).

Example 1.53

2-Amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide

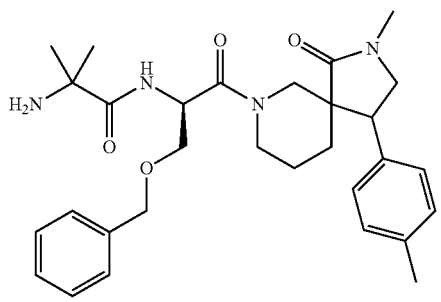 [SMILES: Cc1ccc(C2CN(C)C(=O)C23CCCN(C(=O)[C@@H](COCc2ccccc2)NC(=O)C(C)(C)N)C3)cc1]

Step 1: Tert-butyl 1-((2R)-3-(benzyloxy)-1-(2-methyl-1-oxo-4-p-tolyl-2,7-diazaspiro[4.5]decan-7-yl)-1-oxopropan-2-ylamino)-2-methyl-1-oxopropan-2-ylcarbamate.

To a stirred solution of (R)-3-benzyloxy-2-(2-tert-butoxycarbonylamino-2-methylpropionylamino)-propionic acid (Intermediate 3A) (259 mg, 0.681 mmol) in DMF (5 ml) was added Intermediate 1L (176 mg, 0.681 mmol) and DIPEA (476 I, 2.72 mmol) followed by ®T3P 50% in DMF (795 ul, 1.362 mmol) and the reaction mixture was left to stir at room temperature overnight. The reaction mixture was added to DCM (15 ml) and washed with water (15 ml). The combined organics were washed with sat. sodium bicarbonate solution (15 ml), brine (2×15 ml), dried (MgSO4) and concentrated to give the crude product as a yellow oil. The crude material was purified by silica chromatography eluting with 30-100% isohexane/EtOAc. The relevant fractions concentrated to give the desired product.

LC-MS Method 10minLC_v003; Rt 4.74 min; MS m/z 621.8 [M+H

Step 2: 2-Amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide To a stirred solution of tert-butyl 1-((2R)-3-(benzyloxy)-1-(2-methyl-1-oxo-4-p-tolyl-2,7-diazaspiro[4.5]decan-7-yl)-1-oxopropan-2-ylamino)-2-methyl-1-oxopropan-2-ylcarbamate (302 mg, 0.486 mmol) in DCM (3 ml) was added TFA (562 I, 7.30 mmol) at 5° C. The reaction mixture was then left to stir at 5-10° C. overnight. The reaction mixture was added to 2M NaOH (2 ml) and extracted with DCM (3×5 ml). The extracts were washed with brine (5 ml), dried (MgSO4) and concentrated to give the mixture of diastereomers. The desired isomer was isolated via SFC chromatography.

SFC Method OD45MeOH_AA, peak 2 Rt 3.4 min.
LC-MS Method 2minLC_v003; Rt 0.99 min; MS m/z 521.5 [M+H]+;

$^1$H NMR (d6-DMSO, 500 MHz, 398K) δ 1.13-1.24 (2H, m), 1.26 (3H, s), 1.27 (3H, s), 1.42-1.51 (1H, m), 1.58-1.69 (1H, m), 2.28 (3H, s), 2.70-2.92 (2H, br signal), 2.85 (3H, s), 3.02-3.14 (1H, m), 3.15-3.23 (1H, m), 3.26 (1H, dd), 3.30 (1H, dd), 3.64 (1H, dd), 3.66-3.73 (1H, m), 3.76 (1H, dd), 3.79 (1H, dd), 3.89-4.03 (1H, m), 4.48-4.59 (2H, m), 4.98 (1H, dd), 7.03 (2H, d), 7.09 (2H, d), 7.23-7.38 (5H, m).

In another embodiment of the invention there is provided crystalline forms I and II of the L-malate salt of the compound of Example 1.53, 2-Amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide, and a process to make said crystalline forms. The disclosed crystalline L-malate salt forms provide a significant improvement in processing properties compared to the free base amorphous form, and physicochemical properties (e.g. higher melting point, increased aqueous solubility).

Process to Make Crystalline Forms of the L-Malate Salt of the Compound of Example 1.53

Method A:

50 mg of 2-Amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide were weighed into a glass vial, 12.8 mg L-Malic acid (counterion) was weighed into each vial. Solids were then dissolved in 0.2 mL of Methanol which was then evaporated under vacumme. 500 uL of acetone was added to each vial. The vials were then temperature cycled over 5-35° C. for 2 days. Solids from vials were isolated by centrifugation and dried under vacuum then characterised.

TABLE A

XRPD data of Example 1.53 L-malate salt crystalline form I

| Angle 2-Theta ° | d value Angstrom |
|---|---|
| 7.269 | 12.15150 |
| 9.550 | 9.25365 |
| 17.831 | 4.97035 |
| 20.723 | 4.28275 | error +/−0.2°.

Method B:

250 mg of 2-Amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide were weighed into a glass vial, 64.4 mg L-Malic acid (counterion) was weighed into each vial. 2 mL of Butyl acetate was added to each vial. The vials were then temperature cycled over 5-35° C. for 2 days. Solids from vials were isolated by centrifugation and dried under vacuum then characterised.

TABLE B

XRPD data of Example 1.53 L-malate salt crystalline form II

| Angle 2-Theta ° | d value Angstrom |
|---|---|
| 16.054 | 5.51636 |
| 20.312 | 4.36849 |
| 23.531 | 3.77767 |
| 26.532 | 3.35670 | error +/−0.2°.

Example 2.0(i), 2.0 (ii) and 2.0(iii)

2-Amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide

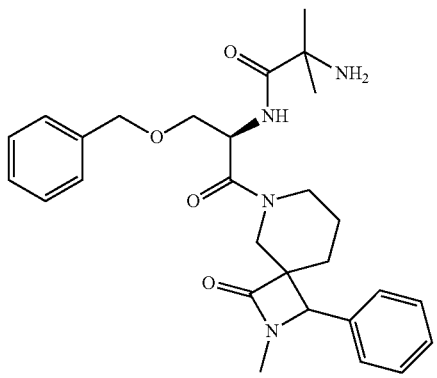 [SMILES: CN1C(=O)C2(CCCN(C(=O)[C@@H](COCc3ccccc3)NC(=O)C(C)(C)N)C2)C1c1ccccc1]

Step 1: tert-Butyl 1-((2R)-3-(benzyloxy)-1-(2-methyl-1-oxo-3-phenyl-2,6-diazaspiro[3.5]nonan-6-yl)-1-oxopropan-2-ylamino)-2-methyl-1-oxopropan-2-ylcarbamate A mixture comprising (R)-3-(benzyloxy)-2-(2-(tert-butoxycarbonylamino)-2-methyl propanamido)propanoic acid (Intermediate 3A) (300 mg, 0.789 mmol), rac-2-methyl-3-phenyl-2,6-diazaspiro[3.5]nonan-1-one (Intermediate 2A) (182 mg, 0.789 mmol) and DIPEA (0.551 ml, 3.15 mmol) in DMF (4 ml) was treated with ®T3P (amide coupling agent 50% in DMF, 0.460 ml, 1.577 mmol) and stirred at RT for 17 hours. The reaction mixture was diluted with water (5 ml) and extracted with EtOAc. The organic portion was dried (MgSO$_4$) and concentrated in vacuo. Purification of the crude product by chromatography on silica eluting with 1% MeOH in DCM afforded the title compound;

LC-MS Rt 2.45 mins; MS m/z 594[M+H]+; Method LowpH_v002.

Step 2: 2-Amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide A mixture comprising tert-butyl 1-((2R)-3-(benzyloxy)-1-(2-methyl-1-oxo-3-phenyl-2,6-diazaspiro[3.5]nonan-6-yl)-1-oxopropan-2-ylamino)-2-methyl-1-oxopropan-2-ylcarbamate (290.8 mg, 0.491 mmol) and TFA (0.378 ml, 4.91 mmol) in DCM (3 ml) was stirred at room temperature for 90 minutes. The solvent was removed in vacuo to afford a colourless oil. The oil was dissolved with methanol (3 ml) and passed through a 10 g SCX2 cartridge eluting with 2M NH$_3$ in methanol (70 ml). The solvent was removed in vacuo to yield the title compound as diastereomeric mixture.

Example 2.0(i)

2-Amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide; LC-MS Rt 1.99 mins; MS m/z 493[M+H]+; Method LowpH_v002.

Separation of the diastereomers by Supercritical Fluid Chromatography.

Example 2.0(ii)

First eluted peak Rt=3.45 minutes. Diastereomer 1 of 2-amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide $^1$H NMR (d6-DMSO, 500 MHz, 398K) δ 0.87-0.98 (1H, m), 1.26 (6H, s), 1.28-1.42 (2H, m), 1.53-1.63 (1H, m), 2.75 (3H, s), 3.12-3.24 (1H, m), 3.58-3.68 (m, 3H), 3.75 (1H, dd), 4.09 (1H, dd), 4.48-4.62 (2H, m), 5.07 (1H, br t), 7.18-7.23 (2H, m), 7.25-7.30 (1H, m), 7.30-7.40 (7H, m).

LC-MS Rt 0.95 mins; MS m/z 493[M+H]+; Method 2min-LC_v003.

SFC Rt 3.45 mins; Method OD40MeOH_AA

Example 2.0(iii)

Second eluted peak Rt=6.76 min. Diastereomer 2 of 2-amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide LC-MS Rt 0.95 mins; MS m/z 493[M+H]+; Method 2min-LC_v003.

SFC Rt 6.76 mins; Method OD40MeOH_AA

Example 3.0(i), 3.0 (ii) and 3.0(iii)

N-((2R)-3-(1H-Indol-3-yl)-1-(2-isopropyl-1-oxo-4-phenyl-2,7-diazaspiro[4.5]decan-7-yl)-1-oxopropan-2-yl)-2-amino-2-methylpropanamide

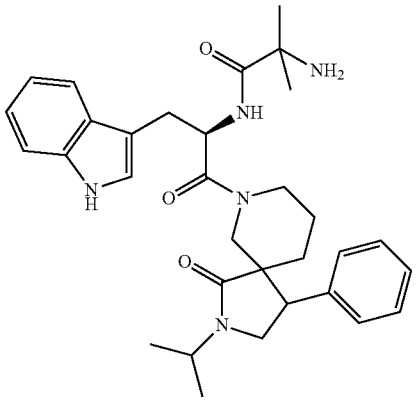 [SMILES: CC(C)N1CC(c2ccccc2)C2(CCCN(C(=O)[C@@H](Cc3c[nH]c4ccccc34)NC(=O)C(C)(C)N)C2)C1=O]

Step 1: tert-butyl 1-((2R)-3-(1H-indol-3-yl)-1-(2-isopropyl-1-oxo-4-phenyl-2,7-diazaspiro[4.5]decan-7-yl)-1-oxopropan-2-ylamino)-2-methyl-1-oxopropan-2-ylcarbamate A mixture comprising 2-isopropyl-4-phenyl-2,7-diazaspiro[4.5]decan-1-one (ASW MedChem) (278 mg, 0.899 mmol), (R)-2-(2-(tert-butoxycarbonylamino)-2-methylpropanamido)-3-(1H-indol-3-yl)propanoic acid (Intermediate 3C) (350 mg, 0.899 mmol) and DIPEA (0.628 ml, 3.59 mmol) in DMF (4 ml) was treated with ®T3P (50% in DMF, 0.525 ml, 1.797 mmol) and stirred at RT for 2 h 20 min. The reaction mixture was diluted with water (5 ml) and extracted with EtOAc. The organic portion was dried (MgSO$_4$) and concentrated in vacuo Purification of the crude product by chromatography on silica eluting with 1% MeOH in DCM afforded the title compound;

LC-MS Rt 2.63 mins; MS m/z 645 [M+H]+; Method LowpH_v002.

Step 2: N-((2R)-3-(1H-indol-3-yl)-1-(2-isopropyl-1-oxo-4-phenyl-2,7-diazaspiro[4.5]decan-7-yl)-1-oxopropan-2-yl)-2-amino-2-methylpropanamide A mixture comprising tert-butyl 1-((2R)-3-(1H-indol-3-yl)-1-(2-isopropyl-1-oxo-4-phenyl-2,7-diazaspiro[4.5]decan-7-yl)-1-oxopropan-2-ylamino)-2-methyl-1-oxopropan- 2-ylcarbamate (450.21 mg, 0.699 mmol) (step 1) and TFA (0.539 ml, 6.99 mmol) in DCM (5 ml) was stirred at room temperature for 17 hours. The solvent was removed in vacuo to afford a purple oil. The oil was dissolved with methanol (3 ml) and passed through a 10 g SCX-2 cartridge eluting with 2M $NH_3$ in methanol (70 ml). The solvent was removed in vacuo to yield the title compound as diastereomeric mixture.

Example 3.0(i)

LC-MS Rt 2.19 mins; MS m/z 545[M+H]+; Method Low-pH_v002.

Separation of the diastereomers by Supercritical Fluid Chromatography.

Example 3.0(ii)

First eluted peak Rt=3.83 minutes. Diastereomer 1 of N-((2R)-3-(1H-indol-3-yl)-1-(2-isopropyl-1-oxo-4-phenyl-2,7-diazaspiro[4.5]decan-7-yl)-1-oxopropan-2-yl)-2-amino-2-methylpropanamide LC-MS Rt 2.16 mins; MS m/z 545[M+H]+; Method Low-pH_v002.

SFC Rt 3.83 mins; Method AD30IPA_AmmAc

Example 3.0(iii)

Second eluted peak Rt=8.33 minutes. Diastereomer 2 of N-((2R)-3-(1H-indol-3-yl)-1-(2-isopropyl-1-oxo-4-phenyl-2,7-diazaspiro[4.5]decan-7-yl)-1-oxopropan-2-yl)-2-amino-2-methylpropanamide $^1$H NMR (d6-DMSO, 500 MHz, 398K) δ 1.02-1.14 (2H, m), 1.16 (3H, d), 1.18 (3H, d), 1.21 (3H, s), 1.23 (3H, s), 1.30-1.40 (1H, m), 1.52-1.63 (1H, m), 2.64-3.43 (6H, m), 3.56-3.74 (2H, m), 4.22 (1H, m), 5.05 (1H, dd), 6.94-7.11 (5H, m), 7.18-7.27 (3H, m), 7.33 (1H, d), 7.59 (1H, d), 7.30-8.29 (1H, br signal), 10.44 (1H, br s)

LC-MS Rt 2.18 mins; MS m/z 545[M+H]+; Method Low-pH_v002.

SFC Rt 8.33 mins; Method AD30IPA_AmmAc

Example 4.0(i) and 4.0(ii)

(R)-2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-3-hydroxy-2-methyl-propionamide and (R)-2-Amino-N—[(R)-1-benzyloxymethyl-2-((4R,5S)-2-methyl-1-oxo-4-phenyl-2,7-diaza-spiro[4.5]dec-7-yl)-2-oxo-ethyl]-3-hydroxy-2-methyl-propionamide

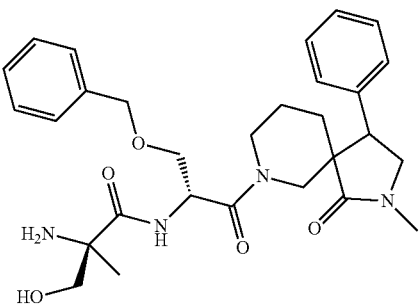 [SMILES: CN1CC(c2ccccc2)C2(CCCN(C(=O)[C@@H](COCc3ccccc3)NC(=O)[C@](C)(N)CO)C2)C1=O]

Step 1: 2-(tert-butoxycarbonylamino)-3-(tert-butyldimethylsilyloxy)-2-methylpropanoic acid A mixture comprising D-2-(tert-butoxycarbonylamino)-3-hydroxy-2-methylpropanoic acid (1 g, 4.56 mmol) and DBU (1.031 ml, 6.84 mmol) in MeCN (6 mL) was treated with TBSCl (1.031 g, 6.84 mmol) in MeCN (1 mL) dropwise at 0° C. The resulting colourless solution was stirred and warmed to room temperature overnight. The reaction mixture was concentrated in vacuo. The resulting crude was diluted with MeOH (4 mL), 6M NaOH solution (4 mL) and water (4 mL) and then stirred for 2 hours at room temperature. The crude solution was neutralised with 10% citric acid solution and extracted with DCM (20 mL). The aqueous phase was further extracted with DCM (3×20 mL). The combined organic portions were washed with water (10 mL), dried ($MgSO_4$), and concentrated in vacuo to afford the title compound. No purification was performed on the title compound.

$^1$H NMR ($CDCl_3$, 400 MHz) δ 5.28 (1H, bs), 3.85 (1H, d), 3.76 (1H, d), 1.45 (3H, s), 1.38 (9H, s), 0.81 (9H, s), 0.00 (6H, s).

Step 2: tert-butyl (2R)-3-(benzyloxy)-1-(2-methyl-1-oxo-4-phenyl-2,7-diazaspiro[4.5]decan-7-yl)-1-oxopropan-2-ylcarbamate A mixture comprising (R)-3-(benzyloxy)-2-(tert-butoxycarbonylamino)propanoic acid (Sigma-Aldrich) (1.052 g, 3.56 mmol) and ®T3P (50% in EtOAc) (4.16 ml, 7.12 mmol) in MeCN (20 mL) was treated dropwise with DIPEA (2.488 ml, 14.25 mmol). The resulting solution was stirred at room temperature for 30 minutes, then a racemic mixture of (4R,5S)-2-Methyl-4-phenyl-2,7-diazaspiro[4.5]decan-1-one and (4S,5R)-2-Methyl-4-phenyl-2,7-diazaspiro[4.5]decan-1-one (Intermediate 1A) (1 g, 3.56 mmol) was added portionwise. The reaction mixture was stirred for 20 hours at room temperature. The reaction mixture was diluted with 0.1M HCl (20 mL) and extracted with DCM (20 mL). The aqueous phase was further extracted with DCM (3×20 mL). The combined organic portions were washed with a saturated solution of sodium bicarbonate (20 mL), water (20 mL), dried ($MgSO_4$), and concentrated in vacuo to afford the title compound. No purification was performed on the title compound.

LC-MS Rt 1.26 mins; MS m/z 522.7 [M+H]+; Method 2minLC_v003.

Step 3: 7-((R)-2-amino-3-(benzyloxy)propanoyl)-2-methyl-4-phenyl-2,7-diazaspiro[4.5]decan-1-one A mixture comprising tert-butyl (2R)-3-(benzyloxy)-1-(2-methyl-1-oxo-4-phenyl-2,7-diazaspiro[4.5]decan-7-yl)-1-oxopropan-2-ylcarbamate (500 mg, 0.959 mmol) and TFA (2.215 ml, 28.8 mmol) in DCM (5 mL) was stirred at room temperature for 2 hours. The reaction mixture was concentrated in vacuo. The crude was then diluted with DCM (10 mL) and washed with a saturated solution of sodium bicarbonate (10 mL). The aqueous phase was further extracted with DCM (3×10 mL). The combined organic portions were dried ($MgSO_4$), and concentrated under reduced pressure to afford the title compound. No purification was performed on the title compound.

LC-MS Rt 0.98 mins; MS m/z 422.7 [M+H]+; Method 2minLC_v003.

Step 4: tert-butyl (4R)-7,10,10,11,11-pentamethyl-4-(2-methyl-1-oxo-4-phenyl-2,7-diazaspiro[4.5]decane-7-carbonyl)-6-oxo-1-phenyl-2,9-dioxa-5-aza-10-siladodecan-7-ylcarbamate A mixture comprising 2-(tert-butoxycarbonylamino)-3-(tert-butyldimethylsilyloxy)-2-methylpropanoic acid (intermediate from step 1) (311 mg, 0.934 mmol) and DIPEA (0.652 ml, 3.73 mmol) in DMF (5 mL) was treated with a solution of ®T3P (50% in EtOAc) (1.090 ml, 1.867 mmol) dropwise at room temperature. The resulting solution was stirred for 15 minutes, then 7-((R)-2-amino-3-(benzyloxy)propanoyl)-2-methyl-4-phenyl-2,7-diazaspiro[4.5]decan-1-one (intermediate from step 3) (500 mg, 0.934 mmol) in DMF (1 mL) was added dropwise at room temperature. The reaction mixture was stirred for 20 hours. The reaction mixture was diluted with 0.1M HCl (10 mL) and extracted with DCM (3×10 mL). The combined organic portions were washed with a saturated solution of sodium bicarbonate (10 mL), brine (10 mL), water (10 mL) and concentrated in vacuo. Purification of the crude product by chromatography on silica eluting with 0-70% EtOAc/iso-hexane afforded the title compound.

LC-MS Rt 2.82 mins; MS m/z 737.60 [M+H]+; Method LowpH_v002.

Step 5: Example 4.0(i) Diastereomeric mixture of (2R)-2-amino-N-((2R)-3-(benzyloxy)-1-(2-methyl-1-oxo-4-phenyl-2,7-diazaspiro[4.5]decan-7-yl)-1-oxopropan-2-yl)-3-hydroxy-2-methylpropanamide A mixture comprising tert-butyl (4R)-7,10,10,11,11-pentamethyl-4-(2-methyl-1-oxo-4-phenyl-2,7-diazaspiro[4.5]decane-7-carbonyl)-6-oxo-1-phenyl-2,9-dioxa-5-aza-10-siladodecan-7-ylcarbamate (Intermediate from step 4) (140 mg, 0.190 mmol) and 2M HCl in Et$_2$O (2.9 mL, 5.70 mmol) was treated with water (300 mg, 16.65 mmol) dropwise and stirred at room temperature for 2 hours. The reaction mixture was concentrated in vacuo. The resulting crude was dried in a vacuum oven for 24 hours at 50° C. to afford the title compound. No purification was performed on the title compound.

LC-MS Rt 2.13 mins; MS m/z 523.49 [M+H]+; Method LowpH_v002.

Separation of the diastereomers by Supercritical Fluid Chromatography.

Example 4.0(ii)

Second eluted peak Rt 8.54 mins. Diastereomer 2: (R)-2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-3-hydroxy-2-methyl-propionamide or (R)-2-Amino-N-[(R)-1-benzyloxymethyl-2-((4R,5S)-2-methyl-1-oxo-4-phenyl-2,7-diaza-spiro[4.5]dec-7-yl)-2-oxo-ethyl]-3-hydroxy-2-methyl-propionamide LC-MS Rt 0.96 mins; MS m/z 523.4 [M+H]+; Method LowpH 2MinLC_v003

SFC Rt 8.54 mins; Method OD30MeOH_DEA

Example 5.0 (i) and 5.0 (ii)

(S)-2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-3-hydroxy-2-methyl-propionamide and (S)-2-Amino-N—[(R)-1-benzyloxymethyl-2-((4R,5S)-2-methyl-1-oxo-4-phenyl-2,7-diaza-spiro[4.5]dec-7-yl)-2-oxo-ethyl]-3-hydroxy-2-methyl-propionamide

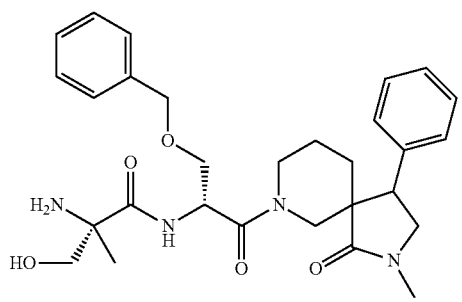 [SMILES: CN1CC(c2ccccc2)C2(CCCN(C(=O)[C@@H](COCc3ccccc3)NC(=O)[C@@](C)(N)CO)C2)C1=O]

Step 1: (S)-2-(tert-butoxycarbonylamino)-3-(tert-butyldimethylsilyloxy)-2-methylpropanoic acid A mixture comprising L-2-(tert-butoxycarbonylamino)-3-hydroxy-2-methylpropanoic acid (900 mg, 4.11 mmol) and DBU (0.928 ml, 6.16 mmol) in MeCN (6 mL) was treated with TBSCl (928 mg, 6.16 mmol) in MeCN (1 mL) dropwise at 0° C. The resulting colourless solution was stirred and warmed to room temperature overnight. The reaction mixture was concentrated in vacuo.

The resulting crude was diluted with MeOH (4 mL), 6M NaOH solution (4 mL) and water (4 mL). The crude solution was neutralised with 10% citric acid solution and extracted with DCM (20 mL). The aqueous phase was further extracted with DCM (3×20 mL). The combined organic portions were washed with water (10 mL), dried (MgSO$_4$), and concentrated in vacuo to afford the title compound. No purification was performed on the title compound.

$^1$H NMR (CDCl$_3$, 400 MHz) δ 5.28 (1H, bs), 3.84 (1H, d), 3.74 (1H, m), 1.45 (3H, s), 1.38 (9H, s), 0.80 (9H, s), 0.00 (6H, s).

Step 2: tert-Butyl (4R)-7,10,10,11,11-pentamethyl-4-(2-methyl-1-oxo-4-phenyl-2,7-diazaspiro[4.5]decane-7-carbonyl)-6-oxo-1-phenyl-2,9-dioxa-5-aza-10-siladodecan-7-ylcarbamate The title compound was prepared analogously to Example 4.

LC-MS Rt 2.82 mins; MS m/z 737.36 [M+H]+; Method LowpH_v002.

Step 3: Example 5.0 (i) Diastereomeric mixture of (2S)-2-amino-N-((2R)-3-(benzyloxy)-1-(2-methyl-1-oxo-4-phenyl-2,7-diazaspiro[4.5]decan-7-yl)-1-oxopropan-2-yl)-3-hydroxy-2-methylpropanamide A mixture comprising tert-butyl (4R)-7,10,10,11,11-pentamethyl-4-(2-methyl-1-oxo-4-phenyl-2,7-diazaspiro[4.5]decane-7-carbonyl)-6-oxo-1-phenyl-2,9-dioxa-5-aza-10-siladodecan-7-ylcarbamate (150 mg, 0.204 mmol) in DCM (5 mL) and 2M HCl in Et$_2$O (3.05 ml, 6.11 mmol) was treated with water (0.3 mL) dropwise at room temperature. The resulting colourless solution was stirred at room temperature for 2 hours. The reaction mixture was concentrated in vacuo. The resulting crude was dried in the vacuum oven at RT for 3 days to afford the title compound.

LC-MS Rt 0.93 mins; MS m/z 523.7 [M+H]+; Method 2minLC_v003.

Separation of the diastereomers by supercritical fluid chromatography.

Example 5.0(ii)

Second eluted peak Rt 4.88 mins. Diastereomer 2: (S)-2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-3-hydroxy-2-methyl-propionamide or (S)-2-Amino-N-[(R)-1-benzyloxymethyl-2-((4R,5S)-2-methyl-1-oxo-4-phenyl-2,7-diaza-spiro[4.5]dec-7-yl)-2-oxo-ethyl]-3-hydroxy-2-methyl-propionamide LC-MS: Rt 2.11 mins; MS m/z 523.51 [M+H]+; Method LowpH_v002.

SFC Rt 4.88 mins; Method OD40IPA_AA.

Example 6.0(i) and 6.0(ii)

Diastereomer 2-Amino-N-[(R)-1-(4-methoxy-benzyloxymethyl)-2-((4S,5R)-2-methyl-1-oxo-4-phenyl-2,7-diaza-spiro[4.5]dec-7-yl)-2-oxo-ethyl]-2-methyl-propionamide and 2-Amino-N-[(R)-1-(4-methoxy-benzyloxymethyl)-2-(4R,5S)-2-methyl-1-oxo-4-phenyl-2,7-diaza-spiro[4.5]dec-7-yl)-2-oxo-ethyl]-2-methyl-propionamide

Example 6.0(i)

Diastereomer 2-Amino-N-[(R)-1-(4-methoxy-benzyloxymethyl)-2-((4S,5R)-2-methyl-1-oxo-4-phenyl-2,7-diaza-spiro[4.5]dec-7-yl)-2-oxo-ethyl]-2-methyl-propionamide or 2-Amino-N-[(R)-1-(4-methoxy-benzyloxymethyl)-2-(4R,5S)-2-methyl-1-oxo-4-phenyl-2,7-diaza-spiro[4.5]dec-7-yl)-2-oxo-ethyl]-2-methyl-propionamide (Diastereomer 1)

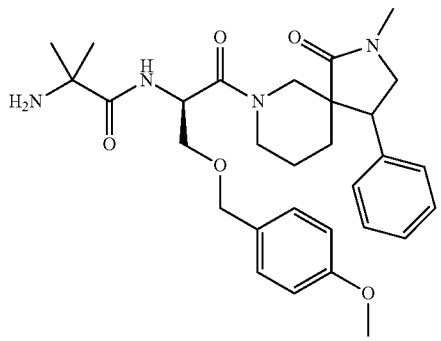 [SMILES: COc1ccc(COC[C@@H](NC(=O)C(C)(C)N)C(=O)N2CCCC3(C2)C(=O)N(C)CC3c2ccccc2)cc1]

Step 1: Diastereomers of [(R)-1-(4-Methoxy-benzyloxymethyl)-2-(2-methyl-1-oxo-4-phenyl-2,7-diaza-spiro[4.5]dec-7-yl)-2-oxo-ethyl]-carbamic acid tert-butyl ester A mixture comprising ((R)-2-tert-Butoxycarbonylamino-3-(4-methoxy-benzyloxy)-propionic acid (Intermediate 4D) (350 mg, 1.08 mmol) and a racemic mixture of (4R,5S)-2-Methyl-4-phenyl-2,7-diazaspiro[4.5]decan-1-one hydrochloride and (4S,5R)-2-Methyl-4-phenyl-2,7-diazaspiro[4.5]decan-1-one hydrochloride (Intermediate 1A) (302 mg, 1.076 mmol) in DMF (8 ml) was treated with DIPEA (0.94 ml, 5.38 mmol) and ®T3P (amide coupling agent 50% in DMF, 1.37 g, 2.15 mmol) and stirred at RT for 1 h. The resulting mixture was diluted with EtOAc (50 ml) and then washed with water (25 ml), NaHCO₃ saturated aqueous solution (25 ml) and brine (25 ml). The combined organic portions were dried (MgSO₄) and concentrated in vacuo. The residue was purified by chromatography on silica eluting with 35-100% EtOAc in iso-hexane to afford the individual diastereomers as white solids:

Diastereomer 1, first eluting compound. LC-MS Rt 1.24 mins; MS m/z 552.7 [M+H]+; Method 2minLC_v003. TLC Rf=0.42 (EtOAc:iHex 8:2)

Diastereomer 2, second eluting compound. LC-MS Rt 1.24 mins; MS m/z 552.7 [M+H]+; Method 2minLC_v003. TLC Rf=0.33 (EtOAc:iHex 8:2)

Step 2: 7-[(R)-2-Amino-3-(4-methoxy-benzyloxy)-propionyl]-2-methyl-4-phenyl-2,7-diaza-spiro[4.5]decan-1-one A solution of [(R)-1-(4-Methoxy-benzyloxymethyl)-2-(2-methyl-1-oxo-4-phenyl-2,7-diaza-spiro[4.5]dec-7-yl)-2-oxo-ethyl]-carbamic acid tert-butyl ester (Diastereomer 1) (168 mg, 0.308 mmol) in 1,4-dioxane (2 ml) was cooled to 8° C. with an water/ice bath and conc. sulfuric acid (0.049 ml, 0.91 mmol) in 1,4-dioxane (0.5 ml) was added dropwise. The reaction mixture was put in a freezer at −20° C. for 72 h. The frozen reaction mixture was quenched with 2M sodium carbonate aqueous solution (10 ml) and extracted with EtOAc (2×25 ml). The organic phase was separated, washed with brine (5 ml), dried (MgSO₄) and concentrated in vacuo. The residue was purified by chromatography on silica eluting with 0-10% MeOH in DCM to afford the title compound.

LC-MS Rt 0.95 mins; MS m/z 452.7 [M+H]+; Method 2minLC_v003.

Step 3: {1-[(R)-1-(4-Methoxy-benzyloxymethyl)-2-(2-methyl-1-oxo-4-phenyl-2,7-diaza-spiro[4.5]dec-7-yl)-2-oxo-ethylcarbamoyl]-1-methyl-ethyl}-carbamic acid 9H-fluoren-9-ylmethyl ester A solution of 2-(9H-Fluoren-9-ylmethoxycarbonylamino)-2-methyl-propionic acid [FMOC-AIB—OH] (Sigma-Aldrich) (39.3 mg, 0.12 mmol) in DMF (2 ml) was treated with DIPEA (0.04 ml, 0.23 mmol) and HATU (52.5 mg, 0.14 mmol). The resulting solution was stirred for 10 minutes before the addition of 7-[(R)-2-Amino-3-(4-methoxy-benzyloxy)-propionyl]-2-methyl-4-phenyl-2,7-diaza-spiro[4.5]decan-1-one (Intermediate from step 2) (52 mg, 0.11 mmol).

The reaction mixture was stirred at RT for 1 hour. The resulting mixture was diluted with EtOAc (25 ml) and then washed with water (10 ml) and brine (5 ml). The combined organic portions were dried (MgSO₄) and concentrated in vacuo. The residue was purified by chromatography on silica eluting with 40-100% EtOAc in iso-hexane to afford the title compound.

LC-MS Rt 1.34 mins; MS m/z 759.8 [M+H]+; Method 2minLC_v003.

Step 4: 2-Amino-N-[(R)-1-(4-methoxy-benzyloxymethyl)-2-(-2-methyl-1-oxo-4-phenyl-2,7-diaza-spiro[4.5]dec-7-yl)-2-oxo-ethyl]-2-methyl-propionamide A solution of {1-[(R)-1-(4-Methoxy-benzyloxymethyl)-2-(2-methyl-1-oxo-4-phenyl-2,7-diaza-spiro[4.5]dec-7-yl)-2-oxo-ethylcarbamoyl]-1-methyl-ethyl}-carbamic acid 9H-fluoren-9-ylmethyl ester (70 mg, 0.09 mmol) in DCM (2 ml) was treated with piperidine (0.20 ml, 2.0 mmol). The resulting solution was stirred for 2 h at RT. The reaction mixture was concentrated in vacuo. The residue was purified by chromatography on silica eluting with 0-10% MeOH in DCM to afford the title compound.

LC-MS Rt 1.06 mins; MS m/z 537.7 [M+H]+; Method 2minLC_hipH_v003.

Example 6.0(ii)

Diastereomer 2-Amino-N-[(R)-1-(4-methoxy-benzyloxymethyl)-2-((4S,5R)-2-methyl-1-oxo-4-phenyl-2,7-diaza-spiro[4.5]dec-7-yl)-2-oxo-ethyl]-2-methyl-propionamide or 2-Amino-N-[(R)-1-(4-methoxy-benzyloxymethyl)-2-(4R,5S)-2-methyl-1-oxo-4-phenyl-2,7-diaza-spiro[4.5]dec-7-yl)-2-oxo-ethyl]-2-methyl-propionamide (Diastereomer 2)

The title compound was prepared by a similar method to that of Example 6(i) from Diastereomer 2 of [(R)-1-(4-Methoxy-benzyloxymethyl)-2-(2-methyl-1-oxo-4-phenyl-2,7-diaza-spiro[4.5]dec-7-yl)-2-oxo-ethyl]-carbamic acid tert-butyl ester (Step 1). The title compound was obtained as a white solid.

LC-MS Rt 1.06 mins; MS m/z 537.7 [M+H]+; Method 2minLC_hipH_v003.

In an alternative procedure for the preparation of Example 6.0(i) and Example 6.0(ii), Diastereomers 1 and 2 from step 1 can be prepared as a mixture in steps 2-4 and the diastereomeric mixture of title compounds can be separated by SFC chromatography.

The compounds of the following tabulated examples (Table 2) were prepared by a similar method to that of Example 6.0(i) and 6.0(ii) from Intermediate 4D and the appropriate spiropiperidine (either commercially available or preparations described hereinafter).

Step 1: Diastereomers of [(R)-1-(4-Fluoro-benzyloxymethyl)-2-(2-methyl-1-oxo-4-phenyl-2,7-diaza-spiro[4.5]dec-7-yl)-2-oxo-ethyl]-carbamic acid tert-butyl ester A mixture comprising (R)-2-tert-Butoxycarbonylamino-3-(4-fluoro-benzyloxy)-propionic acid (Intermediate 4A) (357 mg, 1.14 mmol) and a racemic mixture of (4R,5S)-2-Methyl-4-phenyl-2,7-diazaspiro[4.5]decan-1-one and (4S,5R)-2-Methyl-4-phenyl-2,7-diazaspiro[4.5]decan-1-one (Intermediate 1A) (320 mg, 1.14 mmol) in DMF (6 ml) was treated with DIPEA (0.99 ml, 5.38 mmol) and ®T3P (amide coupling agent 50% in DMF, 1.45 g, 2.28 mmol) and stirred at RT for 1 h. The resulting mixture was diluted with EtOAc (50 ml) and the washed with water (25 ml), NaHCO₃ saturated aqueous solution (25 ml) and brine (25 ml). The combined organic portions were dried (MgSO₄) and concentrated in vacuo. The residue was purified by chromatography on silica eluting with 35-90% EtOAc in iso-hexane to afford the individual diastereomers as white solids:

Diastereomer 1, first eluting compound. LC-MS Rt 1.27 mins; MS m/z 540.4 [M+H]+; Method 2minLC_v003. TLC Rf=0.3 (EtOAc:iHex 8:2)

Diastereomer 2, second eluting compound. LC-MS Rt 1.27 mins; MS m/z 540.4[M+H]+; Method 2minLC_v003. TLC Rf=0.25 (EtOAc:iHex 8:2)

Step 2: 7-[(R)-2-Amino-3-(4-fluoro-benzyloxy)-propionyl]-2-methyl-4-phenyl-2,7-diaza-spiro[4.5]decan-1-one A solution of [(R)-1-(4-Fluoro-benzyloxymethyl)-2-(2-methyl-1-oxo-4-phenyl-2,7-diaza-spiro[4.5]dec-7-yl)-2-oxo-ethyl]-carbamic acid tert-butyl ester (diastereomer 2 from step 1) (185 mg, 0.34 mmol) in DCM (4 ml) was treated with TFA (0.79 ml, 10.3 mmol). The resulting solution was stirred for 2 h at RT. The reaction mixture was diluted with DCM (20 ml) and quenched at 0° C. with 2M NaOH aqueous solution (10 ml). The organic phase was separated, washed with brine (5 ml), dried (MgSO₄) and concentrated in vacuo to afford the title compound.

TABLE 2

| Ex. | Structure | Name | NMR/[M + H]+ SFC Method |
|---|---|---|---|
| 6.1 | 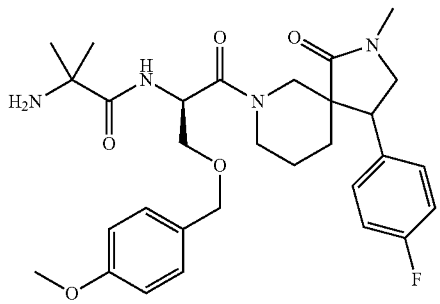 [SMILES: COc1ccc(COC[C@@H](NC(=O)C(C)(C)N)C(=O)N2CCCC3(C2)C(=O)N(C)CC3c2ccc(F)cc2)cc1] | Single diastereomer of 2-Amino-N-[(R)-2-[4-(4-fluoro-phenyl)-2-methyl-1-oxo-2,7-diazaspiro[4.5]dec-7-yl]-1-(4-ethoxy-benzyloxymethyl)-2-oxo-ethyl]-2-methyl-propionamide (Diastereomer 1) | Rt 0.97 mins; MS m/z 555.3 [M + H]+; Method 2minLC_v003 SFC Rt 2.8 min method OD40MeOH_DEA |
| 6.2 | 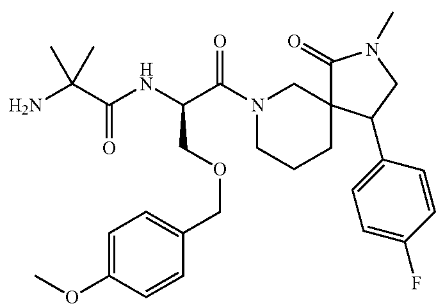 [SMILES: COc1ccc(COC[C@@H](NC(=O)C(C)(C)N)C(=O)N2CCCC3(C2)C(=O)N(C)CC3c2ccc(F)cc2)cc1] | Single diastereomer of 2-Amino-N-[(R)-2-[4-(4-fluoro-phenyl)-2-methyl-1-oxo-2,7-diazaspiro[4.5]dec-7-yl]-1-(4-ethoxy-benzyloxymethyl)-2-oxo-ethyl]-2-methyl-propionamide (Diastereomer 2) | Rt 0.97 mins; MS m/z 555.3 [M + H]+; Method 2minLC_v003 SFC Rt 4.8 min method OD40MeOH_DEA |

Example 7.0

2-Amino-N-[(R)-1-(4-fluoro-benzyloxymethyl)-2-(4S,5R)-2-methyl-1-oxo-4-phenyl-2,7-diaza-spiro[4.5]dec-7-yl)-2-oxo-ethyl]-2-methyl-propionamide or 2-Amino-N-[(R)-1-(4-fluoro-benzyloxymethyl)-2-(4R,5S)-2-methyl-1-oxo-4-phenyl-2,7-diaza-spiro[4.5]dec-7-yl)-2-oxo-ethyl]-2-methyl-propionamide (Diastereomer 2)

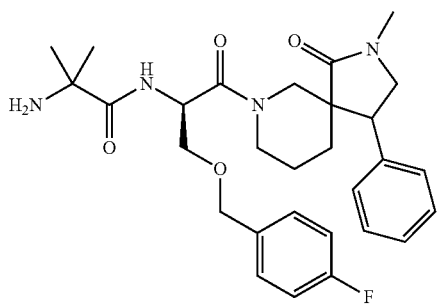 [SMILES: CN1CC(c2ccccc2)C2(CCCN(C(=O)[C@@H](COCc3ccc(F)cc3)NC(=O)C(C)(C)N)C2)C1=O]

LC-MS Rt 0.99 mins; MS m/z 440.3 [M+H]+; Method 2minLC_v003.

Step 3: {1-[(R)-1-(4-Fluoro-benzyloxymethyl)-2-(2-methyl-1-oxo-4-phenyl-2,7-diaza-spiro[4.5]dec-7-yl)-2-oxo-ethyl-carbamoyl]-1-methyl-ethyl}-carbamic acid tert-butyl ester A solution of 7-[(R)-2-Amino-3-(4-fluoro-benzyloxy)-propionyl]-2-methyl-4-phenyl-2,7-diaza-spiro[4.5]decan-1-one (130 mg, 0.3 mmol) (step 2) and 2-tert-Butoxycarbonylamino-2-methyl-propionic acid 2,5-dioxo-pyrrolidin-1-yl ester (synthesis described in EP1486498A1 page 20) (89 mg, 0.3 mmol) in THF (4 ml)/water (1 ml) was treated with TEA (0.12 ml, 0.89 mmol). The resulting mixture was stirred at 50° C. for 6 h. The reaction mixture was concentrated in vacuo and the residue partitioned between EtOAc (25 ml) and 5% citric acid aqueous solution (10 ml). The organic phase was separated, washed with brine (10 ml), dried (MgSO$_4$) and concentrated in vacuo. The residue was purified by chromatography on silica eluting with 50-100% EtOAc in iso-hexane to afford the title compound.

LC-MS Rt 1.21 mins; MS m/z 625.3 [M+H]+; Method 2minLC_v003.

Step 4: 2-Amino-N-[(R)-1-(4-fluoro-benzyloxymethyl)-2-(2-methyl-1-oxo-4-phenyl-2,7-diaza-spiro[4.5]dec-7-yl)-2-oxo-ethyl]-2-methyl-propionamide A solution of {1-[(R)-1-(4-Fluoro-benzyloxymethyl)-2-(2-methyl-1-oxo-4-phenyl-2,7-diaza-spiro[4.5]dec-7-yl)-2-oxo-ethylcarbamoyl]-1-methyl-ethyl}-carbamic acid tert-butyl ester (Intermediate from step 3) (154 mg, 0.24 mmol) in DCM (2.5 ml) was cooled with an ice bath and TFA (0.57 ml, 7.4 mmol) was added. The resulting solution was stirred for 3 h at 0° C. The reaction mixture was diluted with DCM (20 ml) and quenched at 0° C. with 2M NaOH aqueous solution (10 ml). The organic phase was separated, washed with brine (5 ml), dried (MgSO$_4$) and concentrated in vacuo. The residue was purified by chromatography on silica eluting with 0-2.5% MeOH in DCM to afford the title compound.

LC-MS Rt 0.96 mins; MS m/z 525.1 [M+H]+; Method 2minLC_v003.

Example 7.1

Single diastereomer of N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methyl-2-(methylamino)propanamide

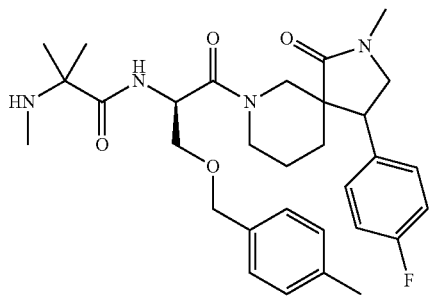 [SMILES: CNC(C)(C)C(=O)N[C@H](COCc1ccc(C)cc1)C(=O)N1CCCC2(C1)C(=O)N(C)CC2c1ccc(F)cc1]

Step 1: 2,5-Dioxopyrrolidin-1-yl 2-(tert-butoxycarbonyl(methyl)amino)-2-methylpropanoate To a solution of 2-(tert-butoxycarbonyl(methyl)amino)-2-methylpropanoic acid (5 g), N-hydroxysuccinamide (2.65 g) in DCM (100 mL) was added triethylamine (6.42 mL) and EDC (4.41 g). The reaction mixture was stirred at room temperature overnight. The reaction mixture was washed with sodium bicarbonate (100 mL), dried with magnesium sulfate, filtered and then concentrated to afford 2,5-dioxopyrrolidin-1-yl 2-(tert-butoxycarbonyl(methyl)amino)-2-methylpropanoate as a colourless oil (5.1 g).

$^1$H NMR (CDCl3, 400 MHz): δ 1.53 (9H, s), 1.64 (6H, s), 2.75-2.88 (4H, m), 2.97 (3H, s).

Step 2: Tert-butyl 1-((2R)-1-(4-(4-fluorophenyl)-2-methyl-1-oxo-2,7-diazaspiro[4.5]decan-7-yl)-3-(4-methylbenzyloxy)-1-oxopropan-2-ylamino)-2-methyl-1-oxopropan-2-yl(methyl)carbamate To 2,5-dioxopyrrolidin-1-yl 2-(tert-butoxycarbonyl(methyl)amino)-2-methylpropanoate (80 mg, 0.254 mmol) and 7-((R)-2-amino-3-(4-methylbenzyloxy)propanoyl)-4-(4-fluorophenyl)-2-methyl-2,7-diazaspiro[4.5]decan-1-one (115 mg, 0.254 mmol) in THF (3 ml) was added DIPEA (0.044 ml, 0.254 mmol) and the mixture stirred at RT overnight. The mixture was diluted with water (10 ml) and extracted with EtOAc (50 ml). The extracts were dried (MgSO4) and concentrated. The residue was applied to a 12 g silica cartridge which was eluted with ethyl acetate. The appropriate fractions were combined and concentrated to give tert-butyl 1-((2R)-1-(4-(4-fluorophenyl)-2-methyl-1-oxo-2,7-diazaspiro[4.5]decan-7-yl)-3-(4-methylbenzyloxy)-1-oxopropan-2-ylamino)-2-methyl-1-oxopropan-2-yl(methyl)carbamate as a foam.

LCMS Method 2minLC_v003, Rt 1.32 mins, MS m/z 653.4 [M+H]+

Step 3: N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methyl-2-(methylamino)propanamide To tert-butyl 1-((2R)-1-(4-(4-fluorophenyl)-2-methyl-1-oxo-2,7-diazaspiro[4.5]decan-7-yl)-3-(4-methylbenzyloxy)-1-oxopropan-2-ylamino)-2-methyl-1-oxopropan-2-yl(methyl)carbamate (128 mg, 0.196 mmol) in DCM (2 ml) was added TFA (0.6 ml, 7.79 mmol). The mixture was stirred at RT for 30 mins then concentrated in vacuo. The residue was suspended in sat. sodium bicarbonate soln. (10 ml) and extracted with EtOAc (2×50 ml). The extracts were dried and concentrated. The residue was applied to a 20 g silica cartridge in DCM and this was eluted with 5% MeOH/DCM [diluted from 10% MeOH/DCM containing 1% aqueous 880 ammonia]. The relevant fractions were combined and concentrated to give a foam. This was dried at 40° C. overnight under vacuum to give the title compound as a glass.

LCMS Method 2minLC_v003, Rt 1.01 mins, MS m/z 553.6 [M+H]+

The appropriate diastereomer of 7-((R)-2-amino-3-(4-methyl benzyloxy)propanoyl)-4-(4-fluorophenyl)-2-methyl-2,7-diazaspiro[4.5]decan-1-one can be isolated analogously to Example 7.0.

Example 7.2

2-Amino-2-methyl-N-((R)-1-((4S,5R)-2-methyl-1-oxo-4-phenyl-2,7-diazaspiro[4.5]decan-7-yl)-1-oxo-4-phenoxybutan-2-yl)propanamide

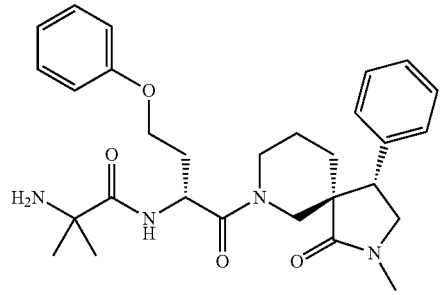 [SMILES: CN1C[C@@H](c2ccccc2)[C@@]2(CCCN(C(=O)[C@@H](CCOc3ccccc3)NC(=O)C(C)(C)N)C2)C1=O]

Step 1: Tert-butyl (R)-4-hydroxy-1-((4S,5R)-2-methyl-1-oxo-4-phenyl-2,7-diazaspiro[4.5]decan-7-yl)-1-oxobutan-2-ylcarbamate 2-Methyl-4-phenyl-2,7-diazaspiro[4.5]decan-1-one (100 mg; 0.409 mmol) was solubilised in acetonitrile (1.4 ml). (R)-2-(Tert-butoxycarbonylamino)-4-hydroxybutanoic acid (90 mg; 0.409 mmol) was added followed by diisopropylethylamine (0.286 ml; 1.637 mmol). ®T3P (50% solution in ethyl acetate) (0.478 ml; 0.819 mmol) was added and the mixture stirred at RT for 2 hr. The reaction was diluted with water and extracted with EtOAc; the organics were combined and washed with brine, dried over MgSO4, filtered and concentrated in vacuo. The residue was purified by chromatography on silica eluting with 0-10% MeOH in DCM with ammonia to afford tert-butyl (R)-4-hydroxy-1-((4S,5R)-2-methyl-1-oxo-4-phenyl-2,7-diazaspiro[4.5]decan-7-yl)-1-oxobutan-2-ylcarbamate.

LC-MS Rt 0.92 mins; MS m/z 446.3[M+H]+; Method 2minLowpH.

Step 2: Tert-butyl (R)-1-((4S,5R)-2-methyl-1-oxo-4-phenyl-2,7-diazaspiro[4.5]decan-7-yl)-1-oxo-4-phenoxybutan-2-ylcarbamate Tert-butyl (R)-4-hydroxy-1-((4S,5R)-2-methyl-1-oxo-4-phenyl-2,7-diazaspiro[4.5]decan-7-yl)-1-oxobutan-2-ylcarbamate (111 mg; 0.249 mmol) was solubilised in THF (2.5 ml). Phenol (24 mg; 0.249 mmol) was added followed by triphenylphosphine (98 mg; 0.374 mmol). The solution was cooled to 0° C. and diisopropyl azodicarboxylate (0.073 ml; 0.374 mmol) was added. The reaction mixture was warmed to RT slowly and stirred overnight. The solution was concentrated in vacuo and purified by chromatography on silica eluting with 0-10% MeOH in DCM with ammonia. The compound eluted with triphenylphospine oxide and was used crude in the next step.

LC-MS Rt 1.17 mins; MS m/z 522.1[M+H]+; Method 2minLowpH

Step 3: (4S,5R)-7-((R)-2-amino-4-phenoxybutanoyl)-2-methyl-4-phenyl-2,7-diazaspiro[4.5]decan-1-one.

Tert-butyl (R)-1-((4S,5R)-2-methyl-1-oxo-4-phenyl-2,7-diazaspiro[4.5]decan-7-yl)-1-oxo-4-phenoxybutan-2-ylcarbamate (242 mg; 0.464 mmol) was solubilised in DCM (1 ml). TFA (0.894 ml; 11.60 mmol) was added and the solution stirred at RT for 20 minutes before being concentrated in vacuo. The residual oil was dissolved with methanol (3 ml) and passed through a 10 g SCX-2 cartridge eluting with 2M $NH_3$ in methanol (70 ml). The solvent was removed in vacuo yielding (4S,5R)-7-((R)-2-amino-4-phenoxybutanoyl)-2-methyl-4-phenyl-2,7-diazaspiro[4.5]decan-1-one.

LC-MS Rt 0.75 mins; MS m/z 422.0[M+H]+; Method 2minLowpH

Step 4: Tert-butyl 2-methyl-1-((R)-1-((4S,5R)-2-methyl-1-oxo-4-phenyl-2,7-diazaspiro[4.5]decan-7-yl)-1-oxo-4-phenoxybutan-2-ylamino)-1-oxopropan-2-ylcarbamate.

(4S,5R)-7-((R)-2-amino-4-phenoxybutanoyl)-2-methyl-4-phenyl-2,7-diazaspiro[4.5]decan-1-one (55 mg; 0.130 mmol) was solubilised in acetonitrile (0.5 ml). 2-(tert-butoxycarbonylamino)-2-methylpropanoic acid (27 mg; 0.130 mmol) was added followed by diisopropylethylamine (0.091 ml; 0.522 mmol). The solution was stirred at RT for 5 minutes before ®T3P (50% solution in ethyl acetate) (0.152 ml; 0.261 mmol) was added. The mixture was stirred overnight, then concentrated in vacuo and purified by chromatography on silica eluting with 0-10% MeOH in TBME with ammonia to yield tert-butyl 2-methyl-1-((R)-1-((4S,5R)-2-methyl-1-oxo-4-phenyl-2,7-diazaspiro[4.5]decan-7-yl)-1-oxo-4-phenoxybutan-2-ylamino)-1-oxopropan-2-ylcarbamate.

LC-MS Rt 1.16 mins; MS m/z 607.5[M+H]+; Method 2minLowpH

Step 5: 2-Amino-2-methyl-N-((R)-1-((4S,5R)-2-methyl-1-oxo-4-phenyl-2,7-diazaspiro[4.5]decan-7-yl)-1-oxo-4-phenoxybutan-2-yl)propanamide Tert-butyl 2-methyl-1-((R)-1-((4S,5R)-2-methyl-1-oxo-4-phenyl-2,7-diazaspiro[4.5]decan-7-yl)-1-oxo-4-phenoxybutan-2-ylamino)-1-oxopropan-2-ylcarbamate (38.7 mg; 0.064 mmol) was solubilised in DCM (0.5 ml). TFA (0.125 ml; 1.622 mmol) was added and the solution stirred at RT for 20 minutes before being concentrated in vacuo. The residual oil was dissolved in methanol (1 ml) and passed through a 1 g SCX-2 cartridge eluting with 2M $NH_3$ in methanol (4 ml. Evaporation gave the title compound.

LC-MS Rt 0.75 mins; MS m/z 507.4[M+H]+; Method 2minLowpH

The compounds of the following tabulated Examples (Table 3) were prepared by a similar method to that of Example 7.0 from commercially available BOC protected amino acids, or Intermediates 4E, 4F, 4G, 4H, 4I, 4J or 4K and the appropriate spiropiperidine (either commercially available or preparations described hereinafter), alternatively coupling with (R)—N-Boc-alpha ethyl alanine or 2,5-Dioxopyrrolidin-1-yl 2-(tert-butoxycarbonyl (methyl)amino)-2-methylpropanoate in the penultimate step, analogously to Example 7.1.

TABLE 3

| Ex. | Structure | Name | NMR/[M + H]+ (LC-MS Method) |
|---|---|---|---|
| 7.3 | 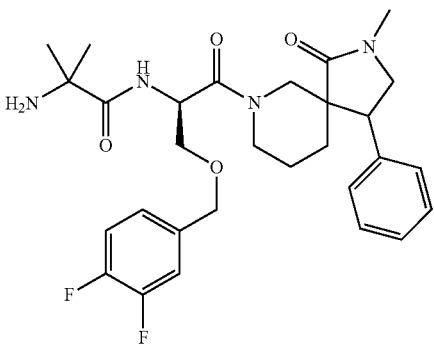 [SMILES: CN1CC(c2ccccc2)C2(CCCN(C(=O)[C@@H](COCc3ccc(F)c(F)c3)NC(=O)C(C)(C)N)C2)C1=O] | Single diastereomer of 2-Amino-N-[(R)-1-(3,4-difluoro-benzyloxymethyl)-2-(2-methyl-1-oxo-4-phenyl-2,7-diaza-spiro[4.5]dec-7-yl)-2-oxo-ethyl]-2-methyl-propionamide | Method 2minLC_v003 Rt 1.00 mins; MS m/z 543.4 [M + H]+; |

TABLE 3-continued

| Ex. | Structure | Name | NMR/[M + H]+ (LC-MS Method) |
|---|---|---|---|
| 7.4 | 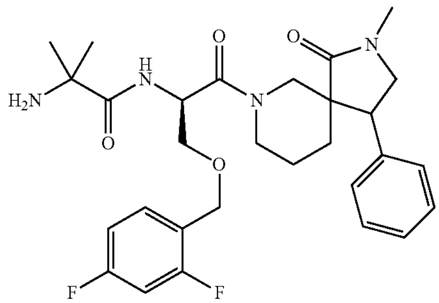 [SMILES: CN1CC(c2ccccc2)C2(CCCN(C(=O)[C@@H](COCc3ccc(F)cc3F)NC(=O)C(C)(C)N)C2)C1=O] | Single diastereomer of 2-Amino-N-[(R)-1-(2,4-difluoro-benzyloxymethyl)-2-(2-methyl-1-oxo-4-phenyl-2,7-diaza-spiro[4.5]dec-7-yl)-2-oxo-ethyl]-2-methyl-propionamide | Method 2minLC_v003 Rt 0.99 mins; MS m/z 543.3 [M + H]+; |
| 7.5 | 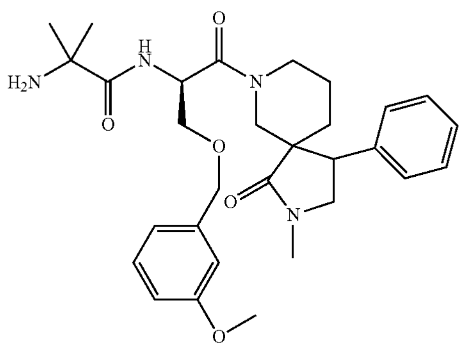 [SMILES: COc1cccc(COC[C@@H](NC(=O)C(C)(C)N)C(=O)N2CCCC3(C2)C(=O)N(C)CC3c2ccccc2)c1] | Single diastereomer of 2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide | Method 2minLC_v003 Rt 0.95 mins; MS m/z 537.4 [M + H]+; SFC Rt 6.36 mins. Method: LUXC2_50MeOH_AA |
| 7.6 | 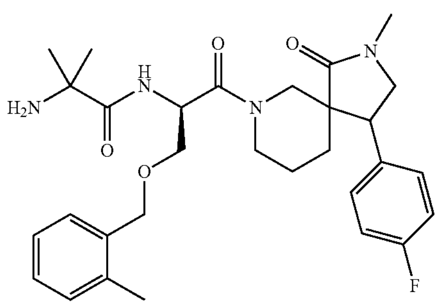 [SMILES: Cc1ccccc1COC[C@@H](NC(=O)C(C)(C)N)C(=O)N1CCCC2(C1)C(=O)N(C)CC2c1ccc(F)cc1] | Single diastereomer of 2-amino-N-((2R)-1-(4-(4-fluorophenyl)-2-methyl-1-oxo-2,7-diazaspiro[4.5]decan-7-yl)-3-(2-methylbenzyloxy)-1-oxopropan-2-yl)-2-methylpropanamide | Method 2minLC_v003; Rt 1.00 min; MS m/z 539.4 [M + H]+ |
| 7.7 | 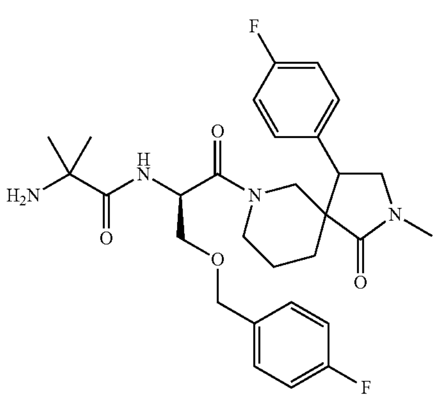 [SMILES: CN1CC(c2ccc(F)cc2)C2(CCCN(C(=O)[C@@H](COCc3ccc(F)cc3)NC(=O)C(C)(C)N)C2)C1=O] | Single diastereomer of 2-amino-N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methylpropanamide | Method 2minLC_v003; Rt 0.98 mins, MS m/z 543.4 [M + 1]+ |

TABLE 3-continued

| Ex. | Structure | Name | NMR/[M + H]+ (LC-MS Method) |
|---|---|---|---|
| 7.8 | 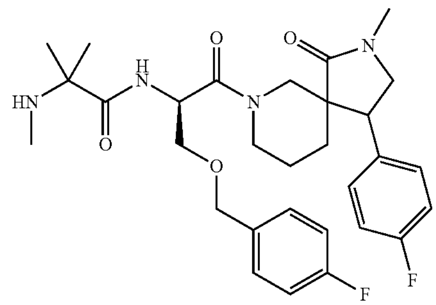 [SMILES: CNC(C)(C)C(=O)N[C@H](COCc1ccc(F)cc1)C(=O)N1CCCC2(C1)C(=O)N(C)CC2c1ccc(F)cc1] | Single diastereomer of N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methyl-2-(methylamino) propanamide | Method 2minLC_v003; Rt 0.98 mins, m/z 557.3 [M + H]+ |
| 7.9 | 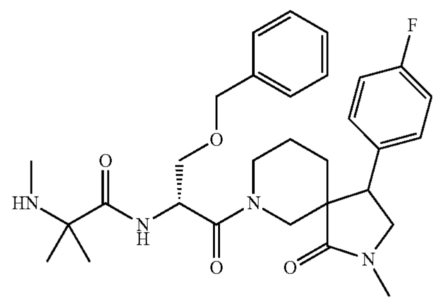 [SMILES: CNC(C)(C)C(=O)N[C@H](COCc1ccccc1)C(=O)N1CCCC2(C1)C(=O)N(C)CC2c1ccc(F)cc1] | Single diastereomer of N-((2R)-3-(benzyloxy)-1-(4-(4-fluorophenyl)-2-methyl-1-oxo-2,7-diazaspiro[4.5]decan-7-yl)-1-oxopropan-2-yl)-2-methyl-2-(methylamino) propanamide | Method 2minLC_v003; Rt 0.95 min; MS m/z 539.4 [M + H]+ |
| 7.10 | 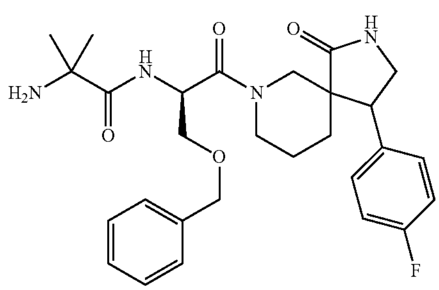 | Single diastereomer of 2-amino-N-((2R)-3-(benzyloxy)-1-(4-(4-fluorophenyl)-1-oxo-2,7-diazaspiro[4.5]decan-7-yl)-1-oxopropan-2-yl)-2-methylpropanamide | Method 2minLC_v003; Rt 0.93 mins; MS m/z 512.1 [M + H]+ |
| 7.11 | 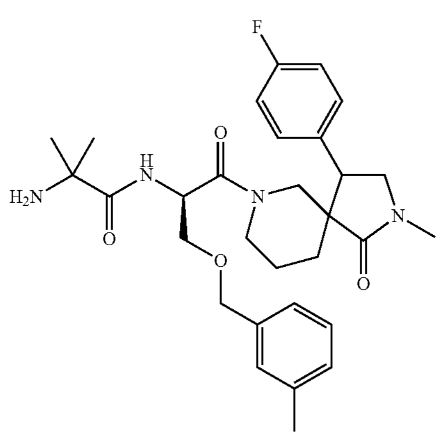 [SMILES: Cc1cccc(COC[C@@H](NC(=O)C(C)(C)N)C(=O)N2CCCC3(C2)C(=O)N(C)CC3c2ccc(F)cc2)c1] | Single diastereomer of 2-amino-N-((2R)-1-(4-(4-fluorophenyl)-2-methyl-1-oxo-2,7-diazaspiro[4.5]decan-7-yl)-3-(3-methylbenzyloxy)-1-oxopropan-2-yl)-2-methylpropanamide | Method 2minLC_v003; Rt 1.01 mins, MS m/z 539.4 [M + 1]+ |

TABLE 3-continued

| Ex. | Structure | Name | NMR/[M + H]+ (LC-MS Method) |
|---|---|---|---|
| 7.12 | 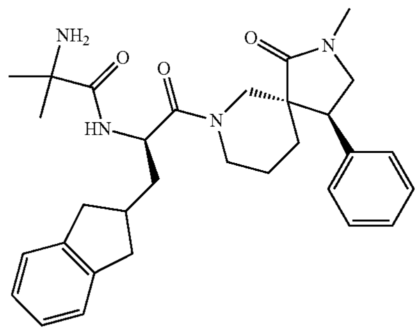 [SMILES: CN1C[C@@H](c2ccccc2)[C@@]2(CCCN(C(=O)[C@@H](CC3Cc4ccccc4C3)NC(=O)C(C)(C)N)C2)C1=O] | Single diastereomer of 2-amino-N-((R)-3-(2,3-dihydro-1H-inden-2-yl)-1-((4S,5R)-2-methyl-1-oxo-4-phenyl-2,7-diazaspiro[4.5]decan-7-yl)-1-oxopropan-2-yl)-2-methylpropanamide | Method 2minLC_v003; Rt 0.81 mins; MS m/z 517.4 [M + H]+ |
| 7.13 | 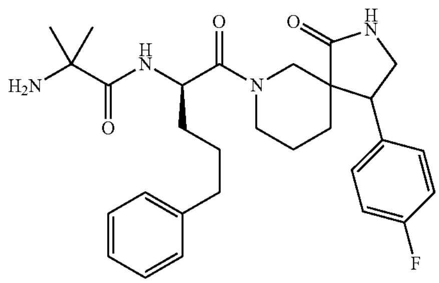 [SMILES: CC(C)(N)C(=O)N[C@H](CCCc1ccccc1)C(=O)N1CCCC2(C1)C(=O)NCC2c1ccc(F)cc1] | Single diastereomer of 2-amino-N-((2R)-1-(4-(4-fluorophenyl)-1-oxo-2,7-diazaspiro[4.5]decan-7-yl)-1-oxo-5-phenylpentan-2-yl)-2-methylpropanamide | Method 2minLC_v003; Rt 0.97 mins; MS m/z 509.4 [M + H]+ |
| 7.14 | 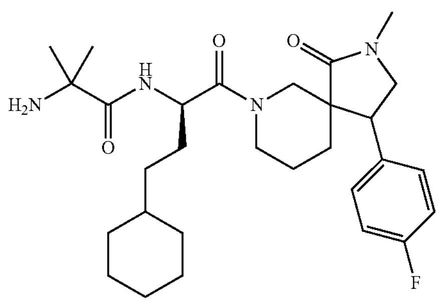 [SMILES: CN1CC(c2ccc(F)cc2)C2(CCCN(C(=O)[C@@H](CCC3CCCCC3)NC(=O)C(C)(C)N)C2)C1=O] | Single diastereomer of 2-amino-N-((2R)-4-cyclohexyl-1-(4-(4-fluorophenyl)-2-methyl-1-oxo-2,7-diazaspiro[4.5]decan-7-yl)-1-oxobutan-2-yl)-2-methylpropanamide | Method 2minLowpH, Rt 0.85 min; MS m/z 515.7 [M + H]+ |
| 7.15 | 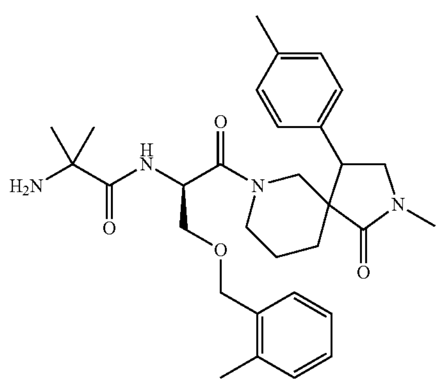 [SMILES: Cc1ccc(C2CN(C)C(=O)C23CCCN(C(=O)[C@@H](COCc2ccccc2C)NC(=O)C(C)(C)N)C3)cc1] | Single diastereomer of 2-amino-2-methyl-N-((2R)-1-(2-methyl-1-oxo-4-p-tolyl-2,7-diazaspiro[4.5]decan-7-yl)-3-(2-methylbenzyloxy)-1-oxopropan-2-yl)propanamide | Method 2minLowpH; Rt 0.82 mins, MS m/z 535.7 [M + 1]+ |
| 7.16 | 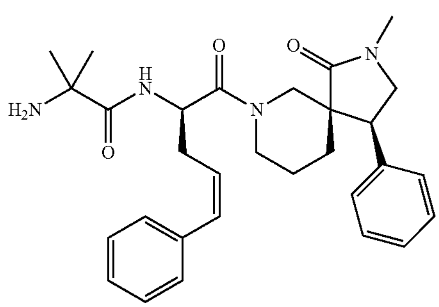 [SMILES: CN1C[C@@H](c2ccccc2)[C@@]2(CCCN(C(=O)[C@@H](C/C=C\c3ccccc3)NC(=O)C(C)(C)N)C2)C1=O] | Single diastereomer of 2-amino-2-methyl-N-((R,Z)-1-((4S,5R)-2-methyl-1-oxo-4-phenyl-2,7-diazaspiro[4.5]decan-7-yl)-1-oxo-5-phenylpent-4-en-2-yl)propanamide | Method 2minLowpH, Rt 0.77 mins; MS m/z 503.4 [M + H]+ |

TABLE 3-continued

| Ex. | Structure | Name | NMR/[M + H]+ (LC-MS Method) |
|---|---|---|---|
| 7.17 | 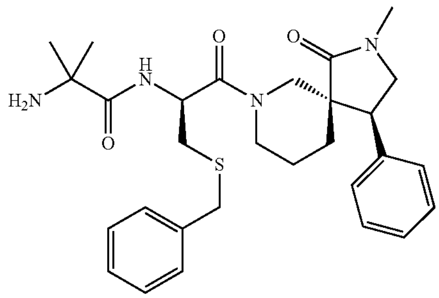 [SMILES: CN1C[C@@H](c2ccccc2)[C@@]2(CCCN(C(=O)[C@@H](CSCc3ccccc3)NC(=O)C(C)(C)N)C2)C1=O] | Single diastereomer of 2-amino-N-((S)-3-(benzylthio)-1-((4S,5R)-2-methyl-1-oxo-4-phenyl-2,7-diazaspiro[4.5]decan-7-yl)-1-oxopropan-2-yl)-2-methylpropanamide | Method 2minLowpH; Rt 0.77 mins; MS m/z 523.4 [M + H]+ |
| 7.18 | 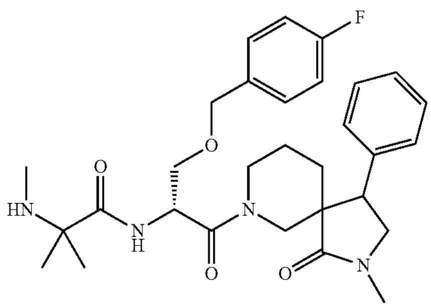 [SMILES: CNC(C)(C)C(=O)N[C@H](COCc1ccc(F)cc1)C(=O)N1CCCC2(C1)C(=O)N(C)CC2c1ccccc1] | Single diastereomer of N-((2R)-3-(4-fluorobenzyloxy)-1-(2-methyl-1-oxo-4-phenyl-2,7-diazaspiro[4.5]decan-7-yl)-1-oxopropan-2-yl)-2-methyl-2-(methylamino)propanamide | Method 2minLowpH; Rt 0.75 MS m/z 539.2 [M + H]+ |
| 7.19 | 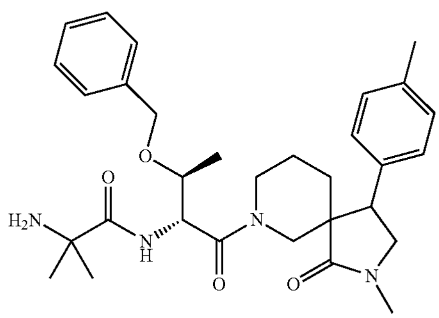 [SMILES: Cc1ccc(C2CN(C)C(=O)C23CCCN(C(=O)[C@H](NC(=O)C(C)(C)N)[C@H](C)OCc2ccccc2)C3)cc1] | Single diastereomer of 2-amino-N-((2R,3S)-3-(benzyloxy)-1-(2-methyl-1-oxo-4-p-tolyl-2,7-diazaspiro[4.5]decan-7-yl)-1-oxobutan-2-yl)-2-methylpropanamide | Method 2minLowpH; Rt 0.81 mins; MS m/z 535.4 [M + H]+ |
| 7.20 | 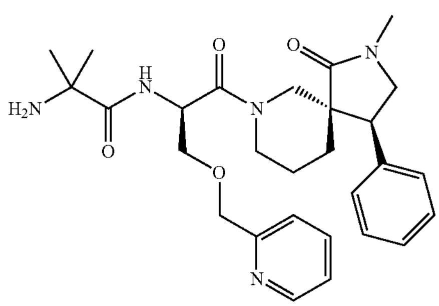 [SMILES: CN1C[C@@H](c2ccccc2)[C@@]2(CCCN(C(=O)[C@@H](COCc3ccccn3)NC(=O)C(C)(C)N)C2)C1=O] | Single diastereomer of 2-amino-2-methyl-N-((R)-1-((4S,5R)-2-methyl-1-oxo-4-phenyl-2,7-diazaspiro[4.5]decan-7-yl)-1-oxo-3-(pyridin-2-ylmethoxy)propan-2-yl)propanamide | Method 2minLowpH; Rt 0.58 mins, MS m/z 508.4 [M + H]+ |
| 7.21 | 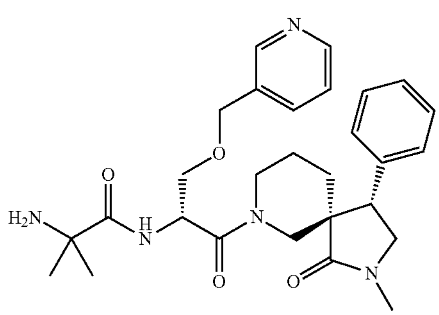 [SMILES: CN1C[C@@H](c2ccccc2)[C@@]2(CCCN(C(=O)[C@@H](COCc3cccnc3)NC(=O)C(C)(C)N)C2)C1=O] | 2-amino-2-methyl-N-((R)-1-((4S,5R)-2-methyl-1-oxo-4-phenyl-2,7-diazaspiro[4.5]decan-7-yl)-1-oxo-3-(pyridin-3-ylmethoxy)propan-2-yl)propanamide | Method 2minLowpH; Rt 0.55 mins; M/z 508.4 [M + H]+ |

| Ex. | Structure | Name | NMR/[M + H]+ (LC-MS Method) |
|---|---|---|---|
| 7.22 | 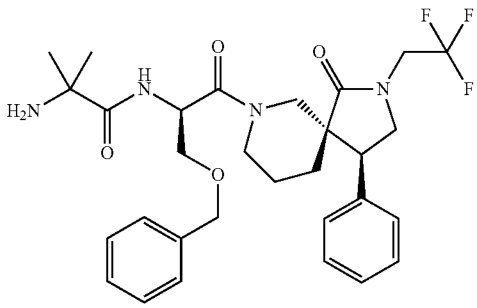 [SMILES: CC(C)(N)C(=O)N[C@H](COCc1ccccc1)C(=O)N1CCC[C@@]2(C1)C(=O)N(CC(F)(F)F)C[C@H]2c1ccccc1] | Single diastereomer of 2-amino-N-((R)-3-(benzyloxy)-1-oxo-1-((4S,5R)-1-oxo-4-phenyl-2-(2,2,2-trifluoroethyl)-2,7-diazaspiro[4.5]decan-7-yl)propan-2-yl)-2-methylpropanamide | Method 2minLowpH; Rt 0.82 mins, m/z 575.4 [M + H]+ |
| 7.23 | 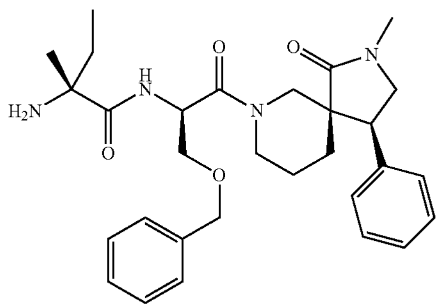 [SMILES: CC[C@@](C)(N)C(=O)N[C@H](COCc1ccccc1)C(=O)N1CCC[C@@]2(C1)C(=O)N(C)C[C@H]2c1ccccc1] | Single diastereomer of (R)-2-amino-N-((R)-3-(benzyloxy)-1-((4S,5R)-2-methyl-1-oxo-4-phenyl-2,7-diazaspiro[4.5]decan-7-yl)-1-oxopropan-2-yl)-2-methylbutanamide | Method 2minLowpH; Rt 0.74 mins; MS m/z 521.4 [M + H]+ |

Example 8.0

Diastereomers of 2-Amino-N-((2R)-3-(benzyloxy)-1-(7-methyl-6-oxo-9-phenyl-2,7-diazaspiro[4.4]nonan-2-yl)-1-oxopropan-2-yl)-2-methylpropanamide

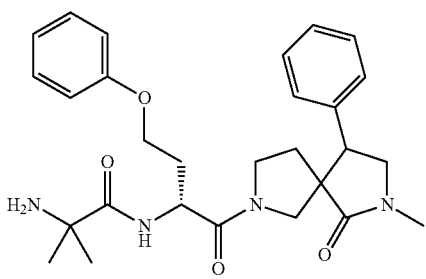 [SMILES: CN1CC(c2ccccc2)C2(CCN(C(=O)[C@@H](CCOc3ccccc3)NC(=O)C(C)(C)N)C2)C1=O]

Step 1: tert-Butyl 7-methyl-6-oxo-9-phenyl-2,7-diazaspiro[4.4]nonane-2-carboxylate A solution of tert-butyl 6-oxo-9-phenyl-2,7-diazaspiro[4.4]nonane-2-carboxylate (commercially available) (1 g, 3.16 mmol)) in DMF (50 mL) was cooled to 0° C. and treated with sodium hydride (126 mg, 3.16 mmol)). The reaction was left to stir at 0° C. for 30 minutes and iodomethane (198 uL, 3.16 mmol) was added. The reaction mixture was left to warm to room temperature. After 3 h 30 mins, the mixture was diluted with water (100 mL) and extracted with EtOAc (100 mL). The organic phase was dried (MgSO₄), filtered and concentrated in vacuo to afford a yellow oil. Purification by chromatography on silica eluting with 0-10% MeOH in TBME afforded the following diastereomers:

Diastereomer 1:
Peak 1:
LC-MS Rt 1.04 mins; MS m/z 331 [M+H]+; Method 2min-LowpH
Diastereomer 2:
Peak 2:
LC-MS Rt 1.01 mins; MS m/z 331 [M+H]+; Method 2min-LowpH

Step 2: 2-Methyl-4-phenyl-2,7-diazaspiro[4.4]nonan-1-one

A solution of tert-butyl 7-methyl-6-oxo-9-phenyl-2,7-diazaspiro[4.4]nonane-2-carboxylate (diastereomer 1, step 1) (488.3 mg, 1.48 mmol) in DCM (10 mL) was treated with TFA (2.3 mL, 29.6 mmol). The reaction mixture was stirred at room temperature for 5 hours and concentrated in vacuo. The residue was dissolved in EtOAc and washed with a saturated sodium bicarbonate solution. The organic portion was dried (MgSO₄), filtered and concentrated in vacuo to afford the title compound which was used in the next step without further purification;
LC-MS Rt 0.33 mins; MS m/z 231 [M+H]+; Method 2min-LowpH

Step 3: tert-Butyl 1-((2R)-3-(benzyloxy)-1-(7-methyl-6-oxo-9-phenyl-2,7-diazaspiro[4.4]nonan-2-yl)-1-oxopropan-2-ylamino)-2-methyl-1-oxopropan-2-ylcarbamate To a solution of (R)-3-(benzyloxy)-2-(2-(tert-butoxycarbonylamino)-2-methyl propanamido) propanoic acid (Intermediate 3A) ((280 mg, 0.736 mmol) and 2-methyl-4-phenyl-2,7-diazaspiro[4.4]nonan-1-one (step 2) (170 mg, 0.736 mmol)) in DMF (5 mL) was added DIPEA (514 uL, 2.94) and followed by ®T3P (amide coupling agent 50% in DMF, 859 uL, 1.47 mmol). The reaction was stirred at room temperature over 3 days. The resulting mixture was diluted with water (50 ml) and extracted with EtOAc (2×100 ml). The combined organic extracts were dried (MgSO₄) and concentrated in vacuo. Purification by chromatography on silica eluting with TBME:MeOH afforded the title compound LC-MS Rt 1.08 mins; MS m/z 593[M+H]+; Method 2min-LowpH.

Step 4: 2-Amino-N-((2R)-3-(benzyloxy)-1-(7-methyl-6-oxo-9-phenyl-2,7-diazaspiro[4.4]nonan-2-yl)-1-oxopropan-2-yl)-2-methylpropanamide A solution of tert-butyl 1-((2R)-3-(benzyloxy)-1-(7-methyl-6-oxo-9-phenyl-2,7-diazaspiro[4.4]nonan-2-yl)-1-oxopropan-2-ylamino)-2-methyl-1-oxopropan-2-ylcarbamate (step 3) (206.5 mg) in DCM (4 mL) was treated with TFA (537 uL, 6.97 mmol). The reaction mixture was stirred at room temperature for 2 days. A further portion of TFA (2 ml) was added and stirring continued for 20 minutes. The mixture was concentrated in vacuo to afford a colourless oil. The oil was dissolved in MeOH and applied to a 10 g pre-wetted (MeOH) SCX-2 cartridge. The column was washed with MeOH (70 mL) and the product was eluted with 2M $NH_3$ in MeOH (70 mL). The clean fractions were concentrated in vacuo to afford a colourless oil. The oil was further purified by mass-directed LC-MS to afford the title compound;

LC-MS Rt 0.71 mins; MS m/z 493[M+H]+; Method 2min-LowpH.

Example 9.0 and 9.0(i), 9.0 (ii), 9.0 (iii) and 9.0(iv)

Diastereomeric mixture and separated diastereomers of 2-Amino-N-((2R)-3-(benzyloxy)-1-(2-methyl-1-oxo-4-phenyl-2,8-diazaspiro[4.6]undecan-8-yl)-1-oxopropan-2-yl)-2-methylpropanamide

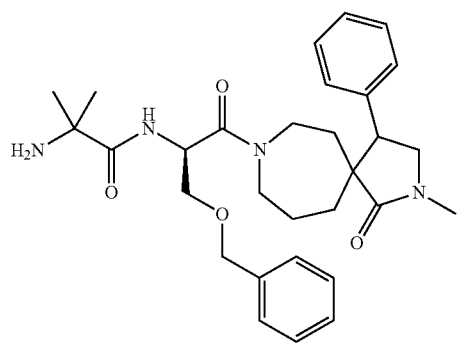 [SMILES: CN1CC(c2ccccc2)C2(CCCN(C(=O)[C@@H](COCc3ccccc3)NC(=O)C(C)(C)N)CC2)C1=O]

Step 1: 1-tert-Butyl 4-methyl azepane-1,4-dicarboxylate 1-(tert-Butoxycarbonyl)azepane-4-carboxylic acid (1.0 g; 4.11 mmol) in DCM (20 ml) and treated with DIPEA (1.5 ml, 8.22 mmol) followed by trimethyloxonium tetrafluoroborate (790 mg, 5.34 mmol) in DCM (5 ml). The mixture was stirred at RT for 3 hours and concentrated in vacuo. The residue was partitioned between EtOAc and water. The organic portion was separated and the aqueous was further extracted with EtOAc. The combined organic extracts were washed with brine, dried over $MgSO_4$ and concentrated in vacuo to afford the title compound which was used without further purification.

Step 2: 1-tert-Butyl 4-methyl 4-(2-nitro-1-phenylethyl)azepane-1,4-dicarboxylate A cooled (−78° C.) solution of diisopropylamine (667 ul, 4.68 mmol) in THF (dry) (4 ml) was treated with n-BuLi (1.6M in hexanes) (2.93 ml, 4.68 mmol). After 5 minutes, the mixture was allowed to warm to RT and then re-cooled to −78° C. This mixture was added dropwise to a cooled (−78° C.) solution of 1-tert-butyl 4-methyl azepane-1,4-dicarboxylate (step 1) (927 mg, 3.6 mmol) in THF (4 ml). The reaction mixture was stirred at −78° C. for 40 minutes. To this mixture was added (E)-(2-nitrovinyl)benzene (537 mg; 3.6 mmol) in THF (4 ml) and the resulting mixture was allowed to warm slowly to RT. The reaction was quenched with saturated ammonium chloride solution and the mixture was extracted with EtOAc. The combined organic extracts were washed with brine, dried (MgSO4), filtered and concentrated in vacuo. Purification of the crude product by chromatography on silica eluting with iso-hexane/EtOAc followed by 10-100% TBME in iso-hexane afforded the title compound as a diastereomeric mixture.

LC-MS Rt 1.28 mins; MS m/z 407.2[M+H]+; Method 2minLC_v003

Step 3: Diastereomeric mixture. of tert-butyl 1-oxo-4-phenyl-2,8-diazaspiro[4.6]undecane-8-carboxylate $NaBH_4$ (570 mg, 15.03 mmol) in EtOH (15 ml) under nitrogen was stirred for 20 minutes and added portionwise (4 aliquots) to a cooled (ice-bath) mixture comprising 1-tert-butyl 4-methyl 4-(2-nitro-1-phenylethyl)azepane-1,4-dicarboxylate (step 2) (1.079 g, 2.504 mmol) and $NiCl_2$ (595 mg, 2.504 mmol) in MeOH (25 ml). After stirring at RT for 1 hour, sat. ammonia solution was added (50 ml) followed by EtOAc (60 ml). The mixture was reduced in vacuo and the resulting slurry was partitioned between sat. ammonia solution and EtOAc. The organic portion was separated and the aqueous was further extracted with EtOAc. The combined organic extracts were washed with brine, dried ($MgSO_4$) and concentrated in vacuo. Purification by chromatography on silica eluting with 1-10% MeOH in TBME afforded the title compound;

LC-MS Rt 1.12 mins; MS m/z 346.3 [M+H]+; Method 2minLC_v003

Step 4: Diastereomeric mixture. of tert-butyl 2-methyl-1-oxo-4-phenyl-2,8-diazaspiro[4.6]undecane-8-carboxylate A diastereomeric mixture. of tert-butyl 1-oxo-4-phenyl-2,8-diazaspiro[4.6]undecane-8-carboxylate (step 4) (669.5 mg; 1.944 mmol) in THF (19.5 ml) under nitrogen was cooled in an ice/brine bath. 1M LHMDS (2.5 ml, 2.53 mmol) was added and the mixture was stirred at 0° C. for 40 minutes. Iodomethane (182 ul, 2.92 mmol) was added and the mixture was allowed to warm slowly to RT overnight. The reaction was quenched with saturated ammonium chloride solution and extracted with EtOAc. The combined organic extracts were washed with brine, dried ($MgSO_4$) and concentrated in vacuo. Purification by chromatography on silica eluting with EtOAc afforded the title compound;

LC-MS Rt 1.18 mins; MS m/z 359 [M+H]+; Method 2min-LC_v003

Step 5: Diastereomeric mixture of 2-methyl-4-phenyl-2,8-diazaspiro[4.6]undecan-1-one A diastereomeric mixture of tert-butyl 2-methyl-1-oxo-4-phenyl-2,8-diazaspiro[4.6]undecane-8-carboxylate (step 4) (683.1 mg; 1.906 mmol) in DCM (6 ml) was treated with TFA (5.8 ml, 76 mmol) and stirred at RT for 10 minutes. The mixture was concentrated in vacuo and the crude product was dissolved in MeOH and applied to a 10 g pre-wetted (MeOH) SCX-2 cartridge. The column was washed with MeOH and the product was eluted with 2M $NH_3$ in MeOH. The clean fractions were concentrated in vacuo to afford the title compound;

LC-MS Rt 0.73 mins; MS m/z 260.3[M+H]+; Method 2minLC_v003

Step 6: Diastereomeric mixture. of tert-butyl 1-((2R)-3-(benzyloxy)-1-(2-methyl-1-oxo-4-phenyl-2,8-diazaspiro[4.6]undecan-8-yl)-1-oxopropan-2-ylamino)-2-methyl-1-oxopropan-2-ylcarbamate A diastereomeric mixture. of 2-methyl-4-phenyl-2,8-diazaspiro[4.6]undecan-1-one (200 mg; 0.774 mmol) in MeCN (2.58 ml) was treated with (R)-3-(benzyloxy)-2-(2-(tert-butoxycarbonylamino)-2-methyl propanamido)propanoic acid (Intermediate 3A) (295 mg; 0.774 mmol) followed by DIPEA (541 ul; 3.10 mmol). After stirring for 5 minutes, ®T3P (amide coupling agent 50% in DMF, 904 ul, 1.548 mmol) was added and the mixture was stirred at RT overnight. The resulting mixture was diluted with water and extracted with EtOAc. The combined organic extracts were dried ($MgSO_4$) and concentrated in vacuo. Purification by chromatography on silica eluting with 50-100% EtOAc in iso-hexane afforded the title compound;

LC-MS Rt 1.13 mins; MS m/z 621.1[M+H]+; Method 2minLowpH.

Step 7: Diastereomers of 2-amino-N-((2R)-3-(benzyloxy)-1-(2-methyl-1-oxo-4-phenyl-2,8-diazaspiro[4.6]undecan-8-yl)-1-oxopropan-2-yl)-2-methylpropanamide A diastereomeric mixture. of tert-butyl 1-((2R)-3-(benzyloxy)-1-(2-methyl-1-oxo-4-phenyl-2,8-diazaspiro[4.6]undecan-8-yl)-1-oxopropan-2-ylamino)-2-methyl-1-oxopropan-2-ylcarbamate (step 6) (309 mg, 0.498 mmol) in DCM (1.5 ml) was treated with TFA (1.5 ml; 19.91 mmol) and stirred at RT for 10 min. The mixture was concentrated in vacuo and the crude product was dissolved in MeOH and applied to a 10 g pre-wetted (MeOH) SCX-2 cartridge. The column was washed with MeOH and the product was eluted with 2M $NH_3$ in MeOH. The clean fractions were concentrated in vacuo to afford the title compound (Example 9.0). The diastereomeric mixture was separated by SFC to afford the following compounds:

Example 9.0(i)

Diastereomer 1:

LC-MS Rt 0.75 mins; MS m/z 521.5[M+H]+; Method 2minLowpH.

SFC First eluted peak Rt 3.4 mins; Method: Chiralpak AS-H 250×10 mm, 5 um Mobile phase: 25% Isopropanol/75% CO2

Example 9.0(ii)

Diastereomer 2:

LC-MS Rt 0.75 mins; MS m/z 521.5[M+H]+; Method 2minLowpH.

SFC Second eluted peak Rt 6.05 mins: Method: Chiralpak AS-H 250×10 mm, 5 um Mobile phase: 25% Isopropanol/75% CO2

Example 9.0(iii)

Diastereomer 3:

LC-MS Rt 0.75 mins; MS m/z 521.5[M+H]+; Method 2minLowpH.

SFC Third eluted peak Rt 12.5 mins; Method: Phenomenex LUX C2 250×10 mm, 5 um (2 columns coupled together). Mobile phase: 50% MeOH+0.1% v/v DEA/50% CO2

Example 9.0(iv)

Diastereomer 4:

LC-MS Rt 0.75 mins; MS m/z 521.5[M+H]+; Method 2minLowpH.

SFC Fourth eluted peak Rt 14.5 mins; Method Phenomenex LUX C2 250×10 mm, 5 um (2 columns coupled together) Mobile phase: 50% MeOH+0.1% v/v DEA/50% CO2

PREPARATION OF INTERMEDIATES

Intermediate 1A

Racemic mixture of (4R,5S)-2-Methyl-4-phenyl-2,7-diazaspiro[4.5]decan-1-one and (4S,5R)-2-Methyl-4-phenyl-2,7-diazaspiro[4.5]decan-1-one

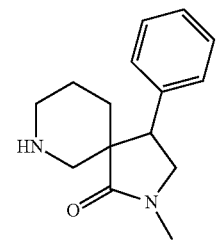 [SMILES: CN1CC(c2ccccc2)C2(CCCNC2)C1=O]

Step 1: Diastereomers of rac-1-tert-butyl 3-ethyl 3-(2-nitro-1-phenylethyl)piperidine-1,3-dicarboxylate To a cooled (−78° C.) solution of diisopropylamine (4.82 ml, 33.8 mmol) in THF (20 ml) was added dropwise 1.6M butyllithium in hexanes (21.13 ml, 33.8 mmol) and the resulting mixture was allowed to warm to 0° C. and then cooled back to −78° C. This mixture was added dropwise to ethyl-1-BOC-3-piperidinecarboxylate (6.18 g, 24 mmol) in THF (20 ml) at −78° C. and stirred at −40° C. for 1 h. The resulting mixture was treated dropwise with a solution of trans-beta-nitrostyrene (3.88 g, 26 mmol) in THF (20 ml) at −40° C. and allowed to warm to RT over 1 h. The reaction was quenched with $NH_4Cl$ solution (200 ml) and extracted with EtOAc (2×200 ml). The combined organic extracts were dried ($MgSO_4$) and concentrated in vacuo. Purification of the crude product by chromatography on silica eluting with 0-24% EtOAc in iso-hexane afforded the individual diastereomers:

Diastereomer 1: LC-MS Rt 2.57 mins; MS m/z 407[M+H]+; Method LowpH_v002

1H NMR (400 MHz, $CDCl_3$) δ 1.30 (3H, t), 1.47 (9H, s), 1.52-1.76 (3H, m), 1.80-1.88 (1H, m), 3.24-3.35 (1H, m), 3.35-3.54 (2H, m), 3.80 (1H, dd), 3.91 (1H, d), 4.14-4.3 (2H, m), 5.0 (1H, t), 5.06 (1H, br s), 7.10-7.17 (2H, m), 7.26-7.37 (3H, m).

Diastereomer 2: LC-MS Rt 2.55 mins; MS m/z 407[M+H]+; Method LowpH_v002.

1H NMR (400 MHz, $CDCl_3$) δ 1.21 (3H, t), 1.35-1.78 (3H, m), 1.43 (9H, s), 2.25 (1H, br d), 2.80-3.10 (2H, m), 3.67-3.78 (2H, m), 3.80-4.22 (3H, m), 4.91 (1H, dd), 5.03 (1H, dd), 7.10-7.18 (2H, m), 7.25-7.36 (3H, m).

Step 2: Racemic mixture of (4R,5S)-1-tert-Butyl 3-ethyl 3-(2-amino-1-phenylethyl)piperidine-1,3-dicarboxylate and (4S,5R)-1-tert-Butyl 3-ethyl 3-(2-amino-1-phenylethyl)piperidine-1,3-dicarboxylate To a racemic mixture of diastereomer 1 (step 1) (3.4 g, 8.36 mmol) in MeOH (50 ml) was added nickel chloride hexahydrate (1.988 g, 8.36 mmol) and the mixture was cooled in an ice bath. Sodium borohydride (3.80 g, 100 mmol) was added and the resulting suspension was stirred and allowed to warm to RT over 1 h. The reaction was quenched with 10% ammonia solution (400 ml) and EtOAc (300 ml) and stirred vigorously at RT until the suspension dissolved to give a purple aqueous solution. The organic solvent was removed and the aqueous portion was extracted with EtOAc (300 ml). The combined organic extracts were dried (MgSO₄) and concentrated in vacuo to afford the title compound which was used without further purification;

LC-MS Rt 1.03 and 1.07 mins; MS m/z 407[M+H]+; Method 2minLC_v003.

Step 3: Racemic mixture of (4R,5S)-tert-Butyl 1-oxo-4-phenyl-2,7-diazaspiro[4.5]decane-7-carboxylate and (4S,5R)-tert-Butyl 1-oxo-4-phenyl-2,7-diazaspiro[4.5]decane-7-carboxylate A racemic mixture of (4R,5S)-1-tert-Butyl 3-ethyl 3-(2-amino-1-phenylethyl)piperidine-1,3-dicarboxylate and (4S,5R)-1-tert-Butyl 3-ethyl 3-(2-amino-1-phenylethyl)piperidine-1,3-dicarboxylate (3.5 g, 8.37 mmol) in toluene (80 ml) was heated at reflux overnight. The resulting mixture was concentrated in vacuo and the residue was purified by chromatography on silica eluting with 0-100% EtOAc in iso-hexane to afford the title compound as a pink solid;

LC-MS Rt 2.46 mins; MS m/z 331 [M+H]+; Method Low-pH_v002

The relative stereochemistry of this compound was determined by X-ray crystallography.

Step 4: Racemic mixture of (4R,5S)-tert-Butyl 2-methyl-1-oxo-4-phenyl-2,7-diazaspiro[4.5]decane-7-carboxylate and (4S,5R)-tert-Butyl 2-methyl-1-oxo-4-phenyl-2,7-diazaspiro[4.5]decane-7-carboxylate To a solution of racemic mixture of (4R,5S)-tert-Butyl 1-oxo-4-phenyl-2,7-diazaspiro[4.5]decane-7-carboxylate and (4S,5R)-tert-Butyl 1-oxo-4-phenyl-2,7-diazaspiro[4.5]decane-7-carboxylate (2.72 g, 8.23 mmol) in THF (80 ml) cooled in an ice/brine bath was added dropwise 1M LHMDS in THF (10.70 ml, 10.70 mmol). After stirring for a few minutes, 2M iodomethane in TBME (6.17 ml, 12.35 mmol) was added. The solution was removed from the ice bath and allowed to warm to RT over 4 hours. The reaction was quenched with water (200 ml) and extracted with EtOAc (2×200 ml). The combined organic extracts were dried (MgSO₄) and concentrated in vacuo. The residue was purified by chromatography on silica eluting with 0-100% EtOAc in iso-hexane to afford the title compound as a white solid;

LC-MS Rt 2.52 mins; MS m/z 345[M+H]+; Method Low-pH_v002

Step 5: Racemic mixture of (4R,5S)-2-Methyl-4-phenyl-2,7-diazaspiro[4.5]decan-1-one and (4S,5R)-2-Methyl-4-phenyl-2,7-diazaspiro[4.5]decan-1-one To a racemic mixture of (4R,5S)-tert-Butyl 2-methyl-1-oxo-4-phenyl-2,7-diazaspiro[4.5]decane-7-carboxylate and (4S,5R)-tert-Butyl 2-methyl-1-oxo-4-phenyl-2,7-diazaspiro[4.5]decane-7-carboxylate (2.24 g, 6.50 mmol) in DCM (40 ml) was added TFA (20 ml, 260 mmol) and the solution was stirred at RT for 1 h. The solvent was removed in vacuo and the residue was dissolved in EtOAc (200 ml) and treated with 2M NaOH (100 ml). The organic portion was separated, dried (MgSO₄) and concentrated in vacuo to afford the title compound;

LC-MS Rt 1.58 mins; MS m/z 245[M+H]+; Method Low-pH_v002

NMR (400 MHz, CDCl₃) δ 1.05-1.15 (1H, m), 1.23-1.34 (1H, m), 1.60-1.76 (2H, m), 2.54 (1H, br s), 2.62 (1H, dt), 2.77 (1H, d), 2.82-2.92 (1H, m), 2.98 (3H, s), 3.02 (1H, d), 3.34 (1H, t), 3.53 (1H, dd), 3.65 (1H, dd), 7.17-7.23 (2H, m), 7.27-7.39 (3H, m).

Intermediate 1AA

Racemic mixture of (4R,5R)-2-Methyl-4-phenyl-2,7-diazaspiro[4.5]decan-1-one and (4S,5S)-2-Methyl-4-phenyl-2,7-diazaspiro[4.5]decan-1-one

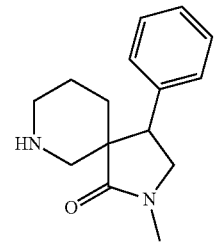 [SMILES: CN1CC(c2ccccc2)C2(CCCNC2)C1=O]

The title compound is prepared analogously to Intermediate 1A but using distereomer 2 produced in step 1 instead of diastereomer 1.

LC-MS Rt 1.52 mins; MS m/z 245[M+H]+; Method Low-pH_v002

NMR (400 MHz, CDCl₃) δ 1.50-1.63 (1H, m), 1.67-1.76 (1H, m), 1.86-2.04 (3H, m), 2.36 (1H, d), 2.57-2.66 (1H, m), 2.78 (1H, d), 2.86 (1H, ddt), 2.98 (3H, s), 3.25 (1H, dd), 3.49 (1H, dd), 3.77 (1H, dd), 7.16-7.23 (2H, m), 7.26-7.38 (3H, m).

Intermediate 1B

Ethyl-4-phenyl-2,7-diazaspiro[4.5]decan-1-one

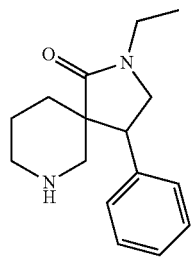 [SMILES: CCN1CC(c2ccccc2)C2(CCCNC2)C1=O]

Step 1: tert-Butyl 2-ethyl-1-oxo-4-phenyl-2,7-diazaspiro[4.5]decane-7-carboxylate tert-Butyl 1-oxo-4-phenyl-2,7-diazaspiro[4,5]decane-7-carboxylate (ASW MedChem) (1 g, 3.03 mmol) was dissolved in THF (20 ml) under an atmosphere of nitrogen. The solution was cooled (ice/brine bath) and treated with sodium hydride (60% in oil) (0.133 g, 3.33 mmol). The reaction mixture was stirred for 10 minutes and iodoethane (0.269 ml, 3.33 mmol) was added dropwise. The ice bath was removed and the reaction mixture was stirred at room temperature overnight. The reaction was quenched with water and extracted with ethyl acetate. The organic phase was washed with brine, dried (MgSO₄) and concentrated in vacuo to afford the title compound. The resulting diastereomeric mixture was used in the next step without further purification.

LC-MS Rt 1.20 and 1.22 mins; MS m/z 359[M+H]+; Method 2minLC_v003.

Step 2: 2-Ethyl-4-phenyl-2,7-diazaspiro[4.5]decan-1-one tert-Butyl 2-ethyl-1-oxo-4-phenyl-2,7-diazaspiro[4.5]decane-7-carboxylate (1.24 g, 3.46 mmol) was dissolved in DCM (15 ml) and 4M HCl in 1,4-dioxane (5 ml, 20.00 mmol) was added. The reaction mixture was stirred at room temperature overnight. The solvent was removed in vacuo and the crude product was dissolved in methanol and loaded onto a pre-wetted 10 g SCX-2 cartridge. Methanol (50 ml) was passed through the cartridge and the product was eluted with 2M NH$_3$ in methanol to afford the title compound as a diastereomeric mixture;

LC-MS Rt 0.74 mins; MS m/z 260[M+H]+; Method 2minLC_v003.

Intermediate 1C

Racemic mixture of (4R,5S)-2-(2,2-Dimethyl-propyl)-4-phenyl-2,7-diaza-spiro[4.5]decan-1-one and (4S,5R)-2-(2,2-Dimethyl-propyl)-4-phenyl-2,7-diaza-spiro[4.5]decan-1-one

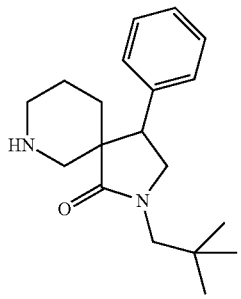 [SMILES: CC(C)(C)CN1CC(c2ccccc2)C2(CCCNC2)C1=O]

Step 1: Racemic mixture of (4R,5S)-2-(2,2-Dimethly-propyl)-1-oxo-4-phenyl-2,7-diaza-spiro[4.5]decane-7-carboxylic acid tert butyl ester and (4S,5R)-2-(2,2-Dimethly-propyl)-1-oxo-4-phenyl-2,7-diaza-spiro[4.5]decane-7-carboxylic acid tert butyl ester A racemic mixture of (4R,5S)-tert-Butyl 1-oxo-4-phenyl-2,7-diazaspiro[4.5]decane-7-carboxylate and (4S,5R)-tert-Butyl 1-oxo-4-phenyl-2,7-diazaspiro[4.5]decane-7-carboxylate (Intermediate 1A, step 3) (500 mg, 1.513 mmol) in DMF (10 ml) was heated at 60° C. Sodium hydride (60% in mineral oil) (91 mg, 2.270 mmol) was added to the heated reaction mixture. The mixture was stirred for a minute, then neopentyl iodide (0.302 ml, 2.270 mmol) was added and the mixture stirred at 60° C. for 3 hours. Sodium hydride (60% in mineral oil) (91 mg, 2.270 mmol) and neopentyl iodide (0.302 ml, 2.270 mmol) were added and the mixture was stirred overnight at 60° C. Sodium hydride (60% in mineral oil) (91 mg, 2.270 mmol) and neopentyl iodide (0.302 ml, 2.270 mmol) were further added. The reaction was stirred at 60° C. for 8 hours. Sodium hydride (60% in mineral oil) (91 mg, 2.270 mmol) and neopentyl iodide (0.302 ml, 2.270 mmol) were added and the mixture was stirred at 70° C. overnight. Reaction was cooled, quenched with water (100 mL) and extracted with EtOAc (100 mL). The organics extracts were combined, washed with water (100 ml), dried (MgSO4), and concentrated in vacuo. Purification of the crude product by chromatography on silica eluting with 0-100% EtOAc in iso-hexane afforded the title compound.

LCMS Rt 2.71 minutes; MS m/z 401[M+H]+; Method LowpH_v002

Step 2: Racemic mixture of (4R,5S)-2-(2,2-Dimethyl-propyl)-4-phenyl-2,7-diaza-spirp[4.5]decane-1-one and (4S,5R)-2-(2,2-Dimethyl-propyl)-4-phenyl-2,7-diaza-spirp[4.5]decane-1-one To a solution of a racemic mixture of (4R,5S)-2-(2,2-Dimethly-propyl)-1-oxo-4-phenyl-2,7-diaza-spiro[4.5]decane-7-carboxylic acid tert butyl ester and (4S,5R)-2-(2,2-Dimethly-propyl)-1-oxo-4-phenyl-2,7-diaza-spiro[4.5]decane-7-carboxylic acid tert butyl ester (518 mg, 1.293 mmol) in DCM (8 ml) was added TFA (4 ml, 51.9 mmol). The resulting solution was stirred at RT for 30 mins. The mixture was concentrated in vacuo, and the residue partitioned between saturated sodium bicarbonate and DCM. The aqueous layer was extracted with DCM. The organics portions were combined, dried (MgSO$_4$), and then concentrated in vacuo to give the title compound.

LCMS Rt 2.02 minutes; MS m/z 301 [M+H]+; Method LowpH_v002.

Intermediate 1D

Racemic mixture of (4R,5S)—N,N-Dimethyl-2-(1-oxo-4-phenyl-2,7-diazaspiro[4.5]decan-2-yl)acetamide and (4S,5R)—N,N-Dimethyl-2-(1-oxo-4-phenyl-2,7-diazaspiro[4.5]decan-2-yl)acetamide

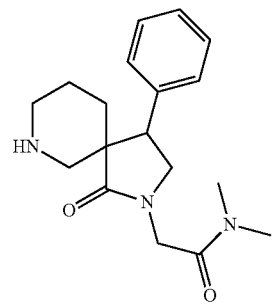 [SMILES: CN(C)C(=O)CN1CC(c2ccccc2)C2(CCCNC2)C1=O]

The title compound is prepared analogously to Intermediate 1A by replacing iodomethane (step 4) with 2-chloro-N,N-dimethylacetamide;

LC-MS Rt 1.62mins; MS m/z 316[M+H]+; Method LowpH_v002

Intermediate 1E

Racemic mixture of (4R,5S)-2-Isobutyl-4-phenyl-2,7-diaza-spiro[4.5]decan-1-one and (4S,5R)-2-Isobutyl-4-phenyl-2,7-diaza-spiro[4.5]decan-1-one

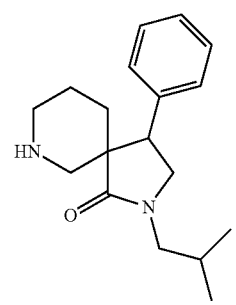 [SMILES: CC(C)CN1CC(c2ccccc2)C2(CCCNC2)C1=O]

Step 1: Racemic mixture of (4R,5S)-2-Isobutyl-1-oxo-4-phenyl-2,7-diaza-spiro[4.5]decane-7-carboxylic acid tert butyl ester and (4S,5R)-2-Isobutyl-1-oxo-4-phenyl-2,7-diaza-spiro[4.5]decane-7-carboxylic acid tert butyl ester To a solution of a racemic mixture of (4R,5S)-tert-Butyl 1-oxo-4-phenyl-2,7-diazaspiro[4.5]decane-7-carboxylate and (4S,5R)-tert-Butyl 1-oxo-4-phenyl-2,7-diazaspiro[4.5]decane-7-carboxylate (Intermediate 1A, step 3) (500 mg, 1.513 mmol) in DMF (10 ml) was added sodium hydride (60% in mineral oil) (91 mg, 2.270 mmol). The reaction mixture was stirred for 10 minutes. 1-Iodo-2-methylpropane (0.264 ml, 2.270 mmol) was added and the mixture heated to 60° C. for 2 hrs. Sodium hydride (60% in mineral oil) (91 mg, 2.270 mmol) was further added and the mixture heated overnight. The following day sodium hydride (60% in mineral oil) (91 mg, 2.270 mmol) was added and the reaction mixture was heated for 1 hour and more sodium hydride (60% in mineral oil) (91 mg, 2.270 mmol) was added. 1-Iodo-2-methylpropane (0.264 ml, 2.270 mmol) was added and the reaction mixture was heated for another hour. The mixture was cooled, diluted with EtOAc (100 mL) and washed with water (100 mL). The organic phase was dried (MgSO$_4$) and concentrated in vacuo. Purification of the crude product by chromatography on silica eluting with 0-100% EtOAc in iso-hexane afforded the title compound.

LCMS Rt 2.66 minutes; MS m/z 387[M+H]+; Method LowpH_v002.

Step 2: Racemic mixture of (4R,5S)-2-Isobutyl-4-phenyl-2,7-diaza-spiro[4.5]decan-1-one and (4S,5R)-2-Isobutyl-4-phenyl-2,7-diaza-spiro[4.5]decan-1-one To a solution of racemic mixture of (4R,5S)-2-Isobutyl-1-oxo-4-phenyl-2,7-diaza-spiro[4.5]decane-7-carboxylic acid tert butyl ester and (4S,5R)-2-Isobutyl-1-oxo-4-phenyl-2,7-diaza-spiro[4.5]decane-7-carboxylic acid tert butyl ester (397 mg, 1.027 mmol) in DCM (6 ml) was added TFA (3 ml, 38.9 mmol). The resulting solution was stirred at RT for 30 mins. The mixture was concentrated in vacuo and partitioned between saturated sodium bicarbonate and DCM. The aqueous layer was further extracted with DCM. The organics portions were combined, dried (MgSO$_4$) and concentrated in vacuo to afford the title compound.

LCMS Rt 1.93 minutes; MS m/z 287[M+H]+; Method LowpH_v002

Intermediate 1F

Racemic mixture of 2-Methyl-4-phenyl-2,3,7-triaza-spiro[4.5]dec-3-en-1-one

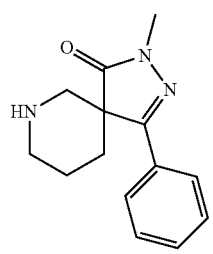 [SMILES: CN1N=C(c2ccccc2)C2(CCCNC2)C1=O]

Step 1: Racemic mixture of 3-benzoyl-piperidine-1,3-dicarboxylic acid 1-tert-butyl ester 3-ethyl ester Piperidine-1,3-dicarboxylic acid 1-tert-butyl ester 3-ethyl ester (Manchester Organics) (3 g, 11.6 mmol) was dissolved in THF (20 ml) and cooled to −78° C. before adding 1M LiHMDS solution in THF (11.6 ml, 11.6 mmol). The reaction was allowed to warm to RT over 30 mins before cooling again to −78° C. Benzoyl chloride (1.5 ml, 12.8 mmol) was added. The reaction mixture was left to warm to RT for 1.5 hrs. The solvent volume was reduced in vacuo before adding EtOAc (20 ml) and washing sequentially with sat. bicarb solution (20 ml), 1M HCl solution (20 ml) and brine (20 ml). The organics portions were dried (MgSO$_4$) and concentrated in vacuo. Purification of the crude product by chromatography on silica eluting with 0-15% EtOAc in iso-hexane afforded the title compound.

LC-MS Rt 2.19 mins; MS m/z 262[M+H]+; Method LowpH_30_v002

Step 2: Racemic mixture of 4-Oxo-1-phenyl-2,3,7-triaza-spiro[4.5]dec-1-ene-7-carboxylic acid tert-butyl ester To a solution of racemic mixture of 3-benzoyl-piperidine-1,3-dicarboxylic acid 1-tert-butyl ester 3-ethyl ester (step 1) (400 mg, 1.1 mmol) in EtOH (4 ml) was added hydrazine hydrate (166 mg, 3.3 mmol). The reaction mixture was stirred at RT for 30 min before heating in the microwave at 120° C. for 3 hours. The reaction mixture was concentrated in vacuo, dissolved in EtOAc (10 ml) and washed with brine (20 ml). The aqueous phase was further washed with EtOAc (10 ml). The organics portions were combined, dried (MgSO$_4$) and concentrated in vacuo. Purification of the crude product by chromatography on silica eluting with 0-60% EtOAc in iso-hexane afforded the title compound.

LCMS: Rt 1.95 min; MS m/z 330 [M+H]+; Method: LowpH_30_v002

Step 3: Racemic mixture of 3-Methyl-4-oxo-1-phenyl-2,3,7-triaza-spiro[4.5]dec-1-ene-7-carboxylic acid tert-butyl ester To a solution of racemic mixture of 4-Oxo-1-phenyl-2,3,7-triaza-spiro[4.5]dec-1-ene-7-carboxylic acid tert-butyl ester (150 mg, 0.45 mmol) in THF (3 ml) under nitrogen at −78° C. was added 1M LiHMDS solution in THF (0.55 ml, 0.55 mol). The reaction mixture was allowed to warm to RT for 30 mins before cooling back to −78° C. and adding 2M MeI in THF solution (0.45 ml, 0.9 mmol). The reaction mixture was left to warm to RT overnight. The mixture was diluted with EtOAc (10 ml) and washed with brine (20 ml). The aqueous phase was extracted with a further EtOAc (10 ml). The organics portions were combined, dried (MgSO$_4$) and concentrated in vacuo. Purification of the crude product by chromatography on silica eluting with 0-50% EtOAc in iso-hexane afforded the title compound.

LCMS Rt 2.11 min; MS m/z 344 [M+H]+; Method: LowpH_30_v002

Step 4: Racemic mixture of 2-Methyl-4-phenyl-2,3,7-triaza-spiro[4.5]dec-3-en-1-one To a solution of a racemic mixture of 3-Methyl-4-oxo-1-phenyl-2,3,7-triaza-spiro[4.5]dec-1-ene-7-carboxylic acid tert-butyl ester (110 mg, 0.32 mmol) in DCM (5 ml) was added TFA (0.5 ml). The reaction mixture was stirred at RT for 1 hour. The reaction mixture was applied to a 1 g SCX-2 cartridge. The impurities were eluted with 1:1 DCM:MeOH, followed by 0.05M ammonia in 1:1 DCM:MeOH. The product was eluted with 1M ammonia in 1:1 DCM:MeOH and the clean fractions were concentrated in vacuo to afford the title compound. No further purification was performed on the title compound.

LCMS: Rt 1.54 min; MS m/z 244 [M+H]+; Method: LowpH_v002.

Intermediate 1G

Racemic mixture of 3-Methyl-1-phenyl-1,3,7-triaza-spiro[4.5]decan-4-one

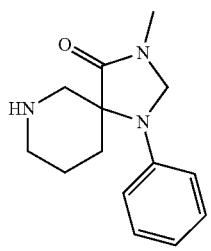 [SMILES: CN1CN(c2ccccc2)C2(CCCNC2)C1=O]

Step 1: Racemic mixture of 3-Cyano-3-phenylamino-piperidine-1-carboxylic acid tert-butyl ester A solution comprising of 3-Oxo-piperidine-1-carboxylic acid tert-butyl ester (2.5 g, 12.55 mol) and aniline (1.28 g, 13.8 mmol) in acetic acid (10 ml) was stirred at RT for 60 mins under nitrogen. Trimethylsilyl cyanide (1.57 ml, 12.55 mmol) was added carefully into the reaction mixture. The reaction mixture was left to stir at RT for a further 90 mins. The reaction mixture was cannulated into a rapidly stirring flask containing crushed ice (50 ml) and concentrated ammonium hydroxide (30 ml) for 10 minutes, resulting in a precipitate. This solution was allowed to stir for a further 15 mins to ensure no HCN remained before adding EtOAc (150 ml) to dissolve the precipitate. The organics were then separated and the aqueous washed with a further EtOAc (50 ml). The organics portions were combined, washed with brine (100 ml), dried (MgSO$_4$) and concentrated in vacuo to afford an oil. Purification of the crude product by chromatography on silica eluting with 0-50% EtOAc in iso-hexane afforded the title compound.

LCMS: Rt 1.97 min; MS m/z 302 [M+H]+; Method: LowpH_30_v002

Step 2: Racemic mixture of 3-Carbamoyl-3-phenylamino-piperidine-1-carboxylic acid tert-butyl ester To a solution of 3-cyano-3-phenylamino-piperidine-1-carboxylic acid tert-butyl ester (1.1 g, 3.65 mmol) in DMSO (10 ml) was added potassium carbonate (76 mg, 0.54 mmol) and hydrogen peroxide (35% in water solution) (0.73 ml, 8.4 mmol). The reaction mixture was stirred at RT overnight. Further portions of potassium carbonate (76 mg, 0.54 mmol) and hydrogen peroxide (35% in water solution) (0.73 ml, 8.4 mmol) were added and stirring continued for 24 hrs. The mixture was diluted with EtOAc (10 ml) and washed with brine (30 ml). The organics were separated and the aqueous was extracted with EtOAc (10 mL). The combined organic extracts were dried (MgSO$_4$) and concentrated in vacuo. Purification of the crude product by chromatography on silica eluting with 0-50% EtOAc in iso-hexane afforded the title compound.

LCMS: Rt 1.82 min; MS m/z 320 [M+H]+; Method: LowpH_30_v002

Step 3: Racemic mixture of 4-Oxo-1-phenyl-1,3,7-triaza-spiro[4.5]dec-2-ene-7-carboxylic acid tert-butyl ester To a solution of 3-carbamoyl-3-phenylamino-piperidine-1-carboxylic acid tert-butyl ester (300 mg, 0.94 mmol) in toluene (10 ml) was added triethyl orthoformate (0.47 ml, 2.8 mmol) and acetic acid (0.5 ml, 8.7 mmol). The mixture was heated at reflux overnight. The reaction mixture was cooled and washed with a saturated solution of sodium bicarbonate (25 ml). The organics were separated and the aqueous extracted with EtOAc (10 ml). The organics portions were combined, dried (MgSO$_4$) and concentrated in vacuo to afford an oil. Purification of the crude product by chromatography on silica eluting with 0-50% EtOAc in iso-hexane afforded the title compound.

LCMS: Rt 1.60 min; MS m/z 330 [M+H]+; Method: LowpH_30_v002

Step 4: Racemic mixture of 4-oxo-1-phenyl-1,3,7-triaza-spiro[4.5]decane-7-carboxylic acid tert-butyl ester To a solution of 4-oxo-1-phenyl-1,3,7-triaza-spiro[4.5]dec-2-ene-7-carboxylic acid tert-butyl ester (130 mg, 0.39 mmol) in methanol (3 ml) was added sodium borohydride (22 mg, 0.59 mmol). The reaction mixture was stirred at RT for 1 hour. The reaction mixture was concentrated in vacuo. The residue was dissolved with EtOAc (5 ml) and washed with a saturated solution of sodium bicarbonate (10 ml). The aqueous phase was extracted with further EtOAc (5 ml). The organics portions were combined, dried (MgSO$_4$) and concentrated in vacuo to afford an oil. Purification of the crude product by chromatography on silica eluting with 0-50% EtOAc in iso-hexane afforded the title compound.

LCMS: Rt 2.06 min; MS m/z 332 [M+H]+; Method: LowpH_30_v002

Step 5: Racemic mixture of 3-Methyl-4-oxo-1-phenyl-1,3,7-triaza-spiro[4.5]decane-7-carboxylic acid tert-butyl ester A solution of 4-oxo-1-phenyl-1,3,7-triaza-spiro[4.5]decane-7-carboxylic acid tert-butyl ester (130 mg, 0.45 mmol) in dry THF (3 ml) under nitrogen was cooled to −78° C. and treated with 1M LHMDS in THF (0.55 ml, 0.55 mol). The reaction was allowed to warm to RT for 30 mins before cooling back to −78° C. and adding 2M MeI in THF solution (0.45 ml, 0.9 mmol). The reaction was left to warm to RT overnight. The reaction mixture was diluted with EtOAc (10 ml) and washed with brine (20 ml). The aqueous phase was extracted with EtOAc (10 ml). Organics portions were combined, dried (MgSO$_4$) and concentrated in vacuo. Purification of the crude product by chromatography on silica eluting with 0-50% EtOAc in iso-hexane afforded the title compound.

LCMS: Rt 2.10 min; MS m/z 346 [M+H]+; Method: LowpH_30_v002

Step 6: Racemic mixture of 3-methyl-1-phenyl-1,3,7-triaza-spiro[4.5]decan-4-one

To a solution of 3-methyl-4-oxo-1-phenyl-1,3,7-triaza-spiro[4.5]decane-7-carboxylic acid tert-butyl ester (70 mg, 0.2 mmol) in DCM (5 ml) was added TFA (0.5 ml, 6.5 mmol). The reaction mixture was stirred at RT for 1 hour before applying the reaction mixture to a 1 g SCX-2 cartridge. Impurities were eluted with 1:1 DCM:MeOH, followed by 0.05 M ammonia in 1:1 DCM:MeOH. Product was eluted with 1M ammonia in 1:1 DCM:MeOH. The clean fractions were concentrated in vacuo to afford the title compound. No further purification was performed on the title compound.

LCMS: Rt 1.47 min; MS m/z 246 [M+H]+; Method: LowpH_v002

Intermediate 1H

Diastereomers of 2-Methyl-4-pyridin-3-yl-2,7-diaza-spiro[4.5]decan-1-one

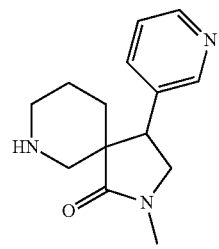 [SMILES: CN1CC(c2cccnc2)C2(CCCNC2)C1=O]

Step 1: 3-(2-Nitro-1-pyridin-3-yl-ethyl)-piperidine-1,3-dicarboxylic acid 1-tert-butyl ester 3-ethyl ester (mixture of four stereoisomers)

To a cooled (−78° C.) solution of ethyl-1-BOC-3-piperidinecarboxylate (1.53 g, 10.20 mmol) in THF (15 ml) was added dropwise 2M LDA in heptane, THF, and ethylbenzene (5.34 ml, 10.69 mmol) and the resulting mixture was allowed to warm to −40° C. over 1 h and then cooled back to −78° C. A solution of 3-(2-nitroethenyl)pyridine (1.53 g, 10.20 mmol) in DMF (5 ml) was added dropwise and the reaction mixture was allowed to warm to RT over 1 h. The reaction was quenched with NH$_4$Cl saturated aqueous solution (50 ml) and extracted with EtOAc (200 ml). The combined organic extracts were dried (MgSO$_4$) and concentrated in vacuo. Purification of the crude product by chromatography on silica eluting with 0-10% MeOH in DCM afforded the title compounds as a yellow oil.

LC-MS Rt 0.98 mins; MS m/z 408.2 [M+H]+; Method 2minLC_v003.

Step 2: 3-(2-Amino-1-pyridin-3-yl-ethyl)-piperidine-1,3-dicarboxylic acid 1-tert-butyl ester 3-ethyl ester (mixture of four stereoisomers)

To a solution of 3-(2-Nitro-1-pyridin-3-yl-ethyl)piperidine-1,3-dicarboxylic acid 1-tert-butyl ester 3-ethyl ester (2.92 g, 7.17 mmol) in MeOH (60 ml) was added nickel chloride hexahydrate (1.70 g, 7.17 mmol) and the mixture was cooled in an ice bath. Sodium borohydride (1.08 g, 28.7 mmol) was portionwise added over 30 minutes and the resulting suspension was stirred for further 30 minutes at 0° C. The reaction was quenched with saturated NH$_4$Cl solution (30 ml) and MeOH was removed in vacuo. The aqueous residue was extracted with EtOAc (2×50 ml) and DCM (2×50 ml). The combined organic extracts were dried (MgSO$_4$) and concentrated in vacuo to afford the title compound which was used without further purification.

LC-MS Rt 0.84 mins; MS m/z 378.2 [M+H]+; Method 2minLC_v003.

Step 3: Diastereomers of 1-Oxo-4-pyridin-3-yl-2,7-diaza-spiro[4.5]decane-7-carboxylic acid tert-butyl ester A solution of 3-(2-Amino-1-pyridin-3-yl-ethyl)-piperidine-1,3-dicarboxylic acid 1-tert-butyl ester 3-ethyl ester (2.5 g, 6.6 mmol) in toluene (21 ml) was heated at reflux overnight. The resulting mixture was concentrated in vacuo and the residue was purified by chromatography on silica eluting with 0-10% MeOH in DCM to afford the individual diastereomers as white solids:

Diastereomer 1 [racemic mixture], first eluting compound.
LC-MS Rt 0.77 mins; MS m/z 332.3 [M+H]+; Method 2minLC_v003.

Diastereomer 2 [racemic mixture], second eluting compound.
LC-MS Rt 0.74 mins; MS m/z 332.3 [M+H]+; Method 2minLC_v003.

Step 4: Racemic mixture of 2-Methyl-1-oxo-4-pyridin-3-yl-2,7-diaza-spiro[4.5]decane-7-carboxylic acid tert-butyl ester (from Diastereomer 1)

To a cooled (−60° C.) solution of 1-oxo-4-pyridin-3-yl-2,7-diaza-spiro[4.5]decane-7-carboxylic acid tert-butyl ester (diastereomer 1) (343 mg, 1.03 mmol) in THF (7 ml) was added dropwise 1M LHMDS in THF (1.34 ml, 1.34 mmol). After stirring for 1 h at −60° C., iodomethane (0.084 ml, 1.34 mmol) in THF (1 ml) was added. The cooling bath was removed and the reaction mixture was allowed to warm to RT and stirred for 3 h. A further portion of 1M LHMDS in THF (0.75 ml, 0.75 mmol) was added to the cooled (−60° C.) reaction mixture. After 30 minutes, iodomethane (0.042 ml, 0.67 mmol) in THF (0.5 ml) was added, the cooling bath was removed and the reaction mixture was allowed to warm to RT and stirred overnight. The reaction was quenched with NH$_4$Cl saturated solution (5 ml) and extracted with EtOAc (2×25 ml). The combined organic extracts were dried (MgSO$_4$) and concentrated in vacuo. Purification of the crude product by chromatography on silica eluting with 0-5% MeOH in DCM afforded the title compound as a yellow oil.

LC-MS Rt 1.84 mins; MS m/z 346.2 [M+H]+; Method 10minLC_v003.

Step 5: Racemic mixture of 2-Methyl-4-pyridin-3-yl-2,7-diaza-spiro[4.5]decan-1-one (from Diastereomer 1)

A solution of 2-Methyl-1-oxo-4-pyridin-3-yl-2,7-diaza-spiro[4.5]decane-7-carboxylic acid tert-butyl ester [from diastereomer 1] (200 mg, 0.58 mmol) in DCM (5 ml) was cooled with an ice bath and TFA (0.70 ml, 8.68 mmol) was added. The resulting solution was stirred for 3 h at 0° C. The reaction mixture was diluted with DCM (20 ml) and quenched at 0° C. with 2M NaOH solution (8 ml). The organic phase was separated, washed with brine (5 ml), dried (MgSO$_4$) and concentrated in vacuo to afford the title compound as a yellow oil.

LC-MS Rt 0.37 mins (broad); MS m/z 246.2 [M+H]+; Method 2minLC_v003.

Intermediate 1I

Racemic 4-(4-Fluorophenyl)-2-(5-methylisoxazol-3-yl)methyl)-2,7-diazaspiro[4.5]decan-1-one

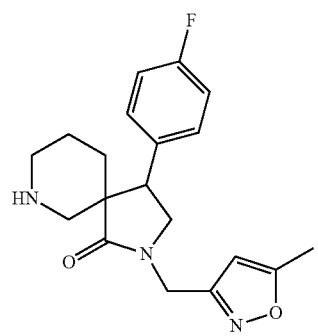 [SMILES: Cc1cc(CN2CC(c3ccc(F)cc3)C3(CCCNC3)C2=O)no1]

Step 1: tert-butyl 4-(4-fluorophenyl)-2-((5-methylisoxazol-3-yl)methyl)-1-oxo-2,7-diazaspiro[4.5]decane-7-carboxylate.

Tert-butyl 4-(4-fluorophenyl)-1-oxo-2,7-diazaspiro[4.5]decane-7-carboxylate (200 mg; 0.574 mmol) was solubilised in DMF (5 ml) and cooled to 0° C. 60% Sodium hydride dispersion in mineral oil (46 mg, 1.148 mmol) was added and the mixture stirred at 0° C. for 45 minutes. 3-(Bromomethyl)-5-methylisoxazole (101 mg; 0.574 mmol) was solubilised in DMF (0.7 ml) and added. The reaction was stirred at 0° C. for 30 minutes then warmed to RT for 3 hr. The mixture was quenched with water and extracted with EtOAc. The organics were combined and washed with brine and dried over magnesium sulphate, filtered and concentrated in vacuo. The resultant oil was purified by chromatography on silica eluting with 50-100% TBME in iso-hexane to yield tert-butyl 4-(4-fluorophenyl)-2-((5-methylisoxazol-3-yl)methyl)-1-oxo-2,7-diazaspiro[4.5]decane-7-carboxylate.

LC-MS Rt 1.16 mins; MS m/z 446.3[M+2H]+; Method 2minLowpH.

Step 2: 4-(4-Fluorophenyl)-2-((5-methylisoxazol-3-yl)methyl)-2,7-diazaspiro[4.5]decan-1-one Tert-butyl 4-(4-fluorophenyl)-2-((5-methylisoxazol-3-yl)methyl)-1-oxo-2,7-diazaspiro[4.5]decane-7-carboxylate (243.6 mg; 0.549 mmol) was solubilised in DCM (1 ml). Trifluoroacetic acid (0.86 ml; 11.14 mmol) was added and the mixture stirred at RT for 20 minutes before being concentrated in vacuo. The oil was dissolved with methanol (5 ml) and passed through a 10 g SCX-2 cartridge eluting with 2M NH3 in methanol (50 ml) and concentrated in vacuo to yield the title compound.

LC-MS Rt 0.63 mins; MS m/z 345.4 [M+2H]+; Method 2minLowpH.

Intermediate 1J

Racemic 4-(4-Fluorophenyl)-2-(oxazol-2-ylmethyl)-2,7-diazaspiro[4.5]decan-1-one

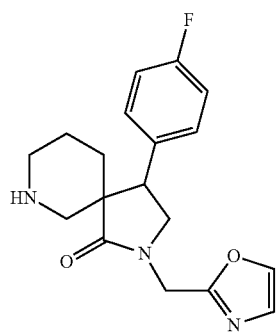 [SMILES: O=C1N(Cc2ncco2)CC(c2ccc(F)cc2)C12CCCNC2]

Step 1: Tert-butyl 4-(4-fluorophenyl)-1-oxo-2,7-diazaspiro[4.5]decane-7-carboxylate (226 mg; 0.649 mmol) was solubilised in DMF (6.5 ml) and cooled in an ice bath. 60% NaH dispersion (78 mg; 1.95 mmol) was added and the mixture stirred for 50 minutes. 2-(Chloromethyl)oxazole (79 ul; 0.649 mmol) was added and the mixture allowed to warm to RT overnight. The solution was quenched with water and extracted with EtOAc; organics were combined and dried (MgSO4), then concentrated in vacuo. The residue was purified by silica chromatography, using a gradient solvent system of 1-10% MeOH with ammonia in DCM. The appropriate fractions were combined and concentrated to give tert-butyl 4-(4-fluorophenyl)-2-(oxazol-2-ylmethyl)-1-oxo-2,7-diazaspiro[4.5]decane-7-carboxylate (148 mg).

LCMS Method 2minLowpH, Rt 1.10 mins, MS m/z 430.3 [M+H]+

Step 2: Tert-butyl 4-(4-fluorophenyl)-2-(oxazol-2-ylmethyl)-1-oxo-2,7-diazaspiro[4.5]decane-7-carboxylate (148 mg; 0.345 mmol) was solubilised in 1 ml DCM. TFA (670 ul; 8.61 mmol) was added and the solution stirred at RT. After 20 minutes, the mixture was concentrated and the residue solubilised in minimal MeOH. This was applied to a 10 g SCX2 cartridge, which was eluted with methanol, then 3× column volumes of 2M ammonia in MeOH. The amonniacal fractions were concentrated to give the title compound.

LCMS Method 2minLowpH, Rt 0.57 mins, MS m/z 331.4 [M+2H]+

Intermediate 1K

Racemic 4-Phenyl-2-(2,2,2-trifluoroethyl)-2,7-diazaspiro[4.5]decan-1-one hydrochloride

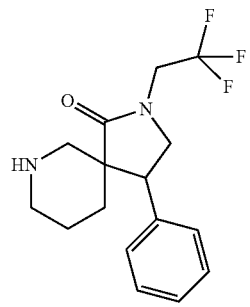 [SMILES: O=C1N(CC(F)(F)F)CC(c2ccccc2)C12CCCNC2]

Step 1: tert-Butyl 1-oxo-4-phenyl-2-(2,2,2-trifluoroethyl)-2,7-diazaspiro[4.5]decane-7-carboxylate Tert-butyl 1-oxo-4-phenyl-2,7-diazaspiro[4.5]decane-7-carboxylate (1 g, 3.03 mmol) in THF (13 ml) cooled to 0° C. was treated with sodium hydride (60% in oil) (4.54 mmol, 0.182 g). The reaction mixture was stirred at 0° C. for 5 minutes and stirred at room temperature for 1 hour. The reaction mixture was cooled back down to 0° C. and treated dropwise with 1,1,1-trifluoroethyl trichloromethanesulfonate (0.547 ml, 3.33 mmol) in THF (2 ml). The reaction mixture was stirred at room temperature for 9 hours. The reaction was quenched with water and extracted with EtOAc. The organic portion was dried (MgSO4) and concentrated in vacuo. The crude product was purified by silica chromatography, eluting with 0-20% ethyl acetate/iso-hexane. The relevant fractions were combined and concentrated in vacuo to give tert-butyl 1-oxo-4-phenyl-2-(2,2,2-trifluoroethyl)-2,7-diazaspiro[4.5] decane-7-carboxylate.

LC-MS Rt 1.19 mins; MS m/z No ionisation Method 2min-LowpH $^1$H NMR (CDCl3, 400 MHz) 7.31 (3H, m), 7.14 (2H, d), 4.05 (4H, m), 3.56 (1H, m), 3.43 (1H, m), 2.95 (1H, m), 2.85 (1H, m), 1.79 (1H, m), 1.55 (9H,$), 1.38 (2H, m), 1.18 (1H, m)

Step 2: Racemic 4-Phenyl-2-(2,2,2-trifluoroethyl)-2,7-diazaspiro[4.5]decan-1-one hydrochloride Tert-butyl 1-oxo-4-phenyl-2-(2,2,2-trifluoroethyl)-2,7-diazaspiro[4.5]decane-7-carboxylate (0.874 g, 2.119 mmol) in DCM (10 ml) was treated with 4M HCl in 1,4-dioxane (4.5 ml, 0.018 mmol). The reaction mixture was stirred at room temperature for 9 hours. The solvent was removed in vacuo to give the title compound.

LC-MS Rt 0.63 mins; MS m/z 313.3 [M+H]+Method 2minLowpH

Intermediate 1L

Racemic
2-Methyl-4-p-tolyl-2,7-diazaspiro[4.5]decan-1-one

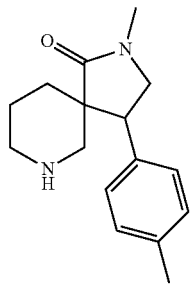 [SMILES: Cc1ccc(C2CN(C)C(=O)C23CCCNC3)cc1]

Step 1: Tert-butyl 1-oxo-4-p-tolyl-2,7-diazaspiro[4.5]decane-7-carboxylate

To a mixture of 4-p-tolyl-2,7-diazaspiro[4.5]decan-1-one hydrochloride (1.00 g, 3.56 mmol) in DCM under nitrogen with ice cooling was added triethylamine (685 ul, 4.91 mmol) followed by di-tert-butyl dicarbonate (1.07 g, 4.91 mmol) and the reaction mixture was left to stir allowing to warm to room temperature overnight. The reaction mixture was concentrated under reduced pressure to give a white waxy solid (2.06 g). The crude material was purified via silica chromatography eluting with 0-100% iso-hexane/EtOAc. The most lipophilic fractions were concentrated under reduced pressure to give a white solid (333 mg), LC-MS: Method 10minLC_v003; Rt 4.03 min; MS m/z 289.2 [M+H-tBu]+

Step 2: Tert-butyl 2-methyl-1-oxo-4-p-tolyl-2,7-diazaspiro[4.5]decane-7-carboxylate To a stirred solution of tert-butyl 1-oxo-4-p-tolyl-2,7-diazaspiro[4.5]decane-7-carboxylate (333 mg, 0.967 mmol) in dry THF (6 ml) at −60° C. under nitrogen was added LiHMDS 1M in THF (1.26 ml, 1.257 mmol) dropwise and the mixture was left to stir at −60° C. for 1 hr. After this time a solution of iodomethane (79 ul, 1.257 mmol) in dry THF (1 ml) was added dropwise at −60° C. and the reaction mixture was allowed to warm from −60° C. to room temperature over 1 hr. After a further 3 hrs at room temperature the reaction mixture was added to sat. ammonium chloride (25 ml), extracted with EtOAc (3×25 ml) and the combined organics were washed with brine (25 ml), dried (MgSO$_4$) and concentrated under reduced pressure to give the crude product as an orange oil. The crude material was purified via silica chromatography eluting with 20-80% iso-hexane/EtOAc. The appropriate fractions were combined and concentrated to give the product as a yellow solid (270 mg).

LC-MS: Method 2minLC_v003; Rt 1.23 min; MS m/z 359.3 [M+H]+

Step 3: 2-Methyl-4-p-tolyl-2,7-diazaspiro[4.5]decan-1-one

To a stirred solution of tert-butyl 2-methyl-1-oxo-4-p-tolyl-2,7-diazaspiro[4.5]decane-7-carboxylate (270 mg, 0.753 mmol) in DCM (5 ml) at 5° C. was added TFA (870 ul, 11.30 mmol) and the reaction mixture was left to stir at 5-10° C. for 1 hr. The reaction mixture was added to 2M NaOH (5 ml) and extracted with DCM (3×5 ml). The organics were combined, washed with brine (5 ml), dried (MgSO4) and concentrated to give the crude product as a white solid (176 mg).

LC-MS: Method 10minLC_v003; Rt 2.08 min; MS m/z 259.5 [M+H]+.

Intermediate 2A

2-Methyl-3-phenyl-2,6-diazaspiro[3.5]nonan-1-one

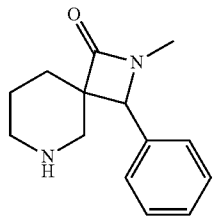 [SMILES: CN1C(=O)C2(CCCNC2)C1c1ccccc1]

Step 1: rac-tert-Butyl 1-oxo-3-phenyl-2,6-diazaspiro[3.5]nonane-6-carboxylate

A solution of 2M LDA in THF/n-heptane/ethylbenzene (10.7 ml, 21.37 mmol) was cooled to −78° C. and a solution of 1-tert-butyl 3-ethyl piperidine-1,3-dicarboxylate (5 g, 19.43 mmol) in THF (5 mL) was added dropwise. The mixture was stirred for 40 minutes and allowed to warm to 0° C. for 10 minutes and cooled again to −78° C. N-benzylidene-1,1,1-trimethylsilanamine (2.63 ml, 21.37 mmol) was added and the mixture was left to stir for 3 h at 0° C. The reaction was quenched with water (5 ml) and the resulting solution was extracted using ethyl acetate. The organic portion was separated, dried (MgSO$_4$) and concentrated in vacuo to yield a yellow oil. Purification by flash chromatography on silica (220 g column) eluting with 20-70% EtOAc in iso-hexane afforded the title compound;

LC-MS Rt 2.33 mins; MS m/z 317 [M+H]+; Method LowpH_v002

Step 2: rac-tert-Butyl 2-methyl-1-oxo-3-phenyl-2,6-diazaspiro[3.5]nonane-6-carboxylate A stirred solution of rac-tert-butyl 1-oxo-3-phenyl-2,6-diazaspiro[3.5]nonane-6-carboxylate (1.18 g, 3.73 mmol) in DMF (20 ml) was cooled to 0° C. and treated with NaH (194 mg, 4.85 mmol) followed by iodomethane (303 ul, 4.85 mmol). The mixture was left to warm to room temperature. After 5 hours, the reaction was quenched with water and extracted with ethyl acetate. The organic layer was separated and washed with brine, dried (MgSO$_4$) and concentrated in vacuo to yield a the title compound as a yellow oil;

LC-MS Rt 2.39 mins; MS m/z 331 [M+H]+; Method LowpH_v002

Step 3: rac-2-Methyl-3-phenyl-2,6-diazaspiro[3.5]nonan-1-one

A solution comprising tert-butyl 2-methyl-1-oxo-3-phenyl-2,6-diazaspiro[3.5]nonane-6-carboxylate (1.2 g, 3.63 mmol) and TFA (1.399 ml, 18.16 mmol) in DCM (20 ml) was stirred at RT for 4 days. The reaction mixture was concentrated in vacuo and the resulting crude product was dissolved with methanol (5 ml) and passed through a 10 g SCX-2 cartridge. The product was eluted with 2M NH$_3$ in methanol (70 ml) and the relevant fractions were combined and concentrated in vacuo to afford the title compound as a yellow oil;

LC-MS Rt 0.73 mins; MS m/z 232 [M+H]+; Method Low-pH_v002

Intermediate 2B 3-(4-Fluoro-phenyl)-2-methyl-2,6-diaza-spiro[3.5]nonan-1-one

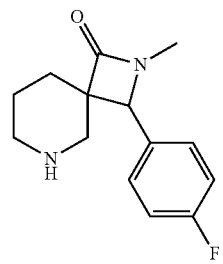 [SMILES: CN1C(=O)C2(CCCNC2)C1c1ccc(F)cc1]

Step 1: rac-1-(4-Fluoro-phenyl)-3-oxo-2,6-diaza-spiro[3.5]nonane-6-carboxylic acid tert-butyl ester A solution of 1M LHMDS (8.55 mL, 8.55 mmol) in THF was cooled to −78° C. and to this mixture 4-fluorobenzaldehyde (839 ul, 7.77 mmol) in THF (25 mL) was added dropwise. The mixture was left to stir for 50 minutes and allowed to warm to 0° C. for 10 minutes and cooled again to −78° C. In a different flask a solution of 1M LHMDS (8.55 mL, 8.55 mmol) was cooled to −78° C. and a solution of piperidine-1,3-dicarboxylic acid 1-tert-butyl ester 3-ethyl ester (2 g, 7.77 mmol) in THF (25 mL) was added dropwise. The mixture was left to stir for 40 minutes and allowed to warm to 0° C. for 10 minutes and cooled again to −78° C. The solution of trimethylsilylenamine was added dropwise to the solution of enolate maintaining the temperature below 0° C. After the addition was complete, the reaction was left to stir for 3 hours at 0° C. and allowed to warm to room temperature overnight. The reaction was quenched with water (5 ml) and the resulting solution was extracted using ethyl acetate. The organic portion was separated, dried (MgSO$_4$) and concentrated in vacuo to yield a yellow oil. Purification by flash chromatography on silica (80 g column) eluting with 0-100% EtOAc in isohexane afforded the title compound;

LC-MS Rt 2.44 mins; MS m/z 335 [M+H]+; Method Low-pH_v002

Step 2: rac-1-(4-Fluoro-phenyl)-2-methyl-3-oxo-2,6-diaza-spiro[3.5]nonane-6-carboxylic acid tert-butyl ester A stirred solution of rac-1-(4-Fluoro-phenyl)-3-oxo-2,6-diaza-spiro[3.5]nonane-6-carboxylic acid tert-butyl ester (850 mg, 2.54 mmol) in THF (15 ml) was treated with 1M LHMDS in THF (3.30 ml, 3.30 mmol) followed by the addition of iodomethane (0.238 ml, 3.81 mmol). The solution was stirred at RT. After 4 hours, the reaction was quenched with water (30 mL) and extracted with ethyl acetate. The organic layer was separated, dried (MgSO$_4$) and concentrated in vacuo to yield the title compound as a yellow oil;

LC-MS Rt 0.98 mins; MS m/z 349 [M+H]+; Method 2min-LC_v003

Step 3: rac-3-(4-Fluoro-phenyl)-2-methyl-2,6-diaza-spiro[3.5]nonan-1-one

A solution comprising of rac-1-(4-Fluoro-phenyl)-2-methyl-3-oxo-2,6-diaza-spiro[3.5]nonane-6-carboxylic acid tert-butyl ester (830 mg, 2.38 mmol) and TFA (1 ml, 12.98 mmol) in DCM (15 ml) was stirred at RT overnight. The reaction mixture was concentrated in vacuo and the resulting crude product was dissolved with ethyl acetate and washed with a saturated solution of sodium bicarbonate. The organic layer was separated, dried (MgSO$_4$) and concentrated in vacuo to yield a the title compound as a yellow oil;

LC-MS Rt 1.66 mins; MS m/z 249 [M+H]+; Method Low-pH_v002

Intermediate 3A (R)-3-Benzyloxy-2-(2-tert-butoxycarbonylamino-2-methylpropionylamino)-propionic acid

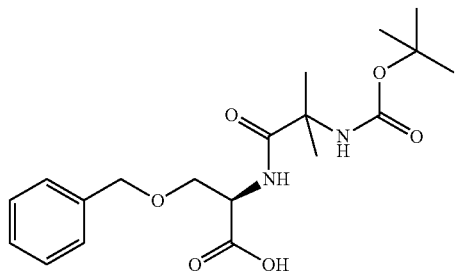 [SMILES: CC(C)(C)OC(=O)NC(C)(C)C(=O)N[C@H](COCc1ccccc1)C(=O)O]

The title compound was prepared according to the procedure described in WO 98/58949 page 88.

Intermediate 3B (R)-3-Benzyloxy-2-[2-(tert-butoxycarbonyl-methyl-amino)-2-methyl-propionylamino]-propionic acid

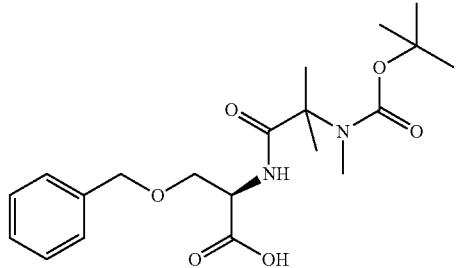 [SMILES: CN(C(=O)OC(C)(C)C)C(C)(C)C(=O)N[C@H](COCc1ccccc1)C(=O)O]

The title compound was prepared according to the procedure described in WO99/08699 page 379

Intermediate 3C (R)-2-(2-(tert-Butoxycarbonylamino)-2-methylpropanamido)-3-(1H-indol-3-yl)propanoic acid

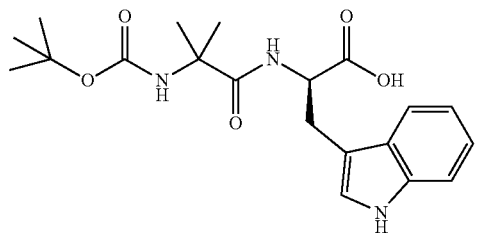 [SMILES: CC(C)(C)OC(=O)NC(C)(C)C(=O)N[C@H](Cc1c[nH]c2ccccc12)C(=O)O]

The title compound was prepared according to the procedure described in WO 98/58949 page 70.

Intermediate 3D (R)-2-(2-(tert-Butoxycarbonylamino)-2-methylpropanamido)-3-(1-methyl-1H-indol-3-yl)propanoic acid

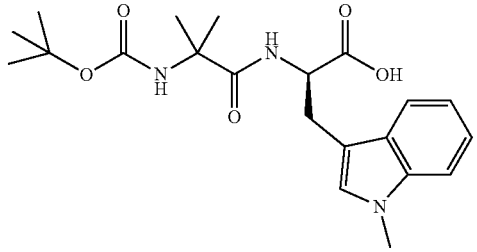 [SMILES: Cn1cc(C[C@@H](NC(=O)C(C)(C)NC(=O)OC(C)(C)C)C(=O)O)c2ccccc21]

The title compound was prepared according to the procedure described in WO 96/38471 page 117.

Intermediate 3E (R)-2-(2-(tert-Butoxycarbonylamino)-2-methylpropanamido)-4-phenylbutanoic acid

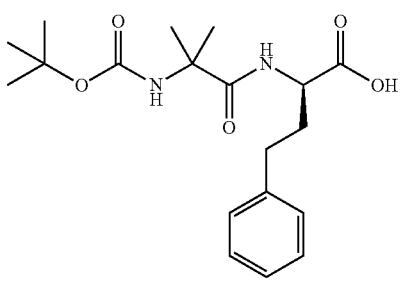 [SMILES: CC(C)(C)OC(=O)NC(C)(C)C(=O)N[C@H](CCc1ccccc1)C(=O)O]

A mixture comprising of tert-Butyl 1-(2,5-dioxopyrrolidin-1-yl)-2-methyl-1-oxopropan-2-ylcarbamate (1 g, 3.52 mmol) (prepared according to the procedure described in EP1486498A1 page 20) and H-D-Homophe-OH (0.630 g, 3.52 mmol) in THF (16 ml)/water (4 ml) was treated with triethylamine (1.471 ml, 10.55 mmol). The reaction mixture was stirred at 50° C. for 9 hours. THF was removed in vacuo. The aqueous solution was further diluted with water and the pH adjusted to pH 2-3 using 1M HCl. The resulting aqueous phase was extracted with EtOAc. The organic portion was dried (MgSO$_4$) and concentrated in vacuo to afford the title compound.

LC-MS Rt 1.05 mins; MS m/z 365.3 [M+H]+; Method 2minLC_v003.

Intermediate 3F (R)-2-(2-(tert-butoxycarbonylamino)-2-methylpropanamido)-5-phenylpentanoic acid

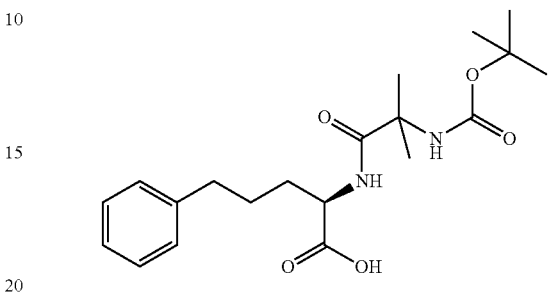

The title compound was prepared according to the procedure described in Example 6 of WO/03087036 page 11.

Intermediate 3G (2R,3S)-3-(Benzyloxy)-2-(2-(tert-butoxycarbonylamino)-2-methylpropanamido)butanoic acid

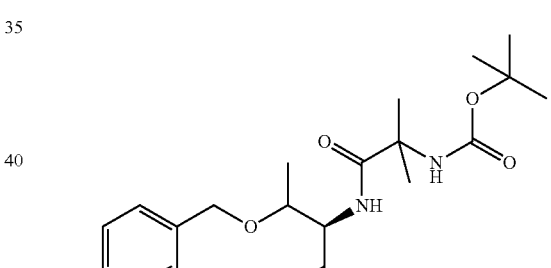

A mixture comprising of tert-butyl 1-(2,5-dioxopyrrolidin-1-yl)-2-methyl-1-oxopropan-2-ylcarbamate (1 g, 3.33 mmol) (prepared according to the procedure described in EP1486498A1 page 20) and (2R,3S)-2-amino-3-(benzyloxy)butanoic acid (0.697 g, 3.33 mmol) in THF (40 ml)/water (10 ml) was treated with TEA (1.392 ml, 9.99 mmol) and stirred at 50° C. for 4 hours. The resulting mixture was concentrated in vacuo and EtOAc (20 ml) was added. The pH was adjusted to pH2 with 1M HCl. The organic portion was separated and the aqueous phase was back extracted with EtOAc (30 ml). The combined organic portions were washed with a saturated solution of brine (50 ml), dried (MgSO$_4$), filtered and concentrated in vacuo. The residue was dissolved in DCM and concentrated in vacuo to afford the title compound.

LCMS Rt 2.39 mins; MS m/z [M+H]+ 395.38; Method LowpH_v002

Intermediate 3H (R)-2-(2-tert-Butoxycarbonylamino-2-methyl-propionylamino)-3-(4-methyl-benzyloxy)-propionic acid-benzyloxy)-propionic acid

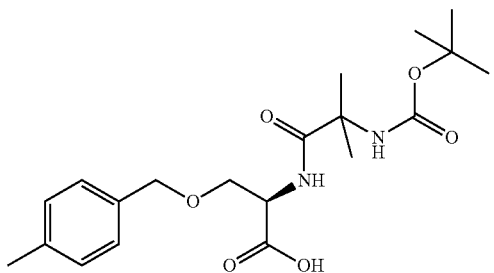 [SMILES: Cc1ccc(COC[C@@H](NC(=O)C(C)(C)NC(=O)OC(C)(C)C)C(=O)O)cc1]

A solution of (R)-2-tert-Butoxycarbonylamino-3-(4-methyl-benzyloxy)-propionic acid (Intermediate 4B) (1.20 g, 3.88 mmol) in 1,4-dioxane (6 ml) was cooled to 10° C. with a water/ice bath and conc. sulfuric acid (0.41 ml, 7.76 mmol) was added dropwise. After stirring at 10° C. for 3 h, the mixture was treated sequentially with TEA (2.97 ml, 21.33 mmol), water (2 ml) and 2-tert-Butoxycarbonylamino-2-methyl-propionic acid 2,5-dioxo-pyrrolidin-1-yl ester (synthesis described in EP1486498A1 page 20) (1.16 g, 3.88 mmol). The resulting suspension was heated to 50° C. and stirred overnight. The reaction mixture was partitioned between EtOAc (150 ml) and water (10 ml). The layers were separated and the organic layer was further extracted with 2M NaOH solution (2×5 ml). The combined aqueous layers were acidified with 5% citric acid solution and back-extracted with EtOAc (2×100 ml). The combined organic layers were washed with brine (50 ml), dried (MgSO$_4$) and concentrated in vacuo to yield the title compound as colourless oil.

LC-MS Rt 1.11 mins; MS m/z 395.6 [M+H]+; Method 2minLC_v003.

Intermediate 3I (R)-2-(2-tert-Butoxycarbonylamino-2-methyl-propionylamino)-3-(4-chloro-benzyloxy)-propionic acid-benzyloxy)-propionic acid

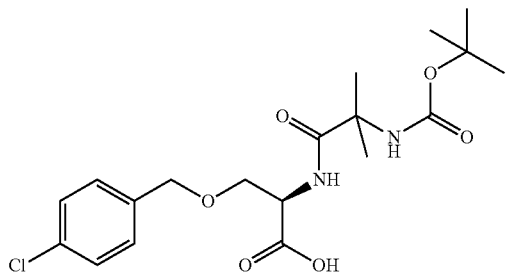 [SMILES: CC(C)(C)OC(=O)NC(C)(C)C(=O)N[C@H](COCc1ccc(Cl)cc1)C(=O)O]

The title compound was prepared according to the general procedure described for Intermediate 3G starting from (R)-2-tert-Butoxycarbonylamino-3-(4-chloro-benzyloxy)-propionic acid (Intermediate 4C).

LC-MS Rt 1.16 mins; MS m/z 437.6 [M+Na]+; Method 2minLC_v003.

Intermediate 3J

R)-2-(2-tert-Butoxycarbonylamino-2-methyl-propionylamino)-3-cyclohexylmethoxy-propionic acid

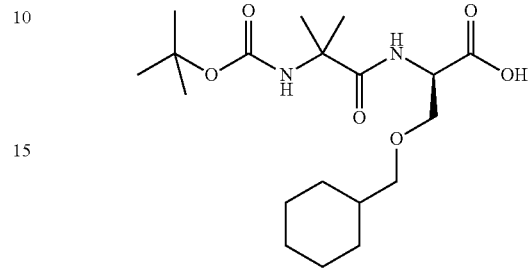

A mixture of 5% rhodium on alumina (80 mg) and (R)-3-benzyloxy-2-(2-tert-butoxy carbonylamino-2-methyl-propionylamino)-propionic acid (500 mg, 1.31 mmol) (intermediate 3A) in isopropanol (12 ml) was stirred under a hydrogen atmosphere at room temperature overnight. To ensure completion, a further 120 mg of catalyst were added and the reaction was left to stir at room temperature under a hydrogen atmosphere for a further 5 h. The reaction mixture was filtered through Celite® (filter material) and concentrated in vacuo to give the title compound as a white solid.

LC-MS Rt 4.06 min; MS m/z 287.3 [M-BOC]+; Method 10minLC_v003

Intermediate 3K 2-(2-(tert-butoxycarbonylamino)-2-methylpropanamido)-4-(tetrahydro-2H-pyran-4-yl)butanoic acid

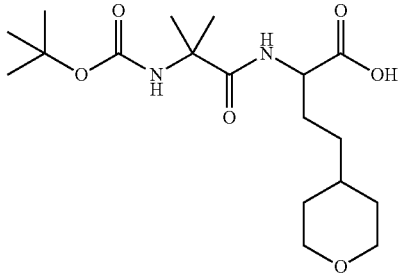 [SMILES: CC(C)(C)OC(=O)NC(C)(C)C(=O)NC(CCC1CCOCC1)C(=O)O]

To a stirred solution of methyl 2-amino-4-(tetrahydro-2H-pyran-4-yl)butanoate hydrochloride (500 mg, 2.103 mmol) in THF (27 ml)/Water (6.7 ml) was added 2,5-dioxopyrrolidin-1-yl 2-(tert-butoxycarbonylamino)-2-methylpropanoate (632 mg, 2.103 mmol) followed by TEA (1.173 ml, 8.41 mmol). The solution was heated to 50° C. and stirred for 6 hours. The solvent was concentrated and the residue partitioned between EtOAc and 5% citric acid. The organic layer was separated and washed with brine, dried over magnesium sulfate, filtered and concentrated under reduced pressure to yield a yellow gum (700 mg). To the gum in MeOH (10 ml)/water (1.5 ml) cooled to 0° C. was added LiOH.H$_2$O (114 mg, 2.72 mmol) portionwise and the reaction stirred at RT for 2 hours. The solvent was evaporated and residue partitioned between EtOAc (5 ml) and water (10 ml). The aqueous layer was acidified with 5% citric acid (10 ml, pH 3) and extracted with EtOAc (2×25 ml) then separated and washed with brine.

This was dried over magnesium sulfate, filtered and concentrated under reduced pressure to yield 2-(2-(tert-butoxycarbonylamino)-2-methylpropanamido)-4-(tetrahydro-2H-pyran-4-yl)butanoic acid.

LCMS Rt 0.95 mins; MS m/z 373.3 [M+1]+; Method 2minLowpH.

Intermediate 4A (R)-2-tert-Butoxycarbonylamino-3-(4-fluoro-benzyloxy)-propionic acid

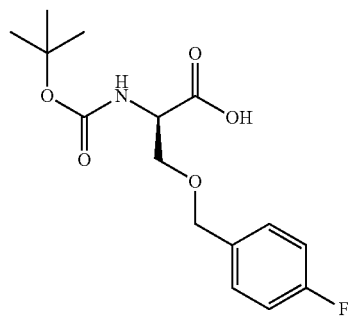 [SMILES: CC(C)(C)OC(=O)N[C@H](COCc1ccc(F)cc1)C(=O)O]

A solution of N—BOC-D-serine (2.00 g, 9.75 mmol) in DMF (25 ml) was cooled to 0° C. under nitrogen atmosphere and sodium hydride (60% in mineral oil) (0.82 g, 20.47 mmol) was added portionwise over 15 minutes. After stirring at 0° C. for 30 minutes, 4-fluorobenzyl bromide (1.82 g, 9.75 mmol) in DMF (5 ml) was added. The ice bath was removed and the reaction mixture was stirred at room temperature overnight. The reaction mixture was partitioned between EtOAc (100 ml) and water (50 ml). The aqueous phase was separated and washed with DCM (2×50 ml). The organic washings were discarded. The aqueous layer was acidified with 5% citric acid aqueous solution and back-extracted with DCM (2×100 ml). The combined organic portions were washed with brine (50 ml), dried (MgSO₄) and concentrated in vacuo to yield the title compound as pale yellow oil.

LC-MS Rt 1.07 mins; MS m/z 314.0 [M+H]+; Method 2minLC_v003.

The following compounds, namely Intermediates 4C-4G were prepared analogously to Intermediate 4A for the appropriate starting compounds;

Intermediate 4B (R)-2-tert-Butoxycarbonylamino-3-(4-methyl-benzyloxy)-propionic acid

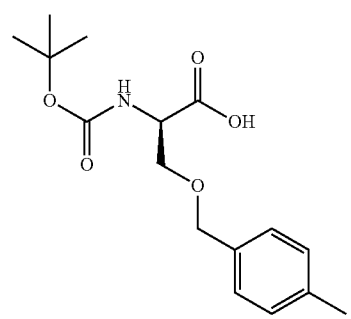 [SMILES: Cc1ccc(COC[C@@H](NC(=O)OC(C)(C)C)C(=O)O)cc1]

The title compound was obtained as a pale yellow oil starting from N—BOC-D-serine and 4-methylbenzyl bromide.

LC-MS Rt 1.14 mins; MS m/z 332.6 [M+H]+; Method 2minLC_v003.

Intermediate 4C (R)-2-tert-Butoxycarbonylamino-3-(4-chloro-benzyloxy)-propionic acid

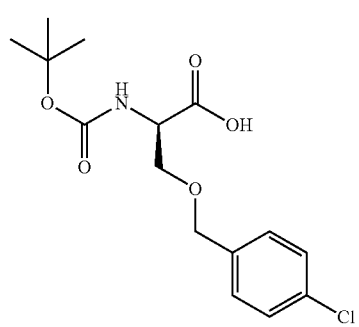 [SMILES: CC(C)(C)OC(=O)N[C@H](COCc1ccc(Cl)cc1)C(=O)O]

The title compound was obtained as a pale yellow oil starting from N—BOC-D-serine and 4-chlorobenzyl bromide.

LC-MS Rt 1.15 mins; MS m/z 352.5 [M+Na]+; Method 2minLC_v003.

Intermediate 4D (R)-2-tert-Butoxycarbonylamino-3-(4-methoxy-benzyloxy)-propionic acid

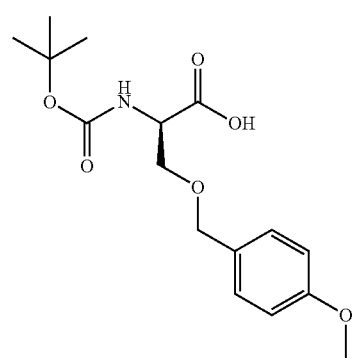 [SMILES: COc1ccc(COC[C@@H](NC(=O)OC(C)(C)C)C(=O)O)cc1]

The title compound was obtained as a pale yellow oil starting from N—BOC-D-serine and 4-methoxybenzyl bromide.

LC-MS Rt 1.07 mins; MS m/z 348.5 [M+Na]+; Method 2minLC_v003.

Intermediate 4E (R)-2-tert-Butoxycarbonylamino-3-(3,4-difluoro-benzyloxy)-propionic acid

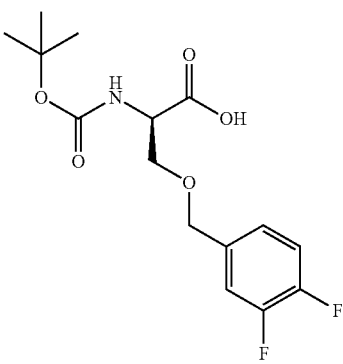 [SMILES: CC(C)(C)OC(=O)N[C@H](COCc1ccc(F)c(F)c1)C(=O)O]

The title compound was obtained as a pale yellow oil starting from N—BOC-D-serine and 3,4-difluorobenzyl bromide.

LC-MS Rt 1.11 min; MS m/z 232.1 [M-BOC]+; Method 2minLC_v003.

Intermediate 4F (R)-2-tert-Butoxycarbonylamino-3-(2,4-difluoro-benzyloxy)-propionic acid

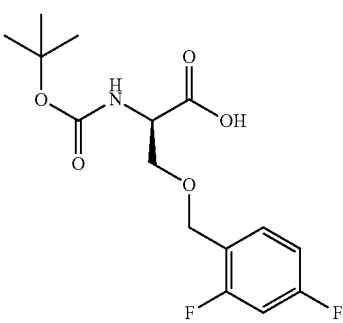 [SMILES: CC(C)(C)OC(=O)N[C@H](COCc1ccc(F)cc1F)C(=O)O]

The title compound was obtained as a pale yellow oil starting from N—BOC-D-serine and 2,4-difluorobenzyl bromide.

LC-MS Rt 1.11 min; MS m/z 232.1 [M-BOC]+; Method 2minLC_v003.

Intermediate 4G (R)-2-tert-Butoxycarbonylamino-3-(3-methoxy-benzyloxy)-propionic acid

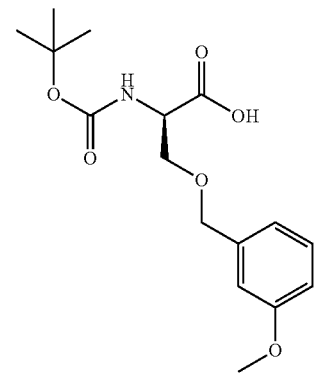 [SMILES: COc1cccc(COC[C@@H](NC(=O)OC(C)(C)C)C(=O)O)c1]

The title compound was obtained as a pale yellow oil starting from N—BOC-D-serine and 3-methoxybenzyl bromide.

LCMS Rt 2.35 mins; MS m/z 326.29 [M+H]+; Method LowpH_v002.

Intermediate 4H (R)-2-tert-Butoxycarbonylamino-3-(2-methyl-benzyloxy)-propionic acid

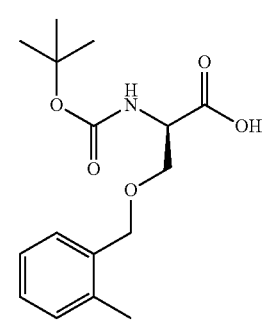 [SMILES: Cc1ccccc1COC[C@@H](NC(=O)OC(C)(C)C)C(=O)O]

The title compound was obtained as a pale yellow oil starting from N—BOC-D-serine and 2-methybenzyl bromide.

LCMS Rt 1.15 min; MS m/z 332.3 [M+Na]+; Method 2minLC_v003.

Intermediate 4I (R)-2-(tert-butoxycarbonylamino)-3-(3-methylbenzyloxy)propanoic acid

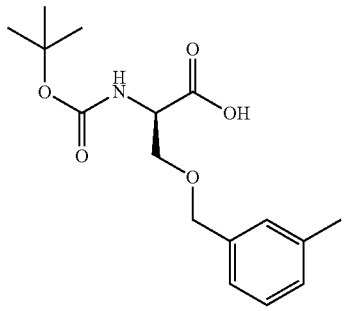 [SMILES: Cc1cccc(COC[C@@H](NC(=O)OC(C)(C)C)C(=O)O)c1]

The title compound was obtained as a pale yellow oil starting from N—BOC-D-serine and 3-methybenzyl bromide.
LCMS Rt 1.15 min; MS m/z 310.2 [M+H]+; Method 2min-LC_v003.

Intermediate 4J (R)-2-(tert-butoxycarbonylamino)-3-(pyridin-2-yl-methoxy)propanoic acid

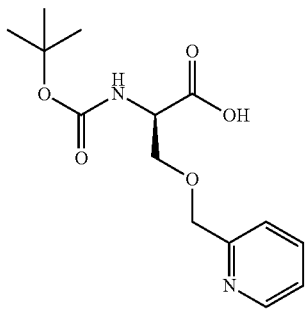 [SMILES: CC(C)(C)OC(=O)N[C@H](COCc1ccccn1)C(=O)O]

The title compound was prepared according to the procedure described in Bioorganic & Medicinal Chemistry (2005), 13(24), 6748-6762, example 10a, page 6753 (Method A) and page 6758.

Intermediate 4K (R)-2-(tert-butoxycarbonylamino)-3-(pyridin-3-yl-methoxy)propanoic acid

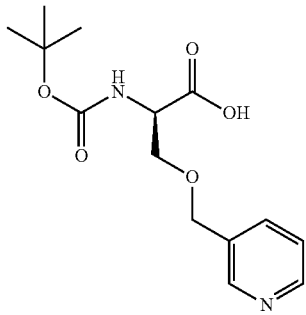 [SMILES: CC(C)(C)OC(=O)N[C@H](COCc1cccnc1)C(=O)O]

The title compound was prepared according to the procedure described in Bioorganic & Medicinal Chemistry (2005), 13(24), 6748-6762, example 10b, page 6753 (Method A) and page 6758.

Intermediate 5A 7-((R)-2-Amino-3-benzyloxy-propionyl)-2-methyl-4-phenyl-2,7-diaza-spiro[4.5]decan-1-one

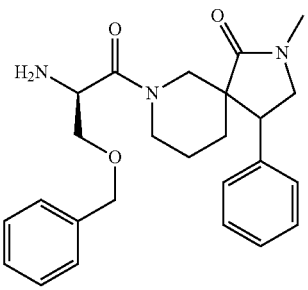 [SMILES: CN1CC(c2ccccc2)C2(CCCN(C(=O)[C@H](N)COCc3ccccc3)C2)C1=O]

The title compound was prepared from commercially available amino acid and spiropiperidine.
LCMS Rt 0.94 mins; MS m/z 423.5 [M+H]$^+$ 0.2min-LC_v003.

Biological Data

The affinities of the compounds as defined in the first, second or third aspect for the ghrelin receptor were determined by the following assays. The compounds as defined in the first, second or third aspect were used in the form as described herein. The compounds of the first, second or third aspect were not necessarily from the same batch. The test compound made in one batch may have been combined with other batch(es) for the assays. All compounds tested have been tested one or more times.

Cell Culture

Chinese hamster ovary (CHO-K1) cells expressing human recombinant ghrelin receptor (GHS-R1a) were purchased from Euroscreen (ES-410-C) and propagated in UltraCHO medium containing glutamine and supplemented with 1% heat inactivated foetal calf serum (FCS), 100 U/ml penicillin, 100 mg/l streptomycin and 0.8 g/l geneticin. Cells were sub-cultured twice a week with a 1:10 dilution. For passaging, cells were washed with 1×DPBS without calcium and magnesium, trypsinised for 10 min with 0.05% Trypsin/EDTA and resuspended in cell culture medium.

CHO TREx cells were obtained from Invitrogen and stably transformed to express the recombinant rat GHS-R1a in an inducible way (using tetracycline as expression inducer). Cells were cultured in RPMI 1640 medium containing glutamine, 10% heat inactivated FCS, 100 U/ml penicillin, 100 mg/l streptomycin and 10 µg/ml blasticidin. Cells were sub-cultured every 2 to 3 days with a 1:10 to 1:30 dilution. For passaging, cells were washed with 1×DPBS without calcium and magnesium, trypsinised for 2-3 min with 0.05% Trypsin/EDTA and resuspended in FCS containing medium. Cells in solution were concentrated by centrifugation (900 rpm, 3 min), washed with DPBS, concentrated again, and finally diluted in cell culture media. Expression of rat GHS-R1a was induced with tetracycline (1 and 3 µg/ml, for calcium and cAMP assays, respectively) for 18-24 h prior to experimentation.

cAMP Assay

The Homogeneous Time-Resolved Fluorescence (HTRF) cAMP dynamic 2 kit (Cisbio International, France) was used as follows. CHO-hGHS-R1a or CHO-rGHS-R1a cells were seeded in a volume of 25 µl culture media at 10,000 cells/well (400,000 cells/ml) in Greiner white 384-well high volume plates and incubated overnight (18-24 h) at 37° C./5% $CO_2$. Then, media was removed and 6 µl assay buffer [HBSS, 10 mM Hepes, 0.2% (w/v) BSA, 1.7 mM IBMX, (pH7.4)] were added to the wells. To generate a dose response up to 30 µM, 10 mM compound stocks in 100% (v/v) DMSO were firstly diluted in 50% (v/v) DMSO followed by a further dilution into assay buffer. Then, 4 µl of 2.5× compound (dose response as 9 point log serial dilution in assay buffer from 30 µM as maximum concentration) were added to each well achieving a final DMSO assay concentration of 0.8% (v/v). 0.1 µM forskolin was added as positive control. After 30 min (rGHS-R1a cell line) or 60 min (hGHS-R1a cell line) incubation at 37° C./5% $CO_2$, 5 µl of cAMP-d2 and 5 µl of anti-cAMP antibody-cryptate, (both made in lysis buffer), were added to the plate followed by 1 h incubation at RT. During this time, cAMP produced by the cells competed with cAMP-d2 for the anti-cAMP antibody-cryptate molecule. Then, the plate was read on the Pherastar instrument (BMG, Germany) at two different emission wavelengths (620 and 650 nm). Increasing levels of endogenous cAMP produced by cells could be followed by a decrease of FRET fluorescent signal and vice-versa. Values represented by a change in arbitrary fluorescence ratios (665/620) were converted into cAMP concentrations by using a standard curve, the reagents for which were supplied with the kit. $EC_{50}$ values of agonists were calculated using the nonlinear logistic function of the Prism 5 software (GraphPad, USA). Emax were expressed as relative values of the ghrelin response, which was defined as 100%.

Calcium Assay

Cells were diluted to achieve $1\times10^6$ cells/ml, seeded in 384-well black clear bottom CellBind plates at 25000 cells/well (25 ul) and incubated overnight at 37° C./5% $CO_2$ Cells were expected to be 85-90% confluent on the day of assay (checked under the microscope) to ensure a high quality assay. Media was manually removed and 40 µl of loading solution containing probenecid and Fluo-4 no wash dye (a calcium indicator, Invitrogen F36206) were added to each well. After 30 min at 37° C. followed by another 30 min at RT, cpds were added to the wells. To generate a dose response up to 30 µM, 10 mM compound stocks in 100% (v/v) DMSO were firstly diluted in 50% (v/v) DMSO. Then, serial dilutions aimed at a full logarithmic dose responses (8 point) were performed in assay buffer [1×HBSS, 20 mM Hepes, 0.1% (w/v) BSA] to give 2.5% (v/v) DMSO and 5× final compound concentrations. The final assay DMSO concentration was 0.5% (v/v). After loading the cells with Fluo-4 containing solution, plates were read on a CellLux instrument (Perkin Elmer). A protocol set up to add 10 µl of 5× compound and to read the plate for 60 sec after adding the compound at 17th sec was used. Fluorescence excitation took place at 494 nm and emission at 516 nm. $EC_{50}$ values of agonists were calculated by fitting the percent stimulation over background [(Max−Min)/Min] using the nonlinear logistic function of the Prism 5 software (GraphPad, USA). Emax were expressed as relative values of the Emax induced by MK-0677 (defined as 100%), as this compound displays the same Emax as ghrelin.

The following Table 4 lists the $EC_K$ values of some of the compounds disclosed herein as determined in the above assays.

TABLE 4

| Ex. | hGHS-R1a Ca assay $EC_{50}/\mu M$ | hGHS-R1a Ca assay Emax/% | hGHS-R1a cAMP assay $EC_{50}/\mu M$ | hGHS-R1a cAMP assay Emax/% |
|---|---|---|---|---|
| 1.0(i) | 0.0023 | 97 | 1.34 | 130 |
| 1.0(ii) | 0.00016 | 100 | 0.043 | 141 |
| 1.2 | 0.0001 | 89 | 0.055 | 197 |
| 1.4 | 0.0002 | 100 | 0.051 | 127 |
| 1.5 | 0.0001 | 96 | 0.020 | 195 |
| 1.8 | 0.0003 | 102 | 0.162 | 149 |
| 1.11 | 0.0003 | 102 | 0.023 | 289 |
| 1.15 | 0.0016 | 112 | 0.128 | 331 |
| 1.16 | 0.0005 | 101 | 0.039 | 210 |
| 1.17 | 0.001 | 107 | 0.082 | 124 |
| 1.20 | 0.0016 | 99 | 2.28 | 169 |
| 1.21 | 0.0021 | 105 | 1.93 | 122 |
| 1.25 | 0.0003 | 103 | 0.043 | 223 |
| 1.28 | 0.00065 | 106.5 | 0.141 | 194 |
| 1.29 | 0.00035 | 102 | 0.049 | 243 |
| 1.32 | 0.0003 | 103 | 0.011 | 176 |
| 1.34 | 0.0005 | 107 | 0.184 | 168 |
| 1.40 | 0.0007 | 86 | 0.034 | 164 |
| 1.47 | 0.0017 | 104 | 0.385 | 145 |
| 1.49 | 0.0006 | 93 | 0.154 | 88 |
| 1.51 | 0.0002 | 98 | 0.067 | 141 |
| 1.53 | 0.00011 | 89 | 0.036 | 212 |
| 1.55 | 0.00013 | 94 | 0.072 | 191 |
| 1.57 | 0.00022 | 84 | 0.043 | 173 |
| 1.60 | 0.0003 | 98 | 0.047 | 171 |
| 1.61 | 0.0029 | 73 | 0.517 | 189 |
| 1.71 | 0.0054 | 108 | 1.139 | 111 |
| 1.72 | 0.005 | 110 | 2.5575 | 147 |
| 1.73 | 3.32 | 79 | 30 | 1 |
| 1.74 | 0.0054 | 103 | 5.9 | 123 |
| 1.75 | 0.0036 | 87 | 0.302 | 176 |
| 2.0(ii) | 0.0011 | 99 | 0.456 | 193 |
| 6.0(ii) | 0.0005 | 103 | 0.109 | 268 |
| 7.0 | 0.00017 | 83 | 0.138 | 153 |
| 8.0 | 0.0046 | 101 | 2.384 | 129 |
| 9.0(iv) | 0.0004 | 96 | 0.086 | 127 |

Rat Fundus Contractility Assay

Male Sprague Dawley rats (180-250 g) were culled by cervical dislocation and the fundus was removed. Each fundus was placed on a Krebs Henseleit (KH) buffer soaked dissection dish and cut along the long curvature to form a flattened sheet that was pinned in each corner. Four adjacent longitudinal strips (10×3 mm) were cut and the mucosa removed by sharp dissection. Each muscle strip was mounted in a 10 ml organ bath containing oxygenated KH at 37° C. Each strip was connected to an isometric force transducer, calibrated initially using a 5 g weight. The signal (g tension) was amplified and responses recorded by a Powerlab data capture system, connected to a computer running Labchart software (version 5.0). Tissues were placed under 1 g tension for an equilibration period of 30 min or until the baseline tension had stabilised. Carbachol (CCh, 100 nM) was then administered to establish the maximum contractile response of each preparation. Tissues were washed thoroughly and left for 30 min to re-equilibrate. Next, the muscle strips underwent electrical field stimulation (EFS). Maximal EFS pulse trains of 12V, 5 Hz, 0.1 msec pulse width, for 2 sec every 60 sec were applied until consistent electrically-stimulated phasic contractions were recorded. The voltage was then reduced in 1V increments until a consistent submaximal ($EC_{50-75}$) EFS response was observed. Ghrelin (100 nM) was administered and left until a maximum response was obtained. Tissues were then washed thoroughly and left for 30 min. Once the EFS-induced contraction had re-stabilised, cumulative additions (10 nM-10 µM) of each test compound were administered. Individual responses were calculated by determining the peak of the EFS-induced contraction minus the baseline.

The maximal increase in the EFS response in the presence of ghrelin was then calculated (defined as 100%) and compound induced effects expressed relative to the ghrelin response. The mean EC50 value for compounds was generated from data obtained on stomach preparations from at least 3 different animals.

The following Table 5 lists the $EC_{50}$ values of some of the compounds disclosed herein as determined in the above rat fundus contractility assay.

TABLE 5

| Ex. | EC50/nM | Emax/% |
|---|---|---|
| 1.0(i) | 1700 | 104 |
| 1.0(ii) | 13 | 66 |
| 1.2 | 7.5 | 100 |
| 1.5 | 35 | 80 |
| 1.6 | 373 | 70 |
| 1.11 | 24 | 99 |
| 1.15 | 36 | 123 |
| 1.16 | 13 | 124 |
| 1.17 | 137 | 113 |
| 1.18 | 148 | 117 |
| 1.19 | 23 | 124 |
| 1.20 | 393 | 39 |
| 1.21 | 84 | 81 |
| 1.29 | 48 | 100 |
| 1.32 | 19 | 109 |
| 1.33 | 84 | 131 |
| 1.34 | 68 | 115 |
| 1.40 | 59 | 117 |
| 2.0(ii) | 17 | 63 |
| 2.0(iii) | 70 | 70 |
| 3.0(ii) | 15 | 85 |

The following are further embodiments of the invention.
Embodiment 1: A compound of formula (I)

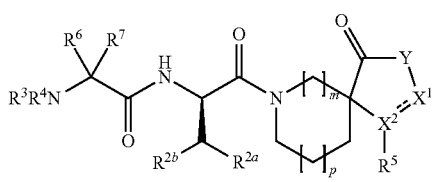

(I)

wherein
---- is a single bond or a double bond;
$X^1$ is $(CR^{x1}H)_n$ and $X^2$ is (CH); or
$X^1$ is $(CR^{x1}H)_n$ and $X^2$ is N; or
$X^1$ is $NR^{x1}$ and $X^2$ is (CH); or
$X^1$ is $NR^{x1}$ and $X^2$ is N; or
$X^1$ is N and $X^2$ is C; wherein the bond between $X^1$ and $X^2$ is a double bond if $X^1$ is N and $X^2$ is C;
n is 0 or 1;
$R^{x1}$ is selected from hydrogen and $C_{1-6}$alkyl;
m is 1 and p is 0; or
m is 1 and p is 1; or
m is 2 and p is 1;
Y is $NR^1$ or O;
$R^1$ is selected from hydrogen, $C_{1-6}$alkyl, $—C_{1-4}$alkylC(O)$NR^{1a}R^{1b}$, $—C_{1-4}$alkylC(O)O$C_{1-4}$alkyl, $—C_{1-4}$alkylC(O)O$C_{1-4}$ haloalkyl, $C_{1-6}$haloalkyl, $C_{3-6}$cycloalkyl, $—C_{1-4}$alkyl-5-6 membered heteroaryl, hydroxy$C_{1-6}$alkyl, $C_{1-6}$alkoxy and $C_{1-4}$alkoxy$C_{1-4}$alkyl;
wherein the 5-6 membered heteroaryl is unsubstituted or substituted with 1 to 3 substituents independently selected from halogen and $C_{1-6}$alkyl;

$R^{1a}$ and $R^{1b}$ are independently selected from hydrogen, $C_{1-6}$alkyl and $C_{1-6}$haloalkyl; or $R^{1a}$ and $R^{1b}$ together with the nitrogen to which they are attached form a 4-6 membered heterocyclic ring containing 0, 1 or 2 additional heteroatoms selected from oxygen, nitrogen and sulphur;
$R^{2a}$ is selected from
(i) -A-phenyl;
(ii) -A-5-6 membered heteroaryl;
(iii) -A-4-6 membered heterocyclyl;
(iv) -A-$C_{5-6}$cycloalkyl;
(v) -D-8-10 membered fused bicyclic ring system;
wherein the phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from halogen, hydroxy, $C_{1-6}$alkyl, $C_{1-6}$alkoxy and $C_{1-6}$haloalkyl;
A is selected from a bond, $—(CR^{A1}R^{A2})—$, $—(CR^{A1}R^{A2})(CR^{A1}R^{A2})—$, $—(CR^{A1}R^{A2})—O—$, $—O—(CR^{A1}R^{A2})—$, $—(CR^{A1}R^{A2})—S—$, $—(CR^{A1}R^{A2})—S(O)—$, $—(CR^{A1}R^{A2})—S(O)_2—$, $—S—(CR^{A1}R^{A2})—$, $—S(O)—(CR^{A1}R^{A2})—$, $—S(O)_2—(CR^{A1}R^{A2})—$, $—NR^{A3}—(CR^{A1}R^{A2})—$, $—(CR^{A1}R^{A2})—NR^{A3}—$ and $—(CR^{A1})=(CR^{A1})—$;
D is a bond, $—O—$ or $—(CR^{D1}R^{D2})—$;
$R^{A1}$, $R^{A2}$ and $R^{A3}$ are independently selected from hydrogen, $C_{1-6}$alkyl and halogen;
$R^{D1}$ and $R^{D2}$ are independently selected from hydrogen, $C_{1-6}$alkyl and halogen;
$R^{2b}$ is hydrogen or $C_{1-4}$alkyl;
$R^3$ and $R^4$ are independently selected from hydrogen, $C_{1-6}$alkyl and $C_{3-6}$cycloalkyl; or $R^3$ and $R^4$ together with the nitrogen to which they are attached form a 4-6 membered heterocyclic ring containing 0, 1 or 2 additional heteroatoms selected from oxygen, nitrogen and sulphur; which 4-6 membered heterocyclic ring is unsubstituted or substituted with 1 or 2 halogen substituents;
$R^6$ and $R^7$ are independently selected from hydrogen, $C_{1-6}$alkyl, $C_{1-6}$hydroxyalkyl and $C_{1-6}$haloalkyl;
$R^5$ is selected from phenyl, a 5-6 membered heteroaryl, $C_{3-6}$cycloalkyl and 4-6 membered heterocyclyl; which phenyl, 5-6 membered heteroaryl, $C_{3-6}$cycloalkyl and 4-6 membered heterocyclyl is unsubstituted or substituted with 1 to 3 substituents independently selected from halogen, $C_{1-6}$alkyl, $C_{1-6}$alkoxy and $C_{1-6}$haloalkyl;
or a pharmaceutically acceptable salt thereof.
Embodiment 2: A compound according to embodiment 1, wherein Y is $NR^1$.
Embodiment 3: A compound according to embodiment 1 or 2, wherein Y is $NR^1$ and $R^1$ is selected from hydrogen, $C_{1-6}$alkyl, $C_{1-6}$haloalkyl, $—C_{1-4}$alkylC(O)$NR^{1a}R^{1b}$, $—C_{1-4}$alkylC(O)O$C_{1-4}$alkyl and $—C_{1-4}$alkyl-5-6 membered heteroaryl, wherein the 5-6 membered heteroaryl is unsubstituted or substituted with 1 to 3 substituents independently selected from halogen and $C_{1-6}$alkyl, for example $R^1$ is selected from hydrogen, $C_{1-6}$alkyl, $C_{1-6}$ haloalkyl, $—C_{1-4}$alkylC(O)$NR^{1a}R^{1b}$ and $—C_{1-4}$alkyl-5-6 membered heteroaryl, wherein the 5-6 membered heteroaryl is unsubstituted or substituted with 1 to 3 substituents independently selected from halogen and $C_{1-6}$alkyl.
Embodiment 4
A compound according to embodiment 3 wherein $R^1$ is selected from hydrogen, methyl, isopropyl, ethyl, 2,2-dimethyl-propyl, isobutyl, 2,2,2-trifluoroethyl, methylisoxazolylmethyl, oxazolylmethyl, $—(CH_2)C(O)N(CH_3)_2$, $—(CH_2)C(O)O(CH_2)(CH_3)$ and $—(CH_2)C(O)O(CH_3)$, for example $R^1$ is selected from hydrogen, methyl, isopropyl, ethyl, 2,2-dimethyl-propyl, isobutyl, 2,2,2-trifluoroethyl, methylisoxazolylmethyl, oxazolylmethyl, and —(CH$_2$)C(O)N(CH$_3$)$_2$, such as hydrogen or methyl.

Embodiment 5: A compound according to any one of embodiments 1 to 4, wherein X$^1$ is (CR$^{x1}$H)$_n$ or N, for example X$^1$ is (CR$^{x1}$H)$_n$.

Embodiment 6: A compound according to any one of embodiments 1 to 5, wherein X$^1$ is (CR$^{x1}$H)$_n$ and n is 0 or 1, for example n is 1.

Embodiment 7: A compound according to embodiment 6, wherein R$^{x1}$ is selected from hydrogen and C$_{1-6}$alkyl.

Embodiment 8: A compound according to embodiment 7, wherein R$^{x1}$ is hydrogen.

Embodiment 9: A compound according to any one of embodiments 1 to 8, wherein R$^5$ is selected from phenyl and a 5-6 membered heteroaryl, which phenyl or 5-6 membered heteroaryl is unsubstituted or substituted with 1 to 3 substituents independently selected from halogen and C$_{1-6}$alkyl.

Embodiment 10: A compound according to embodiment 9, wherein R$^5$ is selected from phenyl and pyridinyl, which phenyl or pyridinyl is unsubstituted or substituted with 1 to 3 substituents independently selected from halogen and C$_{1-6}$alkyl.

Embodiment 11: A compound according to embodiment 10, wherein R$^5$ is selected from phenyl and pyridinyl, which phenyl or pyridinyl is unsubstituted or substituted with 1 to 3, for example 1 or 2, substituents independently selected from fluoro, chloro and methyl.

Embodiment 12: A compound according to embodiment 11, wherein R$^5$ is phenyl, which phenyl is unsubstituted or substituted with 1 to 3, for example 1 or 2, substituents independently selected from fluoro, chloro and methyl, such as 4-fluoro, 4-chloro, 2-methyl, 4-methyl, 3,4-difluoro, 3,3-difluoro, particularly R$^5$ is unsubstituted phenyl or 4-fluorophenyl or 4-methylphenyl.

Embodiment 13: A compound according to any one of embodiments 1 to 12, wherein the compound is of formula (Ia)

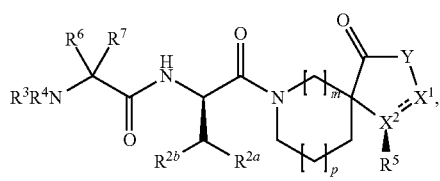

(Ia)

wherein X$^1$ is (CR$^{x1}$H)$_n$ and X$^2$ is (CH) or X$^1$ is NR$^{x1}$ and X$^2$ is (CH).

Embodiment 14: A compound according to any one of embodiments 1 to 12, wherein the compound is of formula (Ib)

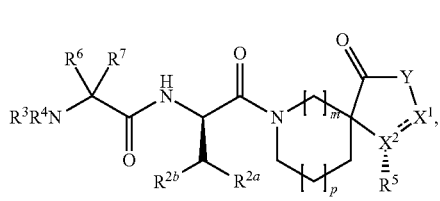

(Ib)

wherein X$^1$ is (CR$^{x1}$H)$_n$ and X$^2$ is (CH) or X$^1$ is NR$^{x1}$ and X$^2$ is (CH).

Embodiment 15: A compound according to any one of embodiments 1 to 12, wherein the compound is of formula (Ic)

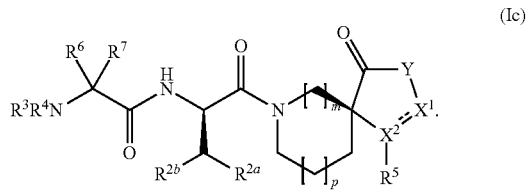

(Ic)

Embodiment 16: A compound according to any one of embodiments 1 to 12, wherein the compound is of formula (Id)

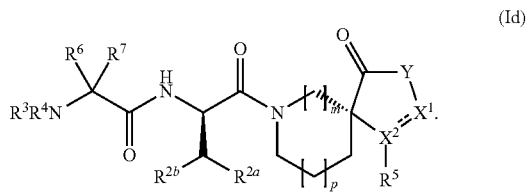

(Id)

Embodiment 17: A compound according to any one of embodiments 1 to 12, wherein the compound is of formula (Ie)

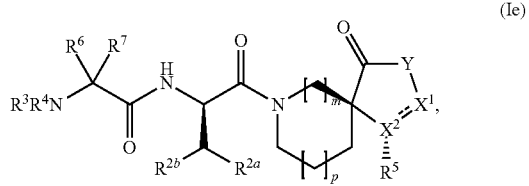

(Ie)

wherein X$^1$ is (CR$^{x1}$H)$_n$ and X$^2$ is (CH) or X$^1$ is NR$^{x1}$ and X$^2$ is (CH).

Embodiment 18: A compound according to any one of embodiments 1 to 12, wherein the compound is of formula (If)

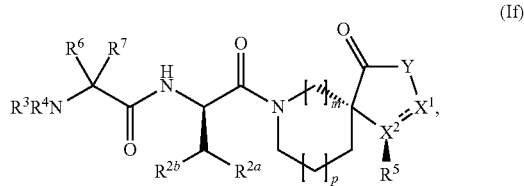

(If)

wherein X$^1$ is (CR$^{x1}$H)$_n$ and X$^2$ is (CH) or X$^1$ is NR$^{x1}$ and X$^2$ is (CH). The compound of formula (I) is particularly a compound of formula (If).

Embodiment 19: A compound according to any one of embodiments 1 to 12, wherein the compound is of formula (Ig)

(Ig)

wherein $X^1$ is $(CR^{x1}H)_n$ and $X^2$ is (CH) or $X^1$ is $NR^{x1}$ and $X^2$ is (CH).

Embodiment 20: A compound according to any one of embodiments 1 to 12, wherein the compound is of formula (Ih)

(Ih)

wherein $X^1$ is $(CR^{x1}H)_n$ and $X^2$ is (CH) or $X^1$ is $NR^{x1}$ and $X^2$ is (CH).

Embodiment 21: A compound according to any one of embodiments 1 to 20, wherein $R^{2a}$ is selected from -A-phenyl, -A-5-6 membered heteroaryl, -A-4-6 membered heterocyclyl, -A-$C_{5-6}$cycloalkyl and a -D-8-10 membered fused bicyclic ring system, which phenyl, 5-6 membered heteroaryl, 4-6 membered heterocyclyl, $C_{5-6}$cycloalkyl and 8-10 membered fused bicyclic ring system are unsubstituted or substituted with 1 to 3 substituents independently selected from $C_{1-6}$alkyl, $C_{1-6}$alkoxy and halogen.

Embodiment 22: A compound according to embodiment 21, wherein $R^{2a}$ is selected from -A-phenyl, -A-pyridyl, -A-tetrahydropyranyl, -A-cyclohexyl, -D-dihydroindenyl and -D-indolyl, which phenyl, pyridyl, tetrahydropyranyl, cyclohexyl, dihydroindenyl and indolyl groups are unsubstituted or substituted with 1 to 3 substituents independently selected from $C_{1-6}$alkyl, $C_{1-6}$alkoxy and halogen.

Embodiment 23: A compound according to any one of embodiments 1 to 22, wherein $R^{2a}$ is -A-phenyl, -A-para-methylphenyl, -A-ortho-methylphenyl, -A-meta-methylphenyl, -A-meta-methoxyphenyl, -A-para-methoxyphenyl, -A-para-chlorophenyl, -A-para-fluorophenyl, -A-ortho, para-difluorophenyl, -A-meta,para-difluorophenyl, -A-cyclohexyl, -A-tetrahydro-2H-pyran-4-yl, -A-pyridin-2-yl, -A-pyridin-3-yl, -D-dihydroindenyl, -D-1H-indol-3-yl or -D-1-methyl-1H-indol-3-yl.

Embodiment 24: A compound according to embodiment 23, wherein $R^{2a}$ is -A-phenyl.

Embodiment 25: A compound according to any one of embodiments 1 to 24, wherein -A- is selected from —$(CR^{A1}R^{A2})$—, —$(CR^{A1}R^{A2})(CR^{A1}R^{A2})$—, —$O(CR^{A1}R^{A2})$—, —$(CR^{A1}R^{A2})$—O—, —S—$(CR^{A1}R^{A2})$—, and —$(CR^{A1})$=$(CR^{A1})$—, and $R^{A1}$, $R^{A2}$ are both hydrogen, particularly -A- is —O—$CH_2$.

Embodiment 26: A compound according to any one of embodiments 1 to 25, wherein -D- is a bond.

Embodiment 27: A compound according to any one of embodiments 1 to 26, wherein $R^{2b}$ is hydrogen or methyl.

Embodiment 28: A compound according to any one of embodiments 1 to 27, wherein $R^{2b}$ is hydrogen.

Embodiment 29: A compound according to any one of embodiments 1 to 28, wherein $R^3$ and $R^4$ are independently selected from hydrogen and $C_{1-6}$alkyl, such as methyl, particularly $R^3$ and $R^4$ are both hydrogen.

Embodiment 30: A compound according to any one of embodiments 1 to 29, wherein $R^6$ and $R^7$ are independently selected from hydrogen, $C_{1-6}$alkyl, $C_{1-6}$haloalkyl and $C_{1-6}$hydroxyalkyl, such as $C_{1-6}$alkyl and $C_{1-6}$hydroxyalkyl.

Embodiment 31: A compound according to embodiment 30, wherein $R^6$ and $R^7$ are both methyl.

Embodiment 32: A compound according to any one of embodiments 1 to 31, wherein m is 1 and p is 1, particularly the compound of formula (I) is:

where $X^1$, $X^2$, $R^{2a}$, $R^{2b}$, $R^3$, $R^4$, $R^5$, $R^6$, $R^7$ and ---- are as defined according to any one of embodiments 1 to 31.

Embodiment 33: A compound according to embodiment 32, wherein the compound of formula (I) is:

where $X^1$, $X^2$, Y, $R^{2a}$, $R^{2b}$, $R^3$, $R^4$, $R^5$, $R^6$, $R^7$ and ---- are as defined according to any one of embodiments 1 to 31.

Embodiment 34: A compound according to embodiment 1, wherein the compound is selected from
2-Amino-N-[(R)-1-benzyloxymethyl-2-(2-methyl-1-oxo-4-phenyl-2,7-diaza-spiro[4.5]dec-7-yl)-2-oxo-ethyl]-2-methyl-propionamide;
2-Amino-N-((2R)-3-(benzyloxy)-1-(4-(4-fluorophenyl)-2-methyl-1-oxo-2,7-diazaspiro[4.5]decan-7-yl)-1-oxopropan-2-yl)-2-methylpropanamide;
2-Amino-N-((2R)-3-(benzyloxy)-1-oxo-1-(1-oxo-4-phenyl-2,7-diazaspiro[4.5]decan-7-yl)propan-2-yl)-2-methylpropanamide;
2-Amino-N-((2R)-3-(benzyloxy)-1-(2-isopropyl-1-oxo-4-phenyl-2,7-diaza spiro[4.5]decan-7-yl)-1-oxopropan-2-yl)-2-methylpropanamide;
2-Amino-N-((2R)-3-(benzyloxy)-1-(4-(4-chlorophenyl)-2-methyl-1-oxo-2,7-diaza spiro[4.5]decan-7-yl)-1-oxopropan-2-yl)-2-methylpropanamide;
2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide;
2-Amino-2-methyl-N-((2R)-1-(2-methyl-1-oxo-4-phenyl-2,7-diazaspiro[4.5]decan-7-yl)-3-(1-methyl-1H-indol-3-yl)-1-oxopropan-2-yl)propanamide;
2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide;

2-Amino-N-((2R)-1-(4-(4-fluorophenyl)-2-isopropyl-1-oxo-2,7-diazaspiro[4.5]decan-7-yl)-3-(1-methyl-1H-indol-3-yl)-1-oxopropan-2-yl)-2-methylpropanamide;

2-amino-N-((2R)-3-(benzyloxy)-1-(2-(2-(dimethylamino)-2-oxoethyl)-1-oxo-4-phenyl-2,7-diaza spiro[4.5]decan-7-yl)-1-oxopropan-2-yl)-2-methylpropanamide;

N-((2R)-3-(Benzyloxy)-1-(2-methyl-1-oxo-4-phenyl-2,7-diazaspiro[4.5]decan-7-yl)-1-oxopropan-2-yl)-2-methyl-2-(methylamino)propanamide;

2-Amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide;

2-Amino-N-((2R)-3-(benzyloxy)-1-(2-methyl-1-oxo-4-phenyl-2,7-diazaspiro[4.5]decan-7-yl)-1-oxopropan-2-yl)-2-methylpropanamide;

N-((2R)-3-(1H-indol-3-yl)-1-(2-methyl-1-oxo-4-phenyl-2,7-diazaspiro[4.5]decan-7-yl)-1-oxopropan-2-yl)-2-amino-2-methylpropanamide;

2-amino-2-methyl-N-((2R)-1-(2-methyl-1-oxo-4-phenyl-2,7-diazaspiro[4.5]decan-7-yl)-1-oxo-5-phenylpentan-2-yl)propanamide;

2-Amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide;

2-amino-2-methyl-N-((2R)-1-(2-methyl-1-oxo-4-phenyl-2,7-diazaspiro[4.5]decan-7-yl)-1-oxo-4-phenylbutan-2-yl)propanamide;

2-amino-N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methylpropanamide;

2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-1-oxo-5-phenylpentan-2-yl)-2-methylpropanamide;

2-amino-2-methyl-N-((2R)-1-(2-methyl-1-oxo-4-phenyl-2,7-diazaspiro[4.5]decan-7-yl)-1-oxo-5-phenylpentan-2-yl)propanamide;

2-amino-N-((2R)-1-(4-(4-fluorophenyl)-2-isopropyl-1-oxo-2,7-diazaspiro[4.5]decan-7-yl)-3-(1H-indol-3-yl)-1-oxopropan-2-yl)-2-methylpropanamide;

2-amino-2-methyl-N-((2R)-1-(2-methyl-1-oxo-3-phenyl-2,6-diazaspiro[3.5]nonan-6-yl)-3-(1-methyl-1H-indol-3-yl)-1-oxopropan-2-yl)propanamide;

2-Amino-N-{(R)-1-benzyloxymethyl-2-[2-(2,2-dimethlypropyl)-1-oxo-4-phenyl-2,7-diaza-spiro[4.5]dec-7-yl]-2-oxo-ethyl}-2-methyl-propionamide;

2-amino-N-((2R)-3-(benzyloxy)-1-(2-methyl-1-oxo-4-phenyl-2,7-diazaspiro[4.5]decan-7-yl)-1-oxobutan-2-yl)-2-methylpropanamide;

2-amino-N-((2R)-3-(benzyloxy)-1-(1-(4-fluorophenyl)-2-methyl-3-oxo-2,6-diazaspiro[3.5]nonan-6-yl)-1-oxopropan-2-yl)-2-methylpropanamide;

2-Amino-N-{(R)-1-benzyloxymethyl-2-(2-isobutyl-1-oxo-4-phenyl-2,7-diaza-spiro[4.5]dec-7-yl)-2-oxo-ethyl}-2-methyl-propionamide;

2-Amino-N-{(R)-1-benzyloxymethyl-2-[4-(4-chloro-phenyl)-2-methyl-1-oxo-2,7-diaza-spiro[4.5]dec-7-yl]-2-oxo-ethyl}-2-methyl-propionamide;

2-Amino-N-[(R)-1-benzyloxymethyl-2-(2-isopropyl-1-oxo-4-phenyl-2,7-diaza-spiro[4.5]dec-7-yl)-2-oxo-ethyl]-2-methyl-propionamide;

2-Amino-N-[(R)-1-benzyloxymethyl-2-(3-methyl-4-oxo-1-phenyl-2,3,7-triaza-spiro[4.5]dec-1-en-7-yl)-2-oxo-ethyl]-2-methyl-propionamide;

2-Amino-N-[(R)-1-benzyloxymethyl-2-(3-methyl-4-oxo-1-phenyl-1,3,7-triaza-spiro[4.5]dec-7-yl)-2-oxo-ethyl]-2-methyl-propionamide;

2-Amino-N-[(R)-1-benzyloxymethyl-2-oxo-2-(1-oxo-4-phenyl-2,7-diaza-spiro[4.5]dec-7-yl)-ethyl]-2-methylpropionamide;

2-amino-N-((2R)-3-(benzyloxy)-1-(2-methyl-1-oxo-4-o-tolyl-2,7-diazaspiro[4.5]decan-7-yl)-1-oxopropan-2-yl)-2-methylpropanamide;

2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide;

2-amino-2-methyl-N-((2R)-1-(2-methyl-1-oxo-4-phenyl-2,7-diazaspiro[4.5]decan-7-yl)-3-(4-methylbenzyloxy)-1-oxopropan-2-yl)propanamide;

2-amino-N-((2R)-3-(4-chlorobenzyloxy)-1-(4-(4-fluorophenyl)-2-methyl-1-oxo-2,7-diazaspiro[4.5]decan-7-yl)-1-oxopropan-2-yl)-2-methylpropanamide;

2-amino-N-((2R)-3-(benzyloxy)-1-(2-methyl-1-oxo-4-(pyridin-3-yl)-2,7-diazaspiro[4.5]decan-7-yl)-1-oxopropan-2-yl)-2-methylpropanamide;

2-amino-N-((2R)-3-(cyclohexylmethoxy)-1-(2-methyl-1-oxo-4-phenyl-2,7-diazaspiro[4.5]decan-7-yl)-1-oxopropan-2-yl)-2-methylpropanamide;

2-amino-N-((2R)-3-(benzyloxy)-1-(3-methyl-4-oxo-1-phenyl-1,3,7-triazaspiro[4.5]decan-7-yl)-1-oxopropan-2-yl)-2-methylpropanamide;

2-amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide;

2-amino-N-((2R)-3-(benzyloxy)-1-(2-methyl-1-oxo-3-phenyl-2,6-diazaspiro[3.5]nonan-6-yl)-1-oxopropan-2-yl)-2-methylpropanamide;

N-((2R)-3-(1H-Indol-3-yl)-1-(2-isopropyl-1-oxo-4-phenyl-2,7-diazaspiro[4.5]decan-7-yl)-1-oxopropan-2-yl)-2-amino-2-methylpropanamide;

2-Amino-N-[(R)-1-benzyloxymethyl-2-(2-methyl-1-oxo-4-phenyl-2,7-diaza-spiro[4.5]dec-7-yl)-2-oxo-ethyl]-3-hydroxy-2-methyl-propionamide;

2-Amino-N-[(R)-1-(4-methoxy-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-2-[4-(4-fluoro-phenyl)-2-methyl-1-oxo-2,7-diaza-spiro[4.5]dec-7-yl]-1-(4-ethoxy-benzyloxymethyl)-2-oxo-ethyl]-2-methyl-propionamide;

2-Amino-N-[(R)-1-(4-fluoro-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-1-(3,4-difluoro-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-1-(2,4-difluoro-benzyloxymethyl)-2-(2-methyl-1-oxo-4-phenyl-2,7-diaza-spiro[4.5]dec-7-yl)-2-oxo-ethyl]-2-methyl-propionamide;

2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide;

2-amino-N-((2R)-3-(2,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-3-(4-fluorobenzyloxy)-1-(2-methyl-1-oxo-4-p-tolyl-2,7-diazaspiro[4.5]decan-7-yl)-1-oxopropan-2-yl)-2-methylpropanamide;

2-amino-N-((2R)-3-(benzyloxy)-1-(4-(3,5-difluorophenyl)-2-methyl-1-oxo-2,7-diazaspiro[4.5]decan-7-yl)-1-oxopropan-2-yl)-2-methylpropanamide;

2-amino-N-((2R)-3-(3,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-3-(benzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-1-(4-(3,4-difluorophenyl)-2-methyl-1-oxo-2,7-diazaspiro[4.5]decan-7-yl)-3-(4-fluorobenzyloxy)-1-oxopropan-2-yl)-2-methylpropanamide;

2-amino-N-(1-(4-(4-fluorophenyl)-2-methyl-1-oxo-2,7-diazaspiro[4.5]decan-7-yl)-1-oxo-4-(tetrahydro-2H-pyran-4-yl)butan-2-yl)-2-methylpropanamide;

2-amino-N-((2R)-3-(benzyloxy)-1-(4-(4-fluorophenyl)-2-((5-methylisoxazol-3-yl)methyl)-1-oxo-2,7-diazaspiro[4.5]decan-7-yl)-1-oxopropan-2-yl)-2-methylpropanamide;

2-amino-N-((2R)-3-(benzyloxy)-1-(4-(4-fluorophenyl)-2-(oxazol-2-ylmethyl)-1-oxo-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-3-(2-methylbenzyloxy)-1-oxopropan-2-yl)-2-methylpropanamide;

2-amino-N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methylpropanamide;

N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methyl-2-(methylamino)propanamide;

N-((2R)-3-(benzyloxy)-1-(4-(4-fluorophenyl)-2-methyl-1-oxo-2,7-diazaspiro[4.5]decan-7-yl)-1-oxopropan-2-yl)-2-methyl-2-(methylamino)propanamide;

2-amino-N-((2R)-3-(benzyloxy)-1-(4-(4-fluorophenyl)-1-oxo-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-3-(3-methylbenzyloxy)-1-oxopropan-2-yl)-2-methylpropanamide;

2-Amino-N-((R)-3-(2,3-dihydro-1H-inden-2-yl)-1-(2-methyl-1-oxo-4-phenyl-2,7-diazaspiro[4.5]decan-7-yl)-1-oxopropan-2-yl)-2-methylpropanamide;

2-amino-N-((2R)-1-(4-(4-fluorophenyl)-1-oxo-2,7-diazaspiro[4.5]decan-7-yl)-1-oxo-5-phenylpentan-2-yl)-2-methylpropanamide;

2-amino-N-((2R)-4-cyclohexyl-1-(4-(4-fluorophenyl)-2-methyl-1-oxo-2,7-diazaspiro[4.5]decan-7-yl)-1-oxobutan-2-yl)-2-methylpropanamide;

2-amino-2-methyl-N-((2R)-1-(2-methyl-1-oxo-4-p-tolyl-2,7-diazaspiro[4.5]decan-7-yl)-3-(2-methylbenzyloxy)-1-oxopropan-2-yl)propanamide;

2-amino-2-methyl-N—((R)-1-(2-methyl-1-oxo-4-phenyl-2,7-diazaspiro[4.5]decan-7-yl)-1-oxo-5-phenylpent-4-en-2-yl)propanamide;

2-Amino-N-((S)-3-(benzylthio)-1-(2-methyl-1-oxo-4-phenyl-2,7-diazaspiro[4.5]decan-7-yl)-1-oxopropan-2-yl)-2-methylpropanamide;

N-((2R)-3-(4-fluorobenzyloxy)-1-(2-methyl-1-oxo-4-phenyl-2,7-diazaspiro[4.5]decan-7-yl)-1-oxopropan-2-yl)-2-methyl-2-(methylamino)propanamide;

2-amino-N-((2R)-3-(benzyloxy)-1-(2-methyl-1-oxo-4-p-tolyl-2,7-diazaspiro[4.5]decan-7-yl)-1-oxobutan-2-yl)-2-methylpropanamide;

2-amino-2-methyl-N—((R)-1-(2-methyl-1-oxo-4-phenyl-2,7-diazaspiro[4.5]decan-7-yl)-1-oxo-3-(pyridin-2-ylmethoxy)propan-2-yl)propanamide;

2-Amino-N-((R)-3-(benzyloxy)-1-oxo-1-(1-oxo-4-phenyl-2-(2,2,2-trifluoroethyl)-2,7-diazaspiro[4.5]decan-7-yl)propan-2-yl)-2-methylpropanamide;

2-Amino-N-((R)-3-(benzyloxy)-1-(2-methyl-1-oxo-4-phenyl-2,7-diazaspiro[4.5]decan-7-yl)-1-oxopropan-2-yl)-2-methylbutanamide;

N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methyl-2-(methylamino)propanamide;

2-Amino-2-methyl-N—((R)-1-(2-methyl-1-oxo-4-phenyl-2,7-diazaspiro[4.5]decan-7-yl)-1-oxo-4-phenoxybutan-2-yl)propanamide;

or a pharmaceutically acceptable salt thereof.

Embodiment 35: A pharmaceutical composition comprising a therapeutically effective amount of a compound or salt according to any one of embodiments 1 to 34 and one or more pharmaceutically acceptable carriers.

Embodiment 36: A combination comprising a therapeutically effective amount of the compound or salt according to any one of embodiments 1 to 34 and one or more therapeutically active co-agents.

Embodiment 37: A combination of embodiment 34, wherein said combination is a pharmaceutical combination.

Embodiment 38: A method of modulating ghrelin receptor activity in a subject,
wherein the method comprises administering to the subject a therapeutically effective amount of the compound according to any one of embodiments 1 to 34.

Embodiment 39: A method of treating a disorder or a disease in a subject mediated by the ghrelin receptor, wherein the method comprises administering to the subject a therapeutically effective amount of the compound according to any one of embodiments 1 to 34.

Embodiment 40: A method in accordance to embodiment 38 or 39, wherein the disorder or the disease is selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis, comprising the step of administering to a subject a therapeutically effective amount of a compound of the first, second or third aspect as defined herein.

Embodiment 41: A compound according to any one of embodiments 1 to 34, for use as a medicament.

Embodiment 42: A compound according to any one of embodiments 1 to 34, for use in the treatment of a disease or disorder mediated by the ghrelin receptor.

Embodiment 43: A compound for use according to embodiment 42 wherein the treatment of a disease or disorder is selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis.

Embodiment 44: Use of a compound according to any one of embodiments 1 to 34 in the manufacture of a medicament for the treatment of a disorder or disease mediated by the ghrelin receptor.

Embodiment 45: Use of a compound according to any one of embodiments 1 to 34, in the manufacture of a medicament for the treatment of a disorder or disease selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis.

Embodiment 46: Pharmaceutical composition for treating a disease or disorder mediated by the ghrelin receptor comprising a compound according to any one of embodiments 1 to 34 as an active ingredient.

Embodiment 47: A pharmaceutical composition according to embodiment 46, wherein said disease or disorder is selected from gastroparesis (e.g. of diabetic, idiopathic or surgical origin), ileus (including post-operative ileus as well as ileus of drug-induced, ischemic, infectious and inflammatory origin), functional dyspepsia, short bowel syndrome, constipation such as associated with the hypomotility phase of irritable bowel syndrome (IBS), chronic intestinal pseudo-obstruction, delayed gastric emptying associated with wasting conditions, GERD, gastric ulcers and Crohn's disease, and emesis.

Embodiment 48: A pharmaceutical composition according to embodiment 46 or 47, wherein said compound is selected from the compounds of embodiment 34.

Embodiment 49: A process of manufacturing a compound of formula (I) or a salt thereof in accordance to the definition of embodiment 1,

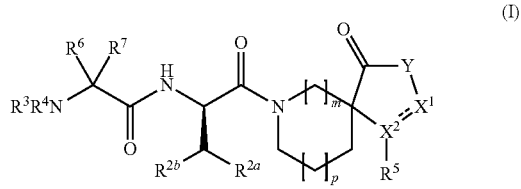

(I)

wherein compounds of formula (I) are as defined in embodiment 1, comprising reacting a compound of formula (II)

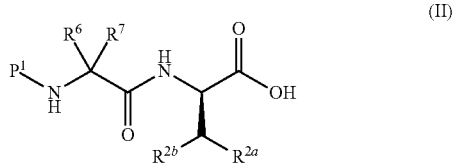

(II)

wherein $R^{22}$, $R^{2b}$, $R^6$, $R^7$ are defined as in embodiment 1, and $P^1$ represents a suitable protection group, for example a BOC (tert-butoxy carbonyl) group,
in a suitable solvent such as DMF in the presence of a suitable amide coupling reagent, for example ®T3P, and a suitable base such as DIPEA with a compound of formula (III)

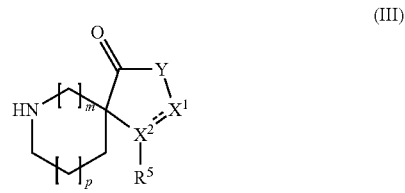

(III)

wherein $R^5$, $X^1$, $X^2$, m, p and Y are defined as in embodiment 1,
at a suitable temperature such as room temperature,
followed by the removal of the protection group $P^1$ so as to obtain a compound of formula (I).

Embodiment 50: A crystalline form I of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 51: The crystalline form according to embodiment 50, characterised by a X-ray diffraction pattern comprising four 2θ values selected from the group consisting of 8.493±0.2°, 15.574±0.2°, 19.339±0.2°, 20.842±0.2° at a temperature of about 22° C.

Embodiment 52: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a X-ray diffraction spectrum substantially the same as the X-ray diffraction spectrum shown in FIG. 1.

Figure 5:
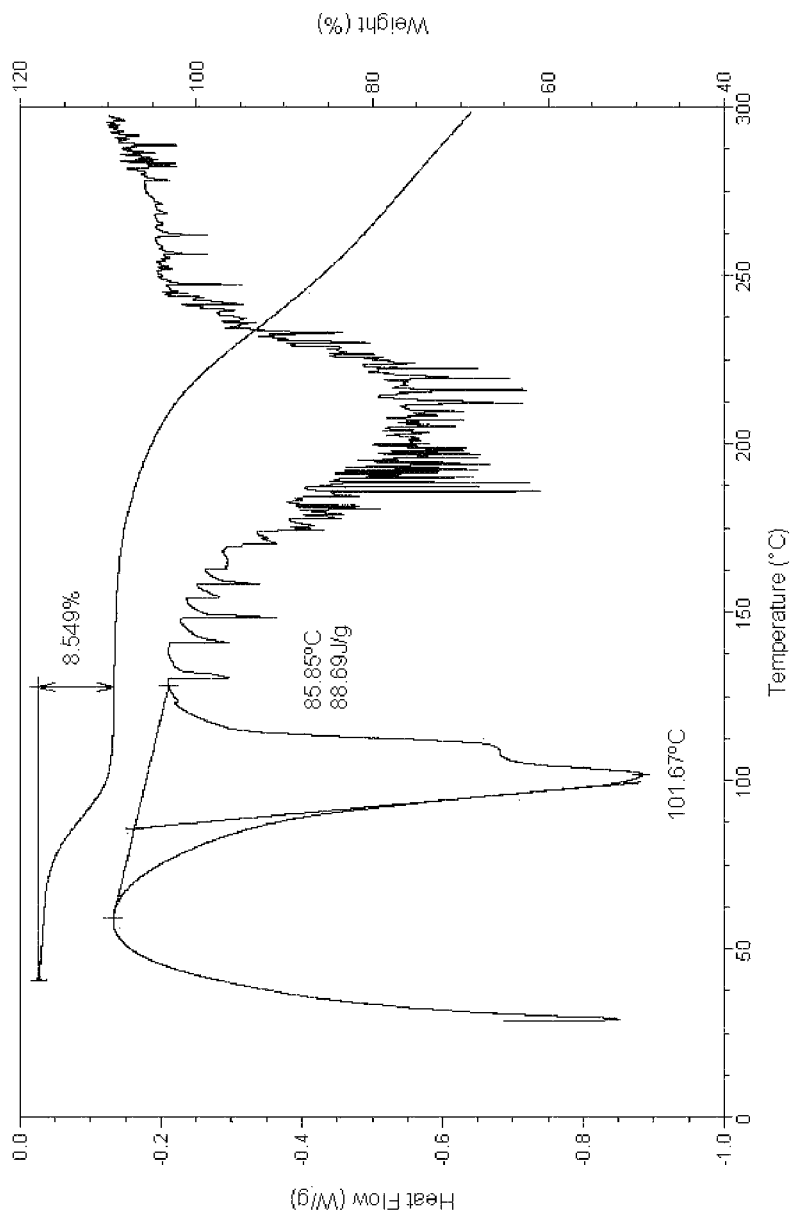
FIG. 5 illustrates the differential scanning calorimetry (DSC) and the thermogravimetric analysis (TGA) of the crystalline form I of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 53: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a thermo gravimetric analysis (TGA) diagram substantially the same as that shown in FIG. 5.

Embodiment 54: A crystalline form II of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 55: The crystalline form according to embodiment 54, characterised by a X-ray diffraction pattern comprising four 2θ values selected from the group consisting of 8.383±0.2°, 11.724±0.2°, 17.918±0.2°, 19.237±0.2° at a temperature of about 22° C.

Embodiment 56: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a X-ray diffraction spectrum substantially the same as the X-ray diffraction spectrum shown in FIG. 2.

Figure 6:
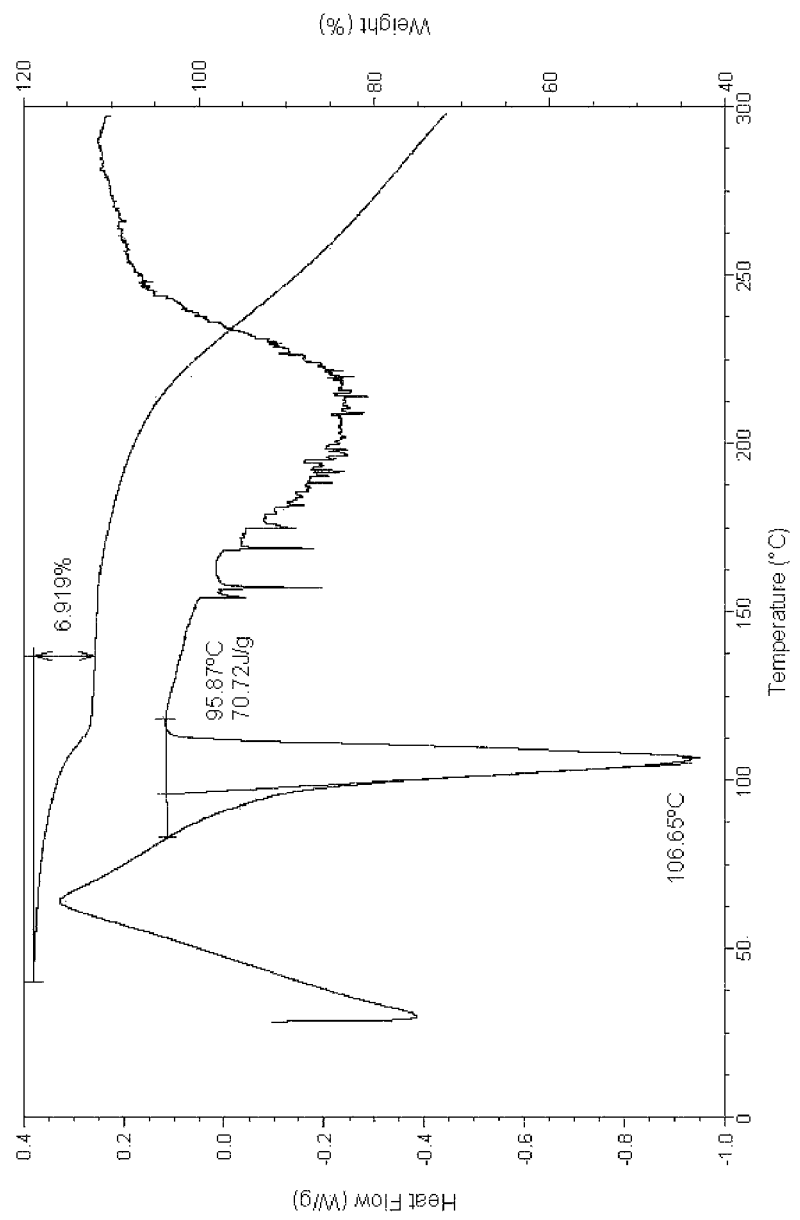
FIG. 6 illustrates the differential scanning calorimetry (DSC) and the thermogravimetric analysis (TGA) of the crystalline form II of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 57: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a thermo gravimetric analysis (TGA) diagram substantially the same as that shown in FIG. 6.

Embodiment 58: A crystalline form III of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 59: The crystalline form according to embodiment 58, characterised by a X-ray diffraction pattern comprising four 2θ values selected from the group consisting of 10.084±0.2°, 16.209±0.2°, 20.166±0.2°, 22.325±0.2° at a temperature of about 22° C.

Embodiment 60: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a X-ray diffraction spectrum substantially the same as the X-ray diffraction spectrum shown in FIG. 3.

Figure 7:
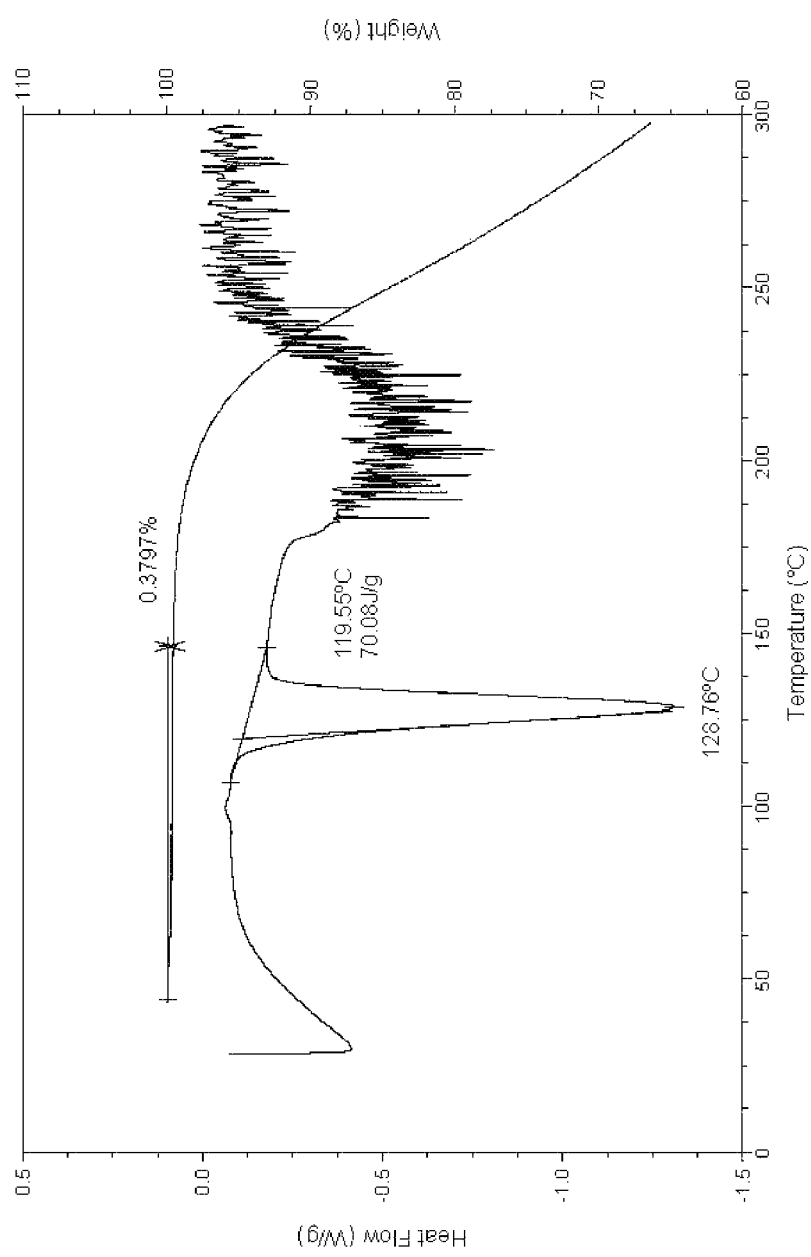
FIG. 7 illustrates the differential scanning calorimetry (DSC) and the thermogravimetric analysis (TGA) of the crystalline form III of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 61: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a thermo gravimetric analysis (TGA) diagram substantially the same as that shown in FIG. 7.

Embodiment 62: A crystalline form IV of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 63: The crystalline form according to embodiment 62, characterised by a X-ray diffraction pattern comprising four 2θ values selected from the group consisting of 10.039±0.2°, 16.169±0.2°, 17.333±0.2°, 20.130±0.2° at a temperature of about 22° C.

Embodiment 64: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a X-ray diffraction spectrum substantially the same as the X-ray diffraction spectrum shown in FIG. 4.

Figure 8:
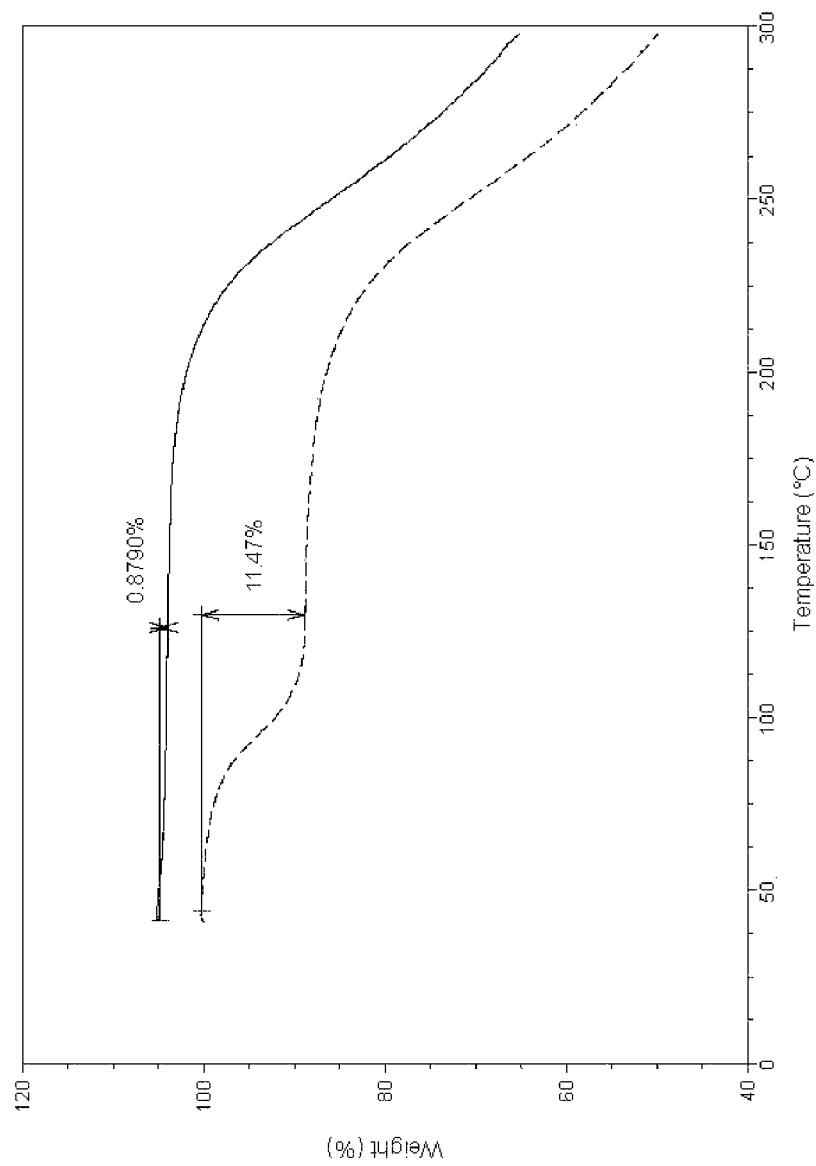
FIG. 8 illustrates the thermogravimetric analysis (TGA) of the crystalline form IV of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt.

Embodiment 65: A crystalline form of 2-Amino-N-[(R)-1-benzyloxymethyl-2-((4S,5R)-2-methyl-1-oxo-4-phenyl-2,7-diaza-spiro[4.5]dec-7-yl)-2-oxo-ethyl]-2-methyl-propionamide L-malate salt having a thermo gravimetric analysis (TGA) diagram substantially the same as that shown in FIG. 8.

Embodiment 66: A crystalline form I of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt.

Embodiment 67: The crystalline form according to embodiment 66, characterised by a X-ray diffraction pattern comprising four 2θ values selected from the group consisting of 7.269±0.2°, 9.550±0.2°, 17.831±0.2°, 20.723±0.2° at a temperature of about 22° C.

Figure 11:
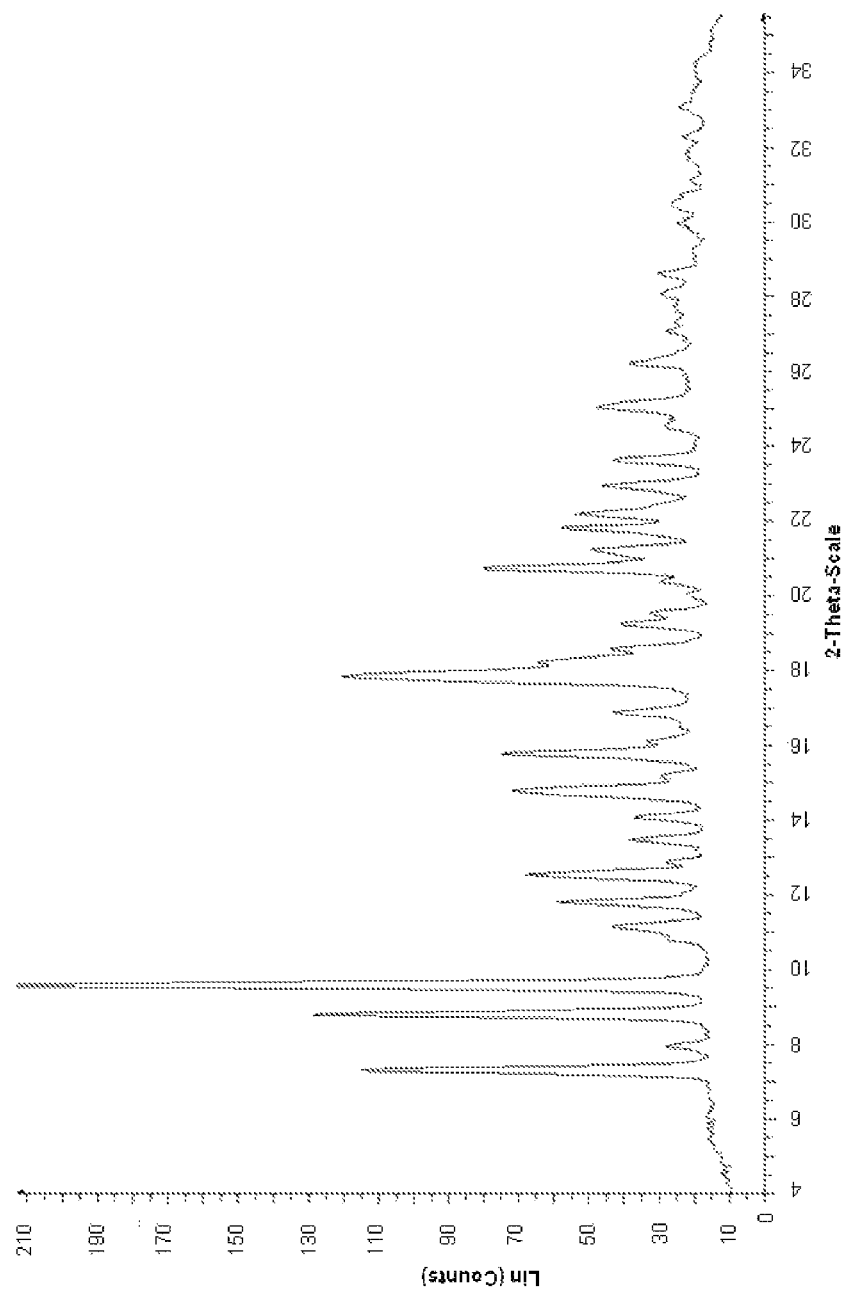
FIG. 11 illustrates the X-ray powder diffraction pattern of the crystalline form I of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt.

Embodiment 68: A crystalline form of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt having a X-ray diffraction spectrum substantially the same as the X-ray diffraction spectrum shown in FIG. 11.

Figure 13:
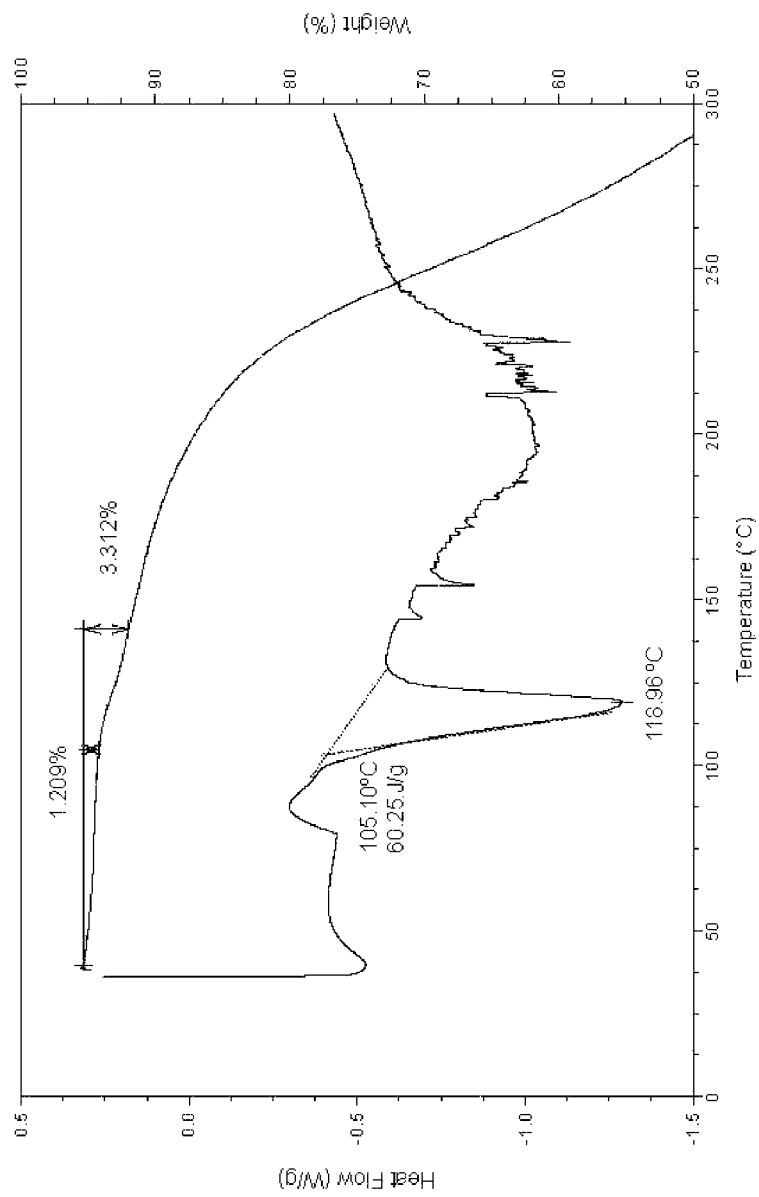
FIG. 13 illustrates the differential scanning calorimetry (DSC) and the thermogravimetric analysis (TGA) of the crystalline form I of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt.

Embodiment 69: A crystalline form of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt having a thermo gravimetric analysis (TGA) diagram substantially the same as that shown in FIG. 13.

Embodiment 70: A crystalline form II of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt.

Embodiment 71: The crystalline form according to embodiment 70, characterised by a X-ray diffraction pattern comprising four 2θ values selected from the group consisting of 16.054±0.2°, 20.312±0.2°, 23.531±0.2°, 26.532±0.2° at a temperature of about 22° C.

Figure 12:
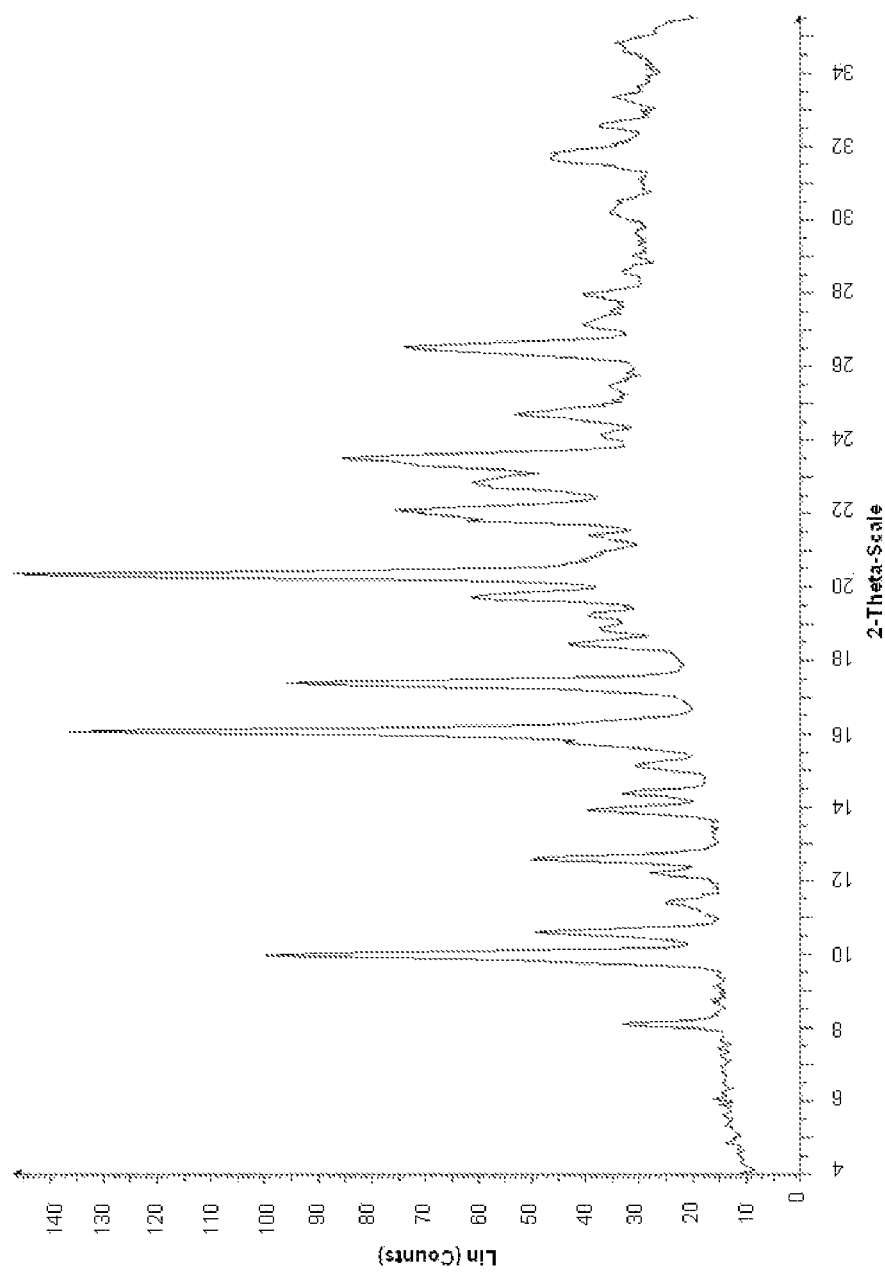
FIG. 12 illustrates the X-ray powder diffraction pattern of the crystalline form II of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt.

Embodiment 72: A crystalline form of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt having a X-ray diffraction spectrum substantially the same as the X-ray diffraction spectrum shown in FIG. 12.

Figure 14:
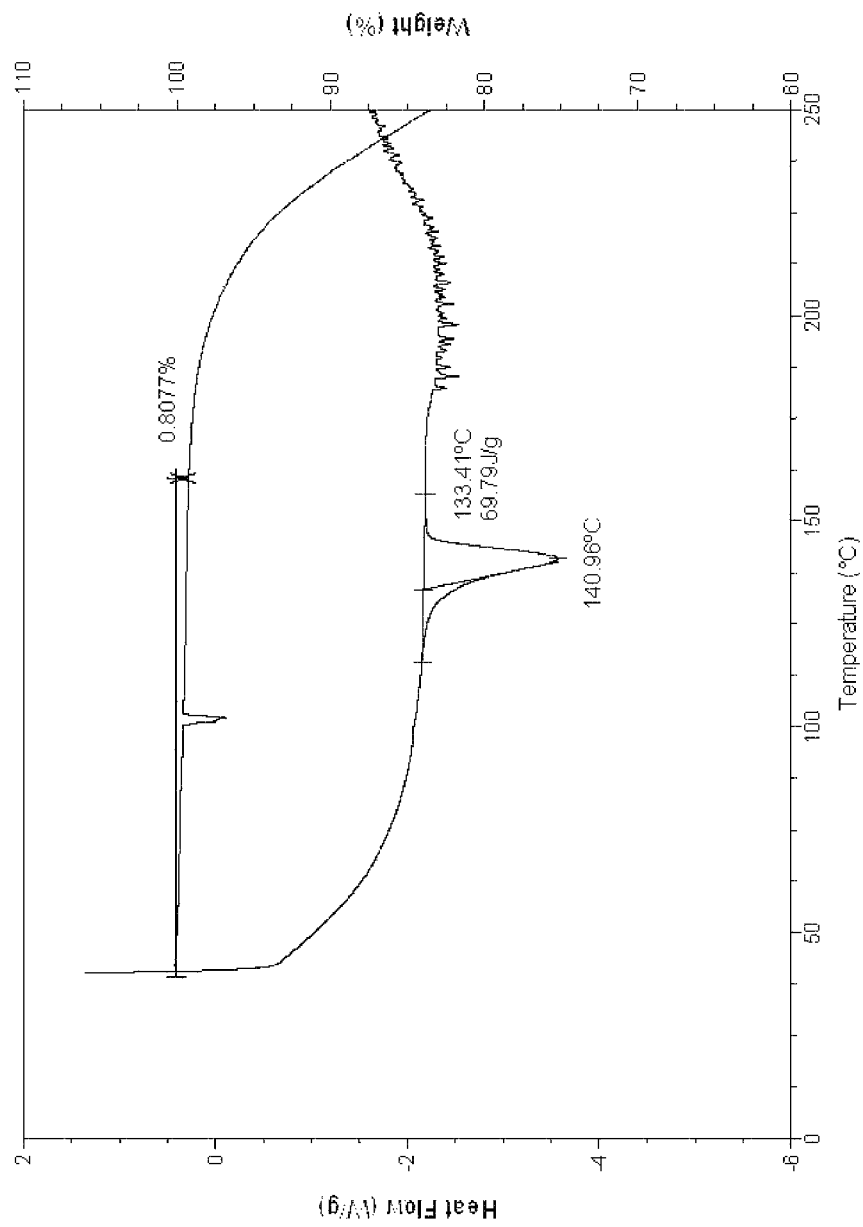
FIG. 14 illustrates the differential scanning calorimetry (DSC) and the thermogravimetric analysis (TGA) of the crystalline form II of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt.

Embodiment 73: A crystalline form of 2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide L-malate salt having a thermo gravimetric analysis (TGA) diagram substantially the same as that shown in FIG. 14.

Embodiment 74: A crystalline form I of 2-Amino-N-{(R)-1-benzyloxymethyl-2-[(4S,5R)-4-fluoro-phenyl)-2-methyl-1-oxo-2,7-diaza-spiro[4.5]dec-7-yl]-2-oxoethyl}2-methyl-propionamide L-malate salt.

Embodiment 75: The crystalline form according to embodiment 74, characterised by a X-ray diffraction pattern comprising four 2θ values selected from the group consisting of 8.767±0.2°, 12.998±0.2°, 17.354±0.2°, 19.847±0.2° at a temperature of about 22° C.

Embodiment 76: A crystalline form of 2-Amino-N-{(R)-1-benzyloxymethyl-2-[(4S,5R)-4-fluoro-phenyl)-2-methyl-1-oxo-2,7-diaza-spiro[4.5]dec-7-yl]-2-oxoethyl}2-methyl-propionamide L-malate salt having a X-ray diffraction spectrum substantially the same as the X-ray diffraction spectrum shown in FIG. 8.

Embodiment 77: A crystalline form of 2-Amino-N-{(R)-1-benzyloxymethyl-2-[(4S,5R)-4-fluoro-phenyl)-2-methyl-1-oxo-2,7-diaza-spiro[4.5]dec-7-yl]-2-oxoethyl}2-methyl-propionamide L-malate salt having a thermo gravimetric analysis (TGA) diagram substantially the same as that shown in FIG. 9.

Embodiment 78: A pharmaceutical composition comprising the crystalline form according to any of embodiments 50 to 53 and a pharmaceutically acceptable carrier or diluent.

Embodiment 79: A pharmaceutical composition comprising the crystalline form according to any of embodiments 54 to 57 and a pharmaceutically acceptable carrier or diluent.

Embodiment 80: A pharmaceutical composition comprising the crystalline form according to any of embodiments 58 to 61 and a pharmaceutically acceptable carrier or diluent.

Embodiment 81: A pharmaceutical composition comprising the crystalline form according to any of embodiments 62 to 65 and a pharmaceutically acceptable carrier or diluent.

Embodiment 82: A pharmaceutical composition comprising the crystalline form according to any of embodiments 66 to 69 and a pharmaceutically acceptable carrier or diluent.

Embodiment 83: A pharmaceutical composition comprising the crystalline form according to any of embodiments 70 to 73 and a pharmaceutically acceptable carried or diluent.

Embodiment 84: A pharmaceutical composition comprising the crystalline form according to any of embodiments 74 to 77 and a pharmaceutically acceptable carrier or diluent.

The invention claimed is:
1. A compound of formula (I)

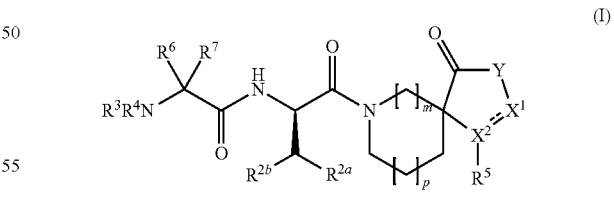

wherein
---- is a single bond;
$X^1$ is $(CR^{x1}H)_n$ and X2 is (CH);
n is 1;
$R^{x1}$ is selected from hydrogen and $C_{1-6}$alkyl;
m is 1 and p is 1; or
Y is $NR^1$;
$R^1$ is selected from hydrogen and $C_{1-6}$alkyl;
$R^{2a}$ is
-A-phenyl;

wherein the phenyl is unsubstituted or substituted with 1 to 3 substituents independently selected from halogen, hydroxy, $C_{1-6}$alkyl, $C_{1-6}$alkoxy and $C_{1-6}$haloalkyl;

A is selected from a bond, —$(CR^{A1}R^{A2})$—, —$(CR^{A1}R^{A2})(CR^{A1}R^{A2})$—, —$(CR^{A1}R^{A2})$—O—, and —O—$(CR^{A1}R^{A2})$—;

$R^{A1}$ and $R^{A2}$ are independently selected from hydrogen and $C_{1-6}$alkyl;

$R^{2b}$ is hydrogen or $C_{1-4}$alkyl;

$R^3$ and $R^4$ are independently selected from hydrogen and $C_{1-6}$alkyl $R^6$ and $R^7$ are independently selected from hydrogen and $C_{1-6}$alkyl;

$R^5$ is phenyl, which is unsubstituted or substituted with 1 to 3 substituents independently selected from halogen, $C_{1-6}$alkyl, $C_{1-6}$alkoxy and $C_{1-6}$haloalkyl;

or a pharmaceutically acceptable salt thereof.

2. The compound according to claim 1, wherein $R^5$ is phenyl and is unsubstituted or substituted with 1 to 3 substituents independently selected from halogen and $C_{1-6}$alkyl.

3. The compound according to claim 1, wherein $R^{2a}$ is -A-phenyl, unsubstituted or substituted with 1 to 3 substituents independently selected from $C_{1-6}$alkyl, $C_{1-6}$alkoxy and halogen.

4. The compound of 1, which is selected from the group consisting of:
2-Amino-N-[(R)-1-benzyloxymethyl-2-(2-methyl-1-oxo-4-phenyl-2,7-diaza-spiro[4.5]dec-7-yl)-2-oxo-ethyl]-2-methyl-propionamide;
2-Amino-N-((2R)-3-(benzyloxy)-1-(4-(4-fluorophenyl)-2-methyl-1-oxo-2,7-diazaspiro [4.5]decan-7-yl)-1-oxopropan-2-yl)-2-methylpropanamide;
2-Amino-N-((2R)-3-(benzyloxy)-1-oxo-1-(1-oxo-4-phenyl-2,7-diazaspiro[4.5]decan-7-yl)propan-2-yl)-2-methylpropanamide;
2-Amino-N-((2R)-3-(benzyloxy)-1-(2-isopropyl-1-oxo-4-phenyl-2,7-diaza spiro[4.5]decan-7-yl)-1-oxopropan-2-yl)-2-methylpropanamide;
2-Amino-N-((2R)-3-(benzyloxy)-1-(4-(4-chlorophenyl)-2-methyl-1-oxo-2,7-diaza spiro[4.5]decan-7-yl)-1-oxopropan-2-yl)-2-methylpropanamide;
2-Amino-N-((2R)-1-(4-(4-fluorophenyl)-2-methyl-1-oxo-2,7-diazaspiro[4.5]decan-7-yl)-3-(1H-indol-3-yl)-1-oxopropan-2-yl)-2-methylpropanamide;
2-Amino-2-methyl-N-((2R)-1-(2-methyl-1-oxo-4-phenyl-2,7-diazaspiro[4.5]decan-7-yl)-3-(1-methyl-1H-indol-3-yl)-1-oxopropan-2-yl)propanamide;
2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide;
2-Amino-N-((2R)-1-(4-(4-fluorophenyl)-2-isopropyl-1-oxo-2,7-diazaspiro[4.5]decan-7-yl)-H-indol-3-yl)-1-oxopropan-2-yl)-2-methyl propanamide;
2-amino-N-((2R)-3-(benzyloxy)-1-(2-(2-(dimethylamino)-2-oxoethyl)-1-oxo-4-phenyl-2,7-diaza spiro[4.5]decan-7-yl)-1-oxopropan-2-yl)-2-methylpropanamide;
2-Amino-N-((2R)-3-(benzyloxy)-1-(4-(4-fluorophenyl)-2-isopropyl-1-oxo-2,7-diazaspiro[4.5]decan-7-yl)-1-oxopropan-2-yl)-2-methylpropanamide;
2-Amino-N-((2R)-3-(benzyloxy)-1-(2-methyl-1-oxo-4-phenyl-2,7-diazaspiro[4.5]decan-7-yl)-1-oxopropan-2-yl)-2-methylpropanamide;
N-((2R)-3-(1H-indol-3-yl)-1-(2-methyl-1-oxo-4-phenyl-2,7-diazaspiro[4.5]decan-7-yl)-1-oxopropan-2-yl)-2-amino-2-methylpropanamide;
2-amino-2-methyl-N-((2R)-1-(2-methyl-1-oxo-4-phenyl-2,7-diazaspiro[4.5]decan-7-yl)-1-oxo-5-phenylpentan-2-yl)propanamide;
2-amino-N-((2R)-3-(benzyloxy)-1-(2-ethyl-1-oxo-4-phenyl-2,7-diazaspiro[4.5]decan-7-yl)-1-oxopropan-2-yl)-2-methylpropanamide;
2-amino-2-methyl-N-((2R)-1-(2-methyl-1-oxo-4-phenyl-2,7-diazaspiro[4.5]decan-7-yl)-1-oxo-4-phenylbutan-2-yl)propanamide;
2-amino-N-((2R)-1-(4-(4-fluorophenyl)-2-methyl-1-oxo-2,7-diazaspiro[4.5]decan-7-yl)-3-(4-methylbenzyloxy)-1-oxopropan-2-yl)-2-methylpropanamide;
2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide;
2-amino-N-((2R)-1-(4-(4-fluorophenyl)-2-methyl-1-oxo-2,7-diazaspiro[4.5]decan-7-yl)-1-oxo-5-phenylpentan-2-yl)-2-methylpropanamide;
2-amino-2-methyl-N-((2R)-1-(2-methyl-1-oxo-4-phenyl-2,7-diazaspiro[4.5]decan-7-yl)-1-oxo-5-phenylpentan-2-yl)propanamide;
2-amino-N-((2R)-1-(4-(4-fluorophenyl)-2-isopropyl-1-oxo-2,7-diazaspiro[4.5]decan-7-yl)-3-(1H-indol-3-yl)-1-oxopropan-2-yl)-2-methylpropanamide;
2-Amino-N-{(R)-1-benzyloxymethyl-2-[2-(2,2-dimethly-propyl)-1-oxo-4-phenyl-2,7-diaza-spiro[4.5]dec-7-yl]-2-oxo-ethyl}-2-methyl-propionamide;
2-amino-N-((2R)-3-(benzyloxy)-1-(2-methyl-1-oxo-4-phenyl-2,7-diazaspiro[4.5]decan-7-yl)-1-oxobutan-2-yl)-2-methylpropanamide;
2-Amino-N-{(R)-1-benzyloxymethyl-2-(2-isobutyl-1-oxo-4-phenyl-2,7-diaza-spiro[4.5]dec-7-yl)-2-oxo-ethyl}-2-methyl-propionamide;
2-Amino-N-{(R)-1-benzyloxymethyl-2-[4-(4-chlorophenyl)-2-methyl-1-oxo-2,7-diaza-spiro[4.5]dec-7-yl]-2-oxo-ethyl}-2-methyl-propionamide;
2-Amino-N-[(R)-1-benzyloxymethyl-2-(2-isopropyl-1-oxo-4-phenyl-2,7-diaza-spiro[4.5]dec-7-yl)-2-oxo-ethyl]-2-methyl-propionamide;
2-Amino-N-[(R)-1-benzyloxymethyl-2-oxo-2-(1-oxo-4-phenyl-2,7-diaza-spiro[4.5]dec-7-yl)ethyl]-2-methyl propionamide;
2-amino-N-((2R)-3-(benzyloxy)-1-(2-methyl-1-oxo-4-o-tolyl-2,7-diazaspiro[4.5]decan-7-yl)-1-oxopropan-2-yl)-2-methylpropanamide;
2-amino-N-((2R)-3-(benzyloxy)-1-(2-methyl-1-oxo-4-p-tolyl-2,7-diazaspiro[4.5]decan-7-yl)-1-oxopropan-2-yl)-2-methylpropanamide;
2-amino-2-methyl-N-((2R)-1-(2-methyl-1-oxo-4-phenyl-2,7-diazaspiro[4.5]decan-7-yl)-3-(4-methylbenzyloxy)-1-oxopropan-2-yl)propanamide;
2-amino-N-((2R)-3-(4-chlorobenzyloxy)-1-(4-(4-fluorophenyl)-2-methyl-1-oxo-2,7-diazaspiro[4.5]decan-7-yl)-1-oxopropan-2-yl)-2-methylpropanamide;
2-amino-N-((2R)-3-(benzyloxy)-1-(2-methyl-1-oxo-4-(pyridin-3-yl)-2,7-diazaspiro[4.5]decan-7-yl)-1-oxopropan-2-yl)-2-methylpropanamide;
2-amino-N-((2R)-3-(cyclohexylmethoxy)-1-(2-methyl-1-oxo-4-phenyl-2,7-diazaspiro[4.5]decan-7-yl)-1-oxopropan-2-yl)-2-methylpropanamide;
N-((2R)-3-(1H-Indol-3-yl)-1-(2-isopropyl-1-oxo-4-phenyl-2,7-diazaspiro[4.5]decan-7-yl)-1-oxopropan-2-yl)-2-amino-2-methylpropanamide;
2-Amino-N-[(R)-1-benzyloxymethyl-2-(2-methyl-1-oxo-4-phenyl-2,7-diaza-spiro[4.5]dec-7-yl)-2-oxo-ethyl]-3-hydroxy-2-methyl-propionamide;

2-Amino-N-[(R)-1-(4-methoxy-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-2-[4-(4-fluoro-phenyl)-2-methyl-1-oxo-2,7-diaza-spiro[4.5]dec-7-yl]-1-(4-ethoxy-benzyloxymethyl)-2-oxo-ethyl]-2-methyl-propionamide;

2-Amino-N-[(R)-1-(4-fluoro-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-1-(3,4-difluoro-benzyloxymethyl)-2-(2-methyl-1-oxo-4-phenyl-2,7-diaza-spiro[4.5]dec-7-yl)-2-oxo-ethyl]-2-methyl-propionamide;

2-Amino-N-[(R)-1-(2,4-difluoro-benzyloxymethyl)-2-(2-methyl-1-oxo-4-phenyl-2,7-diaza-spiro[4.5]dec-7-yl)-2-oxo-ethyl]-2-methyl-propionamide;

2-amino-N-((2R)-3-(3-methoxybenzyloxy)-1-(2-methyl-1-oxo-4-phenyl-2,7-diazaspiro[4.5]decan-7-yl)-1-oxopropan-2-yl)-2-methylpropanamide;

2-amino-N-((2R)-3-(2,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-3-(4-fluorobenzyloxy)-1-(2-methyl-1-oxo-4-p-tolyl-2,7-diazaspiro[4.5]decan-7-yl)-1-oxopropan-2-yl)-2-methylpropanamide;

2-amino-N-((2R)-3-(benzyloxy)-1-(4-(3,5-difluorophenyl)-2-methyl-1-oxo-2,7-diazaspiro[4.5]decan-7-yl)-1-oxopropan-2-yl)-2-methylpropanamide;

2-amino-N-((2R)-3-(3,4-difluorobenzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-3-(benzyloxy)-1-(4-(3,4-difluorophenyl)-2-methyl-1-oxo-2,7-diazaspiro[4.5]decan-7-yl)-1-oxopropan-2-yl)-2-methylpropanamide;

2-amino-N-((2R)-1-(4-(3,4-difluorophenyl)-2-methyl-1-oxo-2,7-diazaspiro[4.5]decan-7-yl)-3-(4-fluorobenzyloxy)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-3-(2-methylbenzyloxy)-1-oxopropan-2-yl)-2-methylpropanamide;

2-amino-N-((2R)-3-(4-fluorobenzyloxy)-1-(4-(4-fluorophenyl)-2-methyl-1-oxo-2,7-diazaspiro[4.5]decan-7-yl)-1-oxopropan-2-yl)-2-methylpropanamide;

2-amino-N-((2R)-3-(benzyloxy)-1-(4-(4-fluorophenyl)-1-oxo-2,7-diazaspiro[4.5]decan-7-yl)-1-oxopropan-2-yl)-2-methylpropanamide;

2-amino-N-((2R)-1-(4-(4-fluorophenyl)-2-methyl-1-oxo-2,7-diazaspiro[4.5]decan-7-yl)-3-(3-methylbenzyloxy)-1-oxopropan-2-yl)-2-methylpropanamide;

2-amino-N-((R)-3-(2,3-dihydro-1H-inden-2-yl)-1-(2-methyl-1-oxo-4-phenyl-2,7-diazaspiro[4.5]decan-7-yl)-1-oxopropan-2-yl)-2-methylpropanamide;

2-amino-N-((2R)-1-(4-(4-fluorophenyl)-1-oxo-2,7-diazaspiro[4.5]decan-7-yl)-1-oxo-5-phenylpentan-2-yl)-2-methylpropanamide;

2-amino-2-methyl-N-((2R)-1-(2-methyl-1-oxo-4-p-tolyl-2,7-diazaspiro [4.5] decan-7-yl)-3-(2-methylbenzyloxy)-1-oxopropan-2-yl)propanamide;

2-amino-2-methyl-N-((R)-1-(2-methyl-1-oxo-4-phenyl-2,7-diazaspiro [4.5]decan-7-yl)-1-oxo-5-phenylpent-4-en-2-yl)propanamide;

2-amino-N-((S)-3-(benzylthio)-1-(2-methyl-1-oxo-4-phenyl-2,7-diazaspiro [4.5] decan-7-yl)-1-oxopropan-2-yl)-2-methylpropanamide;

2-amino-N-((2R)3-(benzyloxy)-1-(2-methyl-1-oxo-4-p-tolyl-2,7-diazaspiro [4.5]decan-7-yl)-1-oxobutan-2-yl)-2-methylpropanamide;

2-amino-2-methyl-N-((R)-1-(2-methyl-1-oxo-4-phenyl-2,7-diazaspiro [4.5] decan-7-yl)-1-oxo-3-(pyridin-2-ylmethoxy)propan-2-yl)propanamide;

2-amino-N-((R)-3-(benzyloxy)-1-oxo-1-(1-oxo-4-phenyl-2-(2,2,2-trifluoroethyl)-2,7-diazaspiro[4.5]decan-7-yl)propan-2-yl)-2-methylpropanamide;

2-amino-N-((R)-3-(benzyloxy)-1-(2-methyl-1-oxo-4-phenyl-2,7-diazaspiro [4.5] decan-7-yl)-1-oxopropan-2-yl)-2-methylbutanamide;

2-Amino-2-methyl-N-((R)-1-(2-methyl-1-oxo-4-phenyl-2,7-diazaspiro [4.5] decan-7-yl)-1-oxo-4-phenoxybutan-2-yl)propanamide;

or a pharmaceutically acceptable salt thereof.

5. A pharmaceutical composition comprising a therapeutically effective amount of a compound or salt according to claim 1 and one or more pharmaceutically acceptable carriers.

6. The compound of claim 1, which is 2-Amino-N-[(R)-1-benzyloxymethyl-2-(2-methyl-1-oxo-4-phenyl-2,7-diazaspiro[4.5]dec-7-yl)-2-oxo-ethyl]-2-methyl-propionamide or a pharmaceutically acceptable salt thereof.

7. The compound of claim 1, which is 2-amino-N-((2R)-3-(benzyloxy)-1-((4S,5R)-4-(4-fluorophenyl)-2-methyl-1-oxo-2,7-diazaspiro [4.5] decan-7-yl)-1-oxopropan-2-yl)-2-methylpropanamide or a pharmaceutically acceptable salt thereof.

8. The compound of claim 1, which is 2-amino-N-((2R)-3-(benzyloxy)-1-(2-methyl-1-oxo-4-p-tolyl-2,7-diazaspiro [4.5] decan-7-yl)-1-oxopropan-2-yl)-2-methylpropanamide or a pharmaceutically acceptable salt thereof.

9. The compound of claim 6, which is an L-malate salt.

10. The compound of claim 7, which is an L-malate salt.

11. The compound of claim 8, which is an L-malate salt.

* * * * *